(12) United States Patent
Cappellini et al.

(10) Patent No.: US 10,548,976 B2
(45) Date of Patent: Feb. 4, 2020

(54) IN VITRO CELL CULTURE METHODS FOR BETA-THALASSEMIA USING ACTIVIN TYPE II RECEPTOR LIGAND TRAPS

(71) Applicants: CELGENE CORPORATION, Summti, NJ (US); Maria Cappellini, Milan (IT)

(72) Inventors: Maria Cappellini, Milan (IT); Victoria Sung, San Francisco, CA (US)

(73) Assignee: Celgene Corporation, Summit, NJ (US)

(*) Notice: Subject to any disclaimer, the term of this patent is extended or adjusted under 35 U.S.C. 154(b) by 0 days.

(21) Appl. No.: 15/574,897

(22) PCT Filed: May 19, 2016

(86) PCT No.: PCT/US2016/033187
§ 371 (c)(1),
(2) Date: Nov. 17, 2017

(87) PCT Pub. No.: WO2016/187378
PCT Pub. Date: Nov. 24, 2016

(65) Prior Publication Data
US 2018/0161426 A1 Jun. 14, 2018

Related U.S. Application Data

(60) Provisional application No. 62/164,367, filed on May 20, 2015, provisional application No. 62/320,032, filed on Apr. 8, 2016.

(51) Int. Cl.
*A61K 39/395* (2006.01)
*A61P 7/00* (2006.01)
*C12Q 1/02* (2006.01)
*G01N 33/483* (2006.01)
*A61K 35/18* (2015.01)
*A61K 38/17* (2006.01)
*A61K 39/00* (2006.01)

(52) U.S. Cl.
CPC .......... *A61K 39/3955* (2013.01); *A61K 35/18* (2013.01); *A61K 38/179* (2013.01); *A61K 39/39541* (2013.01); *A61P 7/00* (2018.01); *C12Q 1/025* (2013.01); *G01N 33/4833* (2013.01); *A61K 2039/505* (2013.01); *A61K 2039/515* (2013.01)

(58) Field of Classification Search
None
See application file for complete search history.

(56) References Cited

U.S. PATENT DOCUMENTS

| | | | |
|---|---|---|---|
| 7,842,663 B2 | 11/2010 | Knopf et al. | |
| 7,988,973 B2 * | 8/2011 | Sherman | C07K 14/71 424/185.1 |
| 8,007,809 B2 | 8/2011 | Sherman | |
| 8,173,601 B2 | 5/2012 | Knopf | |
| 9,138,459 B2 | 9/2015 | Knopf et al. | |
| 9,353,356 B2 | 5/2016 | Knopf et al. | |
| 9,399,669 B2 | 7/2016 | Knopf et al. | |
| 9,526,759 B2 | 12/2016 | Knopf et al. | |
| 9,572,865 B2 | 2/2017 | Knopf et al. | |
| 9,617,319 B2 | 4/2017 | Seehra et al. | |
| 9,745,559 B2 | 8/2017 | Seehra et al. | |
| 9,790,284 B2 | 10/2017 | Knopf et al. | |
| 9,850,298 B2 | 12/2017 | Attie et al. | |
| 9,919,030 B2 | 3/2018 | Sherman et al. | |
| 10,071,135 B2 | 9/2018 | Knopf et al. | |
| 10,093,707 B2 | 10/2018 | Sherman et al. | |
| 10,131,700 B2 | 11/2018 | Seehra et al. | |
| 10,189,882 B2 | 1/2019 | Attie et al. | |
| 10,195,249 B2 | 2/2019 | Sung et al. | |
| 10,259,861 B2 | 4/2019 | Knopf et al. | |
| 2003/0133939 A1 | 7/2003 | Ledbetter et al. | |
| 2005/0181504 A1 | 8/2005 | Merchav et al. | |
| 2005/0238646 A1 | 10/2005 | Ledbetter et al. | |
| 2010/0068215 A1 | 3/2010 | Seehra et al. | |
| 2012/0052067 A1 | 3/2012 | Sherman | |
| 2013/0243743 A1 * | 9/2013 | Seehra | A61K 38/45 424/93.73 |
| 2015/0266950 A1 | 9/2015 | Sung et al. | |
| 2015/0361163 A1 | 12/2015 | Kumar et al. | |
| 2016/0279197 A1 | 9/2016 | Sherman et al. | |
| 2016/0319254 A1 | 11/2016 | Knopf et al. | |

(Continued)

FOREIGN PATENT DOCUMENTS

WO WO 2016/069234 5/1916
WO WO 2016/090077 6/1916

(Continued)

OTHER PUBLICATIONS

Suragani et al., Blood. Jun. 19, 2014;123(25):3864-3872 (Year: 2014).*
Dussiot et al. Nat Med. Apr. 2014;20(4):398-407 (Year: 2014).*
Iancu-Rubin et al., Exp Hematol. Feb. 2013;41(2):155-166.e17 (Year: 2013).*
International Search Report and Written Opinion dated Nov. 24, 2016 for PCT/US16/33187; 9 pages.
European Search Report dated Oct. 2, 2018 for EP Pat. App. No. 16797267.8; 5 pages.
Attisano et al., 1992, "Novel activin receptors: distinct genes and alternative mRNA splicing generate a repertoire of serine/threonine kinase receptors", Cell, 68:97-108.

(Continued)

*Primary Examiner* — Daniel C Gamett
(74) *Attorney, Agent, or Firm* — Jones Day

(57) ABSTRACT

Provided herein are methods of treating beta-thalassemia in a subject comprising administering to the subject an activin type II receptor (ActRII) signaling inhibitor (e.g., an activin ligand trap) and utilizing one or more in vitro cell culture methods provided herein in (i) selection of the subject to be treated according to the methods provided herein; and/or (ii) monitoring of the subject being treated according to the methods provided herein.

14 Claims, 16 Drawing Sheets

Figure 1A:
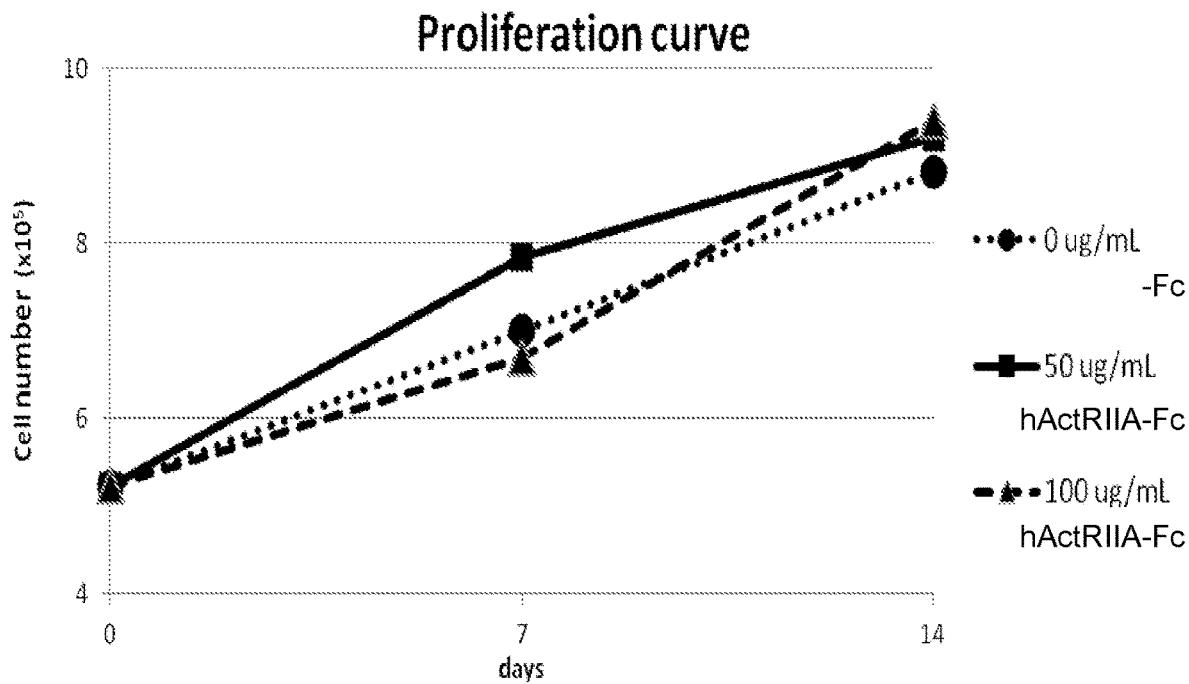

Specification includes a Sequence Listing.

(56) References Cited

U.S. PATENT DOCUMENTS

| | | |
|---|---|---|
| 2017/0137791 A1 | 5/2017 | Seehra et al. |
| 2017/0145074 A1 | 5/2017 | Knopf et al. |
| 2017/0190784 A1 | 7/2017 | Knopf et al. |
| 2017/0274077 A1 | 9/2017 | Kumar et al. |
| 2017/0291935 A1 | 10/2017 | Sherman et al. |
| 2017/0304397 A1 | 10/2017 | Hruska et al. |
| 2017/0320925 A1 | 11/2017 | Seehra et al. |
| 2017/0327800 A1 | 11/2017 | Seehra et al. |
| 2017/0360887 A1 | 12/2017 | Attie et al. |
| 2018/0009872 A1 | 1/2018 | Sherman et al. |
| 2018/0050085 A1 | 2/2018 | Kumar et al. |
| 2018/0050089 A1 | 2/2018 | Kumar et al. |
| 2018/0080012 A1 | 3/2018 | Seehra et al. |
| 2018/0125928 A1 | 5/2018 | Attie et al. |
| 2018/0161426 A1 | 6/2018 | Cappellini et al. |
| 2018/0162954 A1 | 6/2018 | Knopf et al. |
| 2018/0194828 A1 | 7/2018 | Seehra et al. |
| 2018/0194834 A1 | 7/2018 | Attie et al. |
| 2019/0049469 A1 | 2/2019 | Sung et al. |
| 2019/0062392 A1 | 2/2019 | Koncarevic et al. |

FOREIGN PATENT DOCUMENTS

| | | |
|---|---|---|
| WO | WO 2016/090188 | 6/1916 |
| WO | WO 2016/183280 | 11/1916 |
| WO | WO 2016/187378 | 11/1916 |
| WO | WO 2017/079591 | 5/1917 |
| WO | WO 2017/091706 | 6/1917 |
| WO | WO 2018/022762 | 2/1918 |
| WO | WO 2018/231905 | 12/1918 |
| WO | WO 2002/032925 | 4/2002 |
| WO | WO 2002/088171 | 11/2002 |
| WO | WO 2005/037989 | 4/2005 |
| WO | WO 2006/012627 | 2/2006 |
| WO | WO 2006/055689 | 5/2006 |
| WO | WO 2007/062188 | 5/2007 |
| WO | WO 2008/076437 | 6/2008 |
| WO | WO 2010/019261 | 2/2010 |
| WO | WO 2010/083034 | 7/2010 |
| WO | WO 2010/144452 | 12/2010 |
| WO | WO 2010/151426 | 12/2010 |
| WO | WO 2011/020045 | 2/2011 |
| WO | WO 2011/031901 | 3/2011 |
| WO | WO 2013/059347 | 4/2013 |
| WO | WO 2014/066486 | 5/2014 |
| WO | WO 2014/066487 | 5/2014 |
| WO | WO 2014/071158 | 8/2014 |
| WO | WO 2015/161220 | 10/2015 |
| WO | WO 2015/192111 | 12/2015 |

OTHER PUBLICATIONS

Breda et al., 2014, "Modulators of Erythropoiesis", Hematology—Oncology Clinics of North America, 28(2):375-386.

Carrancio et al., 2014, "An activin receptor IIA ligand trap promotes erythropoiesis resulting in a rapid induction of red blood cells and haemoglobin," British Journal of Haematology, vol. 165:870-882.

Chang-Yeol and Whitman, 2001, "Nodal signals to SMADs through Cripto-dependent and Cripto-independent mechanisms," Mol. Cell, 7:949-957.

Colah R, 2010, "Global burden, distribution and prevention of beta-thalassemias and hemoglobin E disorders", Gorakshakar et al., Expert Rev Hematol; 3(1):103-17.

Drueke TB, 2008, "Is parathyroid hormone measurement useful for the diagnosis of renal bone disease?", 73(6):674-676.

Dussiot et al., 2014, "An activin receptor IIA ligand trap corrects ineffective erythropoiesis in B-thalassemia", Nature Medicine, vol. 20:398-407.

Filippone et al., 2010, "Erythroid progenitor cells expanded from peripheral blood without mobilization or preselection: molecular characteristics and functional competence", PLoS ONE, 5(3):e9496.

Galanello and Origa, 2010, "Beta-Thalassemia", Orphanet J Rare Dis., 5(11):1-15.

Genbank NM_001106, Homo sapiens activin A receptor, type IIB (ACVR2B), mRNA, http://www.ncbi.nlm.nih.gov/entrez/viewer.fcgi?db=nucleotide&val=116734707 (Downloaded on Jan. 29, 2007).

Guerra et al., 2018, "Lack of GDF11 does not ameliorate erythropoiesis in beta-thalassemia and does not prevent the activity of the trap-ligand RAP-536", Blood, 132:165.

Herberth et al., 2009, "The five most commonly used intact parathyroid hormone assays are useful for screening but not for diagnosing bone turnover abnormalities in CKD-5 patients", Clinical Nephrology, 72(1):5-14.

Iancu-Rubin et al, 2013, "Stromal cell-mediated inhibition of erythropoiesis can be attentuated by Sotatercept (ACE-011), an activin receptor type II ligand trap", Exp. Hematol., 41:155-166.

Kato and Radbruch, 1993, "Isolation and characterization of CD34+ hematopoietic stem cells from human peripheral blood by high-gradient magnetic cell sorting", Cytometry, 14(4):384-392.

Lee and Mcpherron, 2001, "Regulation of Myostatin Activity and Muscle Growth," PNAS, 98(16):9306-9311.

Lehmann et al., 2008, "Bone histomorphometry and biochemical markers of bone turnover in subjects with chronic kidney disease Stages 3-5", Clin Nephrology, 70(4):296-305.

Mathew et al., 2008, "The mechanism of phosphorus as a cardiovascular risk factor in CKD", J Am Soc Nephrol, 19:1092-1105.

Modell et al., 2007, "Epidemiology of haemoglobin disorders in Europe: an overview", Scand J Clin Lab Invest; 67:39-69.

Modell et al., 2008, "Global epidemiology of haemoglobin disorders and derived service indicators", Bull World Health Organ;86(6):480-487.

Oh et al., 2002, "Activin type IIA and IIB receptors mediate Gdf11 signaling in axial vertebral patterning," Genes & Development, 16:2749-2754.

Okuno and Inaba, 2009, "Biochemical markers of bone turnover. New aspect. Dialysis and bone metabolic marker", Clinical Calcium, 19(8):1084-1091 (English abstract only).

Suragani et al., 2014, "Modified Activin Receptor IIB Ligand Trap Mitigates Ineffective Erythropoiesis and Disease Complications in Murine Beta-Thalassemia", Blood, 123(25):3864-3872.

Thein SL, 2013, "The molecular basis of β-thalassemia", Cold Spring Haiti Perspect Med, 3(5):a011700.

Weatherall DJ, 2001, "Phenotype-genotype relationships in monogenic disease: lessons from the thalassaemias", Nature Reviews Genetics; 2(4):245-255.

Wong et al., 2008, "Ex vivo-generated CD36+ erythroid progenitors are highly permissive to human parvovirus B19 replication", J. Virol., 82:2470-2476.

Yamada et al., 2008, "Utility of serum tartrate-resistant acid phosphatase (TRACP5b) as a bone resorption marker in patients with chronic kidney disease: independence from renal dysfunction", Clin. Endocrinolo. (Oxf)., 69(2):189-96.

Yamashita et al., 1995, "Osteogenic protein-1 binds to activin type II receptors and induces certain activin-like effects", J. Cell Biol., 130:217-226.

Young et al., 2004, "Parvovirus B19", N. Engl. J. Med., 250:586-597.

* cited by examiner

Media pixel density

Media pixel density

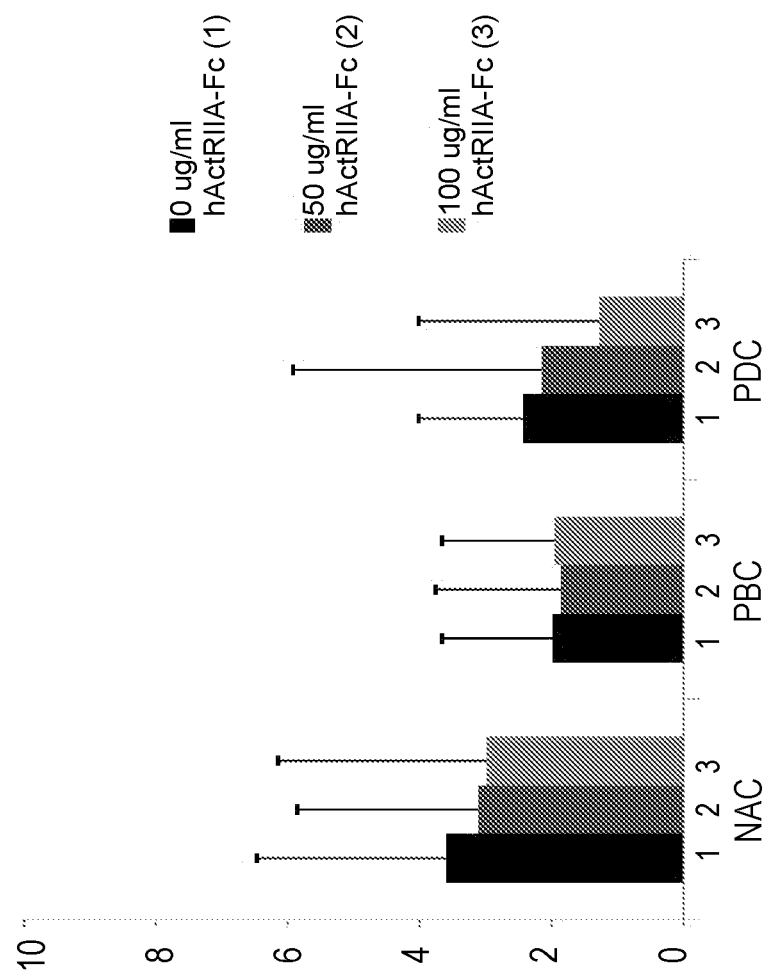
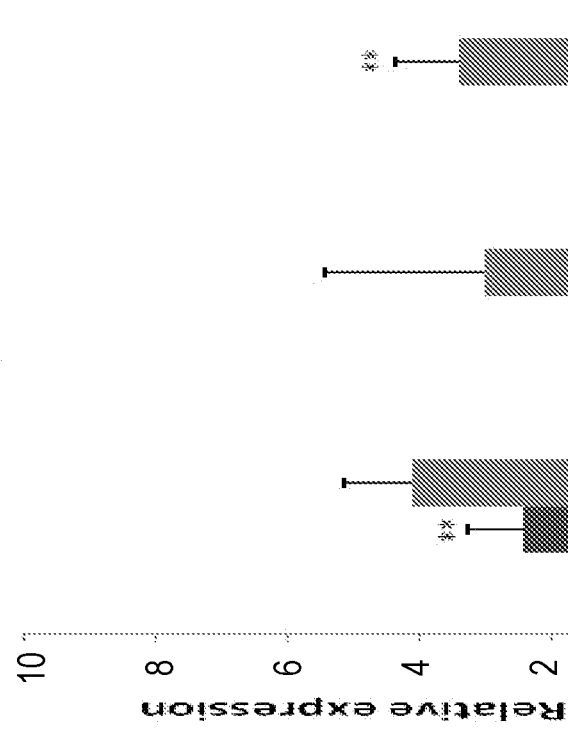

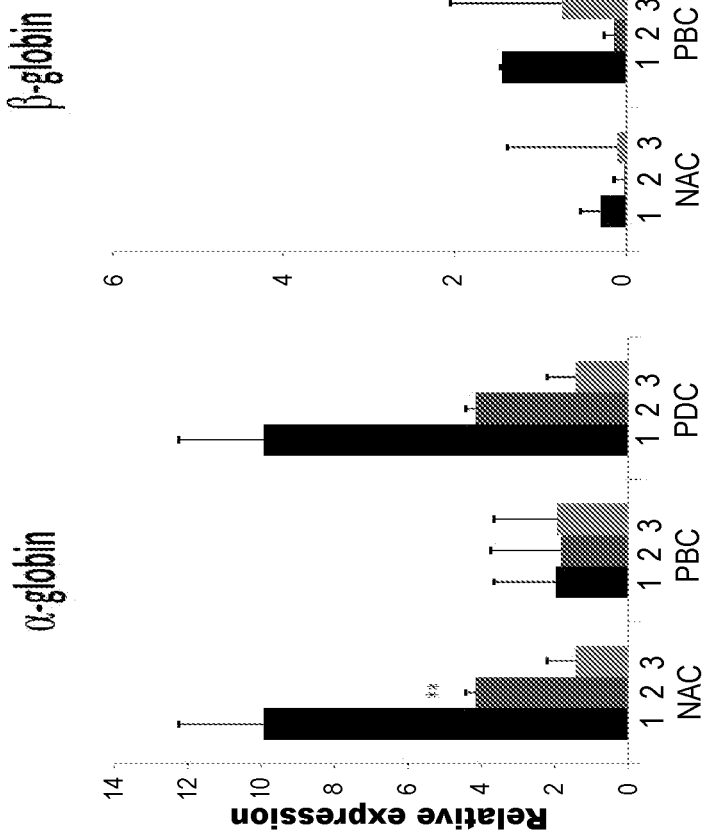
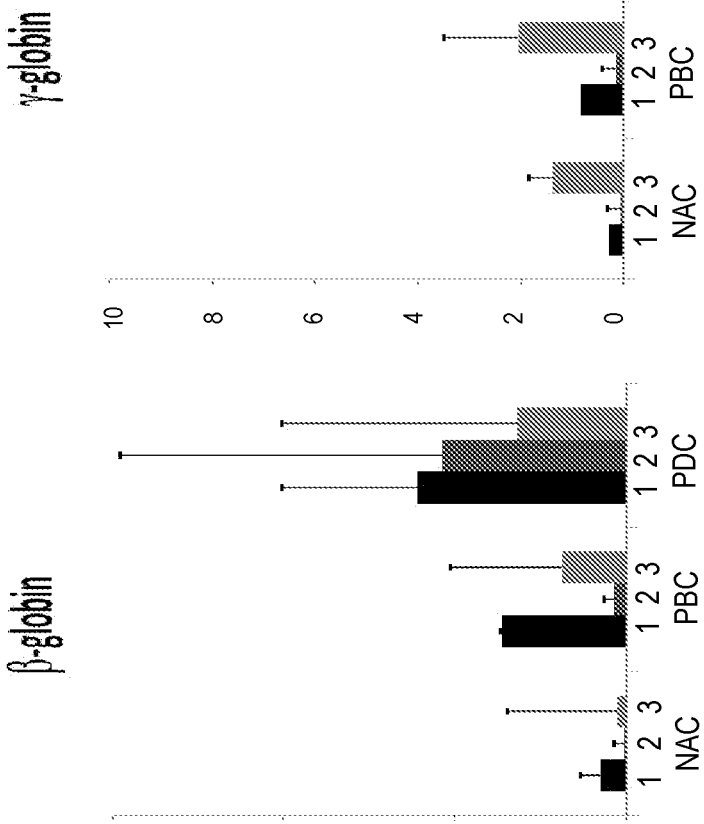
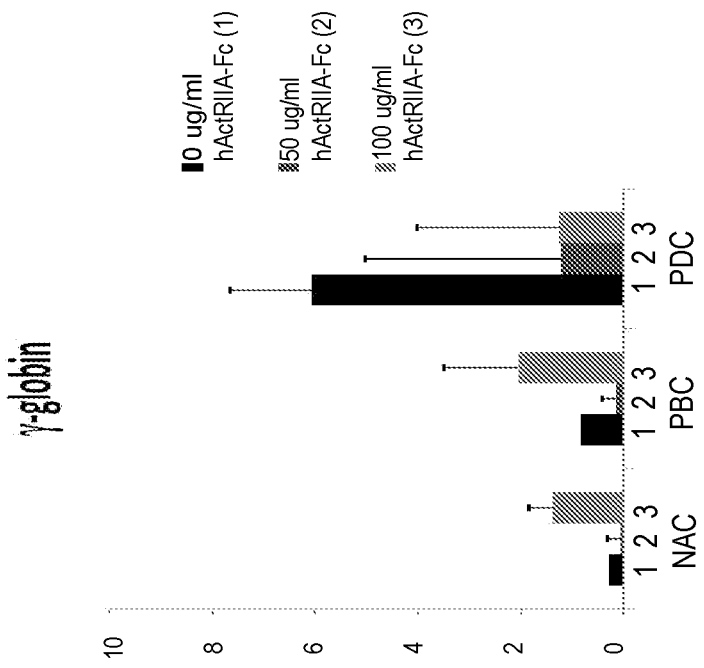

IN VITRO CELL CULTURE METHODS FOR BETA-THALASSEMIA USING ACTIVIN TYPE II RECEPTOR LIGAND TRAPS

1. CROSS-REFERENCE TO RELATED APPLICATIONS

This application is a national stage of International Patent Application No. PCT/US2016/033187, filed on May 19, 2016, which claims the benefit of priority of U.S. Provisional Patent Application No. 62/164,367, filed May 20, 2015, and U.S. Provisional Patent Application No. 62/320,032, filed Apr. 8, 2016, the entire contents of each of which are incorporated herein by reference and for all purposes.

2. SEQUENCE LISTING

The present application is being filed with a Sequence Listing submitted as file name "12827_965_228_SeqListing.txt", of size 93 kilobytes, which was created on May 16, 2016. The Sequence Listing is incorporated herein by reference in its entirety and for all purposes.

3. FIELD

Provided herein are methods of treating beta-thalassemia in a subject comprising administering to the subject an activin type II receptor (ActRII) signaling inhibitor (e.g., an activin ligand trap) and utilizing one or more in vitro cell culture methods provided herein in (i) selection of the subject to be treated according to the methods provided herein; and/or (ii) monitoring of the subject being treated according to the methods provided herein.

4. BACKGROUND

Beta-thalassemia, one of the most common inherited hemoglobinopathies worldwide, is due to autosomal mutations in the gene encoding β-globin which induce an absence or low-level synthesis of this protein in erythropoietic cells (Weatherall D J, 2001, Nature Reviews Genetics; 2(4):245-255). About 80 to 90 million people (~1.5% of the global population) are carriers of beta-thalassemia with approximately 60,000 symptomatic individuals born annually (Modell et al., 2007, Scand J Clin Lab Invest; 67:39-69). The annual incidence of symptomatic individuals is estimated at 1 in 100,000 worldwide and 1 in 10,000 in the European Union (EU) (Galanello R and Origa R, 2010, Orphanet J Rare Dis; 5:11). Incidence is highest in the Mediterranean region, the Middle East, and South East Asia (particularly India, Thailand and Indonesia; this region accounts for approximately 50% of affected births) and incidence is increasing worldwide (e.g., Europe, the Americas and Australia) as a result of migration (Colah R, Gorakshakar et al., 2010; Expert Rev Hematol; 3(1):103-17; Modell et al., 2008, Bull World Health Organ; 86(6):480-7).

Beta-thalassemias are characterized by a reduction of β-globin chains and a subsequent imbalance in globin chains (α:non-α ratio) of the hemoglobin (Hb) molecule, which results in impaired erythropoiesis and other complications. Nearly 200 different mutations have been described in patients with beta-thalassemia that affect the beta-globin gene, for which patients may be either homozygous or compound heterozygous. Phenotypic effects, therefore, range widely in patients from slight impairment to complete inhibition of beta-globin chain synthesis (Thein S L, 2013, Cold Spring Harb Perspect Med; 3(5):a011700). In addition to deficient β-globin chains, patients may also present with β-thalassemia combined with structural variants such as HbE, leading to HbE/beta-thalassemia.

Given the current lack of safe and effective drug therapies to treat beta-thalassemia, for example, transfusion-dependent and non-transfusion-dependent beta-thalassemia, there is significant unmet medical need for the development of new therapies that specifically address the underlying pathophysiology of beta-thalassemia syndromes including anemia and complications of ineffective erythropoiesis, for methods of diagnosing beta-thalassemia, and for methods of monitoring treating of beta-thalassemia.

Two related type II receptors, ActRIIA and ActRIIB, have been identified as the type II receptors for activins (Mathews and Vale, 1991, Cell 65:973-982; Attisano et al., 1992, Cell 68: 97-108). Besides activins, ActRIIA and ActRIIB can biochemically interact with several other TGF-beta family proteins, including BMP7, Nodal, GDF8, and GDF11 (Yamashita et al., 1995, J. Cell Biol. 130:217-226; Lee and McPherron, 2001, Proc. Natl. Acad. Sci. 98:9306-9311; Yeo and Whitman, 2001, Mol. Cell 7: 949-957; Oh et al., 2002, Genes Dev. 16:2749-54). ALK4 is the primary type I receptor for activins, particularly for activin A, and ALK-7 may serve as a receptor for activins as well, particularly for activin B.

ActRII signaling inhibitors have been demonstrated to increase red blood cell levels and treat ineffective erythropoiesis (see, e.g., U.S. Pat. No. 7,988,973 and U.S. patent application Ser. No. 13/654,191, respectively, which are incorporated herein by reference in their entireties). Moreover, an activin ligand trap, consisting of a humanized fusion-protein consisting of the extracellular domain of activin-receptor type IIA (ActRIIA) and the human IgG1 Fc (ActRIIA-hFc), is currently being evaluated in phase II clinical trials for treatment of subjects with beta-thalassemia. An activin ligand trap, consisting of a humanized fusion-protein consisting of the extracellular domain of activin-receptor type IIB (ActRIIB) and the human IgG1 Fc (ActRIIB-hFc), is currently being evaluated in phase II clinical trials for treatment of subjects with beta-thalassemia.

5. SUMMARY

Provided herein are methods of treating beta-thalassemia in a subject comprising administering to the subject an ActRII signaling inhibitor and utilizing one or more in vitro cell culture methods provided herein in (i) selection of the subject to be treated according to the methods provided herein; and/or (ii) monitoring of the subject being treated according to the methods provided herein.

Also provided herein is an in vitro cell culture method, comprising (a) co-culturing an erythroid progenitor cell (EPC) and a stromal cell in the presence of an activin type II receptor (ActRII) signaling inhibitor for a period of time; and (b) determining the level of GYPA, GATA1, GATA2, or alpha-globin in the EPC.

Also provided herein is an in vitro cell culture method, comprising (a) co-culturing an EPC and a stromal cell in the presence of an activin type II receptor (ActRII) signaling inhibitor for a period of time; and (b) determining the level of expansion of the EPC.

Also provided herein is an in vitro cell culture method, comprising (a) culturing a stromal cell in the presence of an activin type II receptor (ActRII) signaling inhibitor for a period of time; and (b) determining the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the supernatant obtained from the culture of step (a).

Also provided herein is an in vitro cell culture method, comprising (a) culturing an EPC in conditioned media for a period of time, wherein the conditioned media has been obtained from a stromal cell cultured in the presence of an ActRII signaling inhibitor; and (b) determining the level of GYPA, GATA1, GATA2, and/or alpha-globin in the EPC and/or the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the supernatant obtained from the culture of step (a).

Also provided herein is an in vitro cell culture method, comprising (a) culturing an EPC in conditioned media for a period of time, wherein the conditioned media has been obtained from a stromal cell cultured in the presence of an ActRII signaling inhibitor; and (b) determining the level of expansion of the EPC.

Also provided herein is an in vitro cell culture method, comprising (a) culturing an EPC in the presence of an ActRII signaling inhibitor for a period of time; and (b) determining the level of GYPA, GATA1, GATA2, or alpha-globin in the EPC and/or the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the supernatant obtained from the culture of step (a).

In certain embodiments, the stromal cell has been obtained from bone marrow of a beta-thalassemic subject. In certain embodiments, the erythroid progenitor cell has been obtained from peripheral blood of a beta-thalassemic subject.

In certain embodiments, the ActRII signaling inhibitor is a polypeptide comprising an amino acid sequence selected from the group consisting of: (a) 90% identical to SEQ ID NO:2; (b) 95% identical to SEQ ID NO:2; (c) 98% identical to SEQ ID NO:2; (d) SEQ ID NO:2; (e) 90% identical to SEQ ID NO:3; (f) 95% identical to SEQ ID NO:3; (g) 98% identical to SEQ ID NO:3; (h) SEQ ID NO:3; (i) 90% identical to SEQ ID NO:6; (j) 95% identical to SEQ ID NO:6; (k) 98% identical to SEQ ID NO:6; (l) SEQ ID NO:6; (m) 90% identical to SEQ ID NO:7; (n) 95% identical to SEQ ID NO:7; (o) 98% identical to SEQ ID NO:7; (p) SEQ ID NO:7; (q) 90% identical to SEQ ID NO:12; (r) 95% identical to SEQ ID NO:12; (s) 98% identical to SEQ ID NO:12; (t) SEQ ID NO:12; (u) 90% identical to SEQ ID NO:17; (v) 95% identical to SEQ ID NO:17; (w) 98% identical to SEQ ID NO:17; (x) SEQ ID NO:17; (y) 90% identical to SEQ ID NO:20; (z) 95% identical to SEQ ID NO:20; (aa) 98% identical to SEQ ID NO:20; (bb) SEQ ID NO:20; (cc) 90% identical to SEQ ID NO:21; (dd) 95% identical to SEQ ID NO:21; (ee) 98% identical to SEQ ID NO:21; (ff) SEQ ID NO:21; (gg) 90% identical to SEQ ID NO:25; (hh) 95% identical to SEQ ID NO:25; (ii) 98% identical to SEQ ID NO:25; and (jj) SEQ ID NO:25.

In certain embodiments, the ActRII signaling inhibitor is an ActRIIA signaling inhibitor.

In certain embodiments, the ActRIIA signaling inhibitor is a polypeptide comprising an amino acid sequence selected from the group consisting of: (a) 90% identical to SEQ ID NO:2; (b) 95% identical to SEQ ID NO:2; (c) 98% identical to SEQ ID NO:2; (d) SEQ ID NO:2; (e) 90% identical to SEQ ID NO:3; (f) 95% identical to SEQ ID NO:3; (g) 98% identical to SEQ ID NO:3; (h) SEQ ID NO:3; (i) 90% identical to SEQ ID NO:6; (j) 95% identical to SEQ ID NO:6; k) 98% identical to SEQ ID NO:6; (l) SEQ ID NO:6; (m) 90% identical to SEQ ID NO:7; (n) 95% identical to SEQ ID NO:7; (o) 98% identical to SEQ ID NO:7; and (p) SEQ ID NO:7. In certain embodiments, the ActRII signaling inhibitor is a polypeptide comprising the amino acid sequence of SEQ ID NO:7. In certain embodiments, the ActRII signaling inhibitor is a humanized fusion-protein consisting of the extracellular domain of ActRIIA and the human IgG1 Fc domain.

In certain embodiments, the wherein the ActRII signaling inhibitor is a signaling inhibitor of ActRIIB In certain embodiments, the ActRIIB signaling inhibitor is a polypeptide comprising an amino acid sequence selected from the group consisting of: (a) 90% identical to SEQ ID NO:17; (b) 95% identical to SEQ ID NO:17; (c) 98% identical to SEQ ID NO:17; (d) SEQ ID NO:17; (e) 90% identical to SEQ ID NO:20; (f) 95% identical to SEQ ID NO:20; (g) 98% identical to SEQ ID NO:20; (h) SEQ ID NO:20; (i) 90% identical to SEQ ID NO:21; (j) 95% identical to SEQ ID NO:21; (k) 98% identical to SEQ ID NO:21; (l) SEQ ID NO:21; (m) 90% identical to SEQ ID NO:25; (n) 95% identical to SEQ ID NO:25; (o) 98% identical to SEQ ID NO:25; and (p) SEQ ID NO:25. In certain embodiments, the ActRII signaling inhibitor is a polypeptide comprising the amino acid sequence of SEQ ID NO:25. In certain embodiments, the ActRII signaling inhibitor is a humanized fusion-protein consisting of the extracellular domain of ActRIIB and the human IgG1 Fc domain.

Also provided herein is use of an in vitro cell culture method provided herein for predicting responsiveness of a subject to treatment of beta-thalassemia, wherein the subject has been administered an ActRII signaling inhibitor, wherein the EPC has been obtained from the subject.

Also provided herein is use of an in vitro cell culture method provided herein for predicting responsiveness of a subject to treatment with an ActRII signaling inhibitor, wherein the stromal cell has been obtained from the subject.

Also provided herein is use of an in vitro cell culture method provided herein for monitoring treatment of beta-thalassemia in a subject administered an initial pharmaceutically effective dose of an ActRII signaling inhibitor, wherein the EPC has been obtained from the subject.

Also provided herein is use of an in vitro cell culture method provided herein for monitoring treatment of beta-thalassemia in a subject administered an initial pharmaceutically effective dose of an ActRII signaling inhibitor, wherein the stromal cell has been obtained from the subject.

Also provided herein is use of an in vitro cell culture method provided herein for selecting a subject to be administered an ActRII signaling inhibitor, wherein the EPC has been obtained from the subject.

Also provided herein is use of an in vitro cell culture method provided herein for selecting a subject to be administered an ActRII signaling inhibitor, wherein the stromal cell has been obtained from the subject.

In certain embodiments, use of an in vitro cell culture method provided herein comprises selecting the subject if use of the in vitro cell culture method results in achieving one or more outcome parameter, wherein the outcome parameter is selected from a group consisting of: (a) an increase in the level of GYPA in the EPC of the in vitro cell culture method as compared to the level of GYPA in a control EPC; (b) an increase in the level of GATA1 in the EPC of the in vitro cell culture method as compared to the level of GATA1 in a control EPC; (c) a decrease in the level of GATA2 in the EPC of the in vitro cell culture method as compared to the level of GATA2 in a control EPC; (d) a decrease in the level of alpha-globin in the EPC of the in vitro cell culture method as compared to the level of alpha-globin in a control EPC; (e) an increase in the level of expansion of the EPC in the in vitro cell culture method as compared to the level of expansion in a control EPC; (f) an increase in the level of ICAM-1 in the supernatant of the in vitro cell culture method as compared to the level of ICAM-1 in a control supernatant; (g) an increase in the level of IL-1Ra in the supernatant of the in vitro cell culture as compared to the level of IL-1Ra in a control supernatant; (h) an increase in the level of survivin in the supernatant of the in vitro cell culture method as compared to the level of survivin in a control supernatant; (i) an increase in the level of Bcl-2 in the supernatant of the in vitro cell culture method as compared to the level of Bcl-2 in a control supernatant; (j) an increase in the level of Bcl-xL in the supernatant of the in vitro cell culture method as compared to the level of Bcl-xL in a control supernatant; (k) an increase in the level of MCP-1 in the supernatant of the in vitro cell culture method as compared to the level of MCP-1 in a control supernatant; (l) an increase in the level of serpinE1 in the supernatant of the in vitro cell culture method as compared to the level of serpinE1 in a control supernatant; (m) an increase in the level of GRO-a in the supernatant of the in vitro cell culture method as compared to the level of GRO-a in a control supernatant, (n) an increase in the level of IL-8 in the supernatant of the in vitro cell culture method as compared to the level of IL-8 in a control supernatant; (o) an increase in the level of IL-10 in the supernatant of the in vitro cell culture method as compared to the level of IL-10 in a control supernatant; (p) an increase in the level of IL-2 in the supernatant of the in vitro cell culture method as compared to the level of IL-2 in a control supernatant; (q) an increase in the level of CIAP1 in the supernatant of the in vitro cell culture method as compared to the level of CIAP1 in a control supernatant; (r) an increase in the level of PON2 in the supernatant of the in vitro cell culture method as compared to the level of PON2 in a control supernatant; (s) a decrease in the level of RANTES in the supernatant of the in vitro cell culture method as compared to the level of RANTES in a control supernatant; (t) a decrease in the level of IP-10 in the supernatant of the in vitro cell culture method as compared to the level of IP-10 in a control supernatant; (u) a decrease in the level of IL-1a in the supernatant of the in vitro cell culture method as compared to the level of IL-1a in a control supernatant; (v) a decrease in the level of IL-1b in the supernatant of the in vitro cell culture method as compared to the level of IL-1b in a control supernatant; (w) a decrease in the level of MIF in the supernatant of the in vitro cell culture method as compared to the level of MIF in a control supernatant; (x) a decrease in the level of G-CSF in the supernatant of the in vitro cell culture method as compared to the level of G-CSF in a control supernatant; (y) a decrease in the level of GMCSF in the supernatant of the in vitro cell culture method as compared to the level of GMCSF in a control supernatant; (z) a decrease in the level of C5a in the supernatant of the in vitro cell culture method as compared to the level of C5a in a control supernatant; (aa) a decrease in the level of IL-6 in the supernatant of the in vitro cell culture method as compared to the level of IL-6 in a control supernatant; (bb) a decrease in the level of HO-2 in the supernatant of the in vitro cell culture method as compared to the level of HO-2 in a control supernatant; (cc) a decrease in the level of HIF-1a in the supernatant of the in vitro cell culture method as compared to the level of HIF-1a in a control supernatant; (dd) a decrease in the level of TRAIL R1 in the supernatant of the in vitro cell culture method as compared to the level of TRAIL R1 in a control supernatant; (ee) a decrease in the level of cleaved caspase-3 in the supernatant of the in vitro cell culture method as compared to the level of cleaved caspase-3 in a control supernatant; (ff) a decrease in the level of p27 in the supernatant of the in vitro cell culture method as compared to the level of p27 in a control supernatant; (gg) a decrease in the level of p21 in the supernatant of the in vitro cell culture method as compared to the level of p21 in a control supernatant; (hh) a decrease in the level of Bax in the supernatant of the in vitro cell culture method as compared to the level of Bax in a control supernatant; and (ii) a decrease in the level of Bad in the supernatant of the in vitro cell culture method as compared to the level of bad in a control supernatant. In certain embodiments, the subject has beta-thalassemia.

Also provided herein is a method of treating beta-thalassemia in a subject, comprising administering an ActRII signaling inhibitor to the subject, wherein the patient has been selected by using an in vitro cell culture method provided herein.

Also provided herein is a method of treating beta-thalassemia in a subject, comprising administering an ActRII signaling inhibitor to the subject, wherein the patient is being monitored by using the in vitro cell culture method provided herein. In certain embodiments, the subject is a human.

6. BRIEF DESCRIPTION OF THE DRAWINGS

Figure 1B:
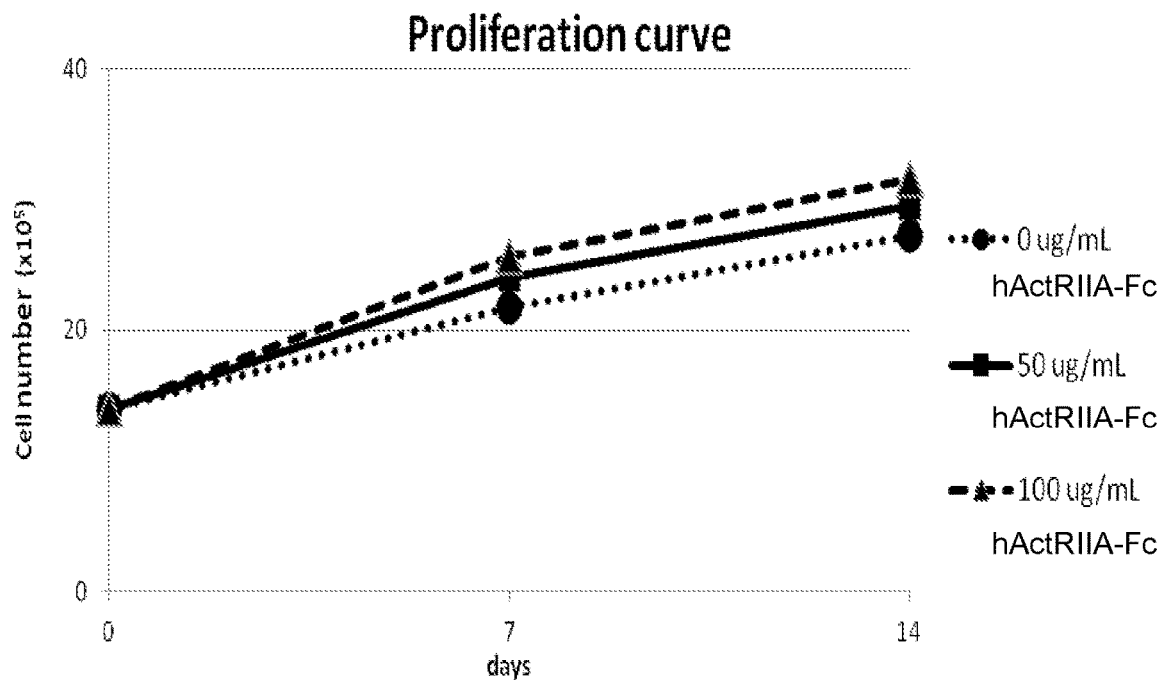
Figure 1C:
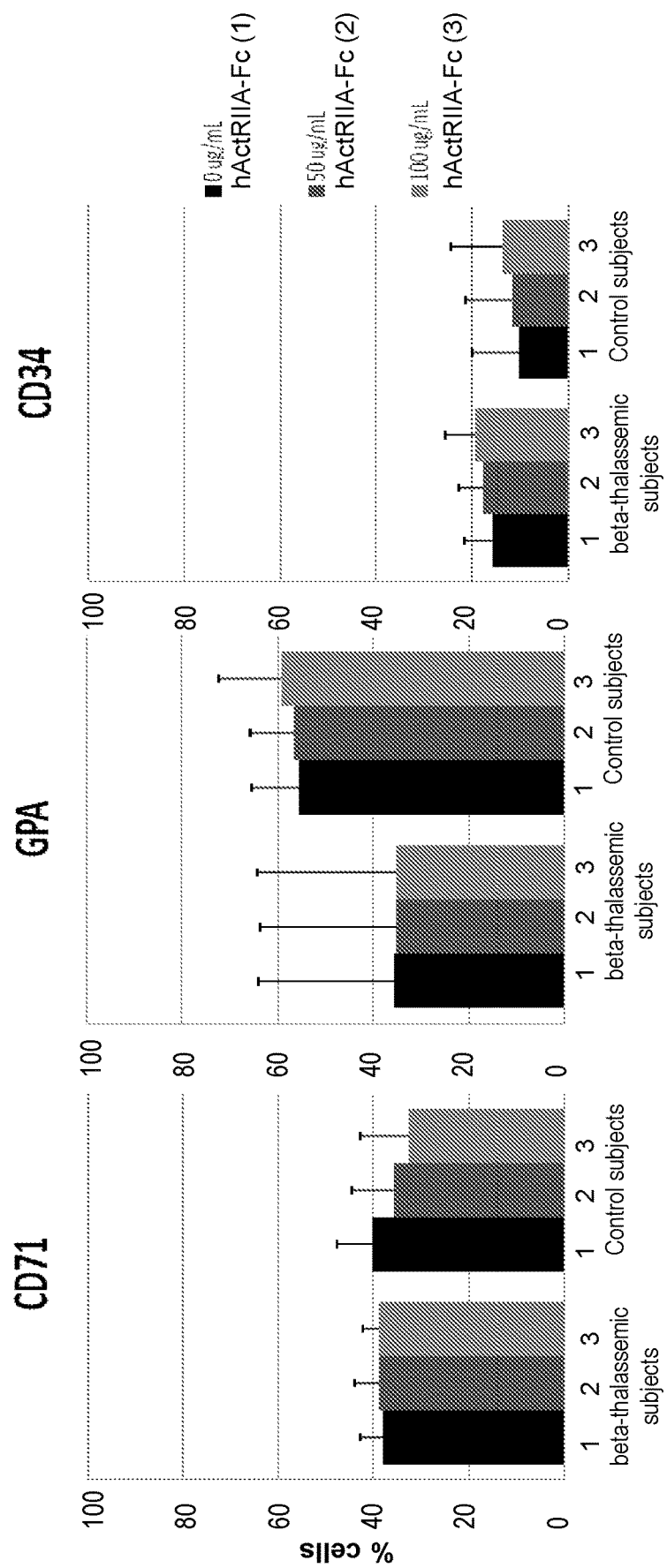

FIG. 1A depicts expansion of total beta-thalassemic subject-derived CD34+ cells in the presence hActRIIA-Fc (SEQ ID NO:7) at different concentrations (circles=0 ug/mL; squares=50 ug/mL; triangles=100 ug/mL) after 2 weeks of culture. FIG. 1B depicts expansion of total control subject-derived CD34+ cells in the presence hActRIIA-Fc (SEQ ID NO:7) at different concentrations (circles=0 ug/mL; squares=50 ug/mL; triangles=100 ug/mL) after 2 weeks of culture. FIG. 1C depicts the flow cytometric analyses of CD71 expression (bottom panel), GPA expression (middle panel), or CD34 expression (top panel) of ex vivo expanded CD34+ cells derived from beta-thalassemic or control subjects treated with different concentrations of hActRIIA-Fc (SEQ ID NO:7). Bars labeled "1" represent data from samples treated with 0 ug/mL of hActRIIA-Fc (SEQ ID NO:7). Bars labeled "2" represent data from samples treated with 50 ug/mL of hActRIIA-Fc (SEQ ID NO:7). Bars labeled "3" represent data from samples treated with 100 ug/mL of hActRIIA-Fc (SEQ ID NO:7). All data for FIG. 1A-FIG. 1C are expressed as the mean±sd.

Figure 2A:
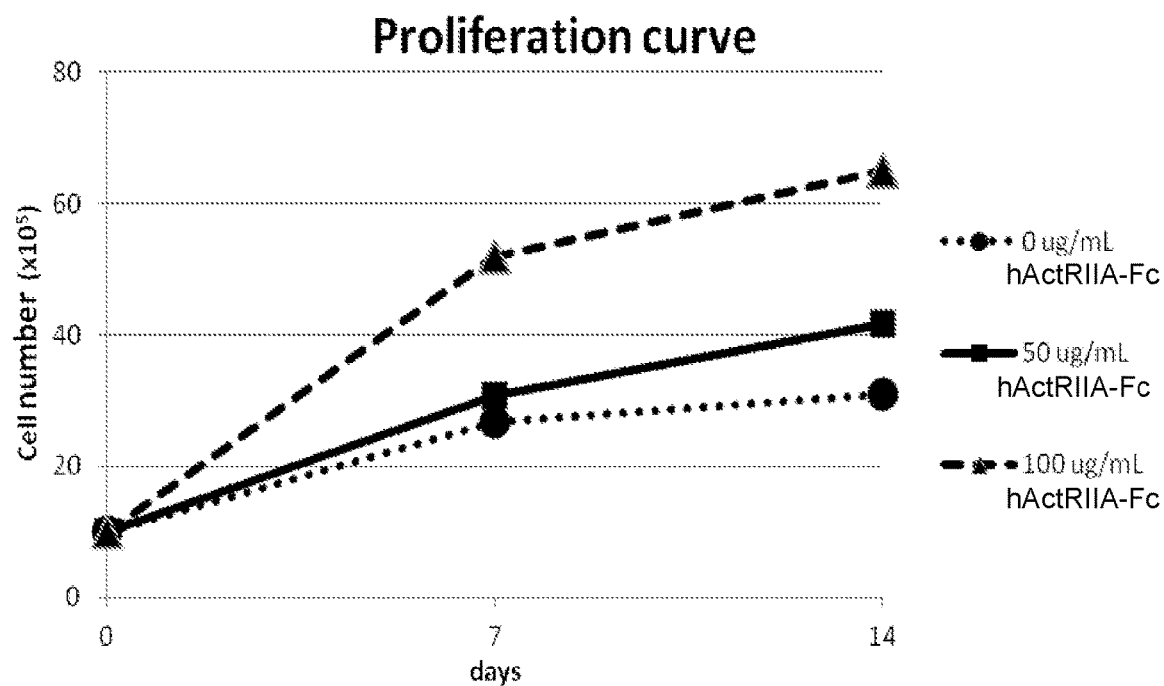
Figure 2B:
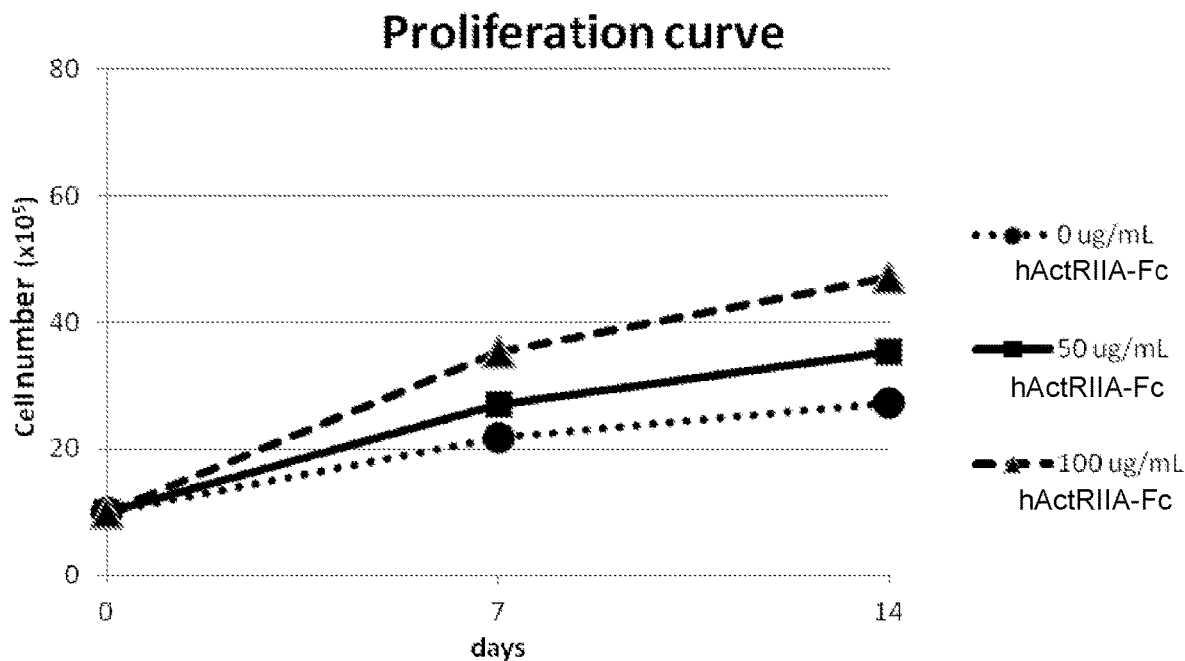
Figure 2C:
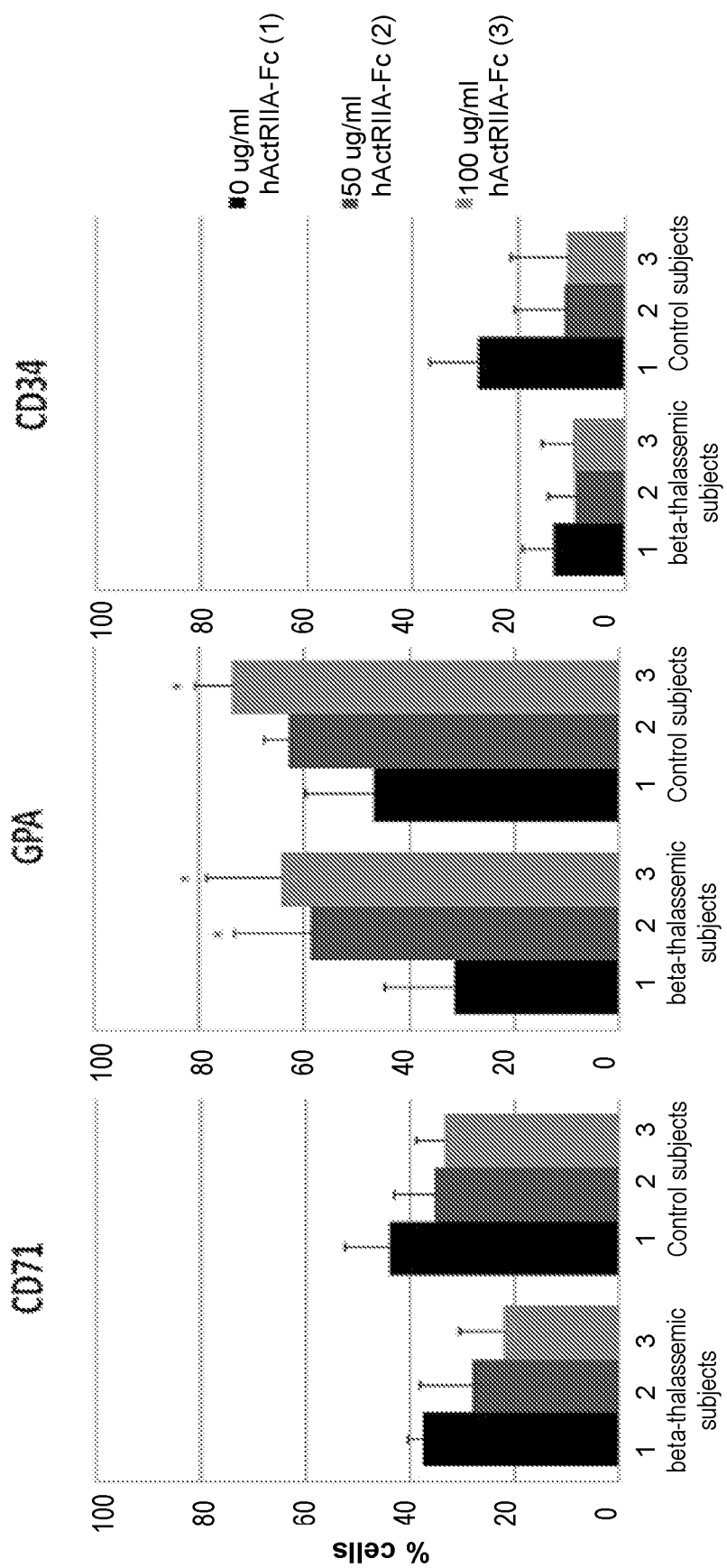

FIG. 2A depicts expansion of total beta-thalassemic subject-derived CD34+ cells in the presence of hActRIIA-Fc (SEQ ID NO:7)-treated cultured medium (CM) at different concentrations (circles=0 ug/mL; squares=50 ug/mL; triangles=100 ug/mL) after 2 weeks of culture. FIG. 2B depicts expansion of total control subject-derived CD34+ cells in the presence of hActRIIA-Fc (SEQ ID NO:7)-treated cultured medium (CM) at different concentrations (circles=0 ug/mL; squares=50 ug/mL; triangles=100 ug/mL) after 2 weeks of culture. FIG. 2C depicts the flow cytometric analyses of CD71 expression (bottom panel), GPA expression (middle panel), or CD34 expression (top panel) of ex vivo expanded CD34+ cells derived from beta-thalassemic or control subjects in the presence of hActRIIA-Fc (SEQ ID NO:7)-treated cultured medium (CM) at different concentrations. Bars labeled "1" represent data from samples treated with 0 ug/mL of hActRIIA-Fc (SEQ ID NO:7). Bars labeled "2" represent data from samples treated with 50 ug/mL of hActRIIA-Fc (SEQ ID NO:7). Bars labeled "3" represent data from samples treated with 100 ug/mL of hActRIIA-Fc (SEQ ID NO:7). All data for FIG. 2A-FIG. 2C are expressed as the mean±sd.

Figure 3A:
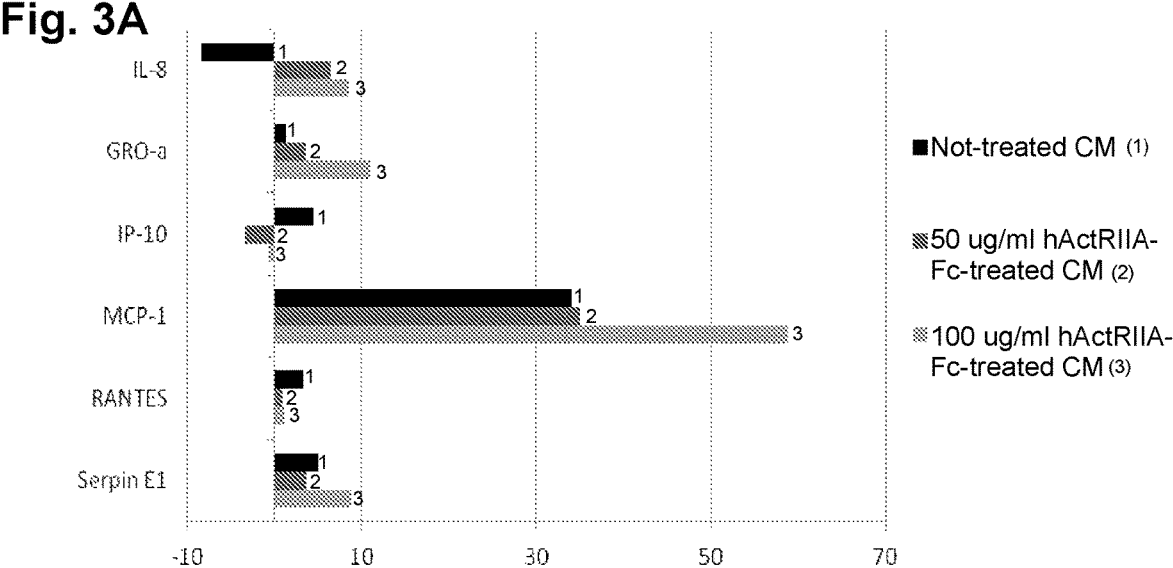
Figure 3B:
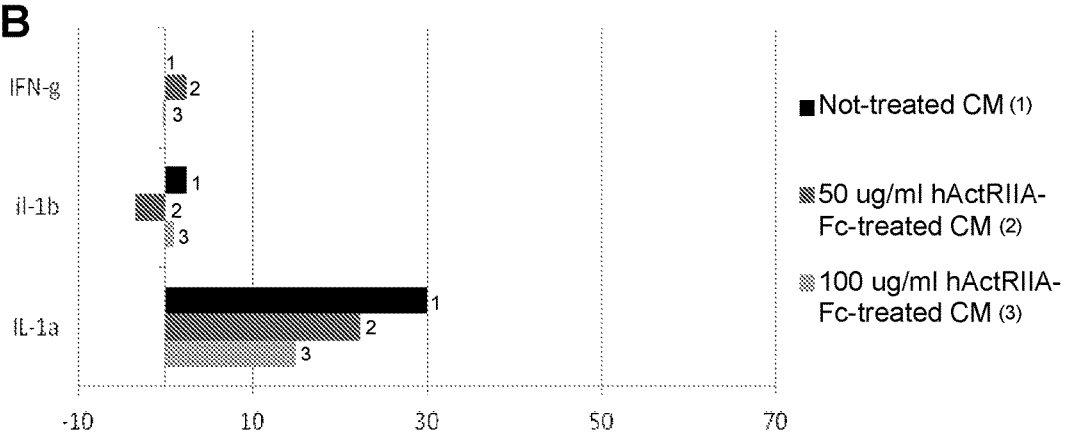
Figure 3C:
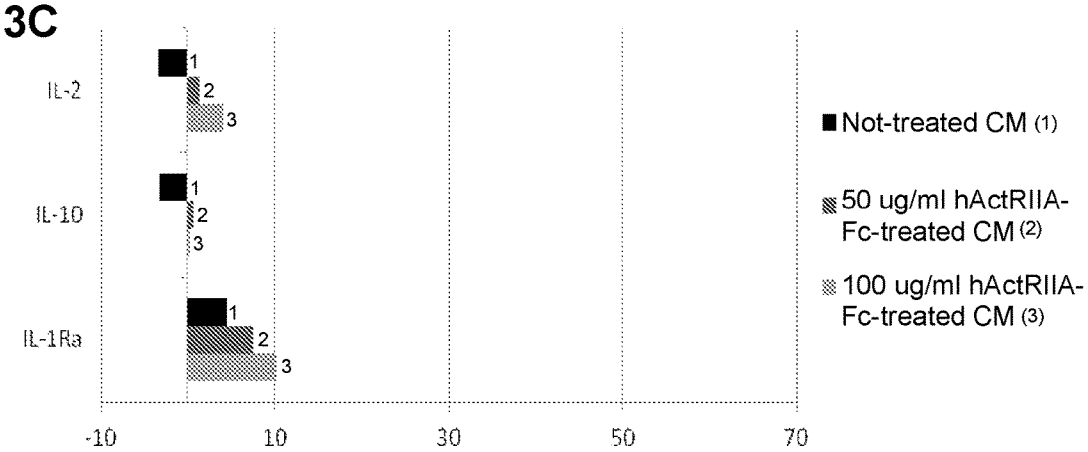
Figure 3D:
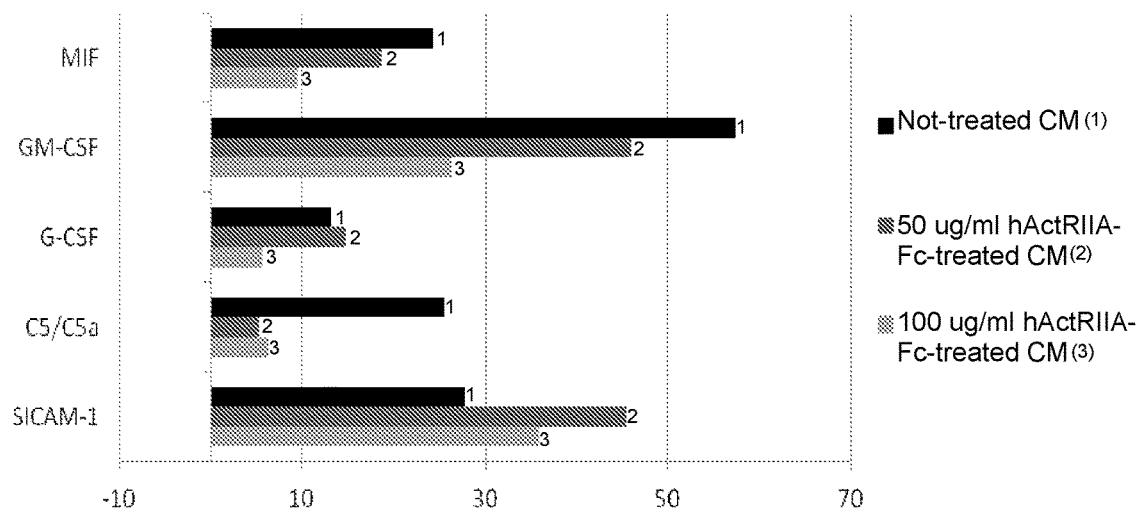
Figure 3E:
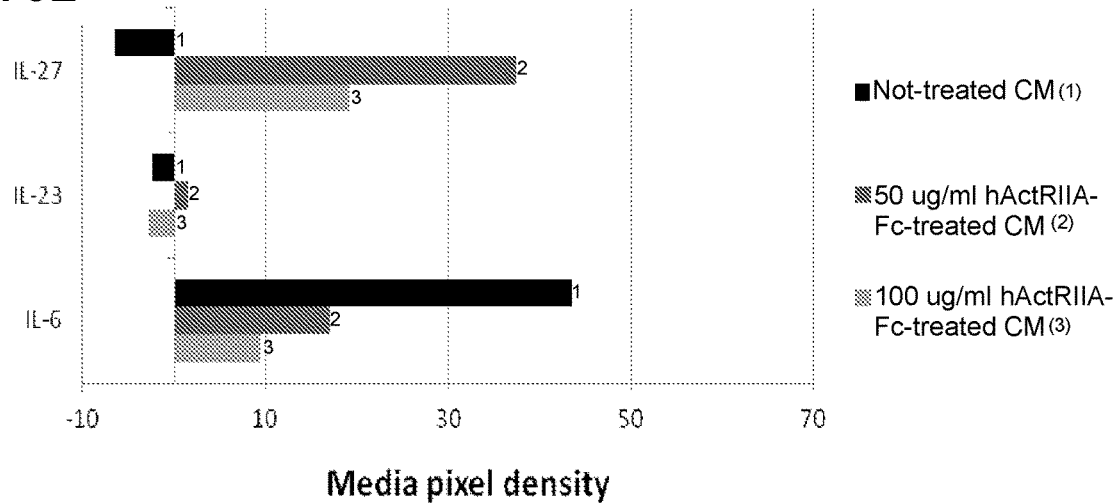

FIG. 3A-FIG. 3E demonstrates that hActRIIA-Fc (SEQ ID NO:7) induces expression anti-inflammatory cytokines and chemokines in conditioned media. FIG. 3A demonstrates the level of IL-I, GRO-a, IP-10, MCP-1, RANTES, and Serpin E1, from top to bottom, respectively, each of which is classified as a chemokine, in cells treated with untreated CM ("1"), CM treated with 50 ug/mL of hActRIIA-Fc ("2"), or CM treated with 100 ug/mL of hActRIIA-Fc ("3"). FIG. 3B demonstrates the level of IFN-gamma, IL-1beta, and IL-1alpha, from top to bottom, respectively, each of which is classified as a Th1 cytokine, in cells treated with untreated CM ("1"), CM treated with 50 ug/mL of hActRIIA-Fc ("2"), or CM treated with 100 ug/mL of hActRIIA-Fc ("3"). FIG. 3C demonstrates the level of IL-2, IL-10, IL-1Ra, from top to bottom, respectively, each of which is classified as an anti-inflammatory cytokine, in cells treated with untreated CM ("1"), CM treated with 50 ug/mL of hActRIIA-Fc ("2"), or CM treated with 100 ug/mL of hActRIIA-Fc ("3"). FIG. 3D demonstrates the level of MIF, GM-CSF, G-CSF, C5/C5a, and SICAM-1, from top to bottom, respectively, each of which is classified as a cytokine involved in inflammation/differentiation, in cells treated with untreated CM ("1"), CM treated with 50 ug/mL of hActRIIA-Fc ("2"), or CM treated with 100 ug/mL of hActRIIA-Fc ("3"). FIG. 3E demonstrates the level of IL-27, IL-23, and IL-6, from top to bottom, respectively, each of which is classified as an –12 and IL-17 family cytokine, in cells treated with untreated CM ("1"), CM treated with 50 ug/mL of hActRIIA-Fc ("2"), or CM treated with 100 ug/mL of hActRIIA-Fc ("3"). The X-axis for FIG. 3A-FIG. 3E is the media pixel density.

Figure 4A:
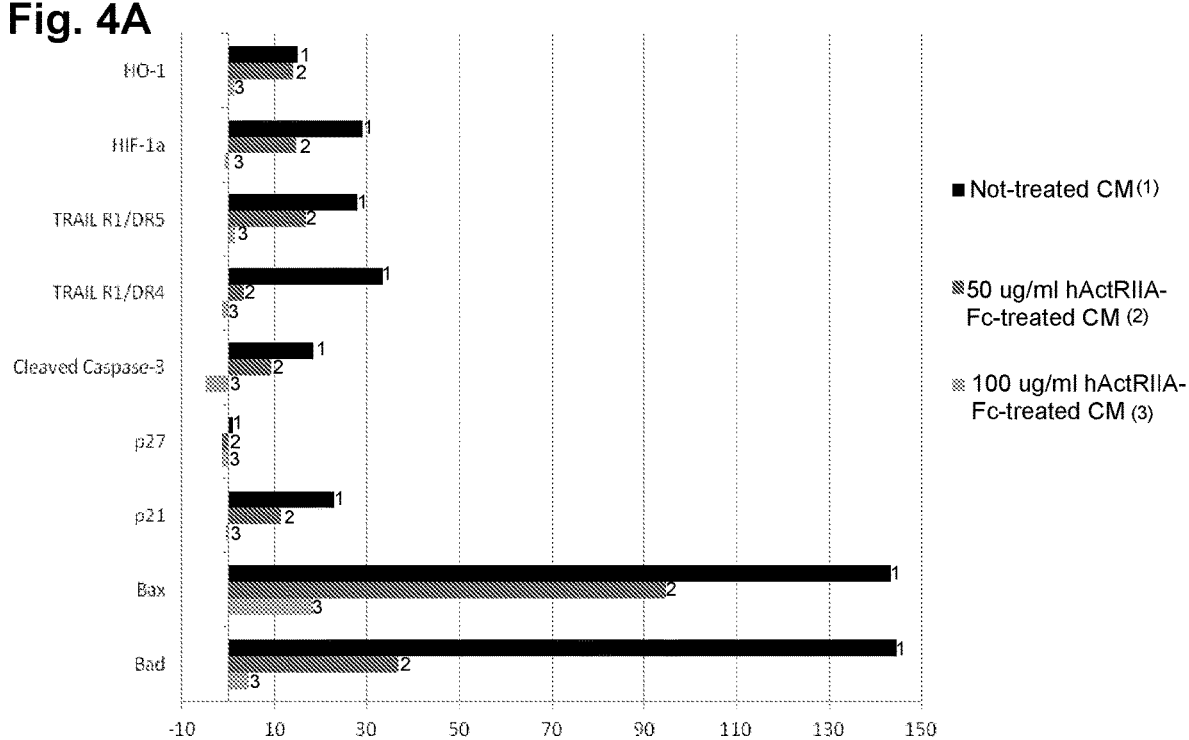
Figure 4B:
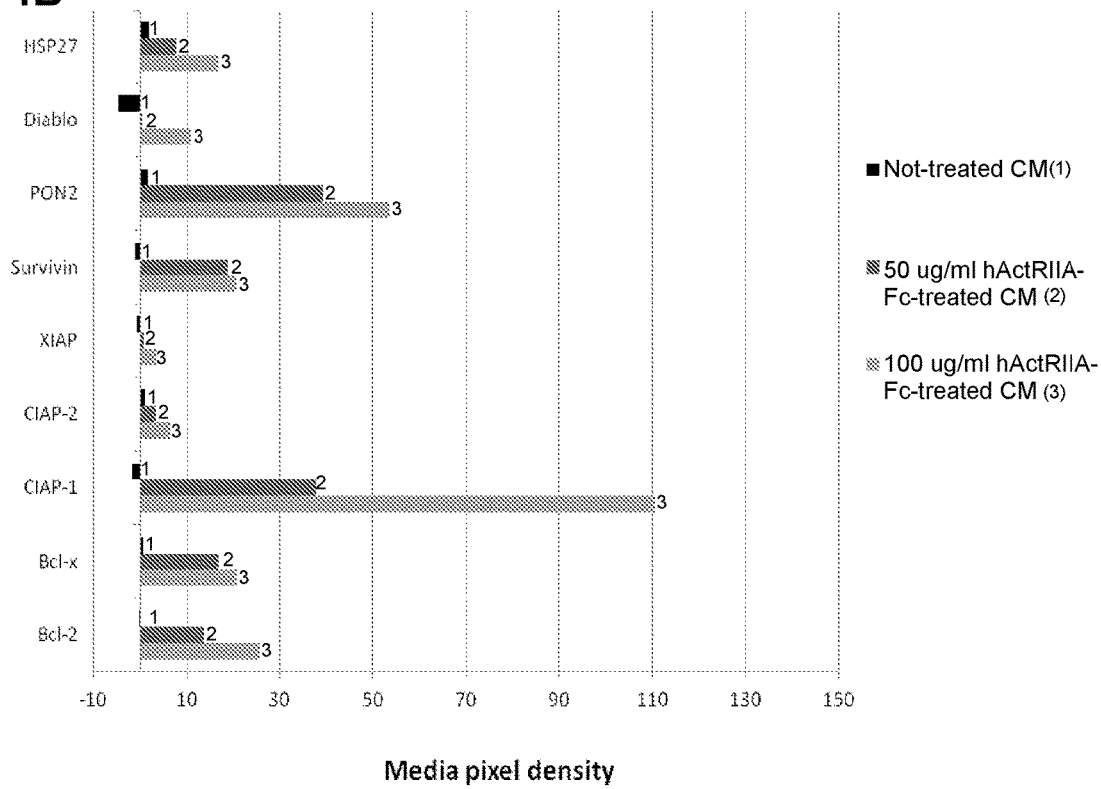

FIG. 4A and FIG. 4B demonstrate that pro-apoptotic effects of hActRIIA-Fc (SEQ ID NO:7) are correlated with alterations in molecules involved in apoptosis and redox status. FIG. 4A depicts the level of HO-1, HIF-1a, TRAIL R1/DR5, TRAIL R1/DR4, Cleaved Caspase-3, p27, p21, Bax, and Bad, from top to bottom, respectively, which are classified as having pro-apoptotic functions, in cells treated with untreated CM ("1"), CM treated with 50 ug/mL of hActRIIA-Fc ("2"), or CM treated with 100 ug/mL of hActRIIA-Fc ("3"). FIG. 4B depicts the level of HSP27, Diablo, PON2, Survivin, XIAP, CIAP-2, CIAP-1, Bcl-x, and Bcl-2, from top to bottom, respectively, which are classified as having anti-apoptotic functions, in cells treated with untreated CM ("1"), CM treated with 50 ug/mL of hActRIIA-Fc ("2"), or CM treated with 100 ug/mL of hActRIIA-Fc ("3"). The X-axis for FIG. 4A and FIG. 4B is the media pixel density.

Figure 5A:
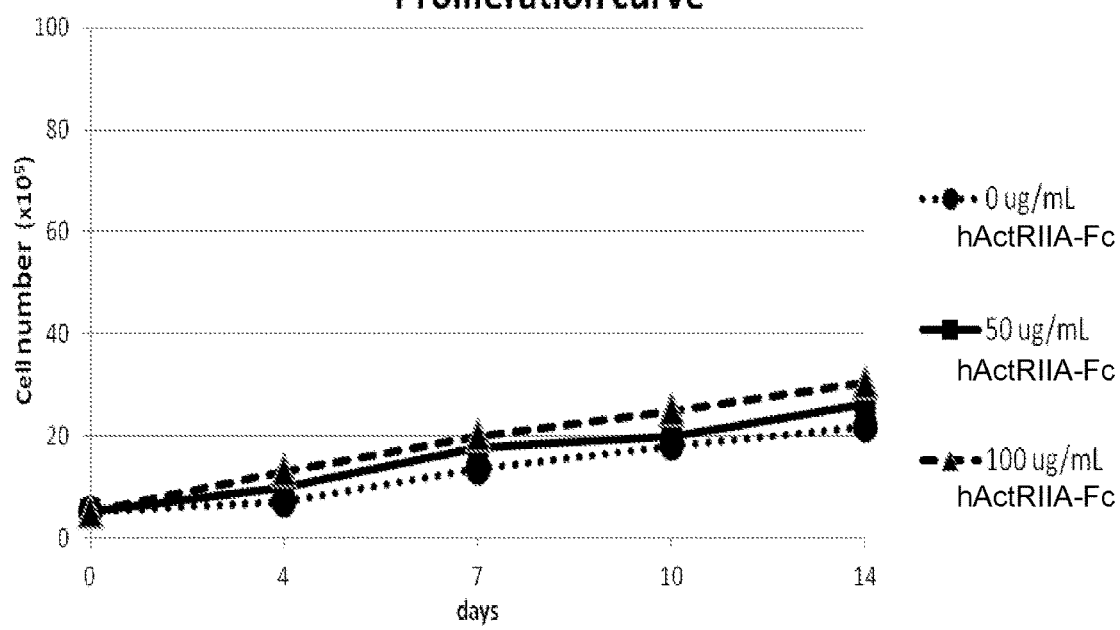
Figure 5B:
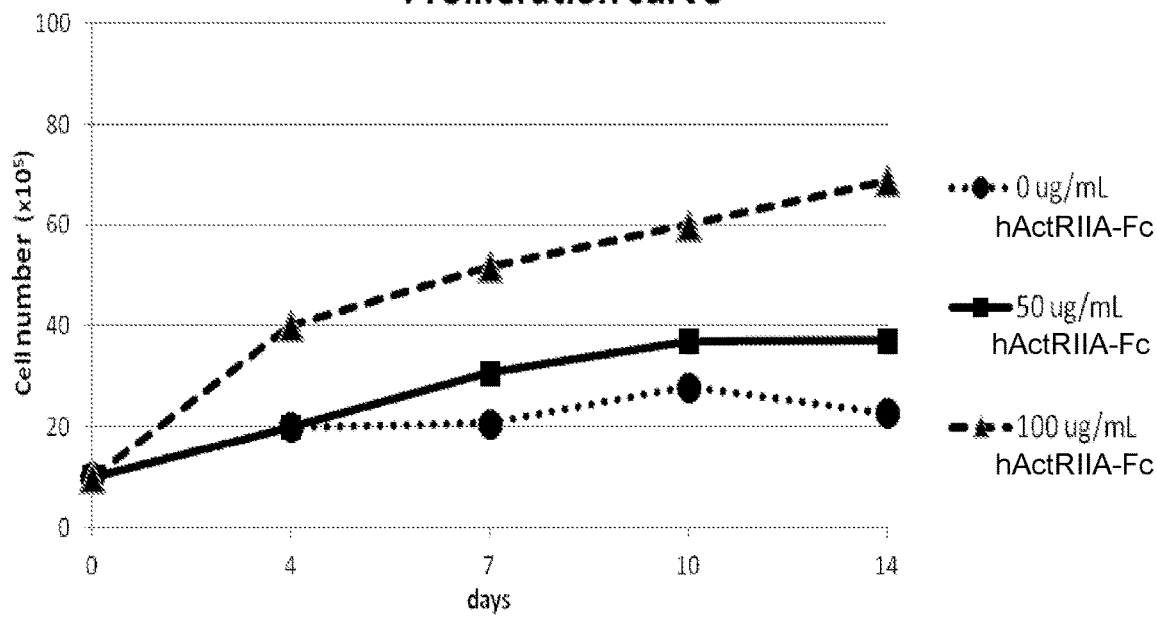
Figure 5C:
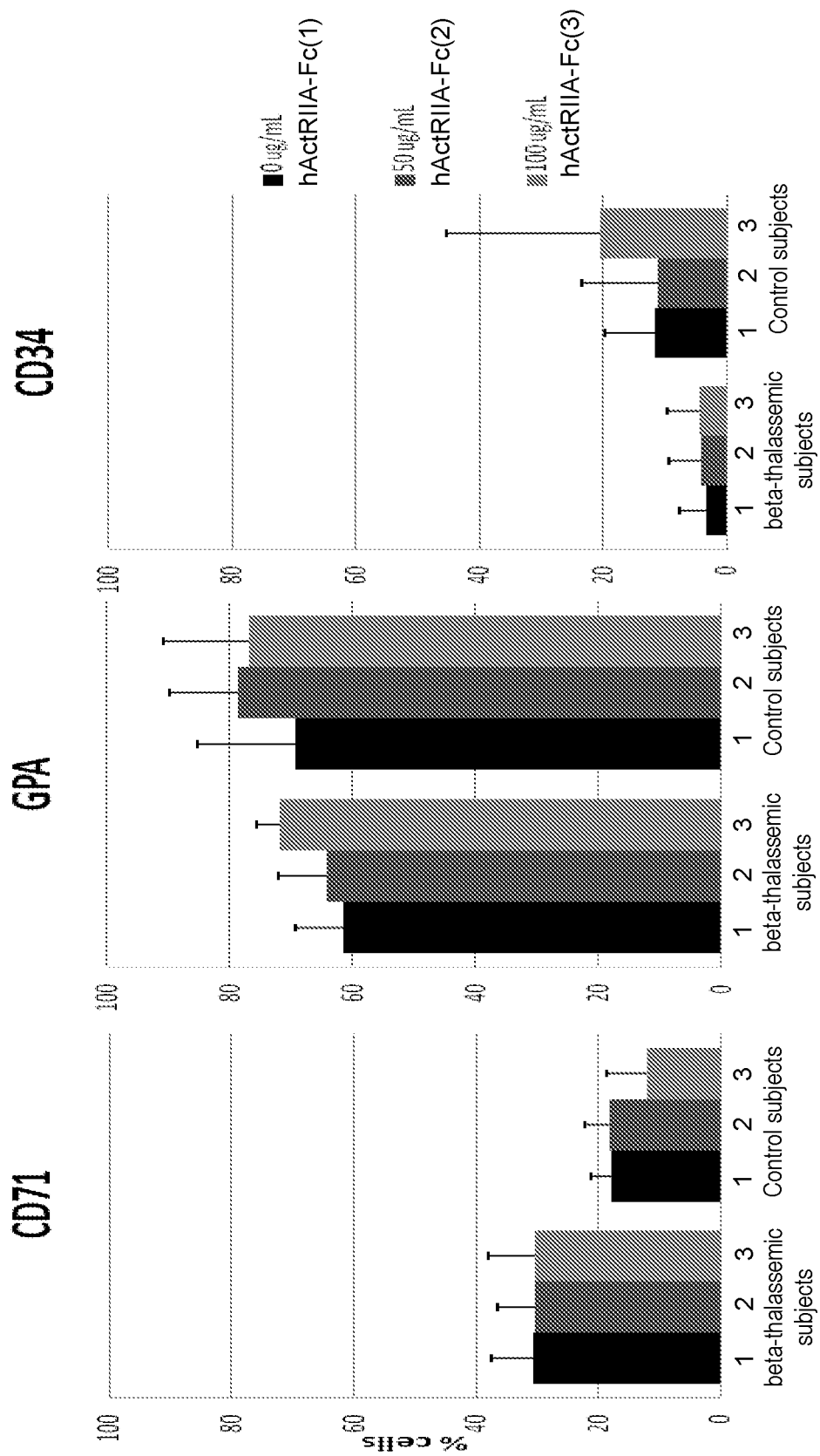

FIG. 5A depicts the expansion fold of total beta-thalassemic subject-derived CD34+ cells over hActRIIA (SEQ ID NO:7)-Fc-treated or not treated HS5 cells (circles=0 ug/mL; squares=50 ug/mL; triangles=100 ug/mL) after two weeks of co-culture. FIG. 5B depicts the expansion fold of total control subject-derived CD34+ cells over hActRIIA-Fc (SEQ ID NO:7)-treated or not treated HS5 cells (circles=0 ug/mL; squares=50 ug/mL; triangles=100 ug/mL) after two weeks of co-culture. FIG. 5C depicts the flow cytometric analyses of CD71 expression (bottom panel), GPA expression (middle panel), or CD34 expression (top panel) of ex vivo expanded CD34+ cells derived from beta-thalassemic or control subjects in co-culture with hActRIIA (SEQ ID NO:7)-Fc-treated or not treated HS5 cells. Bars labeled "1" represent data from samples treated with 0 ug/mL of hActRIIA-Fc (SEQ ID NO:7). Bars labeled "2" represent data from samples treated with 50 ug/mL of hActRIIA-Fc (SEQ ID NO:7). Bars labeled "3" represent data from samples treated with 100 ug/mL of hActRIIA-Fc (SEQ ID NO:7). All data for FIG. 5A-FIG. 5C are expressed as the mean±sd.

Figure 6A:
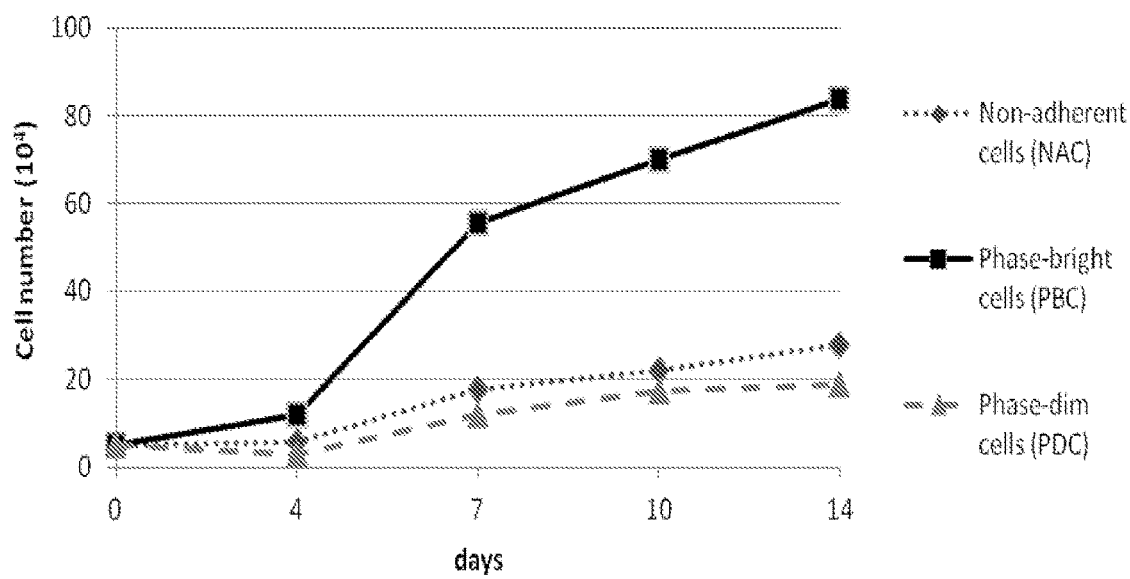
Figure 6B:
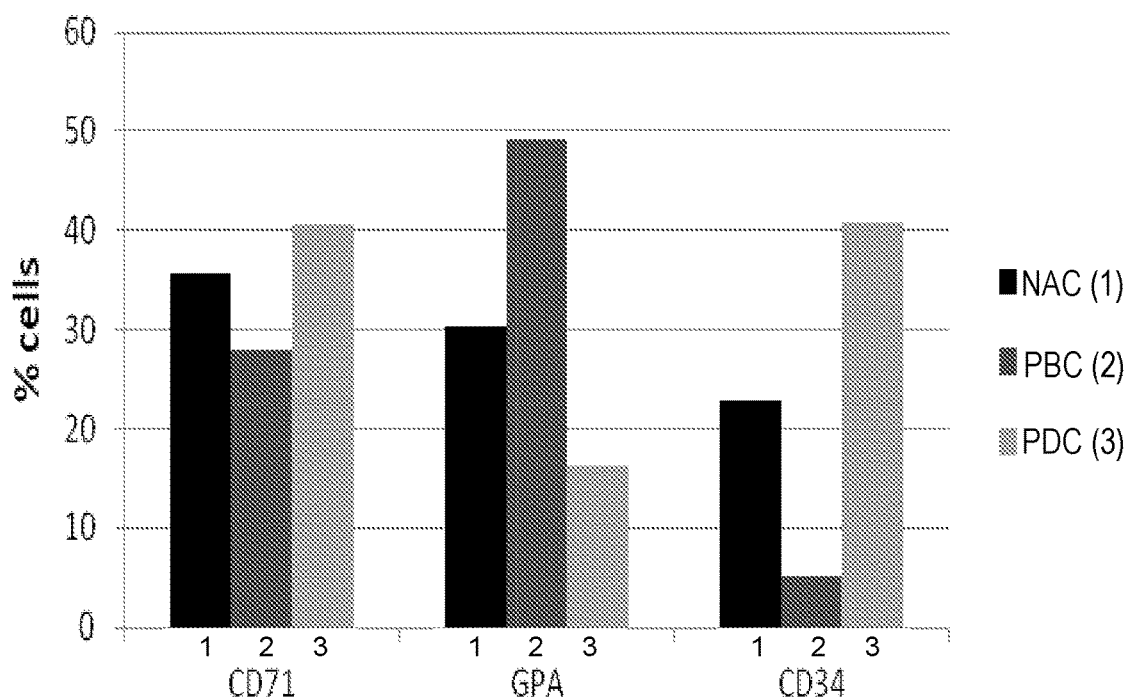

FIG. 6A depicts the cellular proliferation curve of non-adherent cells ("NAC", diamonds), phase-bright cells ("PBC", squares), and phase-dim cells ("PDC", triangles) at the indicated time points. FIG. 6B depicts the proportion of NAC (bars labeled "1"), PBC (bars labeled "2"), and PDC (bars labeled "3") cells FACS sorted for CD71, GPA, or CD34 expression at day 14.

Figure 7A:
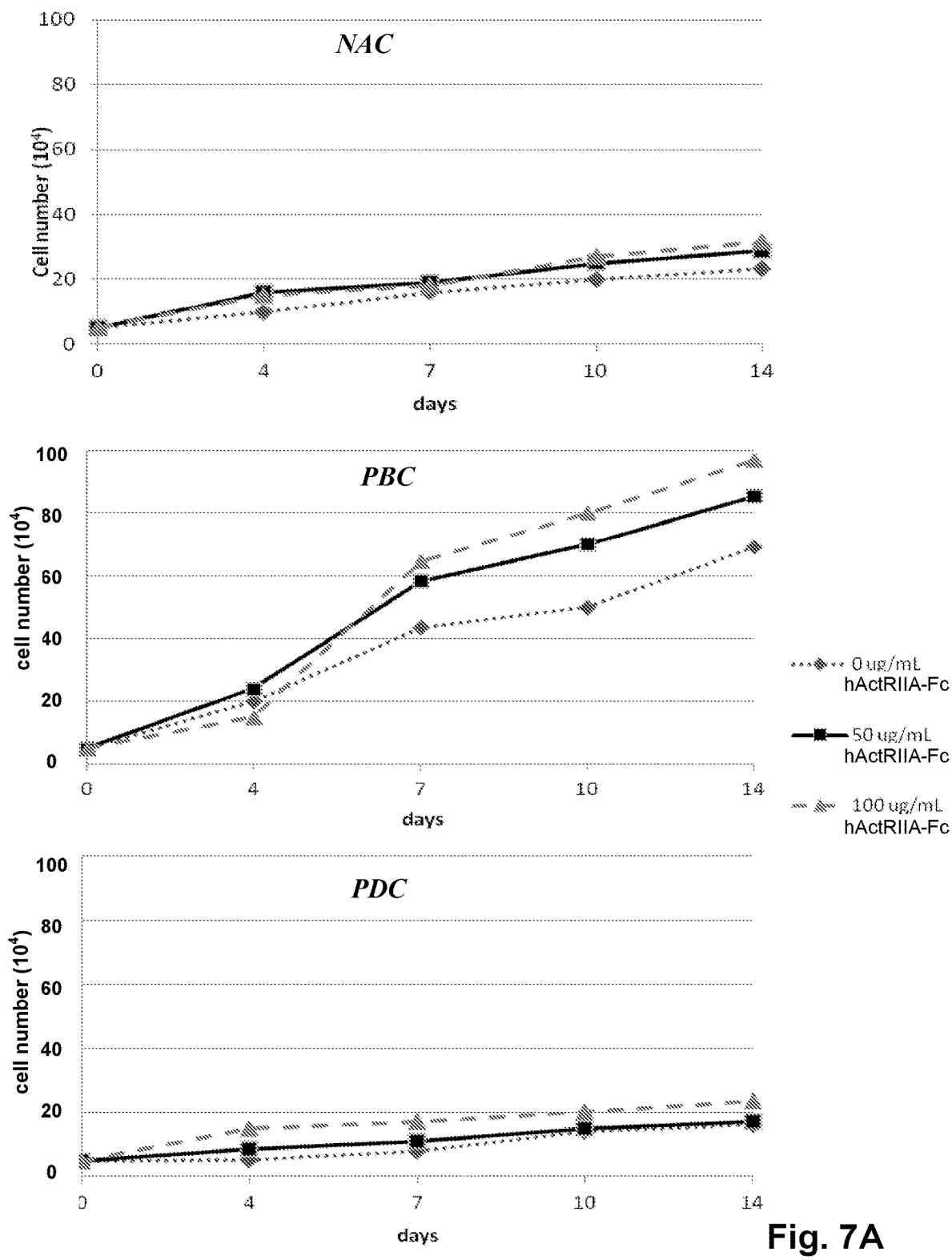
Figure 7B:
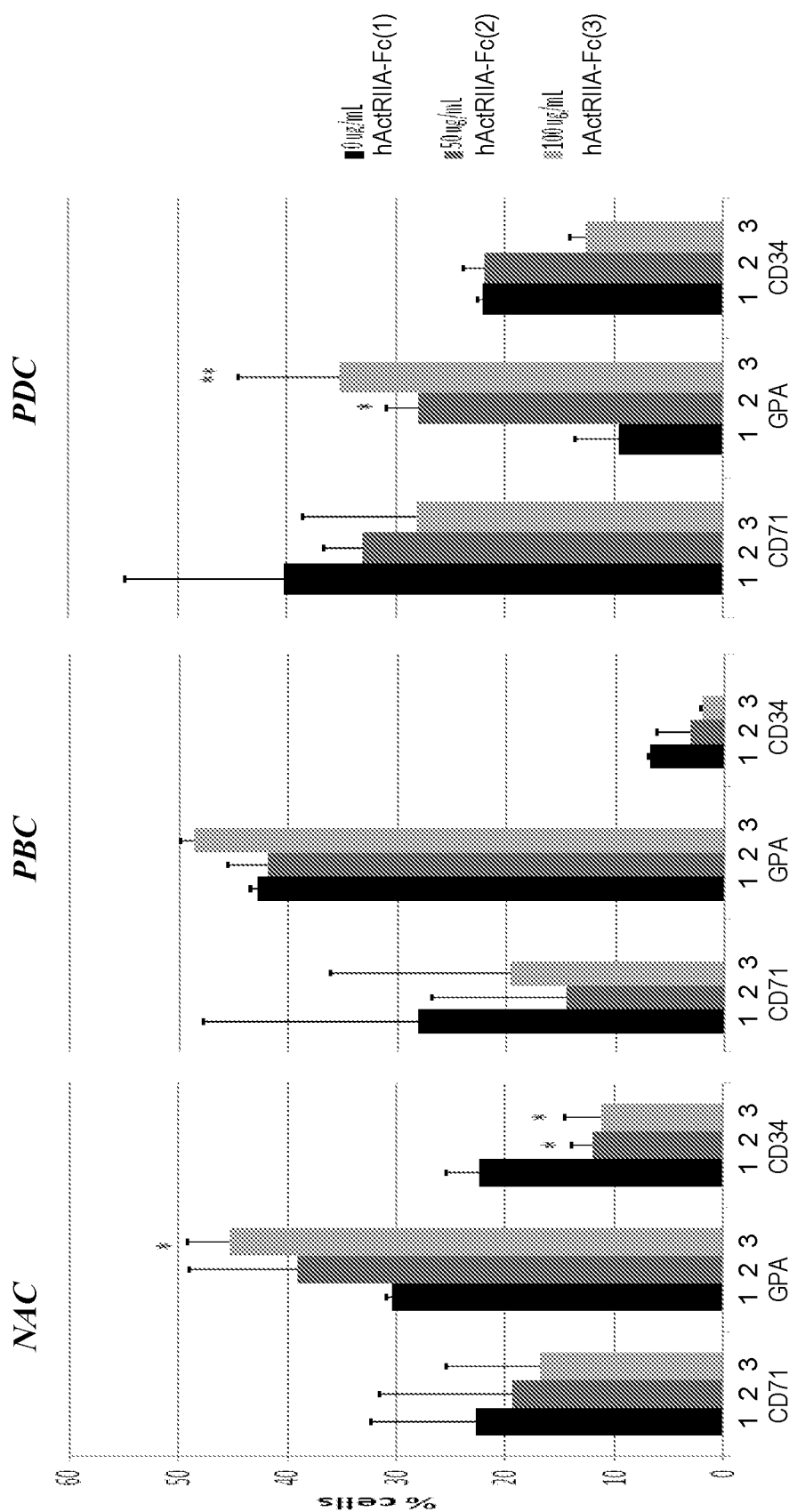

FIG. 7A depicts the cellular proliferation curve of NAC cells (top panel), PBC cells (middle panel), and PDC cells (bottom panel). The cells were co-cultured with HS5 cells treated with hActRIIA-Fc (SEQ ID NO:7) at a concentration of 0 ug/mL (diamonds), 50 ug/mL (squares), or 100 ug/mL (triangles). FIG. 7B depicts a representative FACS analysis of the three cell fractions (top panel: PDC; middle panel: PBC; and bottom panel: NAC) from FIG. 7A. *P<0.05; **P<0.001

Figure 8A:
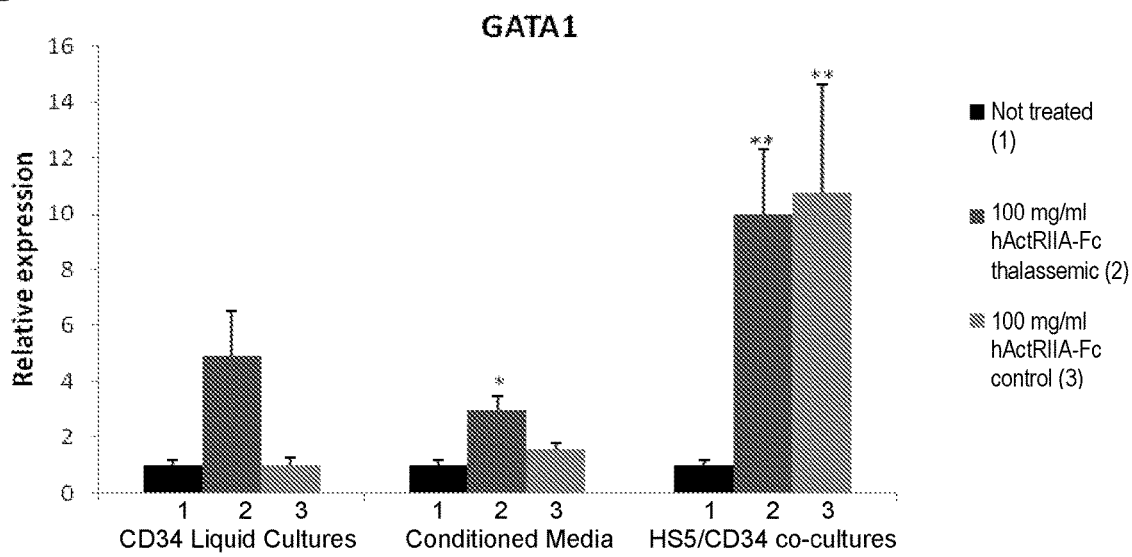
Figure 8B:
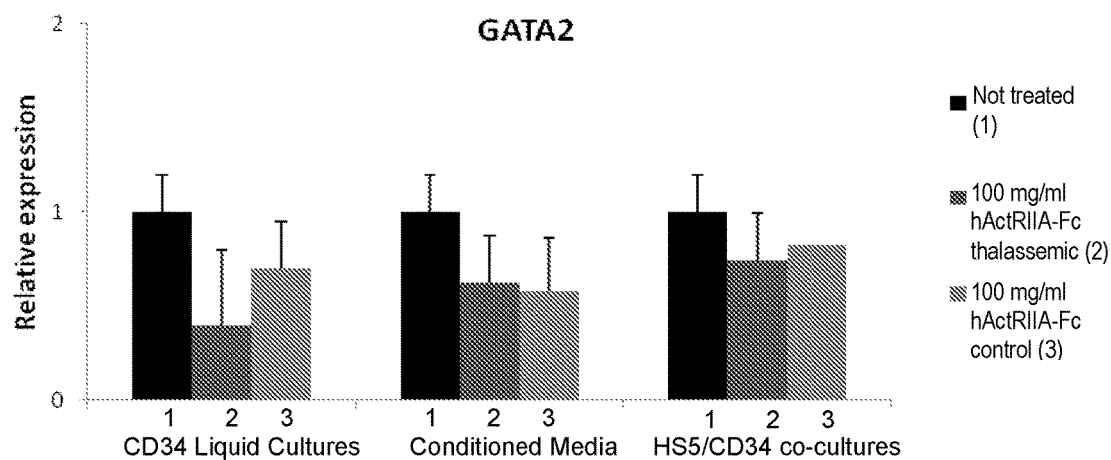
Figure 8C:
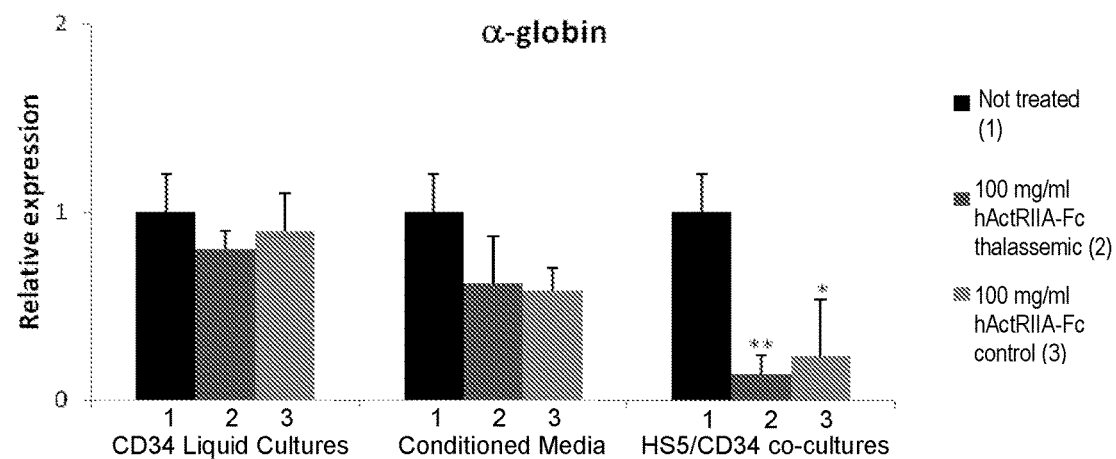
Figure 8D:
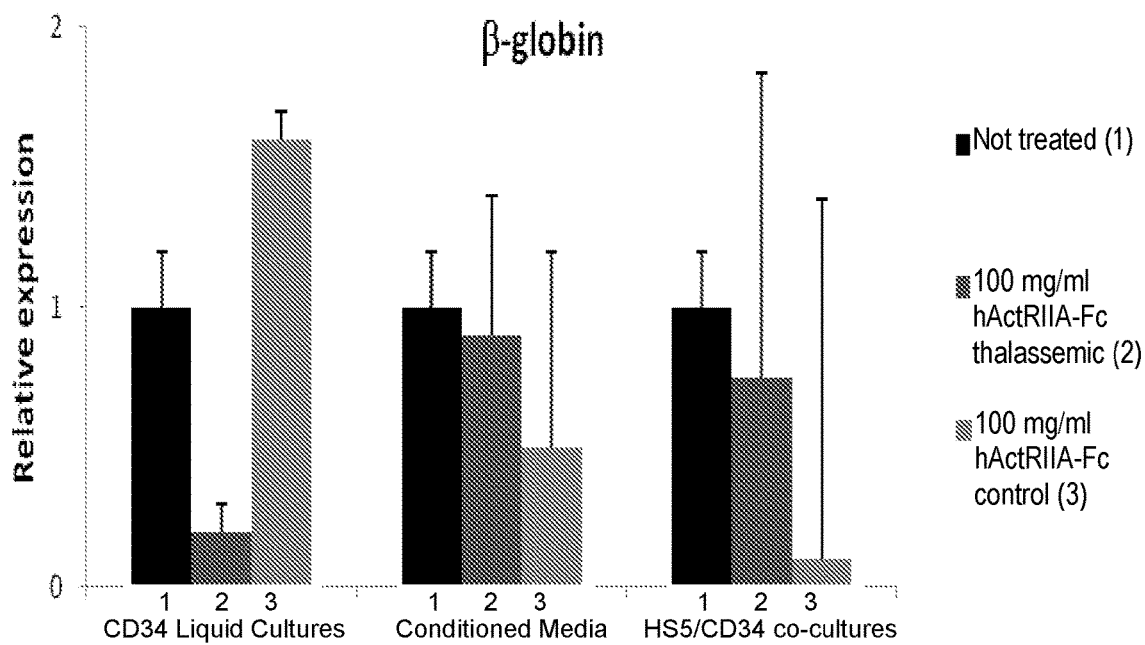
Figure 8E:
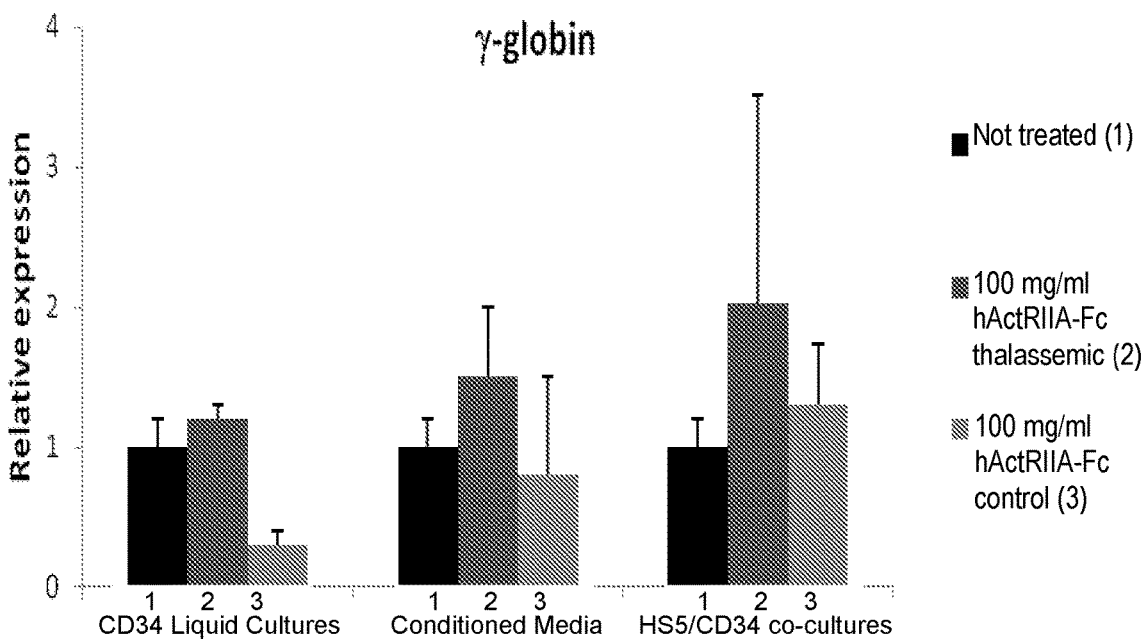

FIG. 8A depicts the relative expression level of GATA1 mRNA as determined by qPCR in CD34 cells derived from beta-thalassemic subjects (bars labeled "2") or control subjects (bars labeled "3") treated with 100 ug/mL of hActRIIA-Fc (SEQ ID NO: 7) or without hActRIIA-Fc (bars labeled "1"). FIG. 8B depicts the relative expression level of GATA2 mRNA as determined by qPCR in CD34 cells derived from beta-thalassemic subjects (bars labeled "2") or control subjects (bars labeled "3") treated with 100 ug/mL of hActRIIA-Fc (SEQ ID NO: 7) or without hActRIIA-Fc (bars labeled "1"). FIG. 8C depicts the relative expression level of alpha-globin mRNA as determined by qPCR in CD34 cells derived from beta-thalassemic subjects (bars labeled "2") or control subjects (bars labeled "3") treated with 100 ug/mL of hActRIIA-Fc (SEQ ID NO: 7) or without hActRIIA-Fc (bars labeled "1"). FIG. 8D depicts the relative expression level of beta-globin mRNA as determined by qPCR in CD34 cells derived from beta-thalassemic subjects (bars labeled "2") or control subjects (bars labeled "3") treated with 100 ug/mL of hActRIIA-Fc (SEQ ID NO: 7) or without hActRIIA-Fc (bars labeled "1"). FIG. 8E depicts the relative expression level of gamma-globin mRNA as determined by qPCR in CD34 cells derived from beta-thalassemic subjects (bars labeled "2") or control subjects (bars labeled "3") treated with 100 ug/mL of hActRIIA-Fc (SEQ ID NO: 7) or without hActRIIA-Fc (bars labeled "1"). All data in FIG. 8A-FIG. 8E are expressed as the mean±sd. *P<0.05 and **P<0.001 for one out of three independent experiments.

FIG. 9A depicts the relative expression level of GATA1 mRNA as determined by qPCR in NAC, PBC, and PDC cells derived from beta-thalassemic subjects (as compared to control subjects) treated with hActRIIA-Fc (SEQ ID NO:7) at 0 ug/mL (bars labeled "1"), 50 ug/mL (bars labeled "2"), or 100 ug/mL (bars labeled "3"). FIG. 9B depicts the relative expression level of GATA2 mRNA as determined by qPCR in NAC, PBC, and PDC cells derived from beta-thalassemic subjects (as compared to control subjects) treated with hActRIIA-Fc (SEQ ID NO:7) at 0 ug/mL (bars labeled "1"), 50 ug/mL (bars labeled "2"), or 100 ug/mL (bars labeled "3"). FIG. 9C depicts the relative expression level of alpha-globin mRNA as determined by qPCR in NAC, PBC, and PDC cells derived from beta-thalassemic subjects (as compared to control subjects) treated with hActRIIA-Fc (SEQ ID NO:7) at 0 ug/mL (bars labeled "1"), 50 ug/mL (bars labeled "2"), or 100 ug/mL (bars labeled "3"). FIG. 9D depicts the relative expression level of beta-globin mRNA as determined by qPCR in NAC, PBC, and PDC cells derived from beta-thalassemic subjects (as compared to control subjects) treated with hActRIIA-Fc (SEQ ID NO:7) at 0 ug/mL (bars labeled "1"), 50 ug/mL (bars labeled "2"), or 100 ug/mL (bars labeled "3"). FIG. 9E depicts the relative expression level of gamma-globin mRNA as determined by qPCR in NAC, PBC, and PDC cells derived from beta-thalassemic subjects (as compared to control subjects) treated with hActRIIA-Fc (SEQ ID NO:7) at 0 ug/mL (bars labeled "1"), 50 ug/mL (bars labeled "2"), or 100 ug/mL (bars labeled "3").

7. DETAILED DESCRIPTION

7.1 Abbreviations and Terminology

"$\beta^0$" refers to an allele associated with a lack of beta globin subunit synthesis.

"$\beta^+$" refers to an allele associated with reduced beta globin subunit synthesis.

As used herein, the term "about" when used in conjunction with a number refers to any number within 1%, 2%, 3%, 4%, 5%, 6%, 7%, 8%, 9%, 10%, 11%, 12%, 13%, 14%, or 15% of the referenced number. In certain embodiments, the term "about" encompasses the exact number recited.

As used herein, "ActRII" refers to activin receptor type II. As used herein, "ActRIIA" refers to activin receptor type IIA. See, for example, Mathews and Vale, 1991, Cell 65:973-982. GenBank™ accession number NM_001-278579.1 provides an exemplary human ActRIIA nucleic acid sequence. GenBank™ accession number NP_001265508.1 provides an exemplary human ActRIIA amino acid sequence. As used herein, "ActRIIB" refers to activin receptor type IIB. See, for example, Attisano et al., 1992, Cell 68: 97-108. GenBank™ accession number NM_001106.3 provides an exemplary human ActRIIB nucleic acid sequence. GenBank™ accession number NP_001097.2 provides an exemplary human ActRIIB amino acid sequence.

As used herein, "ActRIIA-mFc" or "mActRIIA-Fc" refers to a mouse activin type IIA receptor-IgG1 fusion protein. See, for example, U.S. Pat. No. 8,173,601 and Carrancio et al., 2014, British Journal of Haematology, 165:870-882. As used herein, "mActRIIB-Fc" or "ActRIIB-mFc" refers to a mouse activin type IIB receptor-IgG1 fusion protein. See, for example, U.S. Pat. No. 8,173,601. As used herein, "hActRIIA-Fc" or "ActRIIA-hFc" refers to a human activin type IIA receptor-IgG1 fusion protein, such as, e.g., SEQ ID NO:7. See, for example, U.S. Pat. No. 8,173,601. As used herein, "hActRIIB-Fc" or "ActRIIB-hFc" refers to a human activin type IIB receptor-IgG1 fusion protein. See, for example, U.S. Pat. No. 8,173,601.

"AE" refers to adverse events.

"Alpha-globin" refers to alpha-globin, which is also known as "HBA1." GenBank™ Accession No. NP_000508.1 provides an exemplary amino acid sequence of a human alpha globin. GenBank™ Accession No. NM_000558.4 provides an exemplary nucleic acid sequence of a human alpha globin.

"Bad" refers to BCL2-associated agonist of cell death. GenBank™ Accession Nos. NM_032989.2 and NM_004322.3 provide exemplary nucleic acid sequences of human Bad. GenBank™ Accession Nos. NP_116784.1 and NP_004313.1 provide exemplary amino acid sequences of human Bad.

"Bax" refers to BCL2-associated X protein. GenBank™ Accession Nos. NM_001291430.1, NM_001291429.1, NM_001291428.1, NM_138764.4, NM_138761.3, NM_004324.3, NM_001291431.1, and NM_138763.3 provide exemplary nucleic acid sequences of human Bax. GenBank™ Accession Nos. NP_001278359.1, NP_001278360.1, NP_001278358.1, NP_001278357.1, NP_620119.2, NP_620119.2, NP_620118.1, NP_620116.1, and NP_004315.1 provide exemplary amino acid sequences of human Bax.

"Bcl-2" refers to B-cell CLL/lymphoma 2. GenBank™ Accession Nos. NP_000648.2 and NP_000624.2 provide exemplary amino acid sequences of a human Bcl-2. GenBank™ Accession Nos. NM_000633.2 and NM_000657.2 provide exemplary nucleic acid sequences of a human Bcl-2.

"Bcl-xL" refers to Bcl2-like 1. GenBank™ Accession Nos. NP_612815.1 and NP_001182.1 provide exemplary amino acid sequences of a human Bcl-xL. GenBank™ Accession Nos. NM_001191.2 and NM_138578.1 provide exemplary nucleic acid sequences of a human Bcl-xL.

"C5a" refers to the alpha chain of complement component 5. GenBank™ Accession No. NM_001735.2 provides an exemplary nucleic acid sequence of human C5a. GenBank™ Accession No. NP_001726.2 provides an exemplary amino acid sequence of human C5a.

"Caspase-3" refers to caspase 3 or apoptosis-related cysteine peptidase. GenBank™ Accession Nos. NM_032991.2 and NM_004346.3 provide exemplary nucleic acid sequences of human Caspase-3. GenBank™ Accession Nos. NP_004337.2 and NP_116786.1 provide exemplary amino acid sequences of human Caspase-3.

"CIAP1" refers to baculoviral IAP repeat-containing 2. GenBank™ Accession Nos. NM_001256166.1, NM_001256163.1, and NM_001166.4 provide exemplary nucleic acid sequences of human CIAP1. GenBank™ Accession Nos. NP_001243095.1, NP_001243092.1, and NP_001157.1 provide exemplary amino acid sequences of human CIAP1.

"EPC" refers to an erythroid progenitor cell.

"G-CSF" refers to colony stimulating factor 3. GenBank™ Accession Nos. NM_001178147.1, NM_172220.2, NM_172219.2, and NM_000759.3 provide exemplary nucleic acid sequences of human G-CSF. GenBank™ Accession Nos. NP_001171618.1, NP_757374.2, NP_757373.1, and NP_000750.1 provide exemplary amino acid sequences of human G-CSF.

"GMCSF" refers to granulocyte-macrophage colony-stimulating factor. GenBank™ Accession No. NM_000758.3 provides an exemplary nucleic acid sequence of human GMCSF. GenBank™ Accession No. NP_000749.2 provides an exemplary amino acid sequence of human GMCSF.

"GATA1" refers to GATA binding factor 1, also known as globin transcription factor 1. GenBank™ Accession No. NP_002040.1 provides an exemplary amino acid sequence of a human GATA1. GenBank™ Accession No. NM_002049.3 provides an exemplary nucleic acid sequence of a human GATA1.

"GATA2" refers to GATA binding factor 2. GenBank™ Accession Nos. NP_116027.2 and NP_001139134.1 provide exemplary amino acid sequences of a human GATA2. GenBank™ Accession Nos. NM_001145662.1, NM_032638.4, and NM_001145661.1 provide exemplary nucleic acid sequences of a human GATA2.

"GYPA" refers to glycophorin A. GenBank™ Accession Nos. NP_002090.4, NP_001295116.1 and NP_001295119.1 provide exemplary amino acid sequences of a human GYPA. GenBank™ Accession Nos. NM_002099.7, NM_001308187.1 and NM_001308190.1 provide exemplary nucleic acid sequences of a human GYPA.

"GRO-a" refers to growth regulated alpha-protein, also known as CXCL1. GenBank™ Accession No. NP_001502.1 provides an exemplary amino acid sequence of a human GRO-a. GenBank™ Accession No. NM_001511.3 provides an exemplary nucleic acid sequence of a human GRO-a.

In certain embodiments, "Hb" refers to hemoglobin protein. GenBank™ Accession No. NP_000549.1 provides an exemplary amino acid sequence of a human hemoglobin alpha subunit. GenBank™ Accession No. NP_000509.1 provides an exemplary amino acid sequence of a human hemoglobin beta subunit. GenBank™ Accession No. NP_000550.2 provides an exemplary amino acid sequence of a human hemoglobin gamma subunit. Typically, the most common form of hemoglobin in a human adult comprises two alpha subunits and two beta subunits. Fetal hemoglobin, also referred to as "hemoglobin F" or "HbF" comprises two alpha subunits and two gamma subunits.

In certain embodiments, "HbE" or "Hemoglobin E" refers to a mutated form of hemoglobin, for example, human hemoglobin. Hemoglobin E comprises two alpha subunits and two beta subunits, wherein position 26 of the beta subunit is mutated from glutamic acid to lysine (E26K).

In certain embodiments, "HbE/beta-thalassemia" refers to the co-inheritance of hemoglobin E and a β0 allele.

In certain embodiments, "HbS" or "Hemoglobin S" refers to a mutated form of hemoglobin. Hemoglobin S comprises two alpha subunits and two beta subunits, wherein position 6 of the beta subunit is mutated from glutamine to valine (G6V).

"HIF-1a" refers to hypoxia-inducible factor 1, alpha subunit (basic helix-loop-helix transcription factor). GenBank™ Accession Nos. NM_001243084.1, NM_001530.3, and NM_181054.2 provide exemplary nucleic acid sequences of human HIF-1a. GenBank™ Accession Nos. NP_001230013.1, NP_851397.1, and NP_001521.1 provide exemplary amino acid sequences of human HIF-1a.

"HO-2" refers to heme oxygenase (decycling) 2. GenBank™ Accession Nos. NM_001286271.1, NM_001286270.1, NM_001286269.1, NM_001286268.1, NM_001286267.1, NM_001127206.2, NM_001127205.1, NM_001127204.1, and NM_002134.3 provide exemplary nucleic acid sequences of human HO-2. GenBank™ Accession Nos. NP_001273200.1, NP_001273199.1, NP_001273198.1, NP_001273197.1, NP_001273196.1, NP_001120678.1, NP_001120677.1, NP_001120676.1, and NP_002125.3 provide exemplary amino acid sequences of human HO-2.

"IL-1a" refers to interleukin 1, alpha. GenBank™ Accession No. NM_000575.4 provides an exemplary nucleic acid sequence of human IL-1a. GenBank™ Accession No. NP_000566.3 provides an exemplary amino acid sequence of human IL-1a.

"IL-1b" refers to interleukin 1, beta. GenBank™ Accession No. NM000576.2 provides an exemplary nucleic acid sequence of human IL-1b. GenBank™ Accession No. NP_000567.1 provides an exemplary amino acid sequence of human IL-1b.

"IL-2" refers to interleukin 2. GenBank™ Accession No. NM000586.3 provides an exemplary nucleic acid sequence of human IL-2. GenBank™ Accession No. NP_000577.2 provides an exemplary amino acid sequence of human IL-2.

"IL-6" refers to interleukin 6. GenBank™ Accession No. NM_000600.3 provides an exemplary nucleic acid sequence of human IL-6. GenBank™ Accession No. NP_000591.1 provides an exemplary amino acid sequence of human IL-6.

"IL-8" refers to interleukin 8. GenBank™ Accession No. NM_000584.3 provides an exemplary nucleic acid sequence of human IL-8. GenBank™ Accession No. NP_000575.1 provide exemplary amino acid sequences of human IL-8.

"IL-10" refers to interleukin-10. GenBank™ Accession No. NM_000572.2 provides an exemplary nucleic acid sequence of human IL-10. GenBank™ Accession No. NP_000563.1 provides an exemplary amino acid sequence of human IL-10.

"IL-1Ra" refers to interleukin-1 receptor antagonist. GenBank™ Accession Nos. NP_776215.1, NP_776214.1, NP_776213.1, and NP_000568.1 provide exemplary amino acid sequences of a human IL-1Ra. GenBank™ Accession Nos. NM_173842.2, NM_173843.2, NM_173841.2, and NM_000577.4 provide exemplary nucleic acid sequences of a human IL-1Ra.

"IP-10" refers to chemokine (C-X-C motif) ligand 10. GenBank™ Accession No. NM_001565.3 provides an exemplary nucleic acid sequence of human IP-10. GenBank™ Accession No. NP_001556.2 provides an exemplary amino acid sequence of human IP-10.

"MCP-1" refers to monocyte chemoattractant protein 1, also known as CCL2. GenBank™ Accession Nos. NP_001116513.2 and NP_001116868.1 provide exemplary amino acid sequences of a human IL-1Ra. GenBank™ Accession No. NM_002982.3 provides an exemplary nucleic acid sequence of a human MCP-1.

"MIF" refers to Macrophage migration inhibitory factor (glycosylation-inhibiting factor). GenBank™ Accession No. NM_002415.1 provides an exemplary nucleic acid sequence of human MIF. GenBank™ Accession No. NP_002406.1 provides an exemplary amino acid sequence of human MIF.

"p21" refers to cyclin-dependent kinase inhibitor 1A. GenBank™ Accession Nos. NM_001291549.1, NM_001220778.1, NM_001220777.1, NM_078467.2, and NM_000389.4 provide exemplary nucleic acid sequences of human p21. GenBank™ Accession Nos. NP_001278478.1 and NP_001207707.1 provide exemplary amino acid sequences of human p21.

"p27" refers to cyclin-dependent kinase inhibitor 1B. GenBank™ Accession No. NM_004064.4 provides an exemplary nucleic acid sequences of human p27. GenBank™ Accession No. NP_004055.1 provides an exemplary amino acid sequence of human p27.

"PON" refers to paraoxonaase 2 GenBank™ Accession Nos. NM_001018161.1 and NM_000305.2 provide exemplary nucleic acid sequences of human PON2. GenBank™ Accession Nos. NP_001018171.1 and NP_000296.2 provide exemplary amino acid sequences of human PON2.

"RANTES" refers to chemokine (C-C motif) ligand 5. GenBank™ Accession Nos. NM_001278736.1 and NM_002985.2 provide exemplary nucleic acid sequences of human RANTES. GenBank™ Accession Nos. NP_001265665.1 and NP_002976.2 provide exemplary amino acid sequences of human RANTES.

"serpinE1" refers to serpin peptidase inhibitor, clade E (nexin, Plasminogen activator inhibitor type 1), member 1. GenBank™ Accession No. NP_000593.1 provides an exemplary amino acid sequence of human serpinE1. GenBank™ Accession No. NM_000602.4 provides an exemplary nucleic acid sequence of human serpinE1.

"ICAM-1" refers to intracellular adhesion molecule 1. GenBank™ Accession No. NP_000192.2 provides an exemplary amino acid sequence of human ICAM-1. GenBank™ Accession No. NM_000201.2 provides an exemplary nucleic acid sequence of human ICAM-1.

"Survivin" refers to baculoviral IAP repeat containing 5. GenBank™ Accession Nos. NP_001012271.1, NP_001012270.1, and NP_001159.2 provide exemplary amino acid sequences of a human survivin. GenBank™ Accession Nos. NM_001168.2, NM_001012270.1, and NM_001012271.1 provide exemplary nucleic acid sequences of a human survivin.

"TRAIL R1" refers to tumor necrosis factor receptor superfamily, member 10a. GenBank™ Accession No. NM_003844.3 provide exemplary nucleic acid sequences of human TRAIL R1. GenBank™ Accession No. NP_003835.3 provides an exemplary amino acid sequence of human TRAIL R1.

7.2 Overview

Provided herein are methods of treating beta-thalassemia in a subject comprising administering to the subject an ActRII signaling inhibitor (e.g., ActRIIA-hFc (SEQ ID NO:7) or ActRIIB-hFc (SEQ ID NO:25); see Section 7.8) and utilizing one or more in vitro cell culture methods provided herein (see Section 7.4) in (i) selection of the subject (see Section 7.5) to be treated according to the methods provided herein (see Section 7.3); and/or (ii) monitoring of the subject (see Section 7.5) being treated according to the methods provided herein (see Section 7.3).

Without being bound by theory, the responsiveness of erythroid progenitor cells (EPCs) of a beta-thalassemic subject in an in vitro cell culture method provided herein (see Section 7.4 and 7.4.1) can be used to predict whether or not the patient will be responsive to treatment with an ActRII signaling inhibitor (e.g., ActRIIA-hFc (SEQ ID NO:7) or ActRIIB-hFc (SEQ ID NO:25)). In addition, without being bound by theory, the responsiveness of stromal cells of a beta-thalassemic subject in an in vitro cell culture method provided herein (see Section 7.4 and 7.4.1) can be used to predict whether or not the patient will be responsive to treatment with an ActRII signaling inhibitor (e.g., ActRIIA-hFc (SEQ ID NO:7) or ActRIIB-hFc (SEQ ID NO:25)). Similarly, a beta-thalassemic subject can be monitored using an in vitro cell culture method provided herein (see Section 7.4 and 7.4.1) to determine how well the subject responds to treatment of beta-thalassemia with an ActRII signaling inhibitor (e.g., ActRIIA-hFc (SEQ ID NO:7) or ActRIIB-hFc (SEQ ID NO:25)).

For example, without being bound by any theory, if an in vitro cell culture method provided herein results in one or more of the outcome parameters provided in Section 7.4.1, the subject can be selected for treatment with an ActRII signaling inhibitor (e.g., ActRIIA-hFc (SEQ ID NO:7) or ActRIIB-hFc (SEQ ID NO:25)) and is considered to be responsive to said treatment.

In certain embodiments "responsive" or "responsiveness" includes treatment of beta-thalassemia in the subject. In certain embodiments, "treat," "treatment," or "treating," in the context of beta-thalassemia, includes amelioration of at least one symptom of beta-thalassemia. Nonlimiting examples of symptoms of beta include defective red blood cell production in the marrow, ineffective erythropoiesis, deficient hemoglobin levels, multiple organ dysfunction, iron overload, paleness, fatigue, jaundice, and splenomegaly.

7.3 Methods of Treatment

Provided herein is a method of treating beta-thalassemia in a subject, comprising administering a pharmaceutically effective dose of an ActRII signaling inhibitor to the subject, wherein the subject has been selected by using an in vitro cell culture method provided herein (see Section 7.4). Also provided herein is a method for treating beta-thalassemia in a subject, comprising administering a pharmaceutically effective dose of an ActRII signaling inhibitor to the subject, performing an in vitro cell culture method provided herein (see Section 7.4), and determining a subsequent dose of the ActRII signaling inhibitor to administer to the subject based on the in vitro cell culture method. In certain embodiments, the pharmaceutically effective dose is a dose as described in Section 7.6. In certain embodiments, the pharmaceutically effective dose is administered to the subject at a frequency as described in Section 7.6. In certain embodiments, the pharmaceutically effective dose is administered to the subject according to a route of administration as described in Section 7.6. In certain embodiments, the ActRII signaling inhibitor is as described in Section 7.8. In certain embodiments, the ActRII signaling inhibitor is an ActRIIA signaling inhibitor as described in Section 7.8.1. In certain embodiments, the ActRIIA signaling inhibitor is an ActRIIA-Fc such as an ActRIIA-hFc (e.g., SEQ ID NO:7). In certain embodiments, the ActRII signaling inhibitor is an ActRIIB signaling inhibitor as described in Section 7.8.2. In certain embodiments, the ActRIIB signaling inhibitor is an ActRIIB-Fc such as an ActRIIB-hFc (e.g., SEQ ID NO:25). In certain embodiments, the ActRII signaling inhibitor is part of a composition as described in Section 7.7. In certain embodiments, the ActRII signaling inhibitor is administered to the subject in combination with a second pharmaceutically active agent or therapy as described in Section 7.3.1.

Without being bound by theory, the responsiveness of an EPC of a beta-thalassemic subject in an in vitro cell culture method provided herein (see Section 7.4 and 7.4.1) can be used to predict whether or not the patient will be responsive to treatment with an ActRII signaling inhibitor. In addition, without being bound by theory, the responsiveness of a stromal cell of a beta-thalassemic subject in an in vitro cell culture method provided herein (see Section 7.4 and 7.4.1) can be used to predict whether or not the patient will be responsive to treatment with an ActRII signaling inhibitor. Thus, without being bound by theory, an in vitro cell culture method provided herein may be performed (i) to select a subject to be treated according to the methods provided herein, and/or (ii) to determine if a subsequent dose of an ActRII signaling inhibitor administered to the subject should be increased or decreased.

In certain embodiments, the subject is a subject as described in Section 7.5. In certain embodiments, the subject is selected to be treated with an ActRII signaling inhibitor if 1, 2, 3, or more of the outcome parameters provided in Section 7.4.1 are achieved in an in vitro cell culture method provided in Section 7.4, wherein the in vitro cell culture method utilizes an EPC derived from the subject. In certain embodiments, the subject is to be treated with an ActRII signaling inhibitor if 1, 2, 3, or more of the outcome parameters provided in Section 7.4.1 are achieved in an in vitro cell culture method provided in Section 7.4, wherein the in vitro cell culture method utilizes a stromal cell derived from the subject. In certain embodiments, the subject is to be treated with an ActRII signaling inhibitor if 1, 2, 3, or more of the outcome parameters provided in Section 7.4.1 are achieved in an in vitro cell culture method provided in Section 7.4, wherein the in vitro cell culture method utilizes an EPC derived from the subject and a stromal cell derived from a reference population. In certain embodiments, the reference population is as described in Section 7.9.

In certain embodiments, the subject is a subject as described in Section 7.5. In certain embodiments, the subject is predicted to be responsive to treatment with an ActRII signaling inhibitor if 1, 2, 3, or more of the outcome parameters provided in Section 7.4.1 are achieved in an in vitro cell culture method provided in Section 7.4, wherein the in vitro cell culture method utilizes an EPC derived from the subject. In certain embodiments, the subject is predicted to be responsive to treatment with an ActRII signaling inhibitor if 1, 2, 3, or more of the outcome parameters provided in Section 7.4.1 are achieved in an in vitro cell culture method provided in Section 7.4, wherein the in vitro cell culture method utilizes a stromal cell derived from the subject. In certain embodiments, the subject is predicted to be responsive to treatment with an ActRII signaling inhibitor if 1, 2, 3, or more of the outcome parameters provided in Section 7.4.1 are achieved in an in vitro cell culture method provided in Section 7.4, wherein the in vitro cell culture method utilizes an EPC derived from the subject and a stromal cell derived from a reference population. In certain embodiments, the reference population is as described in Section 7.9.

In specific embodiments, one or more in vitro cell culture methods provided herein (see Section 7.4) is performed before a method of treatment provided herein. In specific embodiments, one or more in vitro cell culture methods provided herein (see Section 7.4) is performed after a method of treatment provided herein. In specific embodiments, one or more in vitro cell culture methods provided herein (see Section 7.4) is performed concurrently with a method of treatment provided herein.

In certain embodiments, the in vitro cell culture method (see Section 7.4) is performed a period of time prior to administering a first dose of the ActRII signaling inhibitor to the subject. In certain embodiments, the period of time prior to administering a first dose of the ActRII signaling inhibitor to the subject is within 1 day, 1 week, 2 weeks, 3 weeks, 4 weeks, 1 month, 2 months, 3 months, 4 months, 5 months, 6 months, 7 months, 8 months, 9 months, 10 months, 11 months, or 1 year of administering a first dose of the ActRII signaling inhibitor to the subject.

In certain embodiments, the method of treatment further comprises performing one or more in vitro cell culture methods provided herein (see Section 7.4) a period of time after a first dose of the ActRII signaling inhibitor has been administered to the subject. In certain embodiments, one in vitro cell culture method is performed. In certain embodiments, two in vitro cell culture methods are performed. In certain embodiments, three in vitro cell culture methods are performed. In certain embodiments, four in vitro cell culture methods are performed. In certain embodiments, five in vitro cell culture methods are performed. In certain embodiments, six in vitro cell culture methods are performed. In certain embodiments, the period of time after the first dose of the ActRII signaling inhibitor has been administered to the subject is 1 day, 2 days, 3 days, 4 days, 5 days, 6 days, 1 week, 2 weeks, 3 weeks, 4 weeks, 1 month 2 months, 3 months, 4 months, 5 months, 6 months, 7 months, 8 months, 9 months, 10 months, 11 months, or 12 months.

In certain embodiments, the method of treatment further comprises (i) performing one or more in vitro cell culture methods provided herein (see Section 7.4) a period of time after a first dose of the ActRII signaling inhibitor has been administered to the subject; and (ii) administering a subsequent dose of the ActRII signaling inhibitor to the subject. In certain embodiments, one in vitro cell culture method is performed. In certain embodiments, two in vitro cell culture methods are performed. In certain embodiments, three in vitro cell culture methods are performed. In certain embodiments, four in vitro cell culture methods are performed. In certain embodiments, five in vitro cell culture methods are performed. In certain embodiments, six in vitro cell culture methods are performed. In certain embodiments, the period of time after the first dose of the ActRII signaling inhibitor has been administered to the subject is 1 day, 2 days, 3 days, 4 days, 5 days, 6 days, 1 week, 2 weeks, 3 weeks, 4 weeks, 1 month 2 months, 3 months, 4 months, 5 months, 6 months, 7 months, 8 months, 9 months, 10 months, 11 months, or 12 months. In certain embodiments, the subsequent dose is a subsequent dose as described in Section 7.6. In certain embodiments, the subsequent dose is administered to the subject at a frequency as described in Section 7.6. In certain embodiments, the subsequent dose is administered to the subject according to a route of administration as described in Section 7.6. In certain embodiments, the subsequent dose is less than the first dose (e.g., a reduced concentration or administered at a reduced frequency as compared to the initial dose) if 1, 2, 3, or more of the outcome parameters provided in Section 7.4.1 are achieved in an in vitro cell culture method provided in Section 7.4, wherein the in vitro cell culture method utilizes an EPC derived from the subject. In certain embodiments, the subsequent dose is less than the first dose (e.g., a reduced concentration or administered at a reduced frequency as compared to the initial dose) if 1, 2, 3, or more of the outcome parameters provided in Section 7.4.1 are achieved in an in vitro cell culture method provided in Section 7.4, wherein the in vitro cell culture method utilizes a stromal cell derived from the subject. In certain embodiments, the subsequent dose is less than the first dose (e.g., a reduced concentration or administered at a reduced frequency as compared to the initial dose) if 1, 2, 3, or more of the outcome parameters provided in Section 7.4.1 are achieved in an in vitro cell culture method provided in Section 7.4, wherein the in vitro cell culture method utilizes an EPC derived from the subject and a stromal cell derived from a reference population. In certain embodiments, the reference population is as described in Section 7.9.

In certain embodiments, the subsequent dose is greater than the first dose (e.g., an increased concentration or administered at an increased frequency as compared to the initial dose) if 1, 2, 3, or more of the outcome parameters provided in Section 7.4.1 are not achieved in an in vitro cell culture method provided in Section 7.4, wherein the in vitro cell culture method utilizes an EPC derived from the subject. In certain embodiments, the subsequent dose is greater than the first dose (e.g., an increased concentration or administered at an increased frequency as compared to the initial dose) if 1, 2, 3, or more of the outcome parameters provided in Section 7.4.1 are not achieved in an in vitro cell culture method provided in Section 7.4, wherein the in vitro cell culture method utilizes a stromal cell derived from the subject. In certain embodiments, the subsequent dose is greater than the first dose (e.g., an increased concentration or administered at an increased frequency as compared to the initial dose) if 1, 2, 3, or more of the outcome parameters provided in Section 7.4.1 are not achieved in an in vitro cell culture method provided in Section 7.4, wherein the in vitro cell culture method utilizes an EPC derived from the subject and a stromal cell derived from a reference population. In certain embodiments, the reference population is as described in Section 7.9.

Also provided herein is a method of treating beta-thalassemia in a subject, comprising administering an ActRII signaling inhibitor to the subject, wherein the patient is being monitored by using an in vitro cell culture method provided herein (see Section 7.4). In certain embodiments, the pharmaceutically effective dose is a dose as described in Section 7.6. In certain embodiments, the pharmaceutically effective dose is administered to the subject at a frequency as described in Section 7.6. In certain embodiments, the pharmaceutically effective dose is administered to the subject according to a route of administration as described in Section 7.6. In certain embodiments, the ActRII signaling inhibitor is as described in Section 7.8. In certain embodiments, the ActRII signaling inhibitor is an ActRIIA signaling inhibitor as described in Section 7.8.1. In certain embodiments, the ActRIIA signaling inhibitor is an ActRIIA-Fc such as an ActRIIA-hFc (e.g., SEQ ID NO:7). In certain embodiments, the ActRII signaling inhibitor is an ActRIIB signaling inhibitor as described in Section 7.8.2. In certain embodiments, the ActRIIB signaling inhibitor is an ActRIIB-Fc such as an ActRIIB-hFc (e.g., SEQ ID NO:25). In certain embodiments, the ActRII signaling inhibitor is part of a composition as described in Section 7.7. In certain embodiments, the ActRII signaling inhibitor is administered to the subject in combination with a second pharmaceutically active agent or therapy as described in Section 7.3.1. In certain embodiments, the subject is a subject as described in Section 7.5.

Without being bound by theory, the responsiveness of an EPC of a beta-thalassemic subject in an in vitro cell culture method provided herein (see Section 7.4 and 7.4.1) can be used to monitor the subject to determine whether or not the subject is predicted to be responsive to treatment with an ActRII signaling inhibitor. In addition, without being bound by theory, the responsiveness of a stromal cell of a beta-thalassemic subject in an in vitro cell culture method provided herein (see Section 7.4 and 7.4.1) can be used to monitor whether or not the subject is predicted to be responsive to treatment with an ActRII signaling inhibitor. For example, without being bound by any particular theory, administering of the ActRII signaling inhibitor to a subject exposes an EPC and/or a stromal cell in the subject to the ActRII signaling inhibitor, and thus, an in vitro cell culture method provided herein that utilizes an EPC and/or a stromal cell obtained from a subject who has been administered an ActRII signaling inhibitor may not require addition of the ActRII signaling inhibitor to the in vitro cell culture method. Thus, in certain embodiments, monitoring of the patient by using an in vitro cell culture method provided herein comprises performing an in vitro cell culture method provided herein (see Section 7.4) in the absence of the ActRII signaling inhibitor. In certain embodiments, monitoring of the patient by using an in vitro cell culture method provided herein comprises performing an in vitro cell culture method provided herein (see Section 7.4) in the presence of the ActRII signaling inhibitor.

In certain embodiments, the subject is predicted to be responsive to treatment with an ActRII signaling inhibitor if 1, 2, 3, or more of the outcome parameters provided in Section 7.4.1 are achieved in an in vitro cell culture method provided in Section 7.4, wherein the in vitro cell culture method utilizes an EPC derived from the subject. In certain embodiments, the subject is predicted to be responsive to treatment with an ActRII signaling inhibitor if 1, 2, 3, or more of the outcome parameters provided in Section 7.4.1 are achieved in an in vitro cell culture method provided in Section 7.4, wherein the in vitro cell culture method utilizes a stromal cell derived from the subject. In certain embodiments, the subject is predicted to be responsive to treatment with an ActRII signaling inhibitor if 1, 2, 3, or more of the outcome parameters provided in Section 7.4.1 are achieved in an in vitro cell culture method provided in Section 7.4, wherein the in vitro cell culture method utilizes an EPC derived from the subject and a stromal cell derived from a reference population. In certain embodiments, the reference population is as described in Section 7.9.

In certain embodiments, the in vitro cell culture method (see Section 7.4) is performed a first period of time after administering a first dose of the ActRII signaling inhibitor to the subject. In certain embodiments, the first period of time after administering a first dose of the ActRII signaling inhibitor to the subject is within 1 day, 1 week, 2 weeks, 3 weeks, 4 weeks, 1 month, 2 months, 3 months, 4 months, 5 months, 6 months, 7 months, 8 months, 9 months, 10 months, 11 months, or 1 year of administering a first dose of the ActRII signaling inhibitor to the subject.

In certain embodiments, the method of treatment further comprises performing one or more in vitro cell culture methods provided herein (see Section 7.4) a second period of time after a first dose of the ActRII signaling inhibitor has been administered to the subject. In certain embodiments, one in vitro cell culture method is performed. In certain embodiments, two in vitro cell culture methods are performed. In certain embodiments, three in vitro cell culture methods are performed. In certain embodiments, four in vitro cell culture methods are performed. In certain embodiments, five in vitro cell culture methods are performed. In certain embodiments, six in vitro cell culture methods are performed. In certain embodiments, the second period of time after the first dose of the ActRII signaling inhibitor has been administered to the subject is 1 day, 2 days, 3 days, 4 days, 5 days, 6 days, 1 week, 2 weeks, 3 weeks, 4 weeks, 1 month 2 months, 3 months, 4 months, 5 months, 6 months, 7 months, 8 months, 9 months, 10 months, 11 months, or 12 months.

In certain embodiments, the method of treatment comprises (i) administering the ActRII signaling inhibitor to the subject; (ii) performing one or more in vitro cell culture methods provided herein (see Section 7.4) a first period of time after a first dose of the ActRII signaling inhibitor has been administered to the subject; and (ii) administering a subsequent dose of the ActRII signaling inhibitor to the subject. In certain embodiments, one in vitro cell culture method is performed. In certain embodiments, two in vitro cell culture methods are performed. In certain embodiments, three in vitro cell culture methods are performed. In certain embodiments, four in vitro cell culture methods are performed. In certain embodiments, five in vitro cell culture methods are performed. In certain embodiments, six in vitro cell culture methods are performed. In certain embodiments, the period of time after the first dose of the ActRII signaling inhibitor has been administered to the subject is 1 day, 2 days, 3 days, 4 days, 5 days, 6 days, 1 week, 2 weeks, 3 weeks, 4 weeks, 1 month 2 months, 3 months, 4 months, 5 months, 6 months, 7 months, 8 months, 9 months, 10 months, 11 months, or 12 months. In certain embodiments, the subsequent dose is a subsequent dose as described in Section 7.6. In certain embodiments, the subsequent dose is administered to the subject at a frequency as described in Section 7.6. In certain embodiments, the subsequent dose is administered to the subject according to a route of administration as described in Section 7.6. In certain embodiments, the subsequent dose is less than the first dose (e.g., a reduced concentration or administered at a reduced frequency as compared to the initial dose) if 1, 2, 3, or more of the outcome parameters provided in Section 7.4.1 are achieved in an in vitro cell culture method provided in Section 7.4, wherein the in vitro cell culture method utilizes an EPC derived from the subject. In certain embodiments, the subsequent dose is less than the first dose (e.g., a reduced concentration or administered at a reduced frequency as compared to the initial dose) if 1, 2, 3, or more of the outcome parameters provided in Section 7.4.1 are achieved in an in vitro cell culture method provided in Section 7.4, wherein the in vitro cell culture method utilizes a stromal cell derived from the subject. In certain embodiments, the subsequent dose is less than the first dose (e.g., a reduced concentration or administered at a reduced frequency as compared to the initial dose) if 1, 2, 3, or more of the outcome parameters provided in Section 7.4.1 are achieved in an in vitro cell culture method provided in Section 7.4, wherein the in vitro cell culture method utilizes an EPC derived from the subject and a stromal cell derived from a reference population. In certain embodiments, the reference population is as described in Section 7.9.

In certain embodiments, the subsequent dose is greater than the first dose (e.g., an increased concentration or administered at an increased frequency as compared to the initial dose) if 1, 2, 3, or more of the outcome parameters provided in Section 7.4.1 are not achieved in an in vitro cell culture method provided in Section 7.4, wherein the in vitro cell culture method utilizes an EPC derived from the subject. In certain embodiments, the subsequent dose is greater than the first dose (e.g., an increased concentration or administered at an increased frequency as compared to the initial dose) if 1, 2, 3, or more of the outcome parameters provided in Section 7.4.1 are not achieved in an in vitro cell culture method provided in Section 7.4, wherein the in vitro cell culture method utilizes a stromal cell derived from the subject. In certain embodiments, the subsequent dose is greater than the first dose (e.g., an increased concentration or administered at an increased frequency as compared to the initial dose) if 1, 2, 3, or more of the outcome parameters provided in Section 7.4.1 are not achieved in an in vitro cell culture method provided in Section 7.4, wherein the in vitro cell culture method utilizes an EPC derived from the subject and a stromal cell derived from a reference population. In certain embodiments, the reference population is as described in Section 7.9.

Also provided herein is use of an in vitro cell culture method provided herein (see, Section 7.4) for predicting whether beta-thalassemia will be treated in a subject, wherein an ActRII signaling inhibitor has been administered to the subject. In certain embodiments, the erythroid progenitor utilized in the in vitro cell culture method has been obtained from the subject. In certain embodiments, the stromal cell utilized in the in vitro cell culture method has been obtained from the subject. In certain embodiments, the stromal cell utilized in the in vitro cell culture method has been obtained from a reference population. Without being bound by any particular theory, the occurrence of one or more outcome parameters (see Section 7.4.1) in an in vitro cell culture method provided herein indicate that beta-thalassemia will be treated in the subject upon administering the ActRII signaling inhibitor to the subject, wherein the erythroid progenitor and/or stromal cell in the in vitro cell culture assay has been obtained from the subject.

Also provided herein is use of an in vitro cell culture method provided herein (see, Section 7.4) for selecting a subject to be administered an ActRII signaling inhibitor. In certain embodiments, the subject is selected to be administered an ActRII signaling inhibitor if one or more cells obtained from the subject are utilized in one or more in vitro cell culture methods provided herein (see, Section 7.4) and one or more outcome parameter occurs. In certain embodiments, the outcome parameter is as described in Section 7.4.1.

Also provided herein is use of an in vitro cell culture method provided herein (see, Section 7.4) for monitoring treatment of beta-thalassemia in a subject, wherein an ActRII signaling inhibitor has been administered to the subject.

7.3.1 Combination Therapy

In certain embodiments, the methods provided herein (see, Section 7.3 and Section 7.4) are performed in combination with a second pharmaceutically active agent or therapy. Such combination therapy may be achieved by way of the simultaneous, sequential, or separate dosing of the individual components of the treatment. Additionally, when administered as a component of such combination therapy, the ActRII signaling inhibitor and the second pharmaceutically active agent or therapy may be synergistic, such that the daily dose of either or both of the components may be reduced as compared to the dose of either component that would normally be given as a monotherapy. Alternatively, when administered as a component of such combination therapy, the ActRII signaling inhibitor provided herein and the second pharmaceutically active agent or therapy may be additive, such that the daily dose of each of the components is similar or the same as the dose of either component that would normally be given as a monotherapy.

In certain embodiments, the ActRII signaling inhibitor provided herein is administered on the same day as a second pharmaceutically active agent or therapy. In certain embodiments, the ActRII signaling inhibitor is administered one, two, three, or more days before a second pharmaceutically active agent or therapy. In certain embodiments, the ActRII signaling inhibitor is administered one, two, three or more days after a second pharmaceutically active agent or therapy. In certain embodiments, the ActRII signaling inhibitor is administered within one, two, three or more weeks of a second pharmaceutically active agent or therapy.

In certain embodiments, the second pharmaceutically active agent or therapy is an active agent or therapy, respectively, used to treat beta-thalassemia. Non-limiting examples or pharmaceutically active agents or therapies used to treat beta-thalassemia include red blood cell transfusion, iron chelation therapy, such as, for example, deferoxamine, deferiprone, and/or deferasirox, fetal hemoglobin inducing agents, such as, for example, hydroxyurea, and hematopoietic stem cell transplantation.

7.4 In Vitro Cell Culture Methods

Without being bound by theory, the responsiveness of erythroid progenitor cells (EPCs) of a beta-thalassemic subject in an in vitro cell culture method provided herein can be used to predict whether or not the patient will be responsive to treatment with an ActRII signaling inhibitor (e.g., ActRIIA-hFc (SEQ ID NO:7) or ActRIIB-hFc (SEQ ID NO:25)). In addition, without being bound by theory, the responsiveness of stromal cells of a beta-thalassemic subject in an in vitro cell culture method provided herein can be used to predict whether or not the patient will be responsive to treatment with an ActRII signaling inhibitor (e.g., ActRIIA-hFc (SEQ ID NO:7) or ActRIIB-hFc (SEQ ID NO:25)). Similarly, a beta-thalassemic subject can be monitored using an in vitro cell culture method provided herein to determine how well the subject responds to treatment of beta-thalassemia with an ActRII signaling inhibitor (e.g., ActRIIA-hFc (SEQ ID NO:7) or ActRIIB-hFc (SEQ ID NO:25)). For example, without being bound by any theory, if an in vitro cell culture method provided herein results in one or more of the outcome parameters provided in Section 7.4.1, the subject can be selected for treatment with an ActRII signaling inhibitor (e.g., ActRIIA-hFc (SEQ ID NO:7) or ActRIIB-hFc (SEQ ID NO:25)) and is considered to be responsive to said treatment. In specific embodiments, one or more in vitro cell culture methods provided herein (see Section 7.4) is performed before a method of treatment provided herein. In specific embodiments, one or more in vitro cell culture methods provided herein (see Section 7.4) is performed after a method of treatment provided herein. In specific embodiments, one or more in vitro cell culture methods provided herein (see Section 7.4) is performed concurrently with a method of treatment provided herein. In specific embodiments, the method of treatment is as described in Section 7.3. In specific embodiments, the patient is a patient described in Section 7.5.

Provided herein is an in vitro cell culture method, comprising (a) co-culturing an EPC and a stromal cell in the presence of an activin type II receptor (ActRII) signaling inhibitor for a period of time; and (b) determining the level of GYPA, GATA1, GATA2, or alpha-globin in the EPC. In certain embodiments, the in vitro cell culture method further comprises determining the level of GYPA, GATA1, GATA2, or alpha-globin in the supernatant of the in vitro cell culture method. In certain embodiments, the in vitro cell culture method further comprises determining cell number after the period of time. In certain embodiments, the level of GYPA, GATA1, GATA2, or alpha-globin in the EPC is determined according to an assay as described in Section 7.9 or Section 8.1. In certain embodiments, the level of GYPA, GATA1, GATA2, or alpha-globin in the supernatant is determined according to an assay as described in Section 7.9 or Section 8.1. In certain embodiments, the in vitro cell culture method further comprises determining cell viability of the EPC after the period of time. In certain embodiments, the in vitro cell culture method further comprises determining the number of EPCs in the culture after the period of time. In certain embodiments, the in vitro cell culture method further comprises determining erythroid differentiation after the period of time. In specific embodiments, one or more in vitro cell culture methods provided herein (see Section 7.4) is performed before a method of treatment provided herein. In specific embodiments, one or more in vitro cell culture methods provided herein (see Section 7.4) is performed after a method of treatment provided herein. In specific embodiments, one or more in vitro cell culture methods provided herein (see Section 7.4) is performed concurrently with a method of treatment provided herein. In specific embodiments, the method of treatment is as described in Section 7.3.

Also provided herein is an in vitro cell culture method, comprising (a) co-culturing an EPC and a stromal cell in the presence of an activin type II receptor (ActRII) signaling inhibitor for a period of time; and (b) determining the level of expansion of the EPC. In certain embodiments, the level of expansion of the EPC is determined according to an assay as described in Section 7.9 or Section 8.1. In certain embodiments, the in vitro cell culture method further comprises determining cell viability of the EPC after the period of time. In certain embodiments, the in vitro cell culture method further comprises determining the number of EPCs in the culture after the period of time. In certain embodiments, the in vitro cell culture method further comprises determining erythroid differentiation after the period of time. In specific embodiments, one or more in vitro cell culture methods provided herein (see Section 7.4) is performed before a method of treatment provided herein. In specific embodiments, one or more in vitro cell culture methods provided herein (see Section 7.4) is performed after a method of treatment provided herein. In specific embodiments, one or more in vitro cell culture methods provided herein (see Section 7.4) is performed concurrently with a method of treatment provided herein. In specific embodiments, the method of treatment is as described in Section 7.3.

Also provided herein is an in vitro cell culture method, comprising (a) culturing a stromal cell in the presence of an activin type II receptor (ActRII) signaling inhibitor for a period of time; and (b) determining the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the supernatant obtained from the culture of step (a). In certain embodiments, the method further comprises determining the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the stromal cell. In certain embodiments, the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the supernatant is determined according to an assay as described in Section 7.9. In certain embodiments, the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the stromal cell is determined according to an assay as described in Section 7.9. In certain embodiments, the in vitro cell culture method further comprises determining cell viability of the stromal cell after the period of time. In certain embodiments, the in vitro cell culture method further comprises determining the number of stromal cells in the culture after the period of time. In specific embodiments, one or more in vitro cell culture methods provided herein (see Section 7.4) is performed before a method of treatment provided herein. In specific embodiments, one or more in vitro cell culture methods provided herein (see Section 7.4) is performed after a method of treatment provided herein. In specific embodiments, one or more in vitro cell culture methods provided herein (see Section 7.4) is performed concurrently with a method of treatment provided herein. In specific embodiments, the method of treatment is as described in Section 7.3.

Also provided herein is an in vitro cell culture method, comprising (a) culturing an EPC in conditioned media for a period of time, wherein the conditioned media has been obtained from a stromal cell cultured in the presence of an ActRII signaling inhibitor; and (b) determining the level of GYPA, GATA1, GATA2, and/or alpha-globin in the EPC and/or the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the supernatant obtained from the culture of step (a). In certain embodiments, the method further comprises determining the level of GYPA, GATA1, GATA2, and/or alpha-globin in the supernatant of the in vitro cell culture method. In certain embodiments, the method further comprises determining the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the EPC of the in vitro cell culture method. In certain embodiments, the conditioned media has been obtained from a stromal cell co-cultured with an EPC in the presence of an ActRII signaling inhibitor. In certain embodiments, the level of GYPA, GATA1, GATA2, and/or alpha-globin in the EPC is determined according to an assay as described in Section 7.9 or Section 8.1. In certain embodiments, the level of GYPA, GATA1, GATA2, and/or alpha-globin in the supernatant is determined according to an assay as described in Section 7.9 or Section 8.1. In certain embodiments, the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the supernatant is determined according to an assay as described in Section 7.9 or Section 8.1. In certain embodiments, the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the EPC is determined according to an assay as described in Section 7.9 or Section 8.1. In certain embodiments, the in vitro cell culture method further comprises determining cell viability of the EPC after the period of time. In certain embodiments, the in vitro cell culture method further comprises determining the number of EPCs in the culture after the period of time. In certain embodiments, the in vitro cell culture method further comprises determining erythroid differentiation after the period of time. In specific embodiments, one or more in vitro cell culture methods provided herein (see Section 7.4) is performed before a method of treatment provided herein. In specific embodiments, one or more in vitro cell culture methods provided herein (see Section 7.4) is performed after a method of treatment provided herein. In specific embodiments, one or more in vitro cell culture methods provided herein (see Section 7.4) is performed concurrently with a method of treatment provided herein. In specific embodiments, the method of treatment is as described in Section 7.3.

Also provided herein is an in vitro cell culture method, comprising (a) culturing an EPC in conditioned media for a period of time, wherein the conditioned media has been obtained from a stromal cell cultured in the presence of an ActRII signaling inhibitor; and (b) determining the level of expansion of the EPC. In certain embodiments, the conditioned media has been obtained from a stromal cell co-cultured with an EPC in the presence of an ActRII signaling inhibitor. In certain embodiments, the level of expansion of the EPC is determined according to an assay as described in Section 7.9 or Section 8.1. In certain embodiments, the in vitro cell culture method further comprises determining cell viability of the EPC after the period of time. In certain embodiments, the in vitro cell culture method further comprises determining the number of EPCs in the culture after the period of time. In certain embodiments, the in vitro cell culture method further comprises determining erythroid differentiation after the period of time. In specific embodiments, one or more in vitro cell culture methods provided herein (see Section 7.4) is performed before a method of treatment provided herein. In specific embodiments, one or more in vitro cell culture methods provided herein (see Section 7.4) is performed after a method of treatment provided herein. In specific embodiments, one or more in vitro cell culture methods provided herein (see Section 7.4) is performed concurrently with a method of treatment provided herein. In specific embodiments, the method of treatment is as described in Section 7.3.

Also provided herein is an in vitro cell culture method, comprising (a) culturing an EPC in the presence of an ActRII signaling inhibitor for a period of time; and (b) determining the level of GYPA, GATA1, GATA2, or alpha-globin in the EPC and/or the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the supernatant obtained from step (a). In certain embodiments, the method further comprises determining the level of GYPA, GATA1, GATA2, or alpha-globin in the supernatant of the in vitro cell culture method. In certain embodiments, the method further comprises determining the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the EPC. In certain embodiments, the level of GYPA, GATA1, GATA2, or alpha-globin in the EPC is determined according to an assay as described in Section 7.9 or Section 8.1. In certain embodiments, the level of GYPA, GATA1, GATA2, or alpha-globin in the supernatant is determined according to an assay as described in Section 7.9 or Section 8.1. In certain embodiments, the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the supernatant is determined according to an assay as described in Section 7.9 or Section 8.1. In certain embodiments, the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the EPC is determined according to an assay as described in Section 7.9 or Section 8.1. In certain embodiments, the in vitro cell culture method further comprises determining cell viability of the EPC after the period of time. In certain embodiments, the in vitro cell culture method further comprises determining the number of EPCs in the culture after the period of time. In certain embodiments, the in vitro cell culture method further comprises determining erythroid differentiation after the period of time. In specific embodiments, one or more in vitro cell culture methods provided herein (see Section 7.4) is performed before a method of treatment provided herein. In specific embodiments, one or more in vitro cell culture methods provided herein (see Section 7.4) is performed after a method of treatment provided herein. In specific embodiments, one or more in vitro cell culture methods provided herein (see Section 7.4) is performed concurrently with a method of treatment provided herein. In specific embodiments, the method of treatment is as described in Section 7.3.

In certain embodiments, the period of time is 1, 2, 3, 4, 5, 6, 7, 8, 9, 10, 11, 12, 13, 14, 15, 16, 17, 18, 19, or 20 days. In certain embodiments, the period of time is 14 days. In certain embodiments, the EPC is cultured as described in Section 7.9 or Section 8.1. In certain embodiments the stromal cell is cultured as described in Section 7.9 or Section 8.1. In certain embodiments, the EPC and stromal cell are co-cultured as described in Section 7.9 or Section 8.1.

In certain embodiments, the stromal cell has been obtained from bone marrow. In certain embodiments, the stromal cell has been obtained from a beta-thalassemic subject. In certain embodiments, the stromal cell has been obtained from bone marrow of a beta-thalassemic subject. In certain embodiments, the stromal cell has been obtained from a reference population. In certain embodiments, the stromal cell has been obtained from bone marrow of a reference population. In certain embodiments, the EPC has been obtained from peripheral blood. In certain embodiments, the EPC has been obtained from bone marrow. In certain embodiments, the EPC has been obtained from a beta-thalassemic subject. In certain embodiments, the EPC has been obtained from peripheral blood of a beta-thalassemic subject. In certain embodiments, the EPC has been obtained from bone marrow of a beta-thalassemic subject. In certain embodiments, the EPC has been obtained from a reference population. In certain embodiments, the EPC has been obtained from peripheral blood of a reference population. In certain embodiments, the EPC has been obtained from bone marrow of a reference population. In certain embodiments, the EPC is a $CD34^+$ cell. In certain embodiments, the EPCs is a non-adherent cell in supernatant (NAC). In certain embodiments, the EPC is a phase-bright cells (PBC) adhering to the surface of a stromal cell. In certain embodiments, the EPC is a phase-dim cell (PDC) beneath a stromal cell in a co-culture. In certain embodiments, the stromal cell has been obtained from a reference population and the EPC has been obtained from a beta-thalassemic subject. In certain embodiments, the stromal cell has been obtained from a beta-thalassemic subject and the EPC has been obtained from a beta-thalassemic subject. In certain embodiments, the stromal cell has been obtained from a beta-thalassemic subject and the EPC has been obtained from a reference population. In certain embodiments, the stromal cell has been obtained according to an assay as described in Section 7.9 or Section 8.1. In certain embodiments, the beta-thalassemic subject is a subject as described in Section 7.5. In certain embodiments, the EPC has been obtained according to an assay as described in Section 7.9 or Section 8.1. In certain embodiments, the reference population is a subject from a reference population as described in Section 7.9 or Section 8.1.

In certain embodiments, the ActRII signaling inhibitor is as described in Section 7.8. In certain embodiments, the ActRII signaling inhibitor is an ActRIIB signaling inhibitor as described in Section 7.8.2. In certain embodiments, the ActRIIB signaling inhibitor is an ActRIIB-Fc such as an ActRIIB-hFc (e.g., SEQ ID NO:25). In certain embodiments, the ActRII signaling inhibitor is an ActRIIA signaling inhibitor as described in Section 7.8.1. In certain embodiments, the ActRIIA signaling inhibitor is an ActRIIA-Fc such as an ActRIIA-hFc (e.g., SEQ ID NO:7). In certain embodiments, the ActRII signaling inhibitor is an amount of about 10 µg, about 20 µg, about 30 µg, about 40 µg, about 50 µg, about 60 µg, about 70 µg, about 80 µg, about 90 µg, about 100 µg, about 110 µg, about 120 µg, about 130 µg, about 140 µg, or about 150 µg of an ActRII signaling inhibitor. In certain embodiments, the ActRII signaling inhibitor is an amount of about 50 µg of an ActRII signaling inhibitor. In certain embodiments, the ActRII signaling inhibitor is an amount of about 100 µg of an ActRII signaling inhibitor. In certain embodiments, the ActRII signaling inhibitor is part of a composition as described in Section 7.7.

In certain embodiments, the in vitro cell culture method is used to select a subject to be administered an ActRII signaling inhibitor according to a method of treatment provided herein (see Section 7.3, Section 7.4.1 and Section 7.5). In certain embodiments, the in vitro cell culture method is used to monitor treatment of beta-thalassemia in a subject, wherein the subject is administered an ActRII signaling inhibitor according to a method of treatment provided herein (see Section 7.3, Section 7.4.1, and Section 7.5). In certain embodiments, the in vitro cell culture method is used in combination with a method of treatment provided herein (see Section 7.3, Section 7.4.1, and Section 7.5).

Without being bound by any particular theory, administering of the ActRII signaling inhibitor to a subject exposes an EPC and/or a stromal cell in the subject to the ActRII signaling inhibitor, and thus, an in vitro cell culture method provided herein that utilizes an EPC and/or a stromal cell obtained from a subject who has been administered an ActRII signaling inhibitor may not require addition of the ActRII signaling inhibitor to the in vitro cell culture method. Thus, in certain embodiments, monitoring of the patient by using an in vitro cell culture method provided herein comprises performing an in vitro cell culture method provided herein (see Section 7.4) in the absence of the ActRII signaling inhibitor. In certain embodiments, monitoring of the patient by using an in vitro cell culture method provided herein comprises performing an in vitro cell culture method provided herein (see Section 7.4) in the presence of the ActRII signaling inhibitor.

Thus, in certain embodiments, the in vitro cell culture method, comprises (a) co-culturing an EPC and a stromal cell for a period of time; and (b) determining the level of GYPA, GATA1, GATA2, or alpha-globin in the EPC, wherein the EPC has been obtained from a subject administered a pharmaceutically effective dose of an ActRII signaling inhibitor, and wherein the stromal cell has been obtained from a reference population (e.g., a reference population as described in Section 7.9. In certain embodiments, the in vitro cell culture method, comprises (a) co-culturing an EPC and a stromal cell for a period of time; and (b) determining the level of GYPA, GATA1, GATA2, or alpha-globin in the EPC, wherein the EPC has been obtained from a subject administered a pharmaceutically effective dose of an ActRII signaling inhibitor, and wherein the stromal cell has been obtained from the subject administered a pharmaceutically effective dose of an ActRII signaling inhibitor. In certain embodiments, the in vitro cell culture method further comprises determining the level of GYPA, GATA1, GATA2, or alpha-globin in the supernatant of the in vitro cell culture method. In certain embodiments, the in vitro cell culture method further comprises determining cell number after the period of time. In certain embodiments, the level of GYPA, GATA1, GATA2, or alpha-globin in the EPC is determined according to an assay as described in Section 7.9 or Section 8.1. In certain embodiments, the level of GYPA, GATA1, GATA2, or alpha-globin in the supernatant is determined according to an assay as described in Section 7.9 or Section 8.1. In certain embodiments, the in vitro cell culture method further comprises determining cell viability of the EPC after the period of time. In certain embodiments, the in vitro cell culture method further comprises determining the number of EPCs in the culture after the period of time. In certain embodiments, the in vitro cell culture method further comprises determining erythroid differentiation after the period of time. In specific embodiments, the subject has been administered the pharmaceutically effective dose of an ActRII signaling inhibitor according to the methods of treatment described in Section 7.3. In specific embodiments, the subject is a subject described in Section 7.5.

In certain embodiments, the in vitro cell culture method, comprises (a) co-culturing an EPC and a stromal cell for a period of time; and (b) determining the level of expansion of the EPC, wherein the EPC has been obtained from a subject administered a pharmaceutically effective dose of an ActRII signaling inhibitor, and wherein the stromal cell has been obtained from a reference population (e.g., a reference population as described in Section 7.9. In certain embodiments, the in vitro cell culture method, comprises (a) co-culturing an EPC and a stromal cell for a period of time; and (b) determining the level of expansion of the EPC, wherein the EPC has been obtained from a subject administered a pharmaceutically effective dose of an ActRII signaling inhibitor, and wherein the stromal cell has been obtained from the subject administered a pharmaceutically effective dose of an ActRII signaling inhibitor. In certain embodiments, the level of expansion of the EPC is determined according to an assay as described in Section 7.9 or Section 8.1. In certain embodiments, the in vitro cell culture method further comprises determining cell viability of the EPC after the period of time. In certain embodiments, the in vitro cell culture method further comprises determining the number of EPCs in the culture after the period of time. In certain embodiments, the in vitro cell culture method further comprises determining erythroid differentiation after the period of time. In specific embodiments, the subject has been administered the pharmaceutically effective dose of an ActRII signaling inhibitor according to the methods of treatment described in Section 7.3. In specific embodiments, the subject is a subject described in Section 7.5.

In certain embodiments, the in vitro cell culture method, comprises (a) culturing a stromal cell; and (b) determining the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the supernatant obtained from the culture of step (a), wherein the stromal cell has been obtained from a subject administered a pharmaceutically effective dose of an ActRII signaling inhibitor. In certain embodiments, the method further comprises determining the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the stromal cell. In certain embodiments, the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the supernatant is determined according to an assay as described in Section 7.9. In certain embodiments, the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the stromal cell is determined according to an assay as described in Section 7.9. In certain embodiments, the in vitro cell culture method further comprises determining cell viability of the stromal cell after the period of time. In certain embodiments, the in vitro cell culture method further comprises determining the number of stromal cells in the culture after the period of time. In specific embodiments, the subject has been administered the pharmaceutically effective dose of an ActRII signaling inhibitor according to the methods of treatment described in Section 7.3. In specific embodiments, the subject is a subject described in Section 7.5.

In certain embodiments, the in vitro cell culture method, comprises (a) culturing an EPC in conditioned media for a period of time, wherein the conditioned media has been obtained from culturing a stromal cell; and (b) determining the level of GYPA, GATA1, GATA2, and/or alpha-globin in the EPC and/or the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the supernatant obtained from the culture of step (a), wherein the EPC has been obtained from a subject administered a pharmaceutically effective dose of an ActRII signaling inhibitor, and wherein the stromal cell has been obtained from the subject administered a pharmaceutically effective dose of an ActRII signaling inhibitor. In certain embodiments, the in vitro cell culture method, comprises (a) culturing an EPC in conditioned media for a period of time, wherein the conditioned media has been obtained from culturing a stromal cell; and (b) determining the level of GYPA, GATA1, GATA2, and/or alpha-globin in the EPC and/or the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the supernatant obtained from the culture of step (a), wherein the EPC has been obtained from a reference population (e.g., a reference population as described in Section 7.9), and wherein the stromal cell has been obtained from a subject administered a pharmaceutically effective dose of an ActRII signaling inhibitor. In certain embodiments, the method further comprises determining the level of GYPA, GATA1, GATA2, and/or alpha-globin in the supernatant of the in vitro cell culture method. In certain embodiments, the method further comprises determining the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the EPC of the in vitro cell culture method. In certain embodiments, the conditioned media has been obtained from a stromal cell co-cultured with an EPC in the presence of an ActRII signaling inhibitor. In certain embodiments, the level of GYPA, GATA1, GATA2, and/or alpha-globin in the EPC is determined according to an assay as described in Section 7.9 or Section 8.1. In certain embodiments, the level of GYPA, GATA1, GATA2, and/or alpha-globin in the supernatant is determined according to an assay as described in Section 7.9 or Section 8.1. In certain embodiments, the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the supernatant is determined according to an assay as described in Section 7.9 or Section 8.1. In certain embodiments, the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the EPC is determined according to an assay as described in Section 7.9 or Section 8.1. In certain embodiments, the in vitro cell culture method further comprises determining cell viability of the EPC after the period of time. In certain embodiments, the in vitro cell culture method further comprises determining the number of EPCs in the culture after the period of time. In certain embodiments, the in vitro cell culture method further comprises determining erythroid differentiation after the period of time. In specific embodiments, the subject has been administered the pharmaceutically effective dose of an ActRII signaling inhibitor according to the methods of treatment described in Section 7.3. In specific embodiments, the subject is a subject described in Section 7.5.

In certain embodiments, the in vitro cell culture method, comprises (a) culturing an EPC in conditioned media for a period of time, wherein the conditioned media has been obtained from culturing a stromal cell; and (b) determining the level of expansion of the EPC, wherein the EPC has been obtained from a reference population (e.g., a reference population as described in Section 7.9), and wherein the stromal cell has been obtained from the subject administered a pharmaceutically effective dose of an ActRII signaling inhibitor. In certain embodiments, the in vitro cell culture method, comprises (a) culturing an EPC in conditioned media for a period of time, wherein the conditioned media has been obtained from culturing a stromal cell; and (b) determining the level of expansion of the EPC, wherein the EPC has been obtained from a subject administered a pharmaceutically effective dose of an ActRII signaling inhibitor, and wherein the stromal cell has been obtained from the subject administered a pharmaceutically effective dose of an ActRII signaling inhibitor. In certain embodiments, the conditioned media has been obtained from a stromal cell co-cultured with an EPC in the presence of an ActRII signaling inhibitor. In certain embodiments, the level of expansion of the EPC is determined according to an assay as described in Section 7.9 or Section 8.1. In certain embodiments, the in vitro cell culture method further comprises determining cell viability of the EPC after the period of time. In certain embodiments, the in vitro cell culture method further comprises determining the number of EPCs in the culture after the period of time. In certain embodiments, the in vitro cell culture method further comprises determining erythroid differentiation after the period of time. In specific embodiments, the subject has been administered the pharmaceutically effective dose of an ActRII signaling inhibitor according to the methods of treatment described in Section 7.3. In specific embodiments, the subject is a subject described in Section 7.5.

In certain embodiments, the in vitro cell culture method, comprises (a) culturing an EPC for a period of time; and (b) determining the level of GYPA, GATA1, GATA2, or alpha-globin in the EPC and/or the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the supernatant obtained from step (a), wherein the EPC has been obtained from a subject administered an ActRII signaling inhibitor. In certain embodiments, the method further comprises determining the level of GYPA, GATA1, GATA2, or alpha-globin in the supernatant of the in vitro cell culture method. In certain embodiments, the method further comprises determining the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the EPC. In certain embodiments, the level of GYPA, GATA1, GATA2, or alpha-globin in the EPC is determined according to an assay as described in Section 7.9 or Section 8.1. In certain embodiments, the level of GYPA, GATA1, GATA2, or alpha-globin in the supernatant is determined according to an assay as described in Section 7.9 or Section 8.1. In certain embodiments, the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the supernatant is determined according to an assay as described in Section 7.9 or Section 8.1. In certain embodiments, the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the EPC is determined according to an assay as described in Section 7.9 or Section 8.1. In certain embodiments, the in vitro cell culture method further comprises determining cell viability of the EPC after the period of time. In certain embodiments, the in vitro cell culture method further comprises determining the number of EPCs in the culture after the period of time. In certain embodiments, the in vitro cell culture method further comprises determining erythroid differentiation after the period of time. In specific embodiments, the subject has been administered the pharmaceutically effective dose of an ActRII signaling inhibitor according to the methods of treatment described in Section 7.3. In specific embodiments, the subject is a subject described in Section 7.5.

In certain embodiments, the period of time is 1, 2, 3, 4, 5, 6, 7, 8, 9, 10, 11, 12, 13, 14, 15, 16, 17, 18, 19, or 20 days. In certain embodiments, the period of time is 14 days. In certain embodiments, the EPC is cultured as described in Section 7.9 or Section 8.1. In certain embodiments the stromal cell is cultured as described in Section 7.9 or Section 8.1. In certain embodiments, the EPC and stromal cell are co-cultured as described in Section 7.9 or Section 8.1. In certain embodiments, the stromal cell has been obtained from bone marrow. In certain embodiments, the EPC has been obtained from peripheral blood. In certain embodiments, the EPC has been obtained from bone marrow. In certain embodiments, the EPC is a CD34$^+$ cell. In certain embodiments, the EPCs is a non-adherent cell in supernatant (NAC). In certain embodiments, the EPC is a phase-bright cells (PBC) adhering to the surface of a stromal cell. In certain embodiments, the EPC is a phase-dim cell (PDC) beneath a stromal cell in a co-culture. In certain embodiments, the stromal cell has been obtained according to an assay as described in Section 7.9 or Section 8.1. In certain embodiments, the beta-thalassemic subject is a subject as described in Section 7.5. In certain embodiments, the EPC has been obtained according to an assay as described in Section 7.9 or Section 8.1. In certain embodiments, the reference population is a subject from a reference population as described in Section 7.9 or Section 8.1.

In certain embodiments, the ActRII signaling inhibitor is as described in Section 7.8. In certain embodiments, the ActRII signaling inhibitor is an ActRIIB signaling inhibitor as described in Section 7.8.2. In certain embodiments, the ActRIIB signaling inhibitor is an ActRIIB-Fc such as an ActRIIB-hFc (e.g., SEQ ID NO:25). In certain embodiments, the ActRII signaling inhibitor is an ActRIIA signaling inhibitor as described in Section 7.8.1. In certain embodiments, the ActRIIA signaling inhibitor is an ActRIIA-Fc such as an ActRIIA-hFc (e.g., SEQ ID NO:7). In certain embodiments, the ActRII signaling inhibitor is an amount of about 10 µg, about 20 µg, about 30 µg, about 40 µg, about 50 µg, about 60 µg, about 70 µg, about 80 µg, about 90 µg, about 100 µg, about 110 µg, about 120 µg, about 130 µg, about 140 µg, or about 150 µg of an ActRII signaling inhibitor. In certain embodiments, the ActRII signaling inhibitor is an amount of about 50 µg of an ActRII signaling inhibitor. In certain embodiments, the ActRII signaling inhibitor is an amount of about 100 µg of an ActRII signaling inhibitor. In certain embodiments, the ActRII signaling inhibitor is part of a composition as described in Section 7.7.

7.4.1 In Vitro Cell Culture Method Outcome Parameters

Without being bound by any particular theory, the occurrence of one or more outcome parameters in an in vitro cell culture method provided herein can be utilized to (i) indicate that beta-thalassemia will be treated in the subject upon administering the ActRII signaling inhibitor to the subject; (ii) to select a subject to be administered an ActRII signaling inhibitor according to the methods provided herein; and/or (iii) to monitor treatment of beta-thalassemia in a subject administered an ActRII signaling inhibitor according to the methods provided herein. In specific embodiments, one or more in vitro cell culture methods provided herein is performed before a method of treatment provided herein. In specific embodiments, one or more in vitro cell culture methods provided herein (see Section 7.4) is performed after a method of treatment provided herein. In specific embodiments, one or more in vitro cell culture methods provided herein (see Section 7.4) is performed concurrently with a method of treatment provided herein. In specific embodiments, the method of treatment is as described in Section 7.3. In specific embodiments, the patient is a patient described in Section 7.5.

In certain embodiments, the outcome parameter is an increase in the level of GYPA in the EPC of the in vitro cell culture method as compared to the level of GYPA in a control EPC. In certain embodiments, the level of GYPA is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GYPA in a control EPC. In certain embodiments, the level of GYPA is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GYPA in a control EPC.

In certain embodiments, the outcome parameter is an increase in the level of GYPA in the supernatant of the in vitro cell culture method as compared to the level of GYPA in a control EPC. In certain embodiments, the level of GYPA is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GYPA in a control supernatant. In certain embodiments, the level of GYPA is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GYPA in a control supernatant.

In certain embodiments, the level of GYPA is determined according to an assay as described in Section 7.9 or Section 8.1. In certain embodiments, the level of GYPA is the nucleic acid level of GYPA. In certain embodiments, the level of GYPA is the cDNA level of GYPA. In certain embodiments, the level of GYPA is the mRNA level of GYPA. In certain embodiments, the level of GYPA is the protein level of GYPA.

In certain embodiments, the outcome parameter is an increase in the level of GATA1 in the EPC of the in vitro cell culture method as compared to the level of GATA1 in a control EPC. In certain embodiments, the level of GATA1 is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GATA1 in a control EPC. In certain embodiments, the level of GATA1 is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GATA1 in a control EPC.

In certain embodiments, the outcome parameter is an increase in the level of GATA1 in the supernatant of the in vitro cell culture method as compared to the level of GATA1 in a control supernatant. In certain embodiments, the level of GATA1 is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GATA1 in a control supernatant. In certain embodiments, the level of GATA1 is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GATA1 in a control supernatant.

In certain embodiments, the level of GATA1 is determined according to an assay as described in Section 7.9 or Section 8.1. In certain embodiments, the level of GATA1 is the nucleic acid level of GATA1. In certain embodiments, the level of GATA1 is the cDNA level of GATA1. In certain embodiments, the level of GATA1 is the mRNA level of GATA1. In certain embodiments, the level of GATA1 is the protein level of GATA1.

In certain embodiments, the outcome parameter is a decrease in the level of GATA2 in the EPC of the in vitro cell culture method as compared to the level of GATA2 in a control EPC. In certain embodiments, the level of GATA2 is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GATA2 in a control EPC. In certain embodiments, the level of GATA2 is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GATA2 in a control EPC.

In certain embodiments, the outcome parameter is a decrease in the level of GATA2 in the supernatant of the in vitro cell culture method as compared to the level of GATA2 in a control supernatant. In certain embodiments, the level of GATA2 is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GATA2 in a control supernatant. In certain embodiments, the level of GATA2 is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GATA2 in a control supernatant.

In certain embodiments, the level of GATA2 is determined according to an assay as described in Section 7.9 or Section 8.1. In certain embodiments, the level of GATA2 is the nucleic acid level of GATA2. In certain embodiments, the level of GATA2 is the cDNA level of GATA2. In certain embodiments, the level of GATA2 is the mRNA level of GATA2. In certain embodiments, the level of GATA2 is the protein level of GATA2.

In certain embodiments, the outcome parameter is a decrease in the level of alpha-globin in the EPC of the in vitro cell culture method as compared to the level of alpha-globin in a control EPC. In certain embodiments, the level of alpha-globin is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of alpha-globin in a control EPC. In certain embodiments, the level of alpha-globin is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of alpha-globin in a control EPC.

In certain embodiments, the outcome parameter is a decrease in the level of alpha-globin in the supernatant of the in vitro cell culture method as compared to the level of alpha-globin in a control supernatant. In certain embodiments, the level of alpha-globin is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of alpha-globin in a control supernatant. In certain embodiments, the level of alpha-globin is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of alpha-globin in a control supernatant.

In certain embodiments, the level of alpha-globin is determined according to an assay as described in Section 7.9 or Section 8.1. In certain embodiments, the level of alpha-globin is the nucleic acid level of alpha-globin. In certain embodiments, the level of alpha-globin is the cDNA level of alpha-globin. In certain embodiments, the level of alpha-globin is the mRNA level of alpha-globin. In certain embodiments, the level of alpha-globin is the protein level of alpha-globin.

In certain embodiments, the outcome parameter is an increase in the level of expansion of the EPC in the in vitro cell culture method as compared to the level of expansion in a control EPC. In certain embodiments, the level of expansion of the EPC is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of expansion of the control EPC. In certain embodiments, the level of expansion of the EPC is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of expansion of the control EPC. In certain embodiments, the level of expansion of the EPC in the in vitro cell culture is determined according to an assay as described in Section 7.9 or Section 8.1.

In certain embodiments, the outcome parameter is an increase in the level of ICAM-1 in the EPC of the in vitro cell culture method as compared to the level of ICAM-1 in a control EPC. In certain embodiments, the level of ICAM-1 in the EPC of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of ICAM-1 in a control EPC. In certain embodiments, the level of ICAM-1 in the supernatant of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of ICAM-1 in a control EPC.

In certain embodiments, the outcome parameter is an increase in the level of ICAM-1 in the supernatant of the in vitro cell culture method as compared to the level of ICAM-1 in a control supernatant. In certain embodiments, the level of ICAM-1 in the supernatant of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of ICAM-1 in a control supernatant. In certain embodiments, the level of ICAM-1 in the supernatant of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of ICAM-1 in a control supernatant. In certain embodiments, the level of ICAM-1 is determined according to an assay as described in Section 7.9 or Section 8.1. In certain embodiments, the level of ICAM-1 is the nucleic acid level of ICAM-1. In certain embodiments, the level of ICAM-1 is the cDNA level of ICAM-1. In certain embodiments, the level of ICAM-1 is the mRNA level of ICAM-1. In certain embodiments, the level of ICAM-1 is the protein level of ICAM-1.

In certain embodiments, the outcome parameter is an increase in the level of IL-1Ra in the EPC of the in vitro cell culture as compared to the level of IL-1Ra in a control EPC. In certain embodiments, the level of IL-1Ra in the EPC of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-1Ra in a control EPC. In certain embodiments, the level of IL-1Ra in the EPC of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-1Ra in a control EPC.

In certain embodiments, the outcome parameter is an increase in the level of IL-1Ra in the supernatant of the in vitro cell culture as compared to the level of IL-1Ra in a control supernatant. In certain embodiments, the level of IL-1Ra in the supernatant of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-1Ra in a control supernatant. In certain embodiments, the level of IL-1Ra in the supernatant of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-1Ra in a control supernatant.

In certain embodiments, the level of IL-1Ra is determined according to an assay as described in Section 7.9 or Section 8.1. In certain embodiments, the level of IL-1Ra is the nucleic acid level of IL-1Ra. In certain embodiments, the level of IL-1Ra is the cDNA level of IL-1Ra. In certain embodiments, the level of IL-1Ra is the mRNA level of IL-1Ra. In certain embodiments, the level of IL-1Ra is the protein level of IL-1Ra.

In certain embodiments, the outcome parameter is an increase in the level of survivin in the EPC of the in vitro cell culture method as compared to the level of survivin in a control EPC. In certain embodiments, the level of survivin in the EPC of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of survivin in a control EPC. In certain embodiments, the level of survivin in the EPC of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of survivin in a control EPC.

In certain embodiments, the outcome parameter is an increase in the level of survivin in the supernatant of the in vitro cell culture method as compared to the level of survivin in a control supernatant. In certain embodiments, the level of survivin in the supernatant of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of survivin in a control supernatant. In certain embodiments, the level of survivin in the supernatant of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of survivin in a control supernatant.

In certain embodiments, the level of survivin is determined according to an assay as described in Section 7.9 or Section 8.1. In certain embodiments, the level of survivin is the nucleic acid level of survivin. In certain embodiments, the level of survivin is the cDNA level of survivin. In certain embodiments, the level of survivin is the mRNA level of survivin. In certain embodiments, the level of survivin is the protein level of survivin.

In certain embodiments, the outcome parameter is an increase in the level of Bcl-2 in the EPC of the in vitro cell culture method as compared to the level of Bcl-2 in a control EPC. In certain embodiments, the level of Bcl-2 in the EPC of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of Bcl-2 in a control EPC. In certain embodiments, the level of Bcl-2 in the EPC of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of Bcl-2 in a control EPC.

In certain embodiments, the outcome parameter is an increase in the level of Bcl-2 in the supernatant of the in vitro cell culture method as compared to the level of Bcl-2 in a control supernatant. In certain embodiments, the level of Bcl-2 in the supernatant of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of Bcl-2 in a control supernatant. In certain embodiments, the level of Bcl-2 in the supernatant of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of Bcl-2 in a control supernatant.

In certain embodiments, the level of Bcl-2 is determined according to an assay as described in Section 7.9 or Section 8.1. In certain embodiments, the level of Bcl-2 is the nucleic acid level of Bcl-2. In certain embodiments, the level of Bcl-2 is the cDNA level of Bcl-2. In certain embodiments, the level of Bcl-2 is the mRNA level of Bcl-2. In certain embodiments, the level of Bcl-2 is the protein level of Bcl-2.

In certain embodiments, the outcome parameter is an increase in the level of Bcl-xL in the EPC of the in vitro cell culture method as compared to the level of Bcl-xL in a control EPC. In certain embodiments, the level of Bcl-xL in the EPC of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of Bcl-xL in a control EPC. In certain embodiments, the level of Bcl-xL in the EPC of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of Bcl-xL in a control EPC.

In certain embodiments, the outcome parameter is an increase in the level of Bcl-xL in the supernatant of the in vitro cell culture method as compared to the level of Bcl-xL in a control supernatant. In certain embodiments, the level of Bcl-xL in the supernatant of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of Bcl-xL in a control supernatant. In certain embodiments, the level of Bcl-xL in the supernatant of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of Bcl-xL in a control supernatant.

In certain embodiments, the level of Bcl-xL is determined according to an assay as described in Section 7.9 or Section 8.1. In certain embodiments, the level of Bcl-xL is the nucleic acid level of Bcl-xL. In certain embodiments, the level of Bcl-xL is the cDNA level of Bcl-xL. In certain embodiments, the level of Bcl-xL is the mRNA level of Bcl-xL. In certain embodiments, the level of Bcl-xL is the protein level of Bcl-xL.

In certain embodiments, the outcome parameter is an increase in the level of MCP-1 in the EPC of the in vitro cell culture method as compared to the level of MCP-1 in a control EPC. In certain embodiments, the level of MCP-1 in the EPC of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of MCP-1 in a control EPC. In certain embodiments, the level of MCP-1 in the EPC of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of MCP-1 in a control EPC.

In certain embodiments, the outcome parameter is an increase in the level of MCP-1 in the supernatant of the in vitro cell culture method as compared to the level of MCP-1 in a control supernatant. In certain embodiments, the level of MCP-1 in the supernatant of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of MCP-1 in a control supernatant. In certain embodiments, the level of MCP-1 in the supernatant of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of MCP-1 in a control supernatant.

In certain embodiments, the level of MCP-1 is determined according to an assay as described in Section 7.9 or Section 8.1. In certain embodiments, the level of MCP-1 is the nucleic acid level of MCP-1. In certain embodiments, the level of MCP-1 is the cDNA level of MCP-1. In certain embodiments, the level of MCP-1 is the mRNA level of MCP-1. In certain embodiments, the level of MCP-1 is the protein level of MCP-1.

In certain embodiments, the outcome parameter is an increase in the level of serpinE1 in the EPC of the in vitro cell culture method as compared to the level of serpinE1 in a control EPC. In certain embodiments, the level of serpinE1 in the EPC of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of serpinE1 in a control EPC. In certain embodiments, the level of serpinE1 in the EPC of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of serpinE1 in a control EPC.

In certain embodiments, the outcome parameter is an increase in the level of serpinE1 in the supernatant of the in vitro cell culture method as compared to the level of serpinE1 in a control supernatant. In certain embodiments, the level of serpinE1 in the supernatant of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of serpinE1 in a control supernatant. In certain embodiments, the level of serpinE1 in the supernatant of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of serpinE1 in a control supernatant.

In certain embodiments, the level of serpinE1 is determined according to an assay as described in Section 7.9 or Section 8.1. In certain embodiments, the level of serpinE1 is the nucleic acid level of serpinE1. In certain embodiments, the level of serpinE1 is the cDNA level of serpinE1. In certain embodiments, the level of serpinE1 is the mRNA level of serpinE1. In certain embodiments, the level of serpinE1 is the protein level of serpinE1.

In certain embodiments, the outcome parameter is an increase in the level of GRO-a in the EPC of the in vitro cell culture method as compared to the level of GRO-a in a control EPC. In certain embodiments, the level of GRO-a in the EPC of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GRO-a in a control EPC. In certain embodiments, the level of GRO-a in the EPC of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GRO-a in a control EPC.

In certain embodiments, the outcome parameter is an increase in the level of GRO-a in the supernatant of the in vitro cell culture method as compared to the level of GRO-a in a control supernatant. In certain embodiments, the level of GRO-a in the supernatant of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GRO-a in a control supernatant. In certain embodiments, the level of GRO-a in the supernatant of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GRO-a in a control supernatant.

In certain embodiments, the level of GRO-a is determined according to an assay as described in Section 7.9 or Section 8.1. In certain embodiments, the level of GRO-a is the nucleic acid level of GRO-a. In certain embodiments, the level of GRO-a is the cDNA level of GRO-a. In certain embodiments, the level of GRO-a is the mRNA level of GRO-a. In certain embodiments, the level of GRO-a is the protein level of GRO-a.

In certain embodiments, the outcome parameter is an increase in the level of IL-8 in the EPC of the in vitro cell culture method as compared to the level of IL-8 in a control EPC. In certain embodiments, the level of IL-8 in the EPC of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-8 in a control EPC. In certain embodiments, the level of IL-8 in the EPC of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-8 in a control EPC.

In certain embodiments, the outcome parameter is an increase in the level of IL-8 in the supernatant of the in vitro cell culture method as compared to the level of IL-8 in a control supernatant. In certain embodiments, the level of IL-8 in the supernatant of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-8 in a control supernatant. In certain embodiments, the level of IL-8 in the supernatant of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-8 in a control supernatant.

In certain embodiments, the level of IL-8 is determined according to an assay as described in Section 7.9 or Section 8.1. In certain embodiments, the level of IL-8 is the nucleic acid level of IL-8. In certain embodiments, the level of IL-8 is the cDNA level of IL-8. In certain embodiments, the level of IL-8 is the mRNA level of IL-8. In certain embodiments, the level of IL-8 is the protein level of IL-8.

In certain embodiments, the outcome parameter is an increase in the level of IL-10 in the EPC of the in vitro cell culture method as compared to the level of IL-10 in a control EPC. In certain embodiments, the level of IL-10 in the EPC of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-10 in a control EPC. In certain embodiments, the level of IL-10 in the EPC of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-10 in a control EPC.

In certain embodiments, the outcome parameter is an increase in the level of IL-10 in the supernatant of the in vitro cell culture method as compared to the level of IL-10 in a control supernatant. In certain embodiments, the level of IL-10 in the supernatant of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-10 in a control supernatant. In certain embodiments, the level of IL-10 in the supernatant of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5- fold, 3.0-fold, 3.5-fold, 4.0-fold, or 5.0-fold as compared to the level of IL-10 in a control supernatant.

In certain embodiments, the level of IL-10 is determined according to an assay as described in Section 7.9 or Section 8.1. In certain embodiments, the level of IL-10 is the nucleic acid level of IL-10. In certain embodiments, the level of IL-10 is the cDNA level of IL-10. In certain embodiments, the level of IL-10 is the mRNA level of IL-10. In certain embodiments, the level of IL-10 is the protein level of IL-10.

In certain embodiments, the outcome parameter is an increase in the level of IL-2 in the EPC of the in vitro cell culture method as compared to the level of IL-2 in a control EPC. In certain embodiments, the level of IL-2 in the EPC of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-2 in a control EPC. In certain embodiments, the level of IL-2 in the EPC of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-2 in a control EPC.

In certain embodiments, the outcome parameter is an increase in the level of IL-2 in the supernatant of the in vitro cell culture method as compared to the level of IL-2 in a control supernatant. In certain embodiments, the level of IL-2 in the supernatant of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-2 in a control supernatant. In certain embodiments, the level of IL-2 in the supernatant of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-2 in a control supernatant.

In certain embodiments, the level of IL-2 is determined according to an assay as described in Section 7.9 or Section 8.1. In certain embodiments, the level of IL-2 is the nucleic acid level of IL-2. In certain embodiments, the level of IL-2 is the cDNA level of IL-2. In certain embodiments, the level of IL-2 is the mRNA level of IL-2. In certain embodiments, the level of IL-2 is the protein level of IL-2.

In certain embodiments, the outcome parameter is an increase in the level of CIAP1 in the EPC of the in vitro cell culture method as compared to the level of CIAP1 in a control EPC. In certain embodiments, the level of CIAP1 in the EPC of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of CIAP1 in a control EPC. In certain embodiments, the level of CIAP1 in the EPC of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of CIAP1 in a control EPC.

In certain embodiments, the outcome parameter is an increase in the level of CIAP1 in the supernatant of the in vitro cell culture method as compared to the level of CIAP1 in a control supernatant. In certain embodiments, the level of CIAP1 in the supernatant of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of CIAP1 in a control supernatant. In certain embodiments, the level of CIAP1 in the supernatant of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of CIAP1 in a control supernatant.

In certain embodiments, the level of CIAP1 is determined according to an assay as described in Section 7.9 or Section 8.1. In certain embodiments, the level of CIAP1 is the nucleic acid level of CIAP1. In certain embodiments, the level of CIAP1 is the cDNA level of CIAP1. In certain embodiments, the level of CIAP1 is the mRNA level of CIAP1. In certain embodiments, the level of CIAP1 is the protein level of CIAP1.

In certain embodiments, the outcome parameter is an increase in the level of PON2 in the EPC of the in vitro cell culture method as compared to the level of PON2 in a control EPC. In certain embodiments, the level of PON2 in the EPC of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of PON2 in a control EPC. In certain embodiments, the level of PON2 in the EPC of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of PON2 in a control EPC.

In certain embodiments, the outcome parameter is an increase in the level of PON2 in the supernatant of the in vitro cell culture method as compared to the level of PON2 in a control supernatant. In certain embodiments, the level of PON2 in the supernatant of the culture is increased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of PON2 in a control supernatant. In certain embodiments, the level of PON2 in the supernatant of the culture is increased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of PON2 in a control supernatant.

In certain embodiments, the level of PON2 is determined according to an assay as described in Section 7.9 or Section 8.1. In certain embodiments, the level of PON2 is the nucleic acid level of PON2. In certain embodiments, the level of PON2 is the cDNA level of PON2. In certain embodiments, the level of PON2 is the mRNA level of PON2. In certain embodiments, the level of PON2 is the protein level of PON2.

In certain embodiments, the outcome parameter is an decrease in the level of RANTES in the EPC of the in vitro cell culture method as compared to the level of RANTES in a control EPC. In certain embodiments, the level of RANTES in the EPC of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of RANTES in a control EPC. In certain embodiments, the level of RANTES in the EPC of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of RANTES in a control EPC.

In certain embodiments, the outcome parameter is a decrease in the level of RANTES in the supernatant of the in vitro cell culture method as compared to the level of RANTES in a control supernatant. In certain embodiments, the level of RANTES in the supernatant of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of RANTES in a control supernatant. In certain embodiments, the level of RANTES in the supernatant of the culture is decreased by most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of RANTES in a control supernatant.

In certain embodiments, the level of RANTES is determined according to an assay as described in Section 7.9 or Section 8.1. In certain embodiments, the level of RANTES is the nucleic acid level of RANTES. In certain embodiments, the level of RANTES is the cDNA level of RANTES. In certain embodiments, the level of RANTES is the mRNA level of RANTES. In certain embodiments, the level of RANTES is the protein level of RANTES.

In certain embodiments, the outcome parameter is an decrease in the level of IP-10 in the EPC of the in vitro cell culture method as compared to the level of IP-10 in a control EPC. In certain embodiments, the level of IP-10 in the EPC of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IP-10 in a control EPC. In certain embodiments, the level of IP-10 in the EPC of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IP-10 in a control EPC.

In certain embodiments, the outcome parameter is a decrease in the level of IP-10 in the supernatant of the in vitro cell culture method as compared to the level of IP-10 in a control supernatant. In certain embodiments, the level of IP-10 in the supernatant of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IP-10 in a control supernatant. In certain embodiments, the level of IP-10 in the supernatant of the culture is decreased by most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IP-10 in a control supernatant.

In certain embodiments, the level of IP-10 is determined according to an assay as described in Section 7.9 or Section 8.1. In certain embodiments, the level of IP-10 is the nucleic acid level of IP-10. In certain embodiments, the level of IP-10 is the cDNA level of IP-10. In certain embodiments, the level of IP-10 is the mRNA level of IP-10. In certain embodiments, the level of IP-10 is the protein level of IP-10.

In certain embodiments, the outcome parameter is an decrease in the level of IL-1a in the EPC of the in vitro cell culture method as compared to the level of IL-1a in a control EPC. In certain embodiments, the level of IL-1a in the EPC of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-1a in a control EPC. In certain embodiments, the level of IL-1a in the EPC of the culture is decreased by most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-1a in a control EPC.

In certain embodiments, the outcome parameter is a decrease in the level of IL-1a in the supernatant of the in vitro cell culture method as compared to the level of IL-1a in a control supernatant. In certain embodiments, the level of IL-1a in the supernatant of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-1a in a control supernatant. In certain embodiments, the level of IL-1a in the supernatant of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-1a in a control supernatant.

In certain embodiments, the level of IL-1a is determined according to an assay as described in Section 7.9 or Section 8.1. In certain embodiments, the level of IL-1a is the nucleic acid level of IL-1a. In certain embodiments, the level of IL-1a is the cDNA level of IL-1a. In certain embodiments, the level of IL-1a is the mRNA level of IL-1a. In certain embodiments, the level of IL-1a is the protein level of IL-1a.

In certain embodiments, the outcome parameter is an decrease in the level of IL-1b in the EPC of the in vitro cell culture method as compared to the level of IL-1b in a control EPC. In certain embodiments, the level of IL-1b in the EPC of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-1b in a control EPC. In certain embodiments, the level of IL-1b in the EPC of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-1b in a control EPC.

In certain embodiments, the outcome parameter is a decrease in the level of IL-1b in the supernatant of the in vitro cell culture method as compared to the level of IL-1b in a control supernatant. In certain embodiments, the level of IL-1b in the supernatant of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-1b in a control supernatant. In certain embodiments, the level of IL-1b in the supernatant of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-1b in a control supernatant.

In certain embodiments, the level of IL-1b is determined according to an assay as described in Section 7.9 or Section 8.1. In certain embodiments, the level of IL-1b is the nucleic acid level of IL-1b. In certain embodiments, the level of IL-1b is the cDNA level of IL-1b. In certain embodiments, the level of IL-1b is the mRNA level of IL-1b. In certain embodiments, the level of IL-1b is the protein level of IL-1b.

In certain embodiments, the outcome parameter is an decrease in the level of MIF in the EPC of the in vitro cell culture method as compared to the level of MIF in a control EPC. In certain embodiments, the level of MIF in the EPC of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of MIF in a control EPC. In certain embodiments, the level of MIF in the EPC of the culture is decreased by at most 0.5-fold, 0.6-fold, 0.7-fold, 0.8-fold, 0.9-fold, 1.0-fold, 1.2-fold, 1.4-fold, 1.6-fold, 1.8- fold, 2.0-fold, 2.5-fold, 3.0-fold, 3.5-fold, 4.0-fold, or 5.0-fold as compared to the level of MIF in a control EPC.

In certain embodiments, the outcome parameter is a decrease in the level of MIF in the supernatant of the in vitro cell culture method as compared to the level of MIF in a control supernatant. In certain embodiments, the level of MIF in the supernatant of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of MIF in a control supernatant. In certain embodiments, the level of MIF in the supernatant of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of MIF in a control supernatant.

In certain embodiments, the level of MIF is determined according to an assay as described in Section 7.9 or Section 8.1. In certain embodiments, the level of MIF is the nucleic acid level of MIF. In certain embodiments, the level of MIF is the cDNA level of MIF. In certain embodiments, the level of MIF is the mRNA level of MIF. In certain embodiments, the level of MIF is the protein level of MIF.

In certain embodiments, the outcome parameter is an decrease in the level of G-CSF in the EPC of the in vitro cell culture method as compared to the level of G-CSF in a control EPC. In certain embodiments, the level of G-CSF in the EPC of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of G-CSF in a control EPC. In certain embodiments, the level of G-CSF in the EPC of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of G-CSF in a control EPC.

In certain embodiments, the outcome parameter is a decrease in the level of G-CSF in the supernatant of the in vitro cell culture method as compared to the level of G-CSF in a control supernatant. In certain embodiments, the level of G-CSF in the supernatant of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of G-CSF in a control supernatant. In certain embodiments, the level of G-CSF in the supernatant of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of G-CSF in a control supernatant.

In certain embodiments, the level of G-CSF is determined according to an assay as described in Section 7.9 or Section 8.1. In certain embodiments, the level of G-CSF is the nucleic acid level of G-CSF. In certain embodiments, the level of G-CSF is the cDNA level of G-CSF. In certain embodiments, the level of G-CSF is the mRNA level of G-CSF. In certain embodiments, the level of G-CSF is the protein level of G-CSF.

In certain embodiments, the outcome parameter is an decrease in the level of GMCSF in the EPC of the in vitro cell culture method as compared to the level of GMCSF in a control EPC. In certain embodiments, the level of GMCSF in the EPC of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GMCSF in a control EPC. In certain embodiments, the level of GMCSF in the EPC of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GMCSF in a control EPC.

In certain embodiments, the outcome parameter is a decrease in the level of GMCSF in the supernatant of the in vitro cell culture method as compared to the level of GMCSF in a control supernatant. In certain embodiments, the level of GMCSF in the supernatant of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GMCSF in a control supernatant. In certain embodiments, the level of GMCSF in the supernatant of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of GMCSF in a control supernatant.

In certain embodiments, the level of GMCSF is determined according to an assay as described in Section 7.9 or Section 8.1. In certain embodiments, the level of GMCSF is the nucleic acid level of GMCSF. In certain embodiments, the level of GMCSF is the cDNA level of GMCSF. In certain embodiments, the level of GMCSF is the mRNA level of GMCSF. In certain embodiments, the level of GMCSF is the protein level of GMCSF.

In certain embodiments, the outcome parameter is an decrease in the level of C5a in the EPC of the in vitro cell culture method as compared to the level of C5a in a control EPC. In certain embodiments, the level of C5a in the EPC of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of C5a in a control EPC. In certain embodiments, the level of C5a in the EPC of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of C5a in a control EPC.

In certain embodiments, the outcome parameter is a decrease in the level of C5a in the supernatant of the in vitro cell culture method as compared to the level of C5a in a control supernatant. In certain embodiments, the level of C5a in the supernatant of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of C5a in a control supernatant. In certain embodiments, the level of C5a in the supernatant of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of C5a in a control supernatant.

In certain embodiments, the level of C5a is determined according to an assay as described in Section 7.9 or Section 8.1. In certain embodiments, the level of C5a is the nucleic acid level of C5a. In certain embodiments, the level of C5a is the cDNA level of C5a. In certain embodiments, the level of C5a is the mRNA level of C5a. In certain embodiments, the level of C5a is the protein level of C5a.

In certain embodiments, the outcome parameter is an decrease in the level of IL-6 in the EPC of the in vitro cell culture method as compared to the level of IL-6 in a control EPC. In certain embodiments, the level of IL-6 in the EPC of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-6 in a control EPC. In certain embodiments, the level of IL-6 in the EPC of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-6 in a control EPC.

In certain embodiments, the outcome parameter is a decrease in the level of IL-6 in the supernatant of the in vitro cell culture method as compared to the level of IL-6 in a control supernatant. In certain embodiments, the level of IL-6 in the supernatant of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-6 in a control supernatant. In certain embodiments, the level of IL-6 in the supernatant of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of IL-6 in a control supernatant.

In certain embodiments, the level of IL-6 is determined according to an assay as described in Section 7.9 or Section 8.1. In certain embodiments, the level of IL-6 is the nucleic acid level of IL-6. In certain embodiments, the level of IL-6 is the cDNA level of IL-6. In certain embodiments, the level of IL-6 is the mRNA level of IL-6. In certain embodiments, the level of IL-6 is the protein level of IL-6.

In certain embodiments, the outcome parameter is an decrease in the level of HO-2 in the EPC of the in vitro cell culture method as compared to the level of HO-2 in a control EPC. In certain embodiments, the level of HO-2 in the EPC of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of HO-2 in a control EPC. In certain embodiments, the level of HO-2 in the EPC of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of HO-2 in a control EPC.

In certain embodiments, the outcome parameter is a decrease in the level of HO-2 in the supernatant of the in vitro cell culture method as compared to the level of HO-2 in a control supernatant. In certain embodiments, the level of HO-2 in the supernatant of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of HO-2 in a control supernatant. In certain embodiments, the level of HO-2 in the supernatant of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of HO-2 in a control supernatant.

In certain embodiments, the level of HO-2 is determined according to an assay as described in Section 7.9 or Section 8.1. In certain embodiments, the level of HO-2 is the nucleic acid level of HO-2. In certain embodiments, the level of HO-2 is the cDNA level of HO-2. In certain embodiments, the level of HO-2 is the mRNA level of HO-2. In certain embodiments, the level of HO-2 is the protein level of HO-2.

In certain embodiments, the outcome parameter is an decrease in the level of HIF-1A in the EPC of the in vitro cell culture method as compared to the level of HIF-1A in a control EPC. In certain embodiments, the level of HIF-1A in the EPC of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of HIF-1A in a control EPC. In certain embodiments, the level of HIF-1A in the EPC of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of HIF-1A in a control EPC.

In certain embodiments, the outcome parameter is a decrease in the level of HIF-1A in the supernatant of the in vitro cell culture method as compared to the level of HIF-1A in a control supernatant. In certain embodiments, the level of HIF-1A in the supernatant of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of HIF-1A in a control supernatant. In certain embodiments, the level of HIF-1A in the supernatant of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of HIF-1A in a control supernatant.

In certain embodiments, the level of HIF-1A is determined according to an assay as described in Section 7.9 or Section 8.1. In certain embodiments, the level of HIF-1A is the nucleic acid level of HIF-1A. In certain embodiments, the level of HIF-1A is the cDNA level of HIF-1A. In certain embodiments, the level of HIF-1A is the mRNA level of HIF-1A. In certain embodiments, the level of HIF-1A is the protein level of HIF-1A.

In certain embodiments, the outcome parameter is an decrease in the level of TRAIL R1 in the EPC of the in vitro cell culture method as compared to the level of TRAIL R1 in a control EPC. In certain embodiments, the level of TRAIL R1 in the EPC of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of TRAIL R1 in a control EPC. In certain embodiments, the level of TRAIL R1 in the EPC of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of TRAIL R1 in a control EPC.

In certain embodiments, the outcome parameter is a decrease in the level of TRAIL R1 in the supernatant of the in vitro cell culture method as compared to the level of TRAIL R1 in a control supernatant. In certain embodiments, the level of TRAIL R1 in the supernatant of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of TRAIL R1 in a control supernatant. In certain embodiments, the level of TRAIL R1 in the supernatant of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of TRAIL R1 in a control supernatant.

In certain embodiments, the level of TRAIL R1 is determined according to an assay as described in Section 7.9 or Section 8.1. In certain embodiments, the level of TRAIL R1 is the nucleic acid level of TRAIL R1. In certain embodiments, the level of TRAIL R1 is the cDNA level of TRAIL R1. In certain embodiments, the level of TRAIL R1 is the mRNA level of TRAIL R1. In certain embodiments, the level of TRAIL R1 is the protein level of TRAIL R1.

In certain embodiments, the outcome parameter is an decrease in the level of cleaved caspase-3 in the EPC of the in vitro cell culture method as compared to the level of cleaved caspase-3 in a control EPC. In certain embodiments, the level of cleaved caspase-3 in the EPC of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of cleaved caspase-3 in a control EPC. In certain embodiments, the level of cleaved caspase-3 in the EPC of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of cleaved caspase-3 in a control EPC.

In certain embodiments, the outcome parameter is a decrease in the level of cleaved caspase-3 in the supernatant of the in vitro cell culture method as compared to the level of cleaved caspase-3 in a control supernatant. In certain embodiments, the level of cleaved caspase-3 in the supernatant of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of cleaved caspase-3 in a control supernatant. In certain embodiments, the level of cleaved caspase-3 in the supernatant of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of cleaved caspase-3 in a control supernatant.

In certain embodiments, the level of cleaved caspase-3 is determined according to an assay as described in Section 7.9 or Section 8.1. In certain embodiments, the level of cleaved caspase-3 is the nucleic acid level of cleaved caspase-3. In certain embodiments, the level of cleaved caspase-3 is the cDNA level of cleaved caspase-3. In certain embodiments, the level of cleaved caspase-3 is the mRNA level of cleaved caspase-3. In certain embodiments, the level of cleaved caspase-3 is the protein level of cleaved caspase-3.

In certain embodiments, the outcome parameter is an decrease in the level of p27 in the EPC of the in vitro cell culture method as compared to the level of p27 in a control EPC. In certain embodiments, the level of p27 in the EPC of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of p27 in a control EPC. In certain embodiments, the level of p27 in the EPC of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of p27 in a control EPC.

In certain embodiments, the outcome parameter is a decrease in the level of p27 in the supernatant of the in vitro cell culture method as compared to the level of p27 in a control supernatant. In certain embodiments, the level of p27 in the supernatant of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of p27 in a control supernatant. In certain embodiments, the level of p27 in the supernatant of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of p27 in a control supernatant.

In certain embodiments, the level of p27 is determined according to an assay as described in Section 7.9 or Section 8.1. In certain embodiments, the level of p27 is the nucleic acid level of p27. In certain embodiments, the level of p27 is the cDNA level of p27. In certain embodiments, the level of p27 is the mRNA level of p27. In certain embodiments, the level of p27 is the protein level of p27.

In certain embodiments, the outcome parameter is an decrease in the level of p21 in the EPC of the in vitro cell culture method as compared to the level of p21 in a control EPC. In certain embodiments, the level of p21 in the EPC of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of p21 in a control EPC. In certain embodiments, the level of p21 in the EPC of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of p21 in a control EPC.

In certain embodiments, the outcome parameter is a decrease in the level of p21 in the supernatant of the in vitro cell culture method as compared to the level of p21 in a control supernatant. In certain embodiments, the level of p21 in the supernatant of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of p21 in a control supernatant. In certain embodiments, the level of p21 in the supernatant of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of p21 in a control supernatant.

In certain embodiments, the level of p21 is determined according to an assay as described in Section 7.9 or Section 8.1. In certain embodiments, the level of p21 is the nucleic acid level of p21. In certain embodiments, the level of p21 is the cDNA level of p21. In certain embodiments, the level of p21 is the mRNA level of p21. In certain embodiments, the level of p21 is the protein level of p21.

In certain embodiments, the outcome parameter is an decrease in the level of Bax in the EPC of the in vitro cell culture method as compared to the level of Bax in a control EPC. In certain embodiments, the level of Bax in the EPC of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of Bax in a control EPC. In certain embodiments, the level of Bax in the EPC of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of Bax in a control EPC.

In certain embodiments, the outcome parameter is a decrease in the level of Bax in the supernatant of the in vitro cell culture method as compared to the level of Bax in a control supernatant. In certain embodiments, the level of Bax in the supernatant of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of Bax in a control supernatant. In certain embodiments, the level of Bax in the supernatant of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of Bax in a control supernatant.

In certain embodiments, the level of Bax is determined according to an assay as described in Section 7.9 or Section 8.1. In certain embodiments, the level of Bax is the nucleic acid level of Bax. In certain embodiments, the level of Bax is the cDNA level of Bax. In certain embodiments, the level of Bax is the mRNA level of Bax. In certain embodiments, the level of Bax is the protein level of Bax.

In certain embodiments, the outcome parameter is an decrease in the level of Bad in the EPC of the in vitro cell culture method as compared to the level of Bad in a control EPC. In certain embodiments, the level of Bad in the EPC of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of Bad in a control EPC. In certain embodiments, the level of Bad in the EPC of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of Bad in a control EPC.

In certain embodiments, the outcome parameter is a decrease in the level of Bad in the supernatant of the in vitro cell culture method as compared to the level of Bad in a control supernatant. In certain embodiments, the level of Bad in the supernatant of the culture is decreased by at least 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of Bad in a control supernatant. In certain embodiments, the level of Bad in the supernatant of the culture is decreased by at most 0.5-fold, 0.6-fold, 0.7-fold, 0.8-fold, 0.9-fold, 1.0-fold, 1.2-fold, 1.4-fold, 1.6-fold, 1.8-fold, 2.0-fold, 2.5-fold, 3.0-fold, 3.5-fold, 4.0-fold, or 5.0-fold as compared to the level of Bad in a control supernatant.

In certain embodiments, the level of Bad is determined according to an assay as described in Section 7.9 or Section 8.1. In certain embodiments, the level of Bad is the nucleic acid level of Bad. In certain embodiments, the level of Bad is the cDNA level of Bad. In certain embodiments, the level of Bad is the mRNA level of Bad. In certain embodiments, the level of Bad is the protein level of Bad.

In certain embodiments, the control EPC is an EPC cultured in the absence of an ActRII signaling inhibitor, wherein the EPC has been obtained from the subject. In certain embodiments, the control EPC is cultured in the presence of an ActRII signaling inhibitor, wherein the EPC has been obtained from a reference population. In certain embodiments, the control EPC is an EPC cultured in conditioned media for a period of time, wherein the EPC has been obtained from the subject, wherein the conditioned media has been obtained from a stromal cell cultured in the absence of an ActRII signaling inhibitor, and wherein the stromal cell has been obtained from a reference population. In certain embodiments, the control EPC is an EPC cultured in conditioned media for a period of time, wherein the EPC has been obtained from a reference population, wherein the conditioned media has been obtained from a stromal cell cultured in the presence of an ActRII signaling inhibitor, and wherein the stromal cell has been obtained from a reference population. In certain embodiments, the control EPC is an EPC co-cultured with a stromal cell in the absence of an ActRII signaling inhibitor for a period of time, wherein the control EPC has been obtained from the subject. In certain embodiments, the control EPC is an EPC co-cultured with a stromal cell in the presence of an ActRII signaling inhibitor for a period of time, wherein the control EPC has been obtained from a reference population.

In certain embodiments, the control supernatant is supernatant obtained from culturing a stromal cell in the absence of an ActRII signaling inhibitor for a period of time, wherein the stromal cell has been obtained from the subject. In certain embodiments, the control supernatant is supernatant obtained from culturing a stromal cell in the presence of an ActRII signaling inhibitor for a period of time, wherein the stromal cell has been obtained from a reference population. In certain embodiments, the control supernatant is supernatant obtained from culturing an EPC in conditioned media for a period of time, wherein the EPC has been obtained from the subject, wherein the conditioned media has been obtained from a stromal cell cultured in the absence of an ActRII signaling inhibitor, and wherein the stromal cell has been obtained from the subject. In certain embodiments, the control supernatant is supernatant obtained from culturing an EPC in conditioned media for a period of time, wherein the EPC has been obtained from the subject, wherein the conditioned media has been obtained from a stromal cell cultured in the presence of an ActRII signaling inhibitor, and wherein the stromal cell has been obtained from a reference population.

7.5 Patient Population

The subjects treated in accordance with the methods described herein can be any mammals such as rodents and primates, and in a preferred embodiment, humans. In certain embodiments, the methods described herein can be used to treat beta-thalassemia in a subject, such as, transfusion-dependent beta-thalassemia, non-transfusion-dependent beta-thalassemia, beta-thalassemia major, and beta-thalassemia intermediate, to reduce transfusion burden in a subject with beta-thalassemia, or to monitor said treatment, and/or to select subjects to be treated in accordance with the methods provided herein, in any mammal such as a rodent or primate, and in a preferred embodiment, in a human subject. As used herein, "patient" and "subject" are used interchangeably.

In certain embodiments, the subject treated in accordance with the methods described here can be of any age. In certain embodiments, the subject treated in accordance with the methods described herein is less than 18 years old. In a specific embodiment, the subject treated in accordance with the methods described herein is less than 13 years old. In another specific embodiment, the subject treated in accordance with the methods described herein is less than 12, less than 11, less than 10, less than 9, less than 8, less than 7, less than 6, or less than 5 years old. In another specific embodiment, the subject treated in accordance with the methods described herein is 1-3 years old, 3-5 years old, 5-7 years old, 7-9 years old, 9-11 years old, 11-13 years old, 13-15 years old, 15-20 years old, 20-25 years old, 25-30 years old, or greater than 30 years old. In another specific embodiment, the subject treated in accordance with the methods described herein is 30-35 years old, 35-40 years old, 40-45 years old, 45-50 years old, 50-55 years old, 55-60 years old, or greater than 60 years old. In another specific embodiment, the subject treated in accordance with the methods described herein is 60-65 years old, 65-70 years old, 70-75 years old, 75-80 years old, or greater than 80 years old.

In certain embodiments, the subject treated in accordance with the methods described herein (see Section 7.3) has beta-thalassemia. In certain embodiments, the beta-thalassemia is transfusion-dependent beta-thalassemia. Transfusion-dependent beta-thalassemia is also known as "Cooley's anemia". In certain embodiments, the beta-thalassemia is beta-thalassemia major. In certain embodiments, the transfusion-dependent beta-thalassemia is beta-thalassemia major. In certain embodiments, the beta-thalassemia is non-transfusion-dependent beta-thalassemia. In certain embodiments, the beta-thalassemia is beta-thalassemia intermediate. In certain embodiments, the transfusion-dependent beta-thalassemia is non-beta-thalassemia intermediate. In certain embodiments, the subject has HbE/beta thalassemia. In certain embodiments, the subject (i) has beta-thalassemia major; (ii) has severe HbE/beta-thalassemia; and (iii) is transfusion-dependent. In certain embodiments, the subject (i) has beta-thalassemia intermedia; (ii) has mild/moderate HbE/beta-thalassemia; and (iii) is non-transfusion-dependent.

In certain embodiments, the subject treated in accordance with the methods described herein (see Section 7.3), has transfusion-dependent beta-thalassemia. In certain embodiments, the subject has been diagnosed with transfusion-dependent beta-thalassemia. In certain embodiments, the subject has been diagnosed with beta-thalassemia and hemoglobin E. In certain embodiments, the diagnosis has been confirmed by genetic analysis. In certain embodiments, the transfusion-dependent beta-thalassemia is beta-thalassemia major. In certain embodiments, the transfusion-dependent beta-thalassemia is beta-thalassemia major. In certain embodiments, the subject comprises a genotype comprising homozygosity or compound heterozygosity for a mutant beta globin allele. In certain embodiments, the homozygosity comprises $\beta^0/\beta^0$, wherein $\beta^0$ refers to an allele associated with lack of beta globin chain synthesis. In certain embodiments, the homozygosity comprises $\beta^+/\beta^+$, wherein $\beta^+$ refers to an allele associated with reduced beta globin chain synthesis. In certain embodiments, the compound heterozygosity comprises $\beta^0/\beta^+$, wherein $\beta^0$ refers to an allele associated with lack of beta globin chain synthesis, and wherein $\beta^-$ refers to an allele associated with reduced beta globin chain synthesis. In certain embodiments, the compound heterozygosity comprises $\beta^0$/HbE, wherein $\beta^0$ refers to an allele associated with lack of beta globin chain synthesis, and wherein HbE refers to hemoglobin E. In certain embodiments, the compound heterozygosity comprises $\beta^+$/HbE, wherein $\beta^+$ refers to an allele associated with reduced beta globin chain synthesis, and wherein HbE refers to hemoglobin E. In certain embodiments, the subject has symptomatic thalassemia. In certain embodiments, the subject has co-inherited duplication of the alpha-globin gene. In certain embodiments, the subject has been diagnosed with transfusion-dependent beta-thalassemia. In certain embodiments, the diagnosis has been confirmed by genetic analysis. In certain embodiments, the subject is a human infant subject. In certain embodiments, the subject has hereditary persistence of fetal hemoglobin.

In certain embodiments, the subject requires regular, lifelong red blood cell transfusions. In certain embodiments, the subject has a high transfusion burden. In certain embodiments, high transfusion burden is 12 or more red blood cell units over 24 weeks prior to treatment according to the methods provided herein. In certain embodiments, the subject has a low transfusion burden. In certain embodiments, low transfusion burden is 7-12 red blood cell units over 24 weeks prior to treatment according to the methods provided herein.

In certain embodiments, the subject has one or more transfusion-dependent beta-thalassemia clinical complications. Non-limiting examples of transfusion-dependent beta-thalassemia clinical complications include growth retardation, pallor, jaundice, poor musculature, genu valgum, hepatosplenomegaly, leg ulcers, development of masses from extramedullary hematopoiesis, and skeletal changes resulting from expansion of the bone marrow. In certain embodiments, the subject has one or more complications of chronic red blood cell transfusions. Non-limiting examples of complications of chronic red blood cell transfusions include transfusion-associated infections, such as, for example, hepatitis B virus infection, hepatitis C virus infection, and human immunodeficiency virus infection, alloimmunization, and organ damage due to iron overload, such as, for example, liver damage, heart damage, and endocrine gland damage.

In certain embodiments, the subject treated in accordance with the methods described herein (see Section 7.3), has non-transfusion-dependent beta-thalassemia. In certain embodiments, the subject has been diagnosed with beta-thalassemia. In certain embodiments, the subject has been diagnosed with beta-thalassemia and hemoglobin E. In certain embodiments, the beta-thalassemia has been confirmed by genetic analysis. In certain embodiments, the non-transfusion-dependent beta-thalassemia is beta-thalassemia intermedia. In certain embodiments, the non-transfusion-dependent beta thalassemia is mild-moderate hemoglobin E/beta-thalassemia. In certain embodiments, the non-transfusion-dependent beta-thalassemia does not require regular red blood cell transfusion. In certain embodiments, the subject seldom requires red blood cell transfusions. In certain embodiments, the non-transfusion-dependent beta-thalassemia requires regular red blood cell transfusion later in life. In certain embodiments, the subject has received 0 to 6 red blood cell units during the 24-week period prior to treatment according to the methods provided herein. In certain embodiments, the subject has a mean baseline hemoglobin level of less than 10.0 g/dL.

In certain embodiments, the beta-thalassemia is non-transfusion-dependent beta-thalassemia. In certain embodiments, the beta-thalassemia is beta-thalassemia intermediate. In certain embodiments, the transfusion-dependent beta-thalassemia is non-beta-thalassemia intermediate. In certain embodiments, the subject comprises a genotype comprising compound heterozygosity. In certain embodiments, the compound heterozygosity comprises a $\beta^0$ allele, wherein $\beta^0$ refers to an allele associated with lack of beta globin chain synthesis. In certain embodiments, the compound heterozygosity comprises a $\beta^+$ allele, wherein $\beta^+$ refers to an allele associated with reduced beta globin chain synthesis. In certain embodiments, the compound heterozygosity comprises $\beta^0/\beta^+$, wherein $\beta^0$ refers to an allele associated with lack of beta globin chain synthesis, and wherein $\beta^-$ refers to an allele associated with reduced beta globin chain synthesis. In certain embodiments, the compound heterozygosity comprises one or more hemoglobin variants. In certain embodiments, the hemoglobin variant is hemoglobin E. In certain embodiments, the subject (i) comprises a genotype comprising coinheritance of two severe beta globin chain mutations, and (ii) has alpha-thalassemia. In certain embodiments, the subject (i) comprises a genotype comprising coinheritance of two severe beta globin chain mutations, and (ii) has hereditary persistence of fetal hemoglobin. In certain embodiments, the subject has symptomatic thalassemia. In certain embodiments, the subject has co-inherited duplication of the alpha-globin gene. In certain embodiments, the subject has been diagnosed with beta-thalassemia. In certain embodiments, the diagnosis has been confirmed by genetic analysis.

In certain embodiments, the subject displays one or more non-transfusion-dependent beta-thalassemia clinical complications. Non-limiting examples of non-transfusion-dependent beta-thalassemia clinical complications include endocrine abnormalities, such as, for example, diabetes mellitus, hypothyroidism, hypogonadism, thrombotic events, pulmonary hypertension, hypercoagulability, the development of transfusion-dependency later in life, ineffective erythropoiesis, expansion of the hematopoietic tissue outside of the marrow medulla, formation of extramedullary hematopoiesis masses, skeletal deformities, osteopenia, osteoporosis, bone pain, gallstones, and leg ulcers. In certain embodiments, the subject exhibits alloimmunization.

In certain embodiments, the subject displays mild symptoms beta-thalassemia symptoms. In certain embodiments, the subject has near normal growth.

In certain embodiments, the non-transfusion-dependent beta-thalassemic subject displays severe symptoms. Non-limiting examples of severe symptoms include growth retardation, development retardation, and skeletal deformities.

In certain embodiments, the subject has splenomegaly. In certain embodiments, the splenomegaly develops in the first 6-12 months of the subject's life.

In certain embodiments, the subject has impaired growth during the first 10 years of the subject's life.

In certain embodiments, the subject exhibits microcytic, hypochromic anemia. In certain embodiments, the hemoglobin A2 levels in the subject prior to treatment of the subject according to the methods provided herein are elevated as compared to the hemoglobin A2 levels in a reference population (e.g., a reference population as described in Section 7.9). In certain embodiments, the fetal hemoglobin levels in the subject prior to treatment of the subject according to the methods provided herein is elevated as compared to the fetal hemoglobin levels in a reference population (e.g., a reference population as described in Section 7.9).

In certain embodiments, the subject does not express hemoglobin S.

In certain embodiments, the subject does not express hemoglobin S. In certain embodiments, the subject has not received red blood cell transfusions within 12 weeks prior to treatment according to the methods provided herein, wherein the subject has non-transfusion-dependent beta-thalassemia. In certain embodiments, the subject does not have active hepatitis C infection. In certain embodiments, the subject does not have active hepatitis B infection. In certain embodiments, the subject is not positive for human immunodeficiency virus. In certain embodiments, the subject does not have insulin-dependent diabetes. In certain embodiments, the subject has not been administered an erythropoiesis stimulating agent within 3 months prior to treatment according to the methods provided herein. In certain embodiments, the subject has not undergone iron chelation therapy within 168 days prior to treatment according to the methods provided herein. In certain embodiments, the subject has not undergone hydroxyurea treatment within 168 days prior to treatment according to the methods provided herein. In certain embodiments, the subject has not been administered biphosphonates within the 168 days prior to treatment according to the methods provided herein. In certain embodiments, the subject does not have uncontrolled hypertension. Uncontrolled hypertension refers to >Grade 1 according to NCI CTCAE version 4.0. In certain embodiments, the subject does not have liver disease with ALT greater than 3 times the upper limit of normal. In certain embodiments, the subject does not have liver disease with histopathological evidence of liver cirrhosis/fibrosis as determined by liver biopsy. In certain embodiments, the subject does not have heart disease. Heart disease or heart failure can be classified by the New York Heart Association as classification 3 or higher. In certain embodiments, the subject does not have arrhythmia requiring treatment. In certain embodiments, the subject does not have lung disease. Non-limiting examples of lung disease include pulmonary fibrosis and pulmonary hypertension. In certain embodiments the subject does not have a creatinine clearance rate of less than 60 mL/min as determined by the Cockroff-Gault method. In certain embodiments, the subject does not have folate deficiency. In certain embodiments, the subject does not have proteinuria of Grade 3 or higher. In certain embodiments, the subject does not have adrenal insufficiency. In certain embodiments, the subject has not undergone a major surgery within 30 days prior to treatment according to the methods provided herein, except for wherein the major surgery is splenectomy. In certain embodiments, the subject does not have a history of severe allergic or anaphylactic reactions or hypersensitivity to recombinant proteins. In certain embodiments, the subject has not undergone long-term anticoagulant therapy. Nonlimiting examples of anticoagulant therapy includes heparin and warfarin. In certain embodiments, the subject is not undergoing treatment with cytotoxic agents, systemic corticosteroids, immunosuppressants, or anticoagulant therapy within 28 days prior to treatment according to the methods provided herein.

In certain embodiments, the subject is undergoing other treatment interventions. Non-limiting examples of other treatment interventions include splenectomy, transfusion therapy, iron chelation therapy, and fetal hemoglobin-inducing agents. In certain embodiments, the subject requires iron chelation therapy. See Section 7.3.1 for a description of combination therapies.

7.6 Dosing Regimens

In certain embodiments, the ActRII signaling inhibitor administered to a subject according to the methods provided herein (see Section 7.3) is ActRIIA-hFc (SEQ ID NO:7). In certain embodiments, the dose of ActRIIA-hFc (SEQ ID NO:7) is about 0.1 mg/kg, about 0.3 mg/kg, about 0.5 mg/kg, about 0.75 mg/kg, about 1.0 mg/kg, or about 1.5 mg/kg. In certain embodiments, the dose of ActRIIA-hFc (SEQ ID NO:7) is about 0.1 mg/kg. In certain embodiments, the dose of ActRIIA-hFc (SEQ ID NO:7) is about 0.3 mg/kg. In certain embodiments, the dose of ActRIIA-hFc (SEQ ID NO:7) is about 0.5 mg/kg. In certain embodiments, the dose of ActRIIA-hFc (SEQ ID NO:7) is about 0.75 mg/kg. In certain embodiments, the dose of ActRIIA-hFc (SEQ ID NO:7) is about 1.0 mg/kg. In certain embodiments, the dose of ActRIIA-hFc (SEQ ID NO:7) is about 1.5 mg/kg.

In certain embodiments, the ActRII signaling inhibitor administered to a subject according to the methods provided herein (see Section 7.3) is ActRIIB-hFc (SEQ ID NO:25). In certain embodiments, the dose of ActRIIB-hFc (SEQ ID NO:25) is about 0.3 mg/kg, about 0.45 mg/kg, about 0.6 mg/kg, about 0.8 mg/kg, about 1.0 mg/kg, or about 1.25 mg/kg. In certain embodiments, the dose of ActRIIB-hFc (SEQ ID NO:25) is about 0.3 mg/kg. In certain embodiments, the dose of ActRIIB-hFc (SEQ ID NO:25) is about 0.45 mg/kg. In certain embodiments, the dose of ActRIIB-hFc (SEQ ID NO:25) is about 0.6 mg/kg. In certain embodiments, the dose of ActRIIB-hFc (SEQ ID NO:25) is about 0.8 mg/kg. In certain embodiments, the dose of ActRIIB-hFc (SEQ ID NO:25) is about 1.0 mg/kg. In certain embodiments, the dose of ActRIIB-hFc (SEQ ID NO:25) is about 1.25 mg/kg.

In certain embodiments, the dose of ActRIIA-hFc (SEQ ID NO:7) is an initial dose. In certain embodiments, the initial dose of ActRIIA-hFc (SEQ ID NO:7) is about 0.1 mg/kg, about 0.3 mg/kg, about 0.5 mg/kg, about 0.75 mg/kg, about 1.0 mg/kg, or about 1.5 mg/kg. In certain embodiments, the initial dose of ActRIIA-hFc (SEQ ID NO:7) is about 0.1 mg/kg. In certain embodiments, the initial dose of ActRIIA-hFc (SEQ ID NO:7) is about 0.3 mg/kg. In certain embodiments, the initial dose of ActRIIA-hFc (SEQ ID NO:7) is about 0.5 mg/kg. In certain embodiments, the initial dose of ActRIIA-hFc (SEQ ID NO:7) is about 0.75 mg/kg. In certain embodiments, the initial dose of ActRIIA-hFc (SEQ ID NO:7) is about 1.0 mg/kg. In certain embodiments, the initial dose of ActRIIA-hFc (SEQ ID NO:7) is about 1.5 mg/kg.

In certain embodiments, the dose of ActRIIB-hFc (SEQ ID NO:25) is an initial dose. In certain embodiments, the initial dose of ActRIIB-hFc (SEQ ID NO:25) is about 0.3 mg/kg, about 0.45 mg/kg, about 0.6 mg/kg, about 0.8 mg/kg, about 1.0 mg/kg, or about 1.25 mg/kg. In certain embodiments, the initial dose of ActRIIB-hFc (SEQ ID NO:25) is about 0.3 mg/kg. In certain embodiments, the initial dose of ActRIIB-hFc (SEQ ID NO:25) is about 0.45 mg/kg. In certain embodiments, the initial dose of ActRIIB-hFc (SEQ ID NO:25) is about 0.6 mg/kg. In certain embodiments, the initial dose of ActRIIB-hFc (SEQ ID NO:25) is about 0.8 mg/kg. In certain embodiments, the initial dose of ActRIIB-hFc (SEQ ID NO:25) is about 1.0 mg/kg. In certain embodiments, the initial dose of ActRIIB-hFc (SEQ ID NO:25) is about 1.25 mg/kg.

In certain embodiments, the dose of ActRIIA-hFc (SEQ ID NO:7) is a subsequent dose. In certain embodiments, the subsequent dose of ActRIIA-hFc (SEQ ID NO:7) is determined according to the methods provided in Section 7.3. In certain embodiments, the subsequent dose of ActRIIA-hFc (SEQ ID NO:7) is about 0.1 mg/kg, about 0.3 mg/kg, about 0.5 mg/kg, about 0.75 mg/kg, about 1.0 mg/kg, or about 1.5 mg/kg. In certain embodiments, the subsequent dose of ActRIIA-hFc (SEQ ID NO:7) is about 0.1 mg/kg. In certain embodiments, the subsequent dose of ActRIIA-hFc (SEQ ID NO:7) is about 0.3 mg/kg. In certain embodiments, the subsequent dose of ActRIIA-hFc (SEQ ID NO:7) is about 0.5 mg/kg. In certain embodiments, the subsequent dose of ActRIIA-hFc (SEQ ID NO:7) is about 0.75 mg/kg. In certain embodiments, the subsequent dose of ActRIIA-hFc (SEQ ID NO:7) is about 1.0 mg/kg. In certain embodiments, the subsequent dose of ActRIIA-hFc (SEQ ID NO:7) is about 1.5 mg/kg.

In certain embodiments, the dose of ActRIIB-hFc (SEQ ID NO:25) is a subsequent dose. In certain embodiments, the subsequent dose of ActRIIB-hFc (SEQ ID NO:25) is determined according to the methods provided in Section 7.3. In certain embodiments, the subsequent dose of ActRIIB-hFc (SEQ ID NO:25) is about 0.3 mg/kg, about 0.45 mg/kg, about 0.6 mg/kg, about 0.8 mg/kg, about 1.0 mg/kg, or about 1.25 mg/kg. In certain embodiments, the subsequent dose of ActRIIB-hFc (SEQ ID NO:25) is about 0.3 mg/kg. In certain embodiments, the subsequent dose of ActRIIB-hFc (SEQ ID NO:25) is about 0.45 mg/kg. In certain embodiments, the subsequent dose of ActRIIB-hFc (SEQ ID NO:25) is about 0.6 mg/kg. In certain embodiments, the subsequent dose of ActRIIB-hFc (SEQ ID NO:25) is about 0.8 mg/kg. In certain embodiments, the subsequent dose of ActRIIB-hFc (SEQ ID NO:25) is about 1.0 mg/kg. In certain embodiments, the subsequent dose of ActRIIB-hFc (SEQ ID NO:25) is about 1.25 mg/kg.

In certain embodiments, the subsequent dose is about 2.5 mg, about 5 mg, about 10 mg, about 15 mg, about 20 mg, or about 35 mg greater than the initial dose, or about 0.05 mg/kg, about 0.1 mg/kg, about 0.15 mg/kg, about 0.25 mg/kg, about 0.3 mg/kg, about 0.35 mg/kg, about 0.4 mg/kg, or about 0.5 mg/kg greater than the initial dose.

In certain embodiments, the subsequent dose is administered more frequently than the initial dose. In certain embodiments, the subsequent dose is administered less frequently than the initial dose. In certain embodiments, the subsequent dose is administered at the same frequency as the initial dose. In certain embodiments, the subsequent dose is administered every 14, 15, 16, 17, 18, 19, 20, 21, 22, 23, 24, 25, 26, 27, or 28 days. In certain embodiments, the subsequent dose is administered every 21 days. In certain embodiments, the subsequent dose is administered continuously and/or indefinitely.

In certain embodiments, the dose of the ActRII signaling inhibitor (e.g., ActRIIA-hFc (SEQ ID NO:7) or ActRIIB-hFc (SEQ ID NO:25)) is dosed at intervals and amounts sufficient to achieve serum concentrations of about 0.2 microgram/kg or greater, and serum levels of about 1 microgram/kg or 2 microgram/kg or greater are desirable for achieving significant effects on bone density and strength. Dosing regimens may be designed to reach serum concentrations of between 0.2 and 15 microgram/kg, and optionally between 1 and 5 microgram/kg. In humans, serum levels of 0.2 microgram/kg may be achieved with a single dose of about 0.1 mg/kg or greater and serum levels of 1 microgram/kg may be achieved with a single dose of about 0.3 mg/kg or greater. The observed serum half-life of the molecule is between about 20 and 30 days, substantially longer than most Fc fusion proteins, and thus a sustained effective serum level may be achieved, for example, by dosing with about 0.2-0.4 mg/kg on a weekly or biweekly basis, or higher doses may be used with longer intervals between dosings. For example, doses of about 1-3 mg/kg might be used on a monthly or bimonthly basis, and the effect on bone may be sufficiently durable that dosing is necessary only once every 3, 4, 5, 6, 9, 12 or more months. Serum levels of the ActRII signaling inhibitor can be measured by any means known to the skilled artisan. For example, antibodies against the ActRII signaling inhibitor can be used to determine the serum levels of the ActRII signaling inhibitor using, e.g., an ELISA.

In certain embodiments, the ActRII signaling inhibitor (e.g., ActRIIA-hFc (SEQ ID NO:7) or ActRIIB-hFc (SEQ ID NO:25)) is administered to the subject subcutaneously. In certain embodiments, the ActRII signaling inhibitor (e.g., ActRIIA-hFc (SEQ ID NO:7) or ActRIIB-hFc (SEQ ID NO:25)) is administered to the subject subcutaneously in the upper arm, abdomen, or thigh of the subject. In certain embodiments, the ActRII signaling inhibitor (e.g., ActRIIA-hFc (SEQ ID NO:7) or ActRIIB-hFc (SEQ ID NO:25)) is administered to the subject every 21 days. In certain embodiments, the ActRII signaling inhibitor (e.g., ActRIIA-hFc (SEQ ID NO:7) or ActRIIB-hFc (SEQ ID NO:25)) is administered to the subject every 14, 15, 16, 17, 18, 19, 20, 21, 22, 23, 24, 25, 26, 27, or 28 days. In certain embodiments, the ActRII signaling inhibitor (e.g., ActRIIA-hFc (SEQ ID NO:7) or ActRIIB-hFc (SEQ ID NO:25)) is administered to the subject every 21 days, subcutaneously in the upper arm, abdomen, or thigh of the subject. In certain embodiments, the ActRII signaling inhibitor (e.g., ActRIIA-hFc (SEQ ID NO:7) or ActRIIB-hFc (SEQ ID NO:25)) is administered to the subject every 14, 15, 16, 17, 18, 19, 20, 21, 22, 23, 24, 25, 26, 27, or 28 days, subcutaneously in the upper arm, abdomen, or thigh of the subject.

In certain embodiments, the ActRII signaling inhibitor (e.g., ActRIIA-hFc (SEQ ID NO:7) or ActRIIB-hFc (SEQ ID NO:25)) is part of a composition as described in Section 7.7. In certain embodiments, the ActRII signaling inhibitor (e.g., ActRIIA-hFc (SEQ ID NO:7) or ActRIIB-hFc (SEQ ID NO:25)) is a sterile, preservative-free, lyophilized powder reconstituted in water for injection. In certain embodiments, a single dose of the ActRII signaling inhibitor (e.g., ActRIIA-hFc (SEQ ID NO:7) or ActRIIB-hFc (SEQ ID NO:25)) is reconstituted in a volume of water for injection of greater than 1 mL. In such embodiments, the single dose of the ActRII signaling inhibitor (e.g., ActRIIA-hFc (SEQ ID NO:7) or ActRIIB-hFc (SEQ ID NO:25)) is administered to the subject via two injections of equal volume of reconstituted ActRII signaling inhibitor (e.g., ActRIIA-hFc (SEQ ID NO:7) or ActRIIB-hFc (SEQ ID NO:25)). In certain embodiments, the two injections are administered to the subject at separate sites, e.g., one injection in the right thigh and one injection in the left thigh.

7.7 Pharmaceutical Compositions

In certain embodiments, ActRII signaling inhibitors (e.g., ActRII polypeptides) are formulated with a pharmaceutically acceptable carrier for use with the methods described herein. For example, an ActRII polypeptide can be administered to a subject or utilized in an in vitro cell culture assay alone or as a component of a pharmaceutical formulation (therapeutic composition). The subject compounds may be formulated for administration in any convenient way for use in human or veterinary medicine or for use in an in vitro cell culture method described herein. ActRII can be ActRIIA or ActRIIB In a preferred embodiment, the ActRII signaling inhibitor is formulated for subcutaneous administration.

In another preferred embodiment, the ActRII signaling inhibitor is packaged in a container as a sterile, preservative-free lyophilized powder or cake. In certain embodiments, the container comprises 25 mg of the ActRII signaling inhibitor. In certain embodiments, the container comprising 25 mg of the ActRII signaling inhibitor comprises a total of 37.5 mg of protein. In certain embodiments, ActRII signaling inhibitor in the container comprising 25 mg of the ActRII signaling inhibitor is reconstituted with 0.68 mL of water for injection. In certain embodiments, the container comprises 75 mg of the ActRII signaling inhibitor. In certain embodiments, the container comprising 75 mg of the ActRII signaling inhibitor comprises a total of 87.5 mg of protein. In certain embodiments, ActRII signaling inhibitor in the container comprising 75 mg of the ActRII signaling inhibitor is reconstituted with 1.6 mL of water for injection. In certain embodiments, the ActRII signaling inhibitor in the container is reconstituted with a volume of water for injection, such that the final concentration of the reconstituted ActRII signaling inhibitor in the water for injection is 50 mg/mL with a pH of approximately 6.5. In certain embodiments, the container is stored at between 2° C. and 8° C. In certain embodiments, the container is a 3 mL glass vial with a gray butyl coated stopper.

In certain embodiments, the therapeutic methods provided herein include administering the composition (comprising an ActRII signaling inhibitor) systemically, or locally as an implant or device. When administered, the therapeutic composition for uses provided herein is in a pyrogen-free, physiologically acceptable form. Therapeutically useful agents other than the ActRII signaling inhibitors which may also optionally be included in the composition as described above, may be administered simultaneously or sequentially with the subject compounds (e.g., ActRII polypeptides, such as ActRIIA and/or ActRIIB polypeptides (see, Section 7.8)).

Typically, ActRII signaling inhibitors will be administered parenterally. In a preferred embodiment, the ActRII signaling inhibitor will be administered subcutaneously. Pharmaceutical compositions suitable for parenteral administration may comprise one or more ActRII polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions for use in the methods described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions described herein may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the compounds described herein (e.g., ActRII polypeptides, such as ActRIIA and/or ActRIIB polypeptides (see, Section 7.8)).

In certain embodiments, the ActRII signaling inhibitor is substantially pure in a pharmaceutical composition. Specifically, at most 20%, 10%, 5%, 2.5%, 1%, 0.1%, or at most 0.05% of the compounds in the pharmaceutical composition are compounds other than the ActRII signaling inhibitor and the pharmaceutical acceptable carrier.

7.8 Inhibitors of ActRII Signaling

The ActRII signaling inhibitors described in this Section and known in the art can be used in the methods provided herein. In certain embodiments, the ActRII signaling inhibitors described in this Section can be used in the methods provided herein (see, Section 7.3 and Section 7.4). In certain embodiments, the ActRII signaling inhibitor for use with the present methods comprises an amino acid sequence of SEQ ID NO:7 (i.e., ActRIIA-hFc). In certain embodiments, the ActRII signaling inhibitor for use with the present methods comprises an amino acid sequence of SEQ ID NO:25 (i.e., ActRIIB-hFc).

Inhibitors of ActRII signaling receptors encompassed herein include ActRIIA signaling inhibitors and ActRIIB signaling inhibitors (see below). In certain embodiments, an ActRII signaling inhibitor is specific to ActRIIA signaling. In other embodiments, an ActRII signaling inhibitor is specific to ActRIIB signaling. In certain embodiments, an ActRII signaling inhibitor preferentially inhibits ActRIIA signaling. In other embodiments, an ActRII signaling inhibitor preferentially inhibits ActRIIB signaling. In certain embodiments, an ActRII signaling inhibitor inhibits both ActRIIA signaling and ActRIIB signaling.

In certain embodiments, inhibitors of ActRII signaling can be polypeptides comprising activin-binding domains of ActRII. Without being bound by theory, such activin-binding domain comprising polypeptides sequester activin and thereby prevent activin signaling. These activin-binding domain comprising polypeptides may comprise all or a portion of the extracellular domain of an ActRII (i.e., all or a portion of the extracellular domain of ActRIIA or all or a portion of the extracellular domain of ActRIIB) In specific embodiments, the extracellular domain of an ActRII is soluble.

In certain embodiments, the activin-binding domain comprising polypeptides are linked to an Fc portion of an antibody (i.e., a conjugate comprising an activin-binding domain comprising polypeptide of an ActRII receptor and an Fc portion of an antibody is generated). Without being bound by theory, the antibody portion confers increased stability on the conjugate. In certain embodiments, the activin-binding domain is linked to an Fc portion of an antibody via a linker, e.g., a peptide linker.

The inhibitors of ActRII signaling used in the compositions and methods described herein comprise molecules that inhibit ActRIIA signaling and/or ActRIIB signaling, directly or indirectly, either extracellularly or intracellularly. In some embodiments, the inhibitors of ActRIIA signaling and/or ActRIIB signaling used in the compositions and methods described herein inhibit ActRIIA signaling and/or ActRIIB signaling via interactions with the receptor(s) itself. In other embodiments, the inhibitors of ActRIIA signaling and/or ActRIIB signaling used in the compositions and methods described herein inhibit ActRIIA signaling and/or ActRIIB signaling via interactions with an ActRIIA and/or ActRIIB ligand, e.g., Activin.

In certain embodiments, an ActRII signaling inhibitor for use with the present methods are as described in Section 5.5 of International Publication No. WO 2014/066486, which is incorporated by herein in its entirety. In certain embodiments, such ActRII signaling inhibitors cab be generated and modified as previously described in Section 5.5.1 of International Publication No. WO 2014/066486, which is incorporated by herein in its entirety. In certain embodiments, such ActRII signaling inhibitors cab be generated and modified as previously described in Section 5.5.2 of International Publication No. WO 2014/066486, which is incorporated by herein in its entirety. In certain embodiments, such ActRII signaling inhibitors cab be generated and modified as previously described in Section 5.5.3 of International Publication No. WO 2014/066486, which is incorporated by herein in its entirety.

7.8.1 Inhibitors of ActRIIA Signaling

As used herein, the term "ActRIIA" refers to a family of activin receptor type IIA (ActRIIA) proteins from any species and variants derived from such ActRIIA proteins by mutagenesis or other modification. Reference to ActRIIA herein is understood to be a reference to any one of the currently identified forms. Members of the ActRIIA family are generally transmembrane proteins, composed of a ligand-binding extracellular domain with a cysteine-rich region, a transmembrane domain, and a cytoplasmic domain with predicted serine/threonine kinase activity.

ActRIIA signaling inhibitors to be used in the compositions and methods described herein include, without limitation, activin-binding soluble ActRIIA polypeptides; antibodies that bind to activin (particularly the activin A or B subunits, also referred to as BA or BB) and disrupt ActRIIA binding; antibodies that bind to ActRIIA and disrupt activin binding; non-antibody proteins selected for activin or ActRIIA binding (see e.g., WO/2002/088171, WO/2006/055689, WO/2002/032925, WO/2005/037989, US 2003/0133939, and US 2005/0238646, each of which is incorporated herein by reference in its entirety, for examples of such proteins and methods for design and selection of same); and randomized peptides selected for activin or ActRIIA binding, which can be conjugated to an Fc domain.

In certain embodiments, two or more different proteins (or other moieties) with activin or ActRIIA binding activity, especially activin binders that block the type I (e.g., a soluble type I activin receptor) and type II (e.g., a soluble type II activin receptor) binding sites, respectively, may be linked together to create a bifunctional or multifunctional binding molecule that inhibits ActRIIA signaling and thus can be used in the compositions and methods described herein. In certain embodiments, Activin-ActRIIA signaling axis antagonists that inhibit ActRIIA signaling include nucleic acid aptamers, small molecules and other agents are used in the compositions and methods described herein include.

Such ActIIRA signaling inhibitors can be generated and modified as previously described in Section 5.5.1 of International Publication No. WO 2014/066486, which is incorporated herein in its entirety.

(a) ActRIIA Signaling Inhibitors Comprising ActRIIA Polypeptides

The term "ActRIIA polypeptide" includes polypeptides comprising any naturally occurring polypeptide of an ActRIIA family member as well as any variants thereof (including mutants, fragments, fusions, and peptidomimetic forms) that retain a useful activity. For example, ActRIIA polypeptides include polypeptides derived from the sequence of any known ActRIIA having a sequence at least about 80% identical to the sequence of an ActRIIA polypeptide, and optionally at least 85%, 90%, 95%, 97%, 98%, 99% or greater identity. For example, an ActRIIA polypeptide may bind to and inhibit the function of an ActRIIA protein and/or activin. An ActRIIB polypeptide may be selected for its ability to promote bone growth and bone mineralization. Examples of ActRIIA polypeptides include human ActRIIA precursor polypeptide (SEQ ID NO: 1) and soluble human ActRIIA polypeptides (e.g., SEQ ID NOs: 2, 3, 7 and 12). With respect to the ActRIIA precursor polypeptide whose amino acid sequence is depicted at SEQ ID NO:1, the signal peptide of the human ActRIIA precursor polypeptide located at amino acid positions 1 to 20; the extracellular domain is located at amino acid positions 21 to 135 and the N-linked glycosylation sites of the human ActRIIA precursor polypeptide (SEQ ID NO: 1) are located at amino acid positions 43 and 56 of SEQ ID NO:1. The nucleic acid sequence encoding the human ActRIIB precursor polypeptide of SEQ ID NO:1 is disclosed as SEQ ID NO:4 (nucleotides 164-1705 of Genbank entry NM_001616). The nucleic acid sequence encoding the soluble human ActRIIA polypeptide of SEQ ID NO:2 is disclosed as SEQ ID NO:5. See Table 1 for a description of the sequences.

In specific embodiments, the ActRIIA polypeptides used in the compositions and methods described herein are soluble ActRIIA polypeptides. An extracellular domain of an ActRIIA protein can bind to activin and is generally soluble, and thus can be termed a soluble, activin-binding ActRIIA polypeptide. Thus, as used herein, the term "soluble ActRIIA polypeptide" generally refers to polypeptides comprising an extracellular domain of an ActRIIA protein, including any naturally occurring extracellular domain of an ActRIIA protein as well as any variants thereof (including mutants, fragments and peptidomimetic forms). Soluble ActRIIA polypeptides can bind to activin; however, the wild type ActRIIA protein does not exhibit significant selectivity in binding to activin versus GDF8/11. Native or altered ActRIIA proteins may be given added specificity for activin by coupling them with a second, activin-selective binding agent. Examples of soluble, activin-binding ActRIIA polypeptides include the soluble polypeptides illustrated in SEQ ID NOs: 2, 3, 7, 12 and 13. Other examples of soluble, activin-binding ActRIIA polypeptides comprise a signal sequence in addition to the extracellular domain of an ActRIIA protein, for example, the honey bee mellitin leader sequence (SEQ ID NO: 8), the tissue plasminogen activator (TPA) leader (SEQ ID NO: 9) or the native ActRIIA leader (SEQ ID NO: 10). The ActRIIA-hFc polypeptide illustrated in SEQ ID NO:13 uses a TPA leader.

In certain embodiments, the inhibitors of ActRIIA signaling used in the compositions and methods described herein comprise a conjugate/fusion protein comprising an activin-binding domain of ActRIIA linked to an Fc portion of an antibody. In certain embodiments, the activin-binding domain is linked to an Fc portion of an antibody via a linker, e.g., a peptide linker. Optionally, the Fc domain has one or more mutations at residues such as Asp-265, lysine 322, and Asn-434. In certain cases, the mutant Fc domain having one or more of these mutations (e.g., an Asp-265 mutation) has a reduced ability to bind to the Fcγ receptor relative to a wild-type Fc domain. In other cases, the mutant Fc domain having one or more of these mutations (e.g., an Asn-434 mutation) has an increased ability to bind to the MHC class I-related Fc-receptor (FcRN) relative to a wild-type Fc domain. Exemplary fusion proteins comprising a soluble extracellular domain of ActRIIA fused to an Fc domain are set forth in SEQ ID NOs: 6, 7, 12, and 13.

In a specific embodiment, the ActRIIA signaling inhibitors used in the compositions and methods described herein comprise the extracellular domain of ActRIIA, or a portion thereof, linked to an Fc portion of an antibody, wherein said ActRIIA signaling inhibitor comprises an amino acid sequence that is at least 75% identical to an amino acid sequence selected from SEQ ID NOs: 6, 7, 12, and 13. In another specific embodiment, the ActRIIA signaling inhibitors used in the compositions and methods described herein comprise the extracellular domain of ActRIIA, or a portion thereof, linked to an Fc portion of an antibody, wherein said ActRIIA signaling inhibitor comprises an amino acid sequence that is at least 80%, 85%, 90%, 95%, 96%, 97%, 98%, or 99% identical to an amino acid sequence selected from SEQ ID NOs: 6, 7, 12, and 13.

In certain embodiments, the inhibitors of ActRIIA signaling used in the compositions and methods described herein comprise a truncated form of an extracellular domain of ActRIIA. The truncation can be at the carboxy terminus and/or the amino terminus of the ActRIIA polypeptide. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 amino acids long relative to the mature ActRIIB polypeptide extracellular domain. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 N-terminal amino acids of the mature ActRIIA polypeptide extracellular domain. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 C-terminal amino acids of the mature ActRIIA polypeptide extracellular domain. For example, truncated forms of ActRIIA include polypeptides with amino acids 20-119; 20-128; 20-129; 20-130; 20-131; 20-132; 20-133; 20-134; 20-131; 21-131; 22-131; 23-131; 24-131; and 25-131, wherein the amino acid positions refer to the amino acid positions in SEQ ID NO:1.

In certain embodiments, the inhibitors of ActRIIA signaling used in the compositions and methods described herein comprise an extracellular domain of ActRIIA with one or more amino acid substitutions. In certain embodiments, the inhibitors of ActRIIA signaling used in the compositions and methods described herein comprise a truncated form of an ActRIIA extracellular domain that also carries an amino acid substitution.

In a specific embodiment, the ActRIIA signaling inhibitor to be used in the compositions and methods described herein is a fusion protein between the extracellular domain of the human ActRIIA receptor and the Fc portion of IgG1. In another specific embodiment, the ActRIIA signaling inhibitor to be used in the compositions and methods described herein is a fusion protein between a truncated extracellular domain of the human ActRIIA receptor and the Fc portion of IgG1. In another specific embodiment, the ActRIIA signaling inhibitor to be used in the compositions and methods described herein is a fusion protein between a truncated extracellular domain of the human ActRIIA receptor and the Fc portion of IgG1, wherein the truncated extracellular domain of the human ActRIIA receptor possesses one or more amino acid substitutions.

Functionally active fragments of ActRIIA polypeptides can be obtained, for example, by screening polypeptides recombinantly produced from the corresponding fragment of the nucleic acid encoding an ActRIIA polypeptide. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function as antagonists (inhibitors) of ActRIIA protein or signaling mediated by activin.

In addition, functionally active variants of ActRIIA polypeptides can be obtained, for example, by screening libraries of modified polypeptides recombinantly produced from the corresponding mutagenized nucleic acids encoding an ActRIIA polypeptide. The variants can be produced and tested to identify those that can function as antagonists (inhibitors) of ActRIIA protein or signaling mediated by activin. In certain embodiments, a functional variant of the ActRIIA polypeptides comprises an amino acid sequence that is at least 75% identical to an amino acid sequence selected from SEQ ID NOs: 2 or 3. In certain cases, the functional variant has an amino acid sequence at least 80%, 85%, 90%, 95%, 97%, 98%, 99% or 100% identical to an amino acid sequence selected from SEQ ID NOs: 2 or 3.

In certain aspects, the ActRIIA polypeptides used in the compositions and methods described herein are generated using isolated and/or recombinant nucleic acids encoding any of the ActRIIA polypeptides (e.g., soluble ActRIIA polypeptides), including fragments, functional variants and fusion proteins disclosed herein. For example, SEQ ID NO: 4 encodes the naturally occurring human ActRIIA precursor polypeptide, while SEQ ID NO: 5 encodes the processed extracellular domain of ActRIIA. Such nucleic acids may be single-stranded or double stranded. Such nucleic acids may be DNA or RNA molecules. These nucleic acids may be used, for example, in methods for making ActRIIA polypeptides or as direct therapeutic agents (e.g., in a gene therapy approach).

In certain aspects, nucleic acids encoding ActRIIA polypeptides may include nucleic acids that are variants of SEQ ID NO: 4 or 5. Variant nucleotide sequences include sequences that differ by one or more nucleotide substitutions, additions or deletions, such as allelic variants.

In certain embodiments, isolated or recombinant nucleic acid sequences encoding ActRIIA polypeptides may be least 80%, 85%, 90%, 95%, 97%, 98%, 99% or 100% identical to SEQ ID NO: 4 or 5. One of ordinary skill in the art will appreciate that nucleic acid sequences complementary to SEQ ID NO: 4 or 5, and variants of SEQ ID NO: 4 or 5 may be used in the production of ActRIIA polypeptides suitable for use in the methods and compositions described herein. In further embodiments, such nucleic acid sequences can be isolated, recombinant, and/or fused to a heterologous nucleotide sequence, or be from a DNA library.

7.8.2 Inhibitors of ACTRIIB Signaling

As used herein, the term "ActRIIB" refers to a family of activin receptor type IIB (ActRIIB) proteins from any species and variants derived from such ActRIIB proteins by mutagenesis or other modification. Reference to ActRIIB herein is understood to be a reference to any one of the currently identified forms of the receptor. Members of the ActRIIB family are generally transmembrane proteins, composed of a ligand-binding extracellular domain with a cysteine-rich region, a transmembrane domain, and a cytoplasmic domain with predicted serine/threonine kinase activity.

ActRIIB signaling inhibitors to be used in the compositions and methods described herein include, without limitation, activin-binding soluble ActRIIB polypeptides; antibodies that bind to activin (particularly the activin A or B subunits, also referred to as BA or BB) and disrupt ActRIIB binding; antibodies that bind to ActRIIB and disrupt activin binding; non-antibody proteins selected for activin or ActRIIB binding; and randomized peptides selected for activin or ActRIIB binding, which can be conjugated to an Fc domain.

In certain embodiments, two or more different proteins (or other moieties) with activin or ActRIIB binding activity, especially activin binders that block the type I (e.g., a soluble type I activin receptor) and type II (e.g., a soluble type II activin receptor) binding sites, respectively, may be linked together to create a bifunctional or multifunctional binding molecule that inhibits ActRIIB and thus can be used in the compositions and methods described herein include. In certain embodiments, Activin-ActRIIB signaling axis antagonists that inhibit ActRIIB include nucleic acid aptamers, small molecules and other agents are used in the compositions and methods described herein include.

Such ActIIRB signaling inhibitors can be generated and modified as previously described in Section 5.5.2 of International Publication No. WO 2014/066486, which is incorporated herein in its entirety.

(a) ActRIIB Signaling Inhibitors Comprising ActRIIB Polypeptides

As used herein, the term "ActRIIB polypeptide" refers to polypeptides comprising any naturally occurring polypeptide of an ActRIIB family member as well as any variants thereof (including mutants, fragments, fusions, and peptidomimetic forms) that retain a useful activity. For example, ActRIIB polypeptides include polypeptides derived from the sequence of any known ActRIIB receptor having a sequence at least about 80% identical to the sequence of an ActRIIB polypeptide, and optionally at least 85%, 90%, 95%, 96%, 97%, 98%, 99% or greater identity. For example, an ActRIIB polypeptide may bind to and inhibit the function of an ActRIIB protein and/or activin. An example of an ActRIIB polypeptide includes the human ActRIIB precursor polypeptide (SEQ ID NO:16 or SEQ ID NO:28). With respect to the ActRIIB precursor polypeptide whose amino acid sequence is depicted as SEQ ID NO:16 or SEQ ID NO:28 (i.e., the human ActRIIB precursor polypeptide), the signal peptide of the ActRIIB precursor polypeptide is located at amino acids 1 to 18; the extracellular domain is located at amino acids 19 to 134 and the potential N-linked glycosylation sites are located at amino acid positions 42 and 65. The nucleic acid sequence encoding the human ActRIIB precursor polypeptide of SEQ ID NO:16 is disclosed as SEQ ID NO:19 (SEQ ID NO:19 provides an alanine at the codon corresponding to amino acid position 64, but could be readily modified by one of skill in the art using methods known in the art to provide an arginine at the codon corresponding to amino acid position 64 instead). See Table 1 for a description of the sequences.

The numbering of amino acids for all of the ActRIIB-related polypeptides described herein is based on the amino acid numbering for SEQ ID NO:16 and SEQ ID NO:28 (which only differ in the amino acid expressed at position 64), unless specifically designated otherwise. For example, if an ActRIIB polypeptide is described as having a substitution/mutation at amino acid position 79, then it is to be understood that position 79 refers to the 79th amino acid in SEQ ID NO:16 or SEQ ID NO:28, from which the ActRIIB polypeptide is derived. Likewise, if an ActRIIB polypeptide is described as having an alanine or an arginine at amino acid position 64, then it is to be understood that position 64 refers to the 64th amino acid in SEQ ID NO:16 or SEQ ID NO:28, from which the ActRIIB polypeptide is derived.

In certain embodiments, the inhibitors of ActRIIB signaling used in the compositions and methods described herein comprise polypeptides comprising an activin-binding domain of ActRIIB In some embodiments, the activin-binding domains of ActRIIB comprise the extracellular domain of ActRIIB, or a portion thereof. In specific embodiments, the extracellular domain or portion thereof of ActRIIB is soluble. Illustrative modified forms of ActRIIB polypeptides are disclosed in U.S. Patent Application Publication Nos. 20090005308 and 20100068215, the disclosures of which are incorporated herein by reference in their entireties.

In specific embodiments, the ActRIIB polypeptides used in the compositions and methods described herein are soluble ActRIIB polypeptides. The term "soluble ActRIIB polypeptide" generally refers to polypeptides comprising an extracellular domain of an ActRIIB protein, including any naturally occurring extracellular domain of an ActRIIB protein as well as any variants thereof (including mutants, fragments and peptidomimetic forms). Soluble ActRIIB polypeptides can bind to activin; however, the wild type ActRIIB protein does not exhibit significant selectivity in binding to activin versus GDF8/11. In certain embodiments, altered forms of ActRIIB with different binding properties can be used in the methods provided herein. Such altered forms are disclosed, e.g., in international patent application publication Nos. WO 2006/012627 and WO 2010/019261, the disclosures of which are incorporated herein by reference in their entireties. Native or altered ActRIIB proteins may be given added specificity for activin by coupling them with a second, activin-selective binding agent. Exemplary soluble ActRIIB polypeptides include the extracellular domain of a human ActRIIB polypeptide (e.g., SEQ ID NOs: 17, 18, 23, 26, 27, 29, 30, 31, 32, 33, 36, 37, 42, and 43).

An Fc fusion protein having the ActRIIB extracellular sequence disclosed by Hilden et al. (Blood, 1994, 83(8): 2163-70), which has an alanine at the position corresponding to amino acid 64 of the ActRIIB precursor amino acid sequence, i.e., SEQ ID NO: 16 (herein referred to as "A64"), has been demonstrated to possess a relatively low affinity for activin and GDF-11. By contrast, an Fc fusion protein with an arginine at position 64 of the ActRIIB precursor amino acid sequence (herein referred to as "R64") has an affinity for activin and GDF-11 in the low nanomolar to high picomolar range (see, e.g., U.S. Patent Application Publication No. 20100068215, the disclosure of which is herein incorporated in its entirety). An ActRIIB precursor amino acid sequence with an arginine at position 64 is presented in SEQ ID NO:28. As such, in certain embodiments, the ActRIIB polypeptides used in accordance with the compositions and methods described herein may comprise either (i) an alanine at the position corresponding to amino acid 64 of the ActRIIB precursor amino acid sequence, i.e., SEQ ID NO: 16; or (ii) an arginine at position 64 of the ActRIIB precursor amino acid sequence, i.e., SEQ ID NO: 28. In other embodiments, the ActRIIB polypeptides used in accordance with the compositions and methods described herein may comprise an amino acid that is not alanine or arginine at the position corresponding to amino acid 64 of the ActRIIB precursor amino acid sequence, i.e., SEQ ID NO: 16 or SEQ ID NO:28.

It has been shown that a deletion of the proline knot at the C-terminus of the extracellular domain of ActRIIB reduces the affinity of the receptor for activin (see, e.g., Attisano et al., Cell, 1992, 68(1):97-108). An ActRIIB-Fc fusion protein containing amino acids 20-119 of SEQ ID NO: 28 (i.e., SEQ ID NO:32), "ActRIM(20-119)-Fc" has reduced binding to GDF-11 and activin relative to an ActRIIB-Fc fusion protein containing amino acids 20-134 of SEQ ID NO: 28 (i.e., SEQ ID NO:31), "ActRIIB(20-134)-Fc", which includes the proline knot region and the complete juxtamembrane domain. However, an ActRIIB-Fc fusion protein containing amino acids 20-129 of SEQ ID NO: 28, "ActRIM(20-129)-Fc" retains similar but somewhat reduced activity relative to the non-truncated extracellular domain of ActRIIB, even though the proline knot region is disrupted. Thus, ActRIIB polypeptides comprising extracellular domains that stop at amino acid 134, 133, 132, 131, 130 and 129 of SEQ ID NO: 28 (or SEQ ID NO:16) are all expected to be active, but constructs stopping at amino acid 134 or 133 may be most active. Similarly, mutations at any of residues 129-134 are not expected to alter ligand binding affinity by large margins, as indicated by the fact that mutations of P129 and P130 of SEQ ID NO: 28 do not substantially decrease ligand binding. Therefore, the ActRIIB polypeptides used in accordance with the methods and compositions described herein may end as early as amino acid 109 (i.e., the final cysteine) of SEQ ID NO:28 (or SEQ ID NO:16), however, forms ending at or between amino acid positions 109 and 119 of SEQ ID NO:28 (or SEQ ID NO:16) are expected to have reduced ligand binding ability.

Amino acid 29 of SEQ ID NO:16 and SEQ ID NO:28 represents the initial cysteine in the ActRIIB precursor sequence. It is expected that an ActRIIB polypeptide beginning at amino acid 29 of the N-terminus of SEQ ID NO:16 or SEQ ID NO:28, or before these amino acid positions, will retain ligand binding activity. An alanine to asparagine mutation at position 24 of SEQ ID NO:16 or SEQ ID NO:28 introduces an N-linked glycosylation sequence without substantially affecting ligand binding. This confirms that mutations in the region between the signal cleavage peptide and the cysteine cross-linked region, corresponding to amino acids 20-29 of SEQ ID NO:16 or SEQ ID NO:28, are well tolerated. In particular, ActRIIB polypeptides beginning at amino acid position 20, 21, 22, 23 and 24 of SEQ ID NO:16 or SEQ ID NO:28 will retain activity, and ActRIIB polypeptides beginning at amino acid positions 25, 26, 27, 28 and 29 of SEQ ID NO:16 or SEQ ID NO:28 are also expected to retain activity. An ActRIIB polypeptide beginning at amino acid position 22, 23, 24 or 25 of SEQ ID NO:16 or SEQ ID NO:28 will have the most activity.

Taken together, the active portions (i.e., ActRIIB polypeptides) of the ActRIIB precursor protein (i.e., SEQ ID NO:16 or SEQ ID NO:28) to be used in accordance with the methods and compositions described herein will generally comprise amino acids 29-109 of SEQ ID NO:16 or SEQ ID NO:28, and such ActRIIB polypeptides may, for example, begin at a residue corresponding to any one of amino acids 19-29 of SEQ ID NO:16 or SEQ ID NO:28 and end at a position corresponding to any one of amino acids 109-134 of SEQ ID NO:16 or SEQ ID NO:28. Specific examples of ActRIIB polypeptides encompassed herein include those that begin at an amino acid position from 19-29, 20-29 or 21-29 of SEQ ID NO:16 or SEQ ID NO:28 and end at an amino acid position from 119-134, 119-133 or 129-134, 129-133 of SEQ ID NO:16 or SEQ ID NO:28. Other specific examples of ActRIIB polypeptides encompassed herein include those that begin at an amino acid position from 20-24 (or 21-24, or 22-25) of SEQ ID NO:16 or SEQ ID NO:28 and end at an amino acid position from 109-134 (or 109-133), 119-134 (or 119-133) or 129-134 (or 129-133) of SEQ ID NO:16 or SEQ ID NO:28. Variant ActRIIB polypeptides falling within these ranges are also contemplated, particularly those having at least 80%, 85%, 90%, 91%, 92%, 93%, 94%, 95%, 96%, 97%, 98%, or 99% sequence identity or sequence homology to the corresponding portion of SEQ ID NO:16 or SEQ ID NO:28.

In certain embodiments, the inhibitors of ActRIIB signaling used in the compositions and methods described herein comprise a truncated form of an extracellular domain of ActRIIB The truncation can be at the carboxy terminus and/or the amino terminus of the ActRIIB polypeptide. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 amino acids long relative to the mature ActRIIB polypeptide extracellular domain. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 N-terminal amino acids of the mature ActRIIB polypeptide extracellular domain. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 C-terminal amino acids of the mature ActRIIB polypeptide extracellular domain. For example, truncated forms of ActRIIB include polypeptides with amino acids 20-119; 20-128; 20-129; 20-130; 20-131; 20-132;

20-133; 20-134; 20-131; 21-131; 22-131; 23-131; 24-131; and 25-131, wherein the amino acid positions refer to the amino acid positions in SEQ ID NO:16 or SEQ ID NO:28.

Additional exemplary truncated forms of ActRIIB include (i) polypeptides beginning at amino acids at any of amino acids 21-29 of SEQ ID NO:16 or SEQ ID NO:28 (optionally beginning at 22-25 of SEQ ID NO:16 or SEQ ID NO:28) and ending at any of amino acids 109-134 of SEQ ID NO:16 or SEQ ID NO:28; (ii) polypeptides beginning at any of amino acids 20-29 of SEQ ID NO:16 or SEQ ID NO:28 (optionally beginning at 22-25 of SEQ ID NO:16 or SEQ ID NO:28) and ending at any of amino acids 109-133 of SEQ ID NO:16 or SEQ ID NO:28; (iii) polypeptides beginning at any of amino acids 20-24 of SEQ ID NO:16 or SEQ ID NO:28 (optionally beginning at 22-25 of SEQ ID NO:16 or SEQ ID NO:28) and ending at any of amino acids 109-133 of SEQ ID NO:16 or SEQ ID NO:28; (iv) polypeptides beginning at any of amino acids 21-24 of SEQ ID NO:16 or SEQ ID NO:28 and ending at any of amino acids 109-134 of SEQ ID NO:16 or SEQ ID NO:28; (v) polypeptides beginning at any of amino acids 20-24 of SEQ ID NO:16 or SEQ ID NO:28 and ending at any of amino acids 118-133 of SEQ ID NO:16 or SEQ ID NO:28; (vi) polypeptides beginning at any of amino acids 21-24 of SEQ ID NO:16 or SEQ ID NO:28 and ending at any of amino acids 118-134 of SEQ ID NO:16 or SEQ ID NO:28; (vii) polypeptides beginning at any of amino acids 20-24 of SEQ ID NO:16 or SEQ ID NO:28 and ending at any of amino acids 128-133 of SEQ ID NO:16 or SEQ ID NO:28; (viii) polypeptides beginning at any of amino acids 20-24 of SEQ ID NO:16 or SEQ ID NO:28 and ending at any of amino acids 128-133 of SEQ ID NO:16 or SEQ ID NO:28; (ix) polypeptides beginning at any of amino acids 21-29 of SEQ ID NO:16 or SEQ ID NO:28 and ending at any of amino acids 118-134 of SEQ ID NO:16 or SEQ ID NO:28; (x) polypeptides beginning at any of amino acids 20-29 of SEQ ID NO:16 or SEQ ID NO:28 and ending at any of amino acids 118-133 of SEQ ID NO:16 or SEQ ID NO:28; (xi) polypeptides beginning at any of amino acids 21-29 of SEQ ID NO:16 or SEQ ID NO:28 and ending at any of amino acids 128-134 of SEQ ID NO:16 or SEQ ID NO:28; and (xii) polypeptides beginning at any of amino acids 20-29 of SEQ ID NO:16 or SEQ ID NO:28 and ending at any of amino acids 128-133 of SEQ ID NO:16 or SEQ ID NO:28. In a specific embodiment, an ActRIIB polypeptides comprises, consists essentially of, or consists of, an amino acid sequence beginning at amino acid position 25 of SEQ ID NO:16 or SEQ ID NO:28 and ending at amino acid position 131 of SEQ ID NO:16 or SEQ ID NO:28. In another specific embodiment, an ActRIIB polypeptide consists of, or consists essentially of, the amino acid sequence of SEQ ID NO:17, 18, 23, 26, 27, 29, 30, 31, 32, 33, 36, 37, 42, or 43.

Any of the ActRIIB polypeptides used in the compositions and methods described herein may be produced as a homodimer. Any of the ActRIIB polypeptides used in the compositions and methods described herein may be formulated as a fusion protein having a heterologous portion that comprises a constant region from an IgG heavy chain, such as an Fc domain. Any of the ActRIIB polypeptides used in the compositions and methods described herein may comprise an acidic amino acid at the position corresponding to position 79 of SEQ ID NO:16 or SEQ ID NO:28, optionally in combination with one or more additional amino acid substitutions, deletions or insertions relative to SEQ ID NO:16 or SEQ ID NO:28.

In specific embodiments, the inhibitors of ActRIIB signaling used in the compositions and methods described herein comprise an extracellular domain of ActRIIB with one or more amino acid substitutions/mutations. Such an amino acid substitution/mutation can be, for example, an exchange from the leucine at amino acid position 79 of SEQ ID NO:16 or SEQ ID NO:28 to an acidic amino acid, such as aspartic acid or glutamic acid. For example, position L79 of SEQ ID NO:16 or SEQ ID NO:28 may be altered in ActRIIB extracellular domain polypeptides to confer altered activin-myostatin (GDF-11) binding properties. L79A and L79P mutations reduce GDF-11 binding to a greater extent than activin binding. L79E and L79D mutations retain GDF-11 binding, while demonstrating greatly reduced activin binding.

In certain embodiments, the inhibitors of ActRIIB signaling used in the compositions and methods described herein comprise a truncated form of an ActRIIB extracellular domain that also carries an amino acid substitution, e.g., an exchange from the leucine at amino acid position 79 of SEQ ID NO:16 or SEQ ID NO:28 to an acidic amino acid, such as aspartic acid or glutamic acid. In a specific embodiment, the truncated form of an extracellular domain of ActRIIB polypeptide that also carries an amino acid substitution used in the compositions and methods described herein is SEQ ID NO:23. Forms of ActRIIB that are truncated and/or carry one or more amino acid substitutions can be linked to an Fc domain of an antibody as discussed above.

Functionally active fragments of ActRIIB polypeptides can be obtained, for example, by screening polypeptides recombinantly produced from the corresponding fragment of the nucleic acid encoding an ActRIIB polypeptide. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function as antagonists (inhibitors) of ActRIIB protein or signaling mediated by activin.

In addition, functionally active variants of ActRIIB polypeptides can be obtained, for example, by screening libraries of modified polypeptides recombinantly produced from the corresponding mutagenized nucleic acids encoding an ActRIIB polypeptide. The variants can be produced and tested to identify those that can function as antagonists (inhibitors) of ActRIIB protein or signaling mediated by activin. In certain embodiments, a functional variant of the ActRIIB polypeptides comprises an amino acid sequence that is at least 75% identical to an amino acid sequence selected from SEQ ID NO:17, 18, 23, 26, 27, 29, 30, 31, 32, 33, 36, 37, 42, and 43. In certain embodiments, the functional variant has an amino acid sequence at least 80%, 85%, 90%, 95%, 96%, 97%, 98%, or 99% identical to an amino acid sequence selected from SEQ ID NO:17, 18, 23, 26, 27, 29, 30, 31, 32, 33, 36, 37, 42, and 43.

It has been demonstrated that the ligand binding pocket of ActRIIB is defined by residues Y31, N33, N35, L38 through T41, E47, E50, Q53 through K55, L57, H58, Y60, S62, K74, W78 through N83, Y85, R87, A92, and E94 through F101 of SEQ ID NO:16 or SEQ ID NO:28. At these positions, it is expected that conservative mutations will be tolerated, although a K74A mutation is well-tolerated, as are R40A, K55A, F82A and mutations at position L79. R40 is a K in Xenopus, indicating that basic amino acids at this position will be tolerated. Q53 is R in bovine ActRIIB and K in Xenopus ActRIIB, and therefore amino acids including R, K, Q, N and H will be tolerated at this position. Thus, a general formula for an ActRIIB polypeptide for use in the methods and compositions described herein is one that comprises amino acids 29-109 of SEQ ID NO:16 or SEQ ID NO:28, but optionally beginning at an amino acid position ranging from 20-24 or 22-25 of SEQ ID NO:16 or SEQ ID NO:28 and ending at an amino acid position ranging from 129-134 of SEQ ID NO:16 or SEQ ID NO:28, and comprising no more than 1, 2, 5, or 15 conservative amino acid changes in the ligand binding pocket, and zero, one or more non-conservative alterations at amino acid positions 40, 53, 55, 74, 79 and/or 82 of SEQ ID NO:16 or SEQ ID NO:28 in the ligand binding pocket. Such an ActRIIB polypeptide may retain greater than 80%, 90%, 95% or 99% sequence identity or sequence homology to the sequence of amino acids 29-109 of SEQ ID NO:16 or SEQ ID NO:28. Sites outside the binding pocket, at which variability may be particularly well tolerated, include the amino and carboxy termini of the extracellular domain of ActRIIB, and positions 42-46 and 65-73. An asparagine to alanine alteration at position 65 of SEQ ID NO:16 or SEQ ID NO:28 (N65A) actually improves ligand binding in the A64 background, and is thus expected to have no detrimental effect on ligand binding in the R64 background. This change probably eliminates glycosylation at N65 in the A64 background, thus demonstrating that a significant change in this region is likely to be tolerated. While an R64A change is poorly tolerated, R64K is well-tolerated, and thus another basic residue, such as H may be tolerated at position 64.

In specific embodiments, the inhibitors of ActRIIB signaling used in the compositions and methods described herein comprise a conjugate/fusion protein comprising an extracellular domain (e.g., an activin-binding domain) of an ActRIIB receptor linked to an Fc portion of an antibody. Such conjugate/fusion proteins may comprise any of the ActRIIB polypeptides disclosed herein (e.g., any of SEQ ID NOs:17, 18, 23, 26, 27, 29, 30, 31, 32, 33, 36, 37, 42, or 43), any ActRIIB polypeptides known in the art, or any ActRIIB polypeptides generated using methods known in the art and/or provided herein.

In certain embodiments, the extracellular domain is linked to an Fc portion of an antibody via a linker, e.g., a peptide linker. Exemplary linkers include short polypeptide sequences such as 2-10, 2-5, 2-4, 2-3 amino acid residues (e.g., glycine residues), such as, for example, a Gly-Gly-Gly linker. In a specific embodiment, the linker comprises the amino acid sequence Gly-Gly-Gly (GGG). In another specific embodiment, the linker comprises the amino acid sequence Thr-Gly-Gly-Gly (TGGG). Optionally, the Fc domain has one or more mutations at residues such as Asp-265, lysine 322, and Asn-434. In certain cases, the mutant Fc domain having one or more of these mutations (e.g., an Asp-265 mutation) has a reduced ability to bind to the Fcγ receptor relative to a wild-type Fc domain. In other cases, the mutant Fc domain having one or more of these mutations (e.g., an Asn-434 mutation) has an increased ability to bind to the MHC class I-related Fc-receptor (FcRN) relative to a wild-type Fc domain. Exemplary fusion proteins comprising a soluble extracellular domain of ActRIIB fused to an Fc domain are set forth in SEQ ID NOs:20, 21, 24, 25, 34, 35, 38, 39, 40, 41, 44, 46, and 47.

In a specific embodiment, the ActRIIB signaling inhibitors used in the compositions and methods described herein comprise the extracellular domain of ActRIIB, or a portion thereof, linked to an Fc portion of an antibody, wherein said ActRIIB signaling inhibitor comprises an amino acid sequence that is at least 75% identical to an amino acid sequence selected from SEQ ID NOs:20, 21, 24, 25, 34, 35, 38, 39, 40, 41, 44, 46, and 47. In another specific embodiment, the ActRIIB signaling inhibitors used in the compositions and methods described herein comprise the extracellular domain of ActRIIB, or a portion thereof, linked to an Fc portion of an antibody, wherein said ActRIIB signaling inhibitor comprises an amino acid sequence that is at least 80%, 85%, 90%, 95%, 96%, 97%, 98%, or 99% identical to an amino acid sequence selected from SEQ ID NOs:20, 21, 24, 25, 34, 35, 38, 39, 40, 41, 44, 46, and 47.

In a specific embodiment, the ActRIIB signaling inhibitor to be used in the compositions and methods described herein is a fusion protein between the extracellular domain of the human ActRIIB receptor and the Fc portion of IgG1. In another specific embodiment, the ActRIIB signaling inhibitor to be used in the compositions and methods described herein is a fusion protein between a truncated extracellular domain of the human ActRIIB receptor and the Fc portion of IgG1. In another specific embodiment, the ActRIIB signaling inhibitor to be used in the compositions and methods described herein is a fusion protein between a truncated extracellular domain of the human ActRIIB receptor and the Fc portion of IgG1, wherein the truncated extracellular domain of the human ActRIIB receptor possesses an amino acid substitution at the amino acid position corresponding to amino acid 79 of SEQ ID NO:16 or SEQ ID NO:28. In one embodiment, the amino acid substitution at the amino acid position corresponding to amino acid 79 of SEQ ID NO:16 or SEQ ID NO:28 is substitution of Leucine for Aspartic Acid (i.e., an L79D mutation).

In a specific embodiment, the ActRIIB signaling inhibitor to be used in the compositions and methods described herein is SEQ ID NO:24 or 25, which represents a fusion protein between the extracellular domain of the human ActRIIB receptor and the Fc portion of IgG1, wherein said ActRIIB extracellular domain comprises amino acids 25-131 of SEQ ID NO:28 with an L79D mutation. The nucleic acid sequence encoding the ActRIIB-Fc fusion protein of SEQ ID NO:24 is presented in SEQ ID NO:45.

In another specific embodiment, the ActRIIB signaling inhibitor to be used in the compositions and methods described herein is SEQ ID NO:34 or 35, which represents a fusion protein between the extracellular domain of the human ActRIIB receptor and the Fc portion of IgG1, wherein said ActRIIB extracellular domain comprises amino acids 25-131 of SEQ ID NO:16 with an L79D mutation.

In specific embodiments, mutated ActRIIB polypeptides comprising the addition of a further N-linked glycosylation site (N-X-S/T) that increases the serum half-life of an ActRIIB-Fc fusion protein, relative to the ActRIIB(R64)-Fc form can be used in the methods and compositions described herein. In a specific embodiment, introduction of an asparagine at position 24 of SEQ ID NO:16 or SEQ ID NO:28 (A24N) results in the creation of an NXT sequence that confers a longer half-life. Other NX(T/S) sequences can be found at 42-44 (NQS) and 65-67 (NSS), although the latter may not be efficiently glycosylated with the R at position 64 (i.e., in R64 polypeptides). N-X-S/T sequences may be generally introduced at positions outside the ligand binding pocket of ActRIIB, which is detailed above. Particularly suitable sites for the introduction of non-endogenous N-X-S/T sequences include amino acids 20-29, 20-24, 22-25, 109-134, 120-134 or 129-134 of SEQ ID NO:16 or SEQ ID NO:28. N-X-S/T sequences may also be introduced into the linker between the ActRIIB sequence and the Fc or other fusion component. Such a site may be introduced with minimal effort by introducing an N in the correct position with respect to a pre-existing S or T, or by introducing an S or T at a position corresponding to a pre-existing N. Thus, desirable alterations that would create an N-linked glycosylation site are: A24N, R64N, S67N (possibly combined with an N65A alteration), E106N, R112N, G120N, E123N, P129N, A132N, R112S and R112T (with all amino acid positions corresponding to the positions they can be found in SEQ ID NO:16 or SEQ ID NO:28). Any S that is predicted to be glycosylated may be altered to a T without creating an immunogenic site, because of the protection afforded by the glycosylation. Likewise, any T that is predicted to be glycosylated may be altered to an S. Thus the alterations S67T and S44T are encompassed herein. Likewise, in an A24N variant, an S26T alteration may be used. Accordingly, an ActRIIB polypeptide may include one or more additional, non-endogenous N-linked glycosylation consensus sequences.

In certain embodiments, the methods and compositions described herein use isolated or purified ActRIIB polypeptides, i.e., ActRIIB polypeptides which are isolated from, or otherwise substantially free of, other proteins can be used with the methods and compositions described herein. ActRIIB polypeptides will generally be produced by expression from recombinant nucleic acids.

In certain aspects, the ActRIIB polypeptides used in the methods and compositions described herein are encoded by isolated and/or recombinant nucleic acids, including fragments, functional variants and fusion proteins disclosed herein. For example, SEQ ID NO:19 encodes the naturally occurring human ActRIIB precursor polypeptide. The subject nucleic acids may be single-stranded or double stranded. Such nucleic acids may be DNA or RNA molecules. These nucleic acids may be used, for example, in methods for making ActRIIB polypeptides or as direct therapeutic agents (e.g., in a gene therapy approach).

In certain aspects, the nucleic acids that can be used to produce ActRIIB polypeptides suitable for use in the methods and compositions described herein are further understood to include nucleic acids that are variants of SEQ ID NO: 19 as well as variants of those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43). Variant nucleotide sequences include sequences that differ by one or more nucleotide substitutions, additions or deletions, such as allelic variants.

In certain embodiments, the isolated or recombinant nucleic acid sequences that can be used to produce ActRIIB polypeptides suitable for use in the methods and compositions described herein are at least 80%, 85%, 90%, 95%, 97%, 98%, 99% or 100% identical to SEQ ID NO:19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43). One of ordinary skill in the art will appreciate that nucleic acid sequences complementary to SEQ ID NO:19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43), and variants of SEQ ID NO:19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43) can be used with the methods and compositions described herein. In further embodiments, the nucleic acid sequences can be isolated, recombinant, and/or fused with a heterologous nucleotide sequence, or in a DNA library.

7.9 Assays

7.9.1 Reference Population

In certain embodiments, the size of the reference population can be 1, 5, 10, 25, 50, 75, 100, 200, 250, 300, 400, 500, or 1000 individuals. In certain embodiments, the reference population consists of random volunteers. In certain embodiments, the reference population consists of healthy people. In certain embodiments, the reference population consists of people of the same age, weight, and/or gender as the patient population as described in Section 7.5. In certain embodiments, the reference population consists of people without beta-thalassemia.

7.9.2 Cells and Cell Culture

Cells used in accordance with the methods provided herein can be isolated and/or cultured according to any method known in the art or described herein (see Section 8.1).

EPCs can be isolated according to any method known in the art or described herein. In certain embodiments, EPCs are CD34$^+$ cells. CD34$^+$ cells can be isolated according to any method known in the art or described herein (see Section 8.1). CD34$^+$ cells can be isolated by high-gradient magnetic cell sorting or FACS analysis. See, e.g., Kato and Radbruch, 1993, Cytometry, 14:384-392. In certain embodiments, EPCs are isolated by culturing CD34$^+$ cells following G-CSF mobilization of peripheral blood stem cells. See, e.g., Mortimer et al., 1983, Nature, 302:426-429; Wong et al., 2008, J Virol, 82:2470-2476; and Young et al., 2004, N. Engl. J. Med. 350:586-597, each of which is incorporated herein by reference in its entirety. In certain embodiments, EPCs are isolated as described in Filippone et al., 2010, PLoS ONE, 5(3): e9496, which is incorporated herein by reference in its entirety. In certain embodiments, in the context of a co-culture comprising an EPC and a stromal cell, the EPCs is a non-adherent cell in supernatant (NAC). In certain embodiments, in the context of a co-culture comprising an EPC and a stromal cell, the EPC is a phase-bright cells (PBC) adhering to the surface of a stromal cell. In certain embodiments, in the context of a co-culture comprising an EPC and a stromal cell, the EPC is a phase-dim cell (PDC) beneath a stromal cell in a co-culture.

The level of EPC expansion can be determined according to any method known in the art or described herein (see Section 8.1). For example, erythroid cell expansion can be evaluated by flow cytometry or cell morphology.

Bone marrow stromal cells are a non-hematopoietic cell population residing in the bone marrow. See, e.g., Kagami et al., 2011, Int. J. Biochem. Cell Biol. 43(3):286-289. Bone marrow-derived stromal cells can be isolated according to any method known in the art or described herein. For example, bone marrow stromal cells can be obtained from the adherent cultures of untreated whole bone marrow. Alternatively, bone marrow stromal cells can be isolated by removal of non-bone marrow stromal cells through density gradient centrifugation and/or hemolysis. See, e.g., Horn et al., 2008, Cytotherapy, 10(7):676-685.

7.9.3 Level of Biomarkers

The level of a biomarker, such as GYPA, GATA1, GATA2, alpha-globin, ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2, can be determined by any method known in the art or described herein (see Section 8.1). For example, the nucleic acid level of the biomarker in a sample (e.g., a cell or supernatant from a cell culture) can be determined by assessing (e.g., quantifying) transcribed RNA of the protein in the sample using, e.g., Northern blotting, PCR analysis, real time PCR analysis, or any other technique known in the art or described herein. In one embodiment, the level of the biomarker in a sample (e.g., a cell or supernatant from a cell culture) can be determined by assessing (e.g., quantifying) mRNA of the protein in the sample. The protein level of a biomarker in a sample (e.g., a cell or supernatant from a cell culture) can also be determined by assessing (e.g., quantifying) the level of protein expression of the biomarker in the sample using, e.g., immunohistochemical analysis, Western blotting, ELISA, immunoprecipitation, flow cytometry analysis, or any other technique known in the art or described herein. In particular embodiments, the level of the biomarker is determined by a method capable of quantifying the amount of the protein present in a sample (e.g., a cell or supernatant from a cell culture) of a patient (e.g., in human serum), and/or capable of detecting the correction of the level of protein following treatment with an activin type II receptor signaling inhibitor. In one embodiment, the level of the protein in a sample (e.g., a cell or supernatant from a cell culture) is determined by assessing (e.g., quantifying) protein expression of the biomarker in the sample using ELISA. In certain embodiments, the level of a biomarker, such as GYPA, GATA1, GATA2, alpha-globin, ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2, can be determined according to an assay as described in Section 8.1.

In certain embodiments, the level of GYPA, GATA1, GATA2, or alpha-globin in an EPC is measured in a non-adherent cell in supernatant (NAC). In certain embodiments, the level of GYPA, GATA1, GATA2, or alpha-globin in an EPC is measured in a phase-bright cells (PBC) adhering to the surface of a stromal cell. In certain embodiments, the level of GYPA, GATA1, GATA2, or alpha-globin in an EPC is measured in a phase-dim cell (PDC) beneath a stromal cells in a co-culture.

The level of a biomarker, such as GYPA, GATA1, GATA2, alpha-globin, ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2, can be determined from a location where one skilled in the art would expect the biomarker to be expressed. For example, the level of a secreted biomarker can be determined in supernatant. Alternatively, the level of a secreted biomarker can be determined in a membrane fraction of a cell. As an additional example, the level of an intracellular biomarker can be determined in whole cell lysate or in a subcellular fraction wherein the biomarker is present. In certain embodiments, the level of the biomarker is determined in supernatant. In certain embodiments, the level of the biomarker is determined in whole cell lysate. In certain embodiments, the level of the biomarker is determined in a subcellular fraction.

7.9.4 Screening Assays

Various ActRII polypeptide variants, or soluble ActRII polypeptide variants, may be tested for their ability to inhibit ActRII. In certain aspects, such testing can be performed as previously described in Section 5.3(b) of International Publication No. WO 2014/071158, which is incorporated herein in its entirety. In addition, compounds can be tested for their ability to inhibit ActRII. Once signaling inhibitors of ActRII activity are confirmed, these compounds can be used with the methods provided herein. ActRII can be ActRIIA or ActRIIB 7.10 Clinical Response Various assays known in the art can be utilized to evaluate treatment of beta-thalassemia upon treatment with an ActRII signaling inhibitor according to the methods provided herein. Serum ferritin levels can be determined according to assay(s) known to one skilled in the art. Typically, adult males have a serum ferritin concentration of between 24 and 336 ng/mL. Typically, adult females of between 11 and 307 ng/mL.

Red blood cell morphology can be evaluated according to assay(s) known to one skilled in the art such as, for example, blood smears. The ratio of number of abnormal red blood cells in the subject to the total number of red blood cells in the subject can be determined by, for example, obtaining a blood sample, performing a blood smear, counting the number of abnormal red blood cells in the smear, counting the total number of red blood cells in the smear, and determining the ratio by dividing the number of abnormal red blood cells by the total number of red blood cells in the smear. The ratio of the number of red blood cells with basophilic stippling in the subject to the total number of red blood cells in the subject can be determined by, for example, obtaining a blood sample, performing a blood smear, counting the number of red blood cells with basophilic stippling in the smear, counting the total number of red blood cells in the smear, and determining the ratio by dividing the number of red blood cells with basophilic stippling by the total number of red blood cells in the smear. The ratio of the number of poikilocytic red blood cells in the subject to the total number of red blood cells in the subject can be determined by, for example, obtaining a blood sample, performing a blood smear, counting the number of poikilocytic red blood cells in the smear, counting the total number of red blood cells in the smear, and determining the ratio by dividing the number of poikilocytic red blood cells by the total number of red blood cells in the smear. The ratio of the number of schistocytes in the subject to the total number of red blood cells in the subject can be determined by, for example, obtaining a blood sample, performing a blood smear, counting the number of schistocytes in the smear, counting the total number of red blood cells in the smear, and determining the ratio by dividing the number of schistocytes by the total number of red blood cells in the smear. The ratio of the number of irregularly contracted red blood cells in the subject to the total number of red blood cells in the subject can be determined by, for example, obtaining a blood sample, performing a blood smear, counting the number of irregularly contracted red blood cells in the smear, counting the total number of red blood cells in the smear, and determining the ratio by dividing the number of irregularly contracted red blood cells by the total number of red blood cells in the smear.

Further, erythroid response in a subject treated in accordance with the methods provided herein can be evaluated. In certain embodiments, the erythroid response comprises a reduction in transfusion burden in the subject by at least 33% for at least 12 weeks, wherein the subject has transfusion-dependent beta thalassemia. In certain embodiments, the erythroid response comprises (i) a reduction in transfusion burden in the subject by at least 33% for at least 12 weeks, and (ii) a reduction of at least two units of red blood cells for at least 12 weeks in the subject. The duration of the erythroid response can be calculated for a subject who achieves a response. The algorithm used to calculate the duration of response is as follows: (1) First Day of Response=the first day of the first 12-week interval showing response. Last Day of Response=last day of the last consecutive 129-week interval showing response. Date of Last Assessment=either the last visit date for subjects still on drug or the date of discontinuation for subjects who discontinued from the treatment. The duration of the erythroid response can be calculated as follows, depending on whether or not the response ends before the Date of Last Assessment: (1) a subject whose response does not continue to the end of a treatment period, the duration of response is not censored, and is calculated as: Response Duration=Last Day of Response−First Day of Response+1; (2) a subject who continues to exhibit an erythroid response at the end of a treatment period, the end date of the response is censored and duration of the response is calculated as: Response Duration=Date of Last Response Assessment−First Day of Response+1.

The time to the first erythroid response can be calculated as follows: the day from the first dose of study drug to the First Day of Response starts will be calculated using: Time to Response=First Day of Response−Date of First Study Drug+1.

In addition, transfusion burden can be evaluated in a subject treated in accordance with the methods provided herein. It is estimated that one unit of red blood cells contains approximately 200 mg of iron, while the body typically loses only 1.5 mg of iron per day. Transfusion burden in a subject treated according to the methods provided herein can be determined by determining the subject's transfusion requirement (i.e., the amount and the frequency of red blood cell transfusion). As a nonlimiting example, if a subject requiring transfusion of 2 units of red blood cells every 3 weeks achieves a reduction in frequency in transfusion to every 4 weeks upon treatment according to the methods provided herein, the subject has a 25% reduction in transfusion burden.

In addition, clinical complications associated with beta-thalassemia can be evaluated according to any assay known to one skilled in the art. Extramedullary hematopoietic (EMH) masses in a subject can be evaluated by assay(s) known to one skilled in the art, such as, for example, magnetic resonance imaging (MRI) and computed tomography scanning. In certain embodiments, EMH masses in a subject can be evaluated by MM.

Splenomegaly can be evaluated by assay(s) known to one skilled in the art, such as, for example, magnetic resonance imaging (MM).

Tricuspid regurgitant velocity (TRV) can be evaluated according to assay(s) known to one skilled in the art, such as, for example, echocardiography (ECHO).

Liver iron concentration in a subject can be evaluated by assay(s) known to one skilled in the art, such as, for example, magnetic resonance imaging (MM).

Nonlimiting examples of osteoporosis symptoms include back pain, loss of height over time, stooped posture, easy bone fracturing, and decreased bone mineral density. Bone mineral density in a subject treated according to the methods provided herein can be determined by assay(s) known to one skilled in the art, such as, for example, by bone density scanning (also referred to as dual-energy x-ray absorptiometry (DXA or DEXA) or bone densitometry) and ultrasound. In certain embodiments, bone mineral density in a subject treated according to the methods provided herein is determined by DXA.

Skeletal deformities in subject treated according to the methods provided herein can be determined by assay(s) known to one skilled in the art, such as, for example, by x-ray and imaging techniques, such as, for example, magnetic resonance imaging (MM) and computed tomography.

Various circulating markers of bone turnover can be used to diagnose bone disorders, such as low bone turnover. Circulating markers of bone turnover are markers of bone formation such as bone specific alkaline phosphatase (bAP), osteocalcin, procollagen type I C-terminal propeptide (PICP) and insulin-like growth factor-1 (IGF-1), some being markers of bone resorption such as pyridinoline, deoxypyridinoline, tartrate-resistant acid phosphatase (TRAP), TRAP type 5b, pyridinoline, deoxypyridinoline and procollagen type I C-terminal telopeptide (ICTP), serum or urine collagen cross-links (N-telopeptide or C-telopeptide), and 25 hydroxyvitamin D. Assays to measure the entire parathyroid hormone (PTH) molecule can also be used. The skilled artisan is aware of imaging methods allowing the assessment of bone mineral density (BMD), bone volume, trabecular bone volume, and trabecular thickness. See, e.g., Tilman B. Drueke and Sharon M. Moe, Disturbances of bone and mineral metabolism in chronic kidney disease: an international initiative to improve diagnosis and treatment, Nephrol Dial Transplant (2004) 19: 534-536; Okuno S, Inaba M., Biochemical markers of bone turnover. New aspect. Dialysis and bone metabolic marker, Clin Calcium. 2009 August; 19(8):1084-91; Herberth J, Monier-Faugere M C, Mawad H W, Branscum A J, Herberth Z, Wang G, Cantor T, Malluche H H, The five most commonly used intact parathyroid hormone assays are useful for screening but not for diagnosing bone turnover abnormalities in CKD-5 subjects, Clin Nephrol. 2009 July; 72(1):5-14; Lehmann G, Ott U, Kaemmerer D, Schuetze J, Wolf G., Bone histomorphometry and biochemical markers of bone turnover in subjects with chronic kidney disease Stages 3-5, Clin Nephrol. 2008 October; 70(4):296-305; Drneke T B., Is parathyroid hormone measurement useful for the diagnosis of renal bone disease?, Kidney Int. 2008 March; 73(6):674-6; Yamada S, Inaba M, Kurajoh M, Shidara K, Imanishi Y, Ishimura E, Nishizawa Y., Utility of serum tartrate-resistant acid phosphatase (TRACP5b) as a bone resorption marker in subjects with chronic kidney disease: independence from renal dysfunction., Clin Endocrinol (Oxf). 2008 August; 69(2):189-96. Epub 2008 Jan. 23. See also, Paul D. Miller, Diagnosis and Treatment of Osteoporosis in Chronic Renal Disease, 2009.

Another marker for monitoring bone resorption in CKD subjects with mild renal dysfunction is serum concentration of type I collagen N-telopeptide (S-NTX). See, e.g., Hamano T, Fujii N, Nagasawa Y, Isaka Y, Moriyama T, Okada N, Imai E, Horio M, Ito T., Serum NTX is a practical marker for assessing antiresorptive therapy for glucocorticoid treated subjects with chronic kidney disease, Bone. 2006 November; 39(5):1067-72. Epub 2006 Jun. 16.

Quantitative computed tomography (QCT) can also be used to determine bone turnover.

Markers, such as, for example, Runx2 and A1p can be evaluated to monitor the oseoblastic transition in a subject. Markers, such as, for example, Sm22-alpha can be evaluated to monitor vascular smooth muscle function and the levels of differentiated vascular smooth muscle cells.

Heart size and cardiac hypertrophy can be determined by any method known to the skilled artisan, such as, for example, magnetic resonance imaging, electrocardiography, echocardiography, and noncontrast-enhanced cardiac computed tomography.

To assess the quality of life for a subject treated according to the methods provided herein, the Short Form (36) Health Suvey (SF-26) and/or the Functional Assessment of Cancer Therapy-Anemia (FACT-An) can be utilized.

The SF-36 (Version 2.0) is a self-administered instrument consisting of 8 multi-item scales that assess 8 health domains: (1) Physical functioning (PF), 10 items from 3a to 3j; (2) Role-Physical (RP), 4 items from 4a to 4d; (3) Bodily Pain (BP), items 7 and 8; (4) General Health (GH), items 1 and 11a to 11d, (5) Vitality (VT), items 9a, 9e, 9g, and 9i; (6) Social functioning (SF), items 6 and 10; (7) Role-Emotional (RE), items 5a, 5b, and 5c; and (8) Mental Health (MH), 5 items 9b, 9c, 9d, 9f and 9h. Two overall summary scores can also be obtained: (1) a Physical Component Summary score (PCS); and (2) a Mental Component Summary score (MCS). Health domain scores, as well as the PCS and MCS scores, are transformed to norm based scores (mean of 50 and SD of 10), with higher scores indicating better health. The primary interests of the SF-36 are the health domain norm-based scores, and the PCS and MCS norm-based scores. Summary statistics (n, mean, standard deviation, median, minimum, and maximum) of health domain norm-based scores, PCS and MCS norm-based scores, as well as change from baseline in these norm-based scores can be assessed. Scoring for the SF-36 and methods to address missing values can be accomplished according to directions provided by the instrument developers.

Alternatively, FACT-An can be utilized to determine quality of life for a subject treated according to the methods provided herein. FACT-An is a 47-item, cancer-specific questionnaire consisting of a core 27-item general questionnaire (FACT-General, or FACT-G Total) measuring the four general domains of quality of life (physical, social/family, emotional and functional wellbeing). FACT-An scales are formatted on 1-4 pages, by subscale domain, for self-administration using a 5-point Likert rating scale (0=Not at all; 1=A little bit; 2=Somewhat; 3=Quite a bit; and 4=Very much). Scoring for the FACT instrument can be completed at the total scale level according to directions provided by the instrument developer. The FACT-G total score can be scored by summing the four domains within the general HRQoL instrument.

With regard to common terminology criteria for adverse events (CTCAE, version 4.0), Grade 1 refers to mild adverse events. Specifically, Grade 1 refers to transient or mild discomfort. No limitation in activity and no medical intervention/therapy is required for Grade 1 adverse events. Grade 2 refers to moderate adverse events. Specifically, Grade 2 refers to mild to moderate limitation in activity. Some assistance may be needed, however, no or minimal medical intervention/therapy required for Grade 2 adverse events. Grade 3 refers to severe adverse events. Specifically, Grade 3 refers to marked limitation in activity. Some assistance is usually required and medical intervention/therapy is required, while hospitalization is possible for Grade 3 adverse events. Grade 4 refers to life-threatening adverse events. Specifically, Grade 4 refers to extreme limitation in activity, significant required assistance, significant required medical intervention/therapy, and hospitalization or hospice care is probable for Grade 4 adverse events. Grade 5 adverse event is death.

A hematocrit measures the percentage of red blood cells in a given volume of whole blood and may be included as part of a standard complete blood count. The hematocrit is normally about 45% for men and about 40% for women. However, beta-thalassemia patients typically have a hematocrit lower than that normally seen. Thus, determination of the hematocrit in a beta-thalassemia patient being treated in accordance with the methods provided herein allows for the determination of the efficacy of such treatment.

Hemoglobin concentration can be determined according to an assay known to one skilled in the art. Beta-thalassemia patients typically have a hemoglobin concentration lower than that normally seen. Thus, determination of the hemoglobin concentration in a beta-thalassemia patient being treated in accordance with the methods provided herein allows for the determination of the efficacy of such treatment.

7.11 Kits

Provided herein is a kit comprising one or more containers filled with one or more of the ActRII signaling inhibitors (see Section 7.8) and to provide the in vitro cell culture method of Section 7.4. In certain embodiments, the kit comprises a stromal cell derived from a reference population as described in Section 7.9. In certain embodiments, the kit comprises media for culturing a stromal cell. In certain embodiments, the kit comprises media for culturing an EPC. In certain embodiments, the kit comprises one or more reagents to determine the level of one or more biomarkers described herein. In certain embodiments, the reagent is an antibody specific for the biomarker. In certain embodiments, the reagent is an oligonucleotide that specifically hybridizes to a nucleic acid encoding the biomarker. In certain embodiments, the reagent comprises a primer set for use in PCR amplification of a nucleic acid encoding the biomarker. In certain embodiments, the biomarker is selected from a group consisting of GYPA, GATA1, GATA2, alpha-globin. ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2. In certain embodiments, the biomarker is GYPA. In certain embodiments, the biomarker is GATA1. In certain embodiments, the biomarker is GATA2. In certain embodiments, the biomarker is alpha-globin. In certain embodiments, the biomarker is ICAM-1. In certain embodiments, the biomarker is IL-1Ra. In certain embodiments, the biomarker is survivin. In certain embodiments, the biomarker is Bcl-2. In certain embodiments, the biomarker is Bcl-xL. In certain embodiments, the biomarker is MCP-1. In certain embodiments, the biomarker is serpinE1. In certain embodiments, the biomarker is GRO-a. In certain embodiments, the biomarker is IL-8. In certain embodiments, the biomarker is IL-10. In certain embodiments, the biomarker is IL-2. In certain embodiments, the biomarker is RANTES. In certain embodiments, the biomarker is IP-10. In certain embodiments, the biomarker is IL-1a. In certain embodiments, the biomarker is IL-1b. In certain embodiments, the biomarker is MIF. In certain embodiments, the biomarker is G-CSF. In certain embodiments, the biomarker is GMCSF. In certain embodiments, the biomarker is C5a. In certain embodiments, the biomarker is IL-6. In certain embodiments, the biomarker is HO-2. In certain embodiments, the biomarker is HIF-1a. In certain embodiments, the biomarker is TRAIL R1. In certain embodiments, the biomarker is cleaved caspase-3. In certain embodiments, the biomarker is p27. In certain embodiments, the biomarker is p21. In certain embodiments, the biomarker is Bax. In certain embodiments, the biomarker is Bad. In certain embodiments, the biomarker is CIAP1. In certain embodiments, the biomarker is PON2.

8. EXAMPLES

8.1 Example 1. Erythropoietic Response to a Ligand Trap of Activin Receptor in Cultures from Beta-Thalassemia Patients

8.1.1 Background

The hallmark of beta-thalassemias is ineffective erythropoiesis leading to anemia and tissue hypoxia. Activin has been shown to affect the erythropoiesis in the late-stage of maturation. ActRIIA-hFc (SEQ ID NO:7), a recombinant activin receptor type IIA (ActRIIA) ligand trap, binds with high affinity activin AB and other transforming growth factors. In animal models, ActRIIA-hFc (SEQ ID NO:7) reverses bone loss and increases hemoglobin and hematocrit by mechanisms not yet fully understood.

This example investigates the molecular mechanisms underlying the effect of ActRIIA-mFc (see, e.g., U.S. Pat. No. 8,173,601 and Carrancio et al., 2014, British Journal of Haematology, 165:870-882) on erythropoiesis at different stages of differentiation and maturation from beta-thalassemia patients.

8.1.2 Methods

CD34+-enriched EPCs were isolated from peripheral blood of beta-thalassemia patients and healthy donors by immunoselection. EPCs were cultured in presence or absence of ActRIIA-mFc (50 and 100 µg/mL) for 14 days in two conditions: liquid standard cultures and HS5 stromal cell line co-cultured with EPCs. Erythroid progenitor liquid cultures in medium from HS5 cells conditioned by ActRIIA-mFc (CM) were also set. Conditioned medium was assayed for apoptosis activity and cytokine content with ELISA.

In the co-cultures, the erythroid cells were rescued as non-adherent cells in supernatant (NAC), phase-bright cells adhering to the surface of HS5 cells (PBC) and phase-dim cells beneath the stromal cells (PDC). At day 14 erythroid cells were evaluated for cell number and viability, differentiation (GYPA/CD71/CD34) and gene expression profile.

(a) Isolation of $CD34^+$ Cells

CD34+-enriched cells were obtained from peripheral blood of 5 b-thalassemic patients and 5 healthy donors and prepared with the use of lymphocyte separation medium (Cappel, Aurora, Ohio). $CD34^+$ cells were positively selected by means of the mini-MACS immunomagnetic separation system (Miltenyi Biotec, Auburn, Calif.), according to the manufacturer's instructions. In brief, to obtain normal $CD34^+$ cells, $10^8$ or fewer mononuclear cells were washed twice and then suspended in 300 µL sorting buffer composed of 1× phosphate-buffered saline (PBS), 2 mM EDTA (ethylenediaminetetraacetic acid), and 0.5% bovine serum albumin. Cells were incubated with 100 µL human immunoglobulin—Fc receptor (FcR) blocking antibody and 100 µL monoclonal hapten-conjugated CD34 antibody (clone QBEND/10; Miltenyi Biotec) for 15 minutes at 4° C. After washing, cells were resuspended in 400 µL sorting buffer, and 100 µL paramagnetic microbeads conjugated to antihapten antibody were added, followed by incubation for 15 minutes at 4° C. After washing, cells were resuspended in sorting buffer, passed through a 30 µm nylon mesh, and separated in a column exposed to the magnetic field of the MACS device. The column was washed twice with sorting buffer and removed from the separator. Retained cells were eluted with sorting buffer by means of a plunger and subjected to a second separation. Purity of CD34 cells was 90% to 97% by flow cytometry analysis.

(b) Human Erythroid Progenitor Cell Culture

To reproduce erythropoiesis in vitro, a liquid culture method starting from erythroid progenitors of peripheral blood was utilized to obtain a pure erythroid population at different steps of differentiation and maturation. A total of $5\times10^4$ $CD34^+$ cells were cultured at 37° C. in flat-bottomed 6-well plates (Costar, Cambridge, Mass., USA) in 2 mL of standard medium consisting of alpha-minimal essential medium (a-MEM; GIBCO, Grand Island, N.Y.) supplemented with 30% fetal bovine serum (FBS; GIBCO, Grand Island, N.Y.), 20 ng/mL recombinant human (rH) stem cell factor (SCF, PeproTech, London, UK), 10 ng/mL rH interleukin-3 (IL-3, PeproTech, London, UK) and 3 U/mL rH erythropoietin (rHuepo, Janssen-Cilag, Milan, Italy). Cells were incubated at 37° C. with an atmosphere of 5% $CO_2$ for 14 days. ActRIIA-mFc was added at different concentration (0 µg/ml, 50 µg/ml, or 100 µg/ml) and at different stages of culture in order to determine its effects on erythroid maturation.

(c) Clonogenic Assay

Input $CD34^+$ cells ($5\times10^3$ cells) were plated in triplicate in 35-mm tissue culture dishes containing 1 mL methylcellulose semisolid culture medium (MethoCult H4435, Stem Cell Technologies, Grenoble, France) containing rhSCF 50 ng/mL, rhGM-CSF 20 ng/mL, rhIL-3 20 ng/mL, rhIL-6 20 ng/mL, rhG-CSF 20 ng/mL, and rhEPO 3 U/mL. After 14 days of incubation at 37° C. in 5% $CO_2$, BFU-E colony in culture were subsequently scored with an inverted microscope. Experiments were performed in triplicate. Colonies were defined as clusters consisting of 40 or more cells.

(d) Morphology Analysis

Cells were harvested at different days of culture (days 7 and 14). Cell morphology was analyzed by light microscopy on cytocentrifuged (Shandon Astmoor, England) smears stained with May-Grunwald-Giemsa, by assessing and counting cells in 5 different fields of view, for a total of 500 to 600 cells. Hemoglobin-containing cells were identified by benzidine staining.

(e) Proliferative and Phenotypic Analysis

Cell viability was determined at days 0, 4, 7, 10 and 14 of culture by counting of hematopoietic cells in each well using trypan blue stain (Stem Cell Technologies, USA) and stem cell and lineage markers were analyzed by flow cytometry (Partec, Germany) using fluorescein isothiocyanate (FITC)-conjugate anti-CD71 and phycoerythrin (PE)-conjugated anti-glycophorin A antibodies (BD, Becton Dickinson, San Jose, Calif.) to evaluate erythroid differentiation and phycoerythrin-Cy7 (PE)-conjugated anti-CD34, APC-conjugate anti-CD45 to assess the percentage of stem cells. Flow cytometric analysis was performed by incubating harvested cells with different fluorescent conjugated monoclonal antibodies at 4° C. for 30 minutes. Then the cells were washed in PBS and fixed with 2% paraformaldehyde (Sigma). Isotype controls were used in every experiment. Acquisition and analysis will be performed on a FACSCanto flow cytometer using FACSDiva 5.0 software (BD).

(f) Preparation of HS5 Cell Line

The Human Marrow Stromal cell (MSC) line used for the co-culture study is HS5, which is a multipotent cell line obtained by longterm murine bone marrow cultures and can be used as feeder layers in ex vivo bone marrow cultures or in colony forming assays. HS5 was maintained in Iscove's modified Dulbecco's medium (IMDM) supplemented with 20% fetal bovine serum (FBS) (Invitrogen, Calsbad, Calif., USA) and 10 ng/ml interleukin-3 (IL-3) (Calbiochem, San Diego, Calif., USA). The above cell lines were grown at 37° C. with 5% $CO_2$. Once adherent cells were more than 70% confluent, they were detached with 0.25% trypsin-EDTA (Gibco), counted and replated at a 1:3 dilution under the same culture conditions. ActRII ActRIIA-mFc was added at different concentration (0 µg/ml, 50 µg/ml, or 100 µg/ml) and at different days of culture (0, 3 and 6).

(g) Assessment of Chemokines in Conditioned Culture Media

Chemokine secretion of HS5 preparations was analyzed in conditioned culture media. Medium was conditioned by exposure to semi-confluent cultures of the immortalized human stromal cell lines for one week in presence of ActRIIA-mFc at different concentrations. The culture debris was pelleted by centrifugation at 2000×g for 10 minutes and the supernatant was then aliquoted and frozen at −20° C. Conditioned media was thawed only once prior to use.

Conditioned medium was assayed for colony apoptosis activity with Human Apoptosis Array Kit and for cytokine content with ELISAs using Human Cytokine Array Panel A (R&D Systems, Minneapolis, Minn.) according to manufacturer's specifications. Cells were treated with TNF-α in the presence or absence of apocynin, or untreated, for 24 h and media was collected and incubated with the array membrane. Washes and treatments were performed without deviation from the recommended protocol. Membranes were treated with HyGlo chemiluminescence detection reagent (Denville Scientific, Metuchen, N.J.) and exposed to film to for various time points to detect the signal. Films were scanned using a Canon Lide 100 instrument and subjected to densitometric analysis with ImageJ software (http://rsb.info.nih.gov/ij/). All experiments were carried out in triplicate (h) Co-Culture of Hematopoietic Stem Cells with the HS5 Stromal Cell Layer When HS5 cells reached more than 90% confluence in IMDM, they were washed with PBS and were re-placed in a serum free medium to co-culture with $CD34^+$ cells. $CD34^+$ HSC were suspended in Iscove's modified Dulbecco's medium containing 10% fetal calf serum (Biochrom, Cambridge, UK), 20 ng/mL SCF, 10 ng/mL IL-3 and 4 U/mL erythropoietin. HSC suspensions were plated at a density of $1 \times 10^4$ cells/$cm^2$ on a confluent HS5 layer at 37° C. in 5% $CO_2$. The co-cultures were maintained for 2 weeks with half medium change every 4 days. On each change during the first week $CD34^+$ cells from three distinct localizations in the co-culture were collected separately. Briefly, the supernatant of the co-culture was aspirated and the cells in the supernatant (non-adherent cells (NAC)) were collected. The HS5 layer was gently washed twice with PBS to remove the remaining non-adherent cells. After washing, the cells remaining on the MSC layer (phase-bright cells (PBC)) were collected by further intensive washing steps with PBS. When no phasebright cells could be observed under phase-contrast microscopy, the HS5 layer with the cells underneath the layer (phase-dim cells (PDC)) was trypsinized and collected as well. The three cell fractions were counted using trypan blue (vitality more than 95%).

(i) Gene Expression Analysis

Total cellular RNA was extracted from $CD34^+$ cells by means of TRIzol reagent (Invitrogen, Carlsbad, Calif.) or the High Purity RNA Isolation Kit (Roche Diagnostics, Indianapolis, Ind.), according to the manufacturers' protocols.

Reverse-transcription PCR from 1 µg of total RNA was performed using the High Capacity cDNA Reverse Transcription Kits (Applied Biosystems, Foster city, Calif., USA) in a total final volume of 20 µL. The reaction mixtures for quantitative polymerase chain reaction (PCR) were prepared using Taqman PCR probes specific for the gene of interest according to standard methods and analyzed by 7500 Real-time PCR System (Applied Biosystems, Foster city, Calif., USA). Experiments were performed as triplicate and the data were normalized to GAPDH.

(j) Statistical Analysis

Results obtained from multiple experiments are expressed as the mean±standard deviation (SD). The data were analyzed using the t-test. Probability values<0.05 defined significant differences between test points.

8.1.3 Results

At day 14 no significant differences between liquid cultures treated or not with ActRIIA-mFc were detected in cell number, viability and immunophenotype both in beta-thalassemia and control subjects. In beta-thalassemia co-cultures, no relevant differences in cell number and viability of the three cell fractions, in presence or absence of ActRIIA-mFc were observed; whereas regarding cell surface markers, GYPA was more expressed in NAC (1.5-fold, p<0.05) and in PDC (3.6-fold, p<0.001) treated with ActRIIA-mFc in comparison to non-treated fractions. Similar results were observed in controls. In CM cultures, erythroid precursors from beta-thalassemic patients expanded significantly in treated cells versus not-treated cells (6.5-fold vs. 3.1-fold). No significant differences were found in controls.

High levels of anti-inflammatory, anti-apoptotic cytokine (ICAM-1, IL-1Ra, survivin, Bcl-2 and Bcl-xL), and factors that favored erythroid differentiation (MCP-1, serpinE1 and GRO-a), were detected in CM.

At day 14 in the presence of ActRIIA-mFc, GATA1 expression increased (p<0.005) while GATA2 and alpha-globin expression decreased in erythroid thalassemic cells. In control subjects, no significant differences were observed.

In beta-thalassemic CM and co-cultures treated with ActRIIA-mFc, GATA1 mRNA production was strongly induced (p<0.001), while the levels of GATA2 and alpha-globin mRNA were significantly lower (p<0.005). Similar results were observed in controls.

8.1.4 Conclusions

These data indicate that ActRIIA-mFc does not affect directly the erythroid maturation, but acts through bone marrow-derived factors. Furthermore, ActRIIA-mFc recruits quiescent EPCs with more primitive properties (NAC and PDC) and leads them to differentiate, with a more marked effect on erythroid maturation.

8.2 Example 2. Study of Erythropoiesis Regulation by Sotatercept (ACE-011) in Human Normal and Beta-Thalassemic Erythroid Liquid Culture System 8.2.1 Introduction This example provides a more detailed description of certain of the experiments described in Example 1 (Section 8.1) and additional experiments as compared to Example 1 (Section 8.1).

8.2.2 Materials and Methods (a) Isolation of $CD34^+$ Cells

CD34+-enriched cells were obtained from peripheral blood of 5 b-thalassemic patients and 5 healthy donors and prepared with the use of lymphocyte separation medium (Cappel, Aurora, Ohio). $CD34^+$ cells were positively selected by means of the mini-MACS immunomagnetic separation system (Miltenyi Biotec, Auburn, Calif.), according to the manufacturer's instructions. In brief, to obtain normal $CD34^+$ cells, $10^8$ or fewer mononuclear cells were washed twice and then suspended in 300 µL sorting buffer composed of 1× phosphate-buffered saline (PBS), 2 mM EDTA (ethylenediaminetetraacetic acid), and 0.5% bovine serum albumin. Cells were incubated with 100 µL human immunoglobulin—Fc receptor (FcR) blocking antibody and 100 μL monoclonal hapten-conjugated CD34 antibody (clone QBEND/10; Miltenyi Biotec) for 15 minutes at 4° C. After washing, cells were resuspended in 400 μL sorting buffer, and 100 μL paramagnetic microbeads conjugated to antihapten antibody were added, followed by incubation for 15 minutes at 4° C. After washing, cells were resuspended in sorting buffer, passed through a 30 μm nylon mesh, and separated in a column exposed to the magnetic field of the MACS device. The column was washed twice with sorting buffer and removed from the separator. Retained cells were eluted with sorting buffer by means of a plunger and subjected to a second separation. Purity of CD34 cells was 90% to 97% by flow cytometry analysis.

(b) Human Erythroid Progenitor Cell Culture

To reproduce erythropoiesis in vitro, a liquid culture method starting from erythroid progenitors of peripheral blood was utilized to obtain a pure erythroid population at different steps of differentiation and maturation. A total of $5 \times 10^4$ CD34$^+$ cells were cultured at 37° C. in flat-bottomed 6-well plates (Costar, Cambridge, Mass., USA) in 2 mL of standard medium consisting of alpha-minimal essential medium (a-MEM; GIBCO, Grand Island, N.Y.) supplemented with 30% fetal bovine serum (FBS; GIBCO, Grand Island, N.Y.), 20 ng/mL recombinant human (rH) stem cell factor (SCF, PeproTech, London, UK), 10 ng/mL rH interleukin-3 (IL-3, PeproTech, London, UK) and 3 U/mL rH erythropoietin (rHuepo, Janssen-Cilag, Milan, Italy). Cells were incubated at 37° C. with an atmosphere of 5% $CO_2$ for 14 days. ActRIIA-hFc (SEQ ID NO: 7; also referred to as "Sotatercept") was added at different concentration (0 μg/ml, 50 μg/ml, or 100 μg/ml) and at different stages of culture in order to determine its effects on erythroid maturation.

(c) Clonogenic Assay

Input CD34$^+$ cells ($5 \times 10^3$ cells) were plated in triplicate in 35-mm tissue culture dishes containing 1 mL methylcellulose semisolid culture medium (MethoCult H4435, Stem Cell Technologies, Grenoble, France) containing rhSCF 50 ng/mL, rhGM-CSF 20 ng/mL, rhIL-3 20 ng/mL, rhIL-6 20 ng/mL, rhG-CSF 20 ng/mL, and rhEPO 3 U/mL. After 14 days of incubation at 37° C. in 5% $CO_2$, BFU-E colony in culture were subsequently scored with an inverted microscope. Experiments were performed in triplicate. Colonies were defined as clusters consisting of 40 or more cells.

(d) Morphology Analysis

Cells were harvested at different days of culture (days 7 and 14). Cell morphology was analyzed by light microscopy on cytocentrifuged (Shandon Astmoor, England) smears stained with May-Grunwald-Giemsa, by assessing and counting cells in 5 different fields of view, for a total of 500 to 600 cells. Hemoglobin-containing cells were identified by benzidine staining.

(e) Proliferative and Phenotypic Analysis

Cell viability was determined at days 0, 4, 7, 10 and 14 of culture by counting of hematopoietic cells in each well using trypan blue stain (Stem Cell Technologies, USA) and stem cell and lineage markers were analyzed by flow cytometry (Partec, Germany) using fluorescein isothiocyanate (FITC)-conjugate anti-CD71 and phycoerythrin (PE)-conjugated anti-glycophorin A antibodies (BD, Becton Dickinson, San Jose, Calif.) to evaluate erythroid differentiation and phycoerythrin-Cy7 (PE)-conjugated anti-CD34, APC-conjugate anti-CD45 to assess the percentage of stem cells. Flow cytometric analysis was performed by incubating harvested cells with different fluorescent conjugated monoclonal antibodies at 4° C. for 30 minutes. Then the cells were washed in PBS and fixed with 2% paraformaldehyde (Sigma). Isotype controls were used in every experiment. Acquisition and analysis will be performed on a FACSCanto flow cytometer using FACSDiva 5.0 software (BD).

(f) Preparation of HS5 Cell Line

The Human Marrow Stromal cell (MSC) line used for the co-culture study is HS5, which is a multipotent cell line obtained by longterm murine bone marrow cultures and can be used as feeder layers in ex vivo bone marrow cultures or in colony forming assays. HS5 was maintained in Iscove's modified Dulbecco's medium (IMDM) supplemented with 20% fetal bovine serum (FBS) (Invitrogen, Calsbad, Calif., USA) and 10 ng/ml interleukin-3 (IL-3) (Calbiochem, San Diego, Calif., USA). The above cell lines were grown at 37° C. with 5% $CO_2$. Once adherent cells were more than 70% confluent, they were detached with 0.25% trypsin-EDTA (Gibco), counted and replated at a 1:3 dilution under the same culture conditions. ActRIIA-hFc (SEQ ID NO: 7; also referred to as "Sotatercept") was added at different concentration (0 μg/ml, 50 μg/ml, or 100 μg/ml) and at different days of culture (0, 3 and 6).

(g) Assessment of Chemokines in Conditioned Culture Media

Chemokine secretion of HS5 preparations was analyzed in conditioned culture media. Medium was conditioned by exposure to semi-confluent cultures of the immortalized human stromal cell lines for one week in presence of ActRIIA-hFc (SEQ ID NO: 7; also referred to as "Sotatercept") at different concentrations. The culture debris was pelleted by centrifugation at 2000×g for 10 minutes and the supernatant was then aliquoted and frozen at −20° C. Conditioned media was thawed only once prior to use.

Conditioned medium was assayed for colony apoptosis activity with Human Apoptosis Array Kit and for cytokine content with ELISAs using Human Cytokine Array Panel A (R&D Systems, Minneapolis, Minn.) according to manufacturer's specifications. Cells were treated with TNF-α in the presence or absence of apocynin, or untreated, for 24 h and media was collected and incubated with the array membrane. Washes and treatments were performed without deviation from the recommended protocol. Membranes were treated with HyGlo chemiluminescence detection reagent (Denville Scientific, Metuchen, N.J.) and exposed to film to for various time points to detect the signal. Films were scanned using a Canon Lide 100 instrument and subjected to densitometric analysis with ImageJ software (http://rsb.info.nih.gov/ij/). All experiments were carried out in triplicate (h) Co-Culture of Hematopoietic Stem Cells (HSC) with the HS5 Stromal Cell Layer When HS5 cells reached more than 90% confluence in IMDM, they were washed with PBS and were re-placed in a serum free medium to co-culture with CD34$^+$ cells. CD34$^+$ HSC were suspended in Iscove's modified Dulbecco's medium containing 10% fetal calf serum (Biochrom, Cambridge, UK), 20 ng/mL SCF, 10 ng/mL IL-3 and 4 U/mL erythropoietin. HSC suspensions were plated at a density of $1 \times 10^4$ cells/cm$^2$ on a confluent HS5 layer at 37° C. in 5% $CO_2$. The co-cultures were maintained for 2 weeks with half medium change every 4 days. On each change during the first week CD34$^+$ cells from three distinct localizations in the co-culture were collected separately. Briefly, the supernatant of the co-culture was aspirated and the cells in the supernatant (non-adherent cells (NAC)) were collected. The HS5 layer was gently washed twice with PBS to remove the remaining non-adherent cells. After washing, the cells remaining on the MSC layer (phase-bright cells (PBC)) were collected by further intensive washing steps with PBS.

When no phasebright cells could be observed under phase-contrast microscopy, the HS5 layer with the cells underneath the layer (phase-dim cells (PDC)) was trypsinized and collected as well. The three cell fractions were counted using trypan blue (vitality more than 95%).

(i) Gene Expression Analysis

Total cellular RNA was extracted from CD34$^+$ cells by means of TRIzol reagent (Invitrogen, Carlsbad, Calif.) or the High Purity RNA Isolation Kit (Roche Diagnostics, Indianapolis, Ind.), according to the manufacturers' protocols.

Reverse-transcription PCR from 1 μg of total RNA was performed using the High Capacity cDNA Reverse Transcription Kits (Applied Biosystems, Foster city, Calif., USA) in a total final volume of 20 μL. The reaction mixtures for quantitative polymerase chain reaction (PCR) were prepared using Taqman PCR probes specific for the gene of interest according to standard methods and analyzed by 7500 Realtime PCR System (Applied Biosystems, Foster city, Calif., USA). Experiments were performed as triplicate and the data were normalized to GAPDH.

(j) Statistical Analysis

Results obtained from multiple experiments are expressed as the mean±standard deviation (SD). The data were analyzed using the t-test. Probability values<0.05 defined significant differences between test points.

8.2.3 Results (a) Ex Vivo Expansion of CD34+ Liquid Cultures with hActRIIA-Fc (SEQ ID NO:7)

To identify the effect of hActRIIA-Fc (SEQ ID NO:7) on ex vivo expansion capacity, especially for primitive progenitors, CD34+ cells mobilized from peripheral blood of thalassemic patients (n=5) or control patients (n=5) were cultured with or without hActRIIA-Fc (SEQ ID NO:7; 0 μg/mL, 50 μg/mL, or 100 μg/mL) for 2 weeks.

The viability and the expression levels of CD71 (transferrin receptor expressed on both proliferating cells and early erythroid cells), glycophorin A (GPA, a specific marker of the erythroid lineage), and CD34 were analyzed on the cell surface of intact cells by flow cytometry (FIG. 1). Culturing of the cells obtained from beta-thalassemic patients in the presence of hActRIIA-Fc (SEQ ID NO:7) did not result in alterations in the number or viability of CD34+ cells (0 μg/mL hActRIIA-Fc: 8.82±2.4×10$^5$ cells; 50 μg/mL hActRIIA-Fc: 9.2±1.9×10$^5$ cells; 100 μg/mL hActRIIA-Fc (SEQ ID NO:7): 9.4±2.5×10$^5$ cells; FIG. 1A). A similar result is also observed in the cells obtained from the control patients (FIG. 1B).

Erythropoietic cell differentiation was evaluated by morphological assessment using cytospin slides stained with neutral benzidine. In addition, the expression of surface antigens CD71, GPA, and CD45 (expressed on HSCs and non-erythroid cells such as myeloid cells) was determined by flow cytometry to monitor the differentiation of CD34+ HSCs into RBCs.

Microscopic evaluation showed an average of 30±11.1% reticulocytes and 38.2±8% normoblasts on day 14 in the standard culture. Only a marginal contamination by non-erythroid cells (5.0±3%) was observed on the last culture day. There were no significant differences between the different culture conditions.

CD71, CD34 and GPA-positive cells revealed distinct and progressive temporal changes. After 14 days of liquid cultures, the cells in each condition expressed high levels of GPA (35.0-59.3%), decreased expression of CD71 (32.5-40.3%), and low levels of CD34 (10.5-19.4%). However, the fraction of CD71−/GPA+/CD34− cells generated in the presence of hActRIIA-Fc (SEQ ID NO:7) was comparable to that observed in cells not treated with hActRIIA-Fc, both in thalassemic and control cultures (FIG. 1C).

These data indicate that hActRIIA-Fc (SEQ ID NO:7) has no direct impact on differentiation/proliferation of CD34+ progenitor cells.

(b) Ex Vivo Effect of hActRIIA-Fc (SEQ ID NO:7)-Treated Conditioned Media (CM) on CD34+ Proliferation and Differentiation To analyze the ability of hActRIIA-Fc (SEQ ID NO:7) to indirectly improve CD34+ ex vivo differentiation, purified CD34+ cells were cultured in the presence media obtained from cells cultured in the presence of stromal hActRIIA-Fc (hActRIIA-Fc CM) or in media obtained from stromal cells cultured in the absence of hActRIIA-Fc (control CM). SFT combination was used as growth factors. CD34+ cells were derived from beta-thalassemic patients (n=5) or controls patients (n=5).

The total nucleated cells from beta-thalassemic patients expanded significantly when cultured in the hActRIIA-Fc CM (64.9±26.2×10$^5$ cells) as compared to beta-thalassemic cells cultured in control CM (30.9±19.0×10$^5$ cells) (FIG. 2A). No significant differences were found between control cells cultured in hActRIIA-Fc CM and control cells cultured in control CM (FIG. 2B).

To investigate the impact of CM on CD34+ phenotype, flow cytometry analyses were performed. hActRIIA-Fc CM, at both 50 and 100 μg/mL concentrations, significantly increased the allostimulatory capacity of maturation of CD34+ cells, as demonstrated by high levels of GPA and low levels of CD71 and CD34 markers, both in cells obtained from beta-thalassemic and control subjects. Without being bound by any particular theory, hActRIIA-Fc (SEQ ID NO:7) affects the differentiation capacity of CD34+ cells during erythropoiesis by secretion of additional soluble factors from stromal cells treated with hActRIIA-Fc (SEQ ID NO:7), which may be due to the action of cytokine combination on CD34+ cells, or by a paracrine cross-talk between the expanding CD34+ cells and stromal cells.

(c) Colony-Forming Cell Assays

The clonogenic capacity of CD34+ cells cultured in presence of absence of hActRIIA-Fc (SEQ ID NO:7) was investigated. CD34+ cells were derived from beta-thalassemic patients (n=5) or controls subjects (n=5).

The hActRIIA-Fc (SEQ ID NO:7)-treated fraction produced a significantly higher proportion of BFU-E than the not-treated fraction (0 μg/mL hActRIIA-Fc: 49±1; 50 μg/mL hActRIIA-Fc: 70±0.7; and 100 μg/mL hActRIIA-Fc: 104±5; p<0.001), indicating that the hActRIIA-Fc (SEQ ID NO:7)-treated cells had a higher repopulating capacity.

(d) Chemokine Secretion of Marrow Stromal Cells

Without being bound by any particular theory, hActRIIA-Fc (SEQ ID NO:7)-treated conditioned media may function in modulating erythropoietic responses via induction of cytokines. To elucidate the hActRIIA-Fc (SEQ ID NO:7)-induced cytokine profile in primary human CD34+ cells, a cytokine array was performed to measure expression levels of 36 different cytokines. Cells were cultured in conditioned media obtained from stromal cells cultured with 0 μg/mL hActRIIA-Fc, 50 μg/mL hActRIIA-Fc, or 100 μg/mL hActRIIA for one week and chemokine secretion of marrow stromal cell preparations was analyzed in conditioned culture media using a semiquantitative array for 36 human cytokines and 35 apoptosis-related proteins.

For analysis, the cytokines were grouped as follows: (i) chemokines, (ii) Th1 cytokines, (iii) anti-inflammatory cytokines, (iv) cytokines involved in inflammation and cell differentiation and (v) IL-12 and IL-17 family cytokines (FIG. 3A-FIG. 3E). hActRIIA-Fc (SEQ ID NO:7)-mediated induction of cytokine expression was observed in the chemokine (MCP-1, serpinE, GRO-a, IL-8; FIG. 3A) and in anti-inflammatory (SICAM-1, IL-1Ra, IL-10 and IL-2; FIG. 3C and FIG. 3D) groups of cytokines. Decreases in cytokine levels in response to hActRIIA-Fc (SEQ ID NO:7) treatment were also observed (e.g., RANTES and IP-10 (FIG. 3A); IL-1a and IL-1b (FIG. 3B); MIF, G-CSF, GM-CSF, and C5a (FIG. 3D); and IL-6 (FIG. 3E)).

Without being bound by any particular theory, there was a distinctive pattern that was associated with maintenance of "stemness" status of CD34+ cells and marrow stem cells cultured with hActRIIA-Fc CM produced high levels of the anti-inflammatory molecules and factors that favored erythroid differentiation. IL-1a, IL-6, IL-8, MIF, G-CSF, GM-CSF, MCP1, SICAM1, C5/C5a were highly expressed in all hActRIIA-Fc CM, while there was a lower constitutive expression for various other cytokines (FIG. 3A-FIG. 3E).

To determine whether hActRIIA-Fc (SEQ ID NO:7) can alter the expression of apoptosis-related protein(s) in hActRIIA-Fc CM cultures, a protein array was performed to examine the change in expression of 35 apoptosis-related genes. A number of apoptotic signaling proteins were modulated following treatment with hActRIIA-Fc (SEQ ID NO:7) CM. As shown in FIG. 4A and FIG. 4B, the presence of hActRIIA-Fc (SEQ ID NO:7) CM significantly down-regulated the expression of pro-apoptotic cytokines (FIG. 4A: HO-2, HIF-1a, TRAIL R1, Cleaved Caspase-3, p27, p21, Bax and Bad) compared with control CM. In contrast, the expression of anti-apoptotic proteins CIAP-1, Bcl-2, Bcl-xL, PON2, and Survivin increased in hActRIIA-Fc CM as compared to their expression in control CM (FIG. 4B).

(e) Ex Vivo Expansion and Differentiation of Total CD34+ Cells over hActRIIA-Fc (SEQ ID NO:7)-Treated HS5 Stromal Cells To examine the hematopoiesis-supporting effects of human HS5 stromal cell line treated with hActRIIA-Fc (SEQ ID NO:7) at different concentrations, five thousand purified CD34+ cells, derived from beta-thalassemic patients (n=5) or controls subjects (n=5), were plated on a stromal cell layer after hActRIIA-Fc (SEQ ID NO:7) pretreatment with combinations of EPO, SCF, and IL-3. Cells not adhering and adhering weakly to stromal cells were collected by gentle pipetting after 2 weeks of culture for analysis. For 14 culture days, CD34+ cell numbers were counted by MACS system with CD34 antibody. CD34+ cells were increased after 14 days of culture (0 µg/ml hActRIIA-Fc: up to 4.0 fold, n=21.76±2.28×$10^5$ cells; 50 µg/ml hActRIIA-Fc: up to 5.0-fold, n=26.26±4.90×$10^5$ cells; 100 µg/ml hActRIIA-Fc: up to 6.0-fold, n=30.43±2.00×$10^5$ cells; not statistically relevant; FIG. 5A and FIG. 5B).

The expression of the stem/progenitor cell markers CD34, CD45, GPA and CD71 were examined by FACS analysis. Representative data of flow cytometric analysis of the cells at the start of culture and after 2 weeks of expansion culture are shown in FIG. 5C. Compared to the fraction treated with 0 µg/ml hActRIIA-Fc, the fractions treated with 50 µg/ml hActRIIA-Fc or 100 µg/ml hActRIIA-Fc included more cells with a more differentiated phenotype, such as GPA+ (60±2% vs 55±6%), CD71+ (30±10% vs 28±8%) and CD71+GPA+CD34− (43±2% vs 39±2%). CD34+CD71+ GPA-expressing cells, which, without being bound by any particular theory, are held to be even less differentiated, were rarely detected after 14 culture days and comprised only 10% in both fractions without a significant difference. There were no remarkable differences between hActRIIA-Fc (SEQ ID NO:7)-treated co-cultured conditions and co-cultures not-treated with hActRIIA-Fc.

(f) Ex Vivo Expansion and Differentiation of Total CD34+ Cells over HS5 Stromal Cells in Distinct Localizations CD34+ cells in co-culture are usually considered as a single population, and their localization relative to the marrow stem cell layer has not been investigated intensively. Without being bound by any particular theory, the stromal cells facilitate stem cell maintenance in ex vivo co-culture systems through the secretion of soluble factors and cell-cell contact. In addition, without being bound by any particular theory, a three-dimensional architecture may be important to mimic physiological conditions ex vivo. HS5 stromal cells served as a physical boundary of distinct compartments. The properties and features of CD34+ cells in different sites in relation to hActRIIA-Fc (SEQ ID NO:7) pre-treatment on stromal cells were evaluated to gain insight into the relationship between hActRIIA-Fc (SEQ ID NO:7) and three-dimensional CD34+/HS5 co-culture microenvironment. During the first week, hematopoietic stem cells from three distinct localizations in the co-culture were collected separately: non-adherent cells (NAC) were collected in the supernatant, phase-bright cells (PBC) were collected on the HS5 layer by further intensive washing steps with PBS, and phase-dim cells (PDC) were harvested underneath the layer after trypsin treatment. Finally, the three cell fractions were counted using trypan blue (vitality more than 95%) and measured as described below. Interestingly, the phase-dim fraction showed a slow expansion activity and a more immature phenotype. In contrast, the phase-bright fraction on the marrow stem cell surface revealed significantly more proliferation activity and non-adherent cells had a limited proliferation (FIG. 6A and FIG. 6B).

To determine the influence of cellular localization on CD34+ cell expansion in relationship to hActRIIA-Fc (SEQ ID NO:7) concentrations, cells were counted in their separated environments. CD34+ cells were derived from beta-thalassemic patients (n=5) or control subjects (n=5). Prior to day 4 of co-culture, the numbers of the three fractions increased similarly (FIG. 7A). After day 4 of co-culture, the number of phase-bright cells increased further, while the number of non-adherent cells and phase-dim cells remained almost constant (FIG. 7A). Interestingly, although the cell count was highest for phase-bright cells, the treatment with hActRIIA-Fc (SEQ ID NO:7) did not affect the proliferation activity of all three cellular fractions.

To investigate the impact of the localization on precursor differentiation, CD34+ cell phenotypes were determined by FACS analysis. Both non-adherent cells and phase-dim cells were enriched in GPA+CD71+CD34− in comparison to the phase-bright cells when HS5 stromal cell line were pre-treated with hActRIIA-Fc (SEQ ID NO:7). At day 14, GPA was more highly expressed in non-adherent (1.5-fold, p<0.05) and in phase-dim cells (3.6-fold, p<0.001) when hActRIIA-Fc (SEQ ID NO:7) was added to stromal feeder layer at concentration of 100 µg/ml in comparison to no treatment of stromal cells (FIG. 7B). The proportion of GPA+CD71+CD34− cells in the phase-bright fraction increased after 14 days of co-culture, but the drop was not correlated with the addition of hActRIIA-Fc in the cultures media.

Without being bound by any particular theory, the effect of hActRIIA-Fc (SEQ ID NO:7) on cell proliferation and differentiation differs according to the localization of the cells, suggesting that the more slowly proliferating CD34+ cells (NAC, PDC) grown beneath hActRIIA-Fc (SEQ ID NO:7)-treated stromal layer seem to lose their more primitive stemness features and to be stimulated to differentiate.

(g) Gene Expression Analysis

Gene expression analyses of untreated and treated cells were performed in different conditioned culture conditions to determine the effects of hActRIIA-Fc (SEQ ID NO:7) on erythropoiesis. In particular, GATA1, GATA2, alpha, beta, and gamma-globin gene expression was analyzed in CD34+ cells cultured in liquid method, conditioned media, and co-cultures with HS5. The CD34+ cells were derived from beta-thalassemic patients (n=5) or controls subjects (n=5).

In cells grown in liquid culture, addition of hActRIIA-Fc (SEQ ID NO:7) resulted in a significant increase in the expression of GATA1 ($p<0.005$) and a decrease in the levels of GATA2 and b-globin genes in the beta-thalassemic-derived cells (FIG. 8A-FIG. 8D). In cells derived from control subjects, hActRIIA-Fc (SEQ ID NO:7) stimulation resulted in no significant decrease in the levels of α-globin gene; on the other hand, the presence of hActRIIA-Fc (SEQ ID NO:7) had no effect on GATA1 and GATA2 mRNA expression (FIG. 8A-FIG. 8C)

In cells incubated in conditioned medium, hActRIIA-Fc (SEQ ID NO:7) pre-treatment contributed to the suppression of GATA2 and α-globin expression and enhancement of GATA1 expression ($p<0.005$), both in beta-thalassemic and controls cells (FIG. 8A-FIG. 8C).

GATA1 mRNA production was strongly induced in CD34+ cells co-cultured with hActRIIA-Fc (SEQ ID NO:7)-treated feeder layer ($p<0.001$) (FIG. 8A). In contrast, the level of GATA2 and α-globin mRNA were significantly lower in CD34/HS5 co-cultures containing hActRIIA-Fc (SEQ ID NO:7) at concentration of 100 µg/mL than in cells cultured without hActRIIA-Fc (SEQ ID NO:7) treatment (FIG. 8B and FIG. 8C). These results indicate that the expression of erythroid-specific genes (GATA-1 and GATA-2) and α-globin gene in different culture conditions is mediated directly or indirectly by hActRIIA-Fc (SEQ ID NO:7) signaling.

In NAC and PDC fractions, a significant increase in the expression of GATA1 ($p<0.001$ in NAC fraction at 50 µg/mL hActRIIA-Fc (SEQ ID NO:7) and in PDC fraction at 100 µg/mL hActRIIA-Fc (SEQ ID NO:7)) and a concomitant decrease in GATA2. In contrast, the effect of hActRIIA-Fc (SEQ ID NO:7) on GATA1 and GATA2 gene expression in the PBC did not have statistical significance and was not correlated to the concentrations of hActRIIA-Fc (SEQ ID NO:7) in pre-treated cells (FIG. 9). hActRIIA-Fc (SEQ ID NO:7) induced a decrease in alpha-globin mRNA chains in NAC and PDC cells, but not on beta-globin chains.

8.2.4 Conclusions

Without being bound by any particular theory, the stimulatory effect of hActRIIA-Fc (SEQ ID NO:7) on erythropoiesis does not function directly on erythroid precursors, but is likely is mediated by inhibition of bone marrow-derived factors. hActRIIA-Fc (SEQ ID NO:7) treatment resulted in a specific secreted cytokine profile. Additionally, hActRIIA-Fc (SEQ ID NO:7) is a strong inducer of anti-inflammatory cytokine expression inflammatory (SICAM-1, IL-1Ra, IL-10 and IL-2), while inhibiting basal expression of others (RANTES, IP-10, IL1a, IL1b, MIF, G-CSF, GM-CSF, IL-6). Additionally, certain proteins involved in inhibition of apoptosis, such as survivin, Bcl-2 and Bcl-xL, were induced, and certain pro-apoptotic cytokines were down-regulated. Suppression of RANTES, Il-6, and IL-1 signaling caused less inflammatory rate in expanded cells, and activation of Bcl-2 signaling contributed to enhanced anti-apoptotic effects.

In addition, three different compartments were identified in the co-culture system utilized herein: (i) the supernatant, in which HSC grow without direct contact with MSC; (ii) the surface of MSC; and (iii) the environment beneath the MSC layer. All three locations are dynamically linked with each other, and are characterized by special features. Without being bound by any particular theory, hActRIIA-Fc (SEQ ID NO:7) probably recruits quiescent CD34+ cells with more primitive properties that were non-adherent or had migrated beneath the feeder layer and leads them to differentiate.

Reverse transcriptase PCR analysis revealed a decrease in α-globin (Hbb-a1) and GATA2 gene expression and an increase in GATA1 expression compared to that in controls, which may contribute to the promotion of terminal erythroid maturation and the correction of α-globin precipitation in circulating RBCs.

Without being bound by any particular theory, hActRIIA-Fc (SEQ ID NO:7) promotes erythroid maturation of quiescent mid-late erythroid precursors and reduces inflammation and oxidative stress during the late stages of erythropoiesis.

9. DESCRIPTION OF THE SEQUENCES

TABLE 1

Sequence Information.

| SEQ ID NO. | DESCRIPTION | SEQUENCE |
|---|---|---|
| 1 | human ActRIIA precursor polypeptide | MGAAAKLAFAVFLISCSSGAILGRSETQECLFFNANWEKDRTNQTGVEPCYGDKDKRRH CFATWKNISGSIEIVKQGCWLDDINCYDRTDCVEKKDSPEVYFCCCEGNMCNEKFSYFP EMEVTQPTSNPVTPKPPYYNILLYSLVPLMLIAGIVICAFWVYRHHKMAYPPVLVPTQD PGPPPPSPLLGLKPLQLLEVKARGRFGCVWKAQLLNEYVAVKIFPIQDKQSWQNEYEVY SLPGMKHENILQFIGAEKRGTSVDVDLWLITAFHEKGSLSDFLKANVVSWNELCHIAET MARGLAYLHEDIPGLKDGHKPAISHRDIKSKNVLLKNNLTACIADGFLALKFEAGKSAG DTHGQVGTRRYMAPEVLEGAINFQRDAFLRIDMYAMGLVLWELASRCTAADGPVDEYML PFEEEIGQHPSLEDMQEVVVHKKKRPVLRDYWQKHAGMAMLCETIEECWDHDAEARLSA GCVGERITQMQRLTNIITTEDIVTVVTMVTNVDFPPKESSL |
| 2 | human ActRIIA soluble (extracellular), processed polypeptide sequence | ILGRSETQECLFFNANWEKDRTNQTGVEPCYGDKDKRRHCFATWKNISGSIEIVKQGCW LDDINCYDRTDCVEKKDSPEVYFCCCEGNMCNEKFSYFPEMEVTQPTSNPVTPKPP |
| 3 | human ActRIIA soluble (extracellular), | ILGRSETQECLFFNANWEKDRTNQTGVEPCYGDKDKRRHCFATWKNISGSIEIVKQGCW LDDINCYDRTDCVEKKDSPEVYFCCCEGNMCNEKFSYFPEM |

TABLE 1-continued

Sequence Information.

| SEQ ID NO. | DESCRIPTION | SEQUENCE |
|---|---|---|
| | processed polypeptide sequence with the C-terminal 15 amino acids deleted | |
| 4 | nucleic acid sequence encoding human ActRIIA precursor protein | ATGGGAGCTGCTGCAAAGTTGGCGTTTGCCGTCTTTCTTATCTCCTGTTCTTCAGGTGC TATACTTGGTAGATCAGAAACTCAGGAGTGTCTTTTCTTTAATGCTAATTGGGAAAAAG ACAGAACCAATCAAACTGGTGTTGAACCGTGTTATGGTGACAAAGATAAACGGCGGCAT TGTTTTGCTACCTGGAAGAATATTTCTGGTTCCATTGAAATAGTGAAACAAGGTTGTTG GCTGGATGATATCAACTGCTATGACAGGACTGATTGTGTAGAAAAAAAAGACAGCCCTG AAGTATATTTTTGTTGCTGTGAGGGCAATATGTGTAATGAAAAGTTTTCTTATTTTCCA GAGATGGAAGTCACACAGCCCACTTCAAATCCAGTTACACCTAAGCCACCCTATTACAA CATCCTGCTCTATTCCTTGGTGCCACTTATGTTAATTGCGGGGATTGTCATTTGTGCAT TTTGGGTGTACAGGCATCACAAGATGGCCTACCCTCCTGTACTTGTTCCAACTCAAGAC CCAGGACCACCCCCACCTTCTCCATTACTAGGGTTGAAACCACTGCAGTTATTAGAAGT GAAAGCAAGGGGAAGATTTGGTTGTGTCTGGAAAGCCCAGTTGCTTAACGAATATGTGG CTGTCAAATATTTCCAATACAGGACAAACAGTCATGGCAAAATGAATACGAAGTCTAC AGTTTGCCTGGAATGAAGCATGAGAACATATTACAGTTCATTGGTGCAGAAAAACGAGG CACCAGTGTTGATGTGGATCTTTGGCTGATCACAGCATTTCATGAAAAGGGTTCACTAT CAGACTTTCTTAAGGCTAATGTGGTCTCTTGGAATGAACTGTGTCATATTGCAGAAACC ATGGCTAGAGGATTGGCATATTTACATGAGGATATACCTGGCCTAAAAGATGGCCACAA ACCTGCCATATCTCACAGGGACATCAAAAGTAAAATGTGCTGTTGAAAAACAACCTGA CAGCTTGCATTGCTGACTTTGGGTTGGCCTTAAAATTTGAGGCTGGCAAGTCTGCAGGC GATACCCATGGACAGGTTGGTACCCGGAGGTACATGGCTCCAGAGGTATTAGAGGGTGC TATAAACTTCGAAAGGGATGCATTTTTGAGGATAGATATGTATGCCATGGGATTAGTCC TATGGGAACTGGCTTCTCGCTGTACTGCTGCAGATGGACCTGTAGATGAATACATGTTG CCATTTGAGGAGGAAATTGGCCAGCATCCATCTCTTGAAGACATGCAGGAAGTTGTTGT GCATAAAAAAAAGAGGCCTGTTTTAAGAGATTATTGGCAGAAACATGCTGGAATGGCAA TGCTCTGTGAAACCATTGAAGAATGTTGGGATCACGACGCAGAAGCCAGGTTATCAGCT GGATGTGTAGGTGAAAGAATTACCCAGATGCAGAGACTAACAAATATTATTACCACAGA GGACATTGTAACAGTGGTCACAATGGTGACAAATGTTGACTTTCCTCCCAAAGAATCTA GTCTATGA |
| 5 | nucleic acid sequence encoding a human ActRIIA soluble (extracellular) polypeptide | ATACTTGGTAGATCAGAAACTCAGGAGTGTCTTTTCTTTAATGCTAATTGGGAAAAAGA CAGAACCAATCAAACTGGTGTTGAACCGTGTTATGGTGACAAAGATAAACGGCGGCATT GTTTTGCTACCTGGAAGAATATTTCTGGTTCCATTGAAATAGTGAAACAAGGTTGTTGG CTGGATGATATCAACTGCTATGACAGGACTGATTGTGTAGAAAAAAAAGACAGCCCTGA AGTATATTTTTGTTGCTGTGAGGGCAATATGTGTAATGAAAAGTTTTCTTATTTTCCAG AGATGGAAGTCACACAGCCCACTTCAAATCCAGTTACACCTAAGCCACCC |
| 6 | fusion protein comprising a soluble extracelluar domain of ActRIIA fused to an Fc domain | THTCPPCPAPELLGGPSVFLFPPKPKDTLMISRTPEVTCVVVDX1VSHEDPEVKFNWYV DGVEVHNAKTKPREEQYNSTYRVVSVLTVLHQDWLNGKEYKCKX2VSNAKLPVPIEKTI SKAKGQPREPQVYTLPPSREEMTKNQVSLTCLVKGFYPSDIAVEWESNGQPENNYKTTP PVLDSDGPFFLYSKLTVDKSRWQQGNVFSCSVMHEALHNX3HYTQKSLSLSPGK (wherein X1 is D or A; X2 is K or A and X3 is N or A) |
| 7 | Extracellular domain of human ActRIIA fused to a human Fc domain | ILGRSETQECLFFNANWEKDRTNQTGVEPCYGDKDKRRHCFATWKNISGSIEIVKQGCW LDDINCYDRTDCVEKKDSPEVYFCCCEGNMCNEKFSYFPEMEVTQPTSNPVTPKPPTGG GTHTCPPCPAPELLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKALPVPIEKTISKA KGQPREPQVYTLPPSREEMTKNQVSLTCLVKGFYPSDIAVEWESNGQPENNYKTTPPVL DSDGSFFLYSKLTVDKSRWQQGNVFSCSVMHEALHNHYTQKSLSLSPGK |
| 8 | Leader sequence of Honey bee mellitin (HBML) | MKFLVNVALVFMVVYISYIYA |
| 9 | Leader sequence of Tissue Plasminogen Activator (TPA) | MDAMKRGLCCVLLLCGAVFVSP |
| 10 | Native ActRIIA leader | MGAAAKLAFAVFLISCSSGA |
| 11 | ActRIIA-hFc and mActRIIA-Fc N-terminal sequence | ILGRSETQE |
| 12 | ActRIIA-Fc Protein with deletion of the C-terminal 15 amino acids of the extracellular domain of ActRIIA | ILGRSETQECLFFNANWEKDRTNQTGVEPCYGDKDKRRHCFATWKNISGSIEIVKQGCW LDDINCYDRTDCVEKKDSPEVYFCCCRGNMCNEKFSYFPEMTGGGTHTCPPCPAPELLG GPSVFLFPPKPKDTLMISRTPEVTCVVVDVSHEDPEVKFNWYVDGVEVHNAKTKPREEQ YNSTYRVVSVLTVLHQDWLNGKEYKCKVSNKALPVPIEKTISKAKGQPREPQVYTLPPS REEMTKNQVSLTCLVKGFYPSDIAVEWESNGQPENNYKTTPPVLDSDGSFFLYSKLTVD KSRWQQGNVFSCSVMHEALHNHYTQKSLSLSPGK |

TABLE 1-continued

Sequence Information.

| SEQ ID NO. | DESCRIPTION | SEQUENCE |
|---|---|---|
| 13 | Unprocessed ActRIIA-hFc with TPA leader sequence | MDAMKRGLCCVLLLCGAFVFSPGAAILGRSETQECLFFNANWEKDRTNQTGVEPCYGDK DKRRHCFATWKNISGSIEIVKQGCWLDDINCYDRTDCVEKKDSPEVYFCCCEGNMCNEK FSYFPEMEVTQPTSNPVTPKPPTGGGTHTCPPCPAPELLGGPSVFLFPPKPKDTLMISR TPEVTCVVVDVSHEDPEVKFNWYVDGVEVHNAKTKPREEQYNSTYRVVSVLTVLHQDWL NGKEYKCKVSNKALPVPIEKTISKAKGQPREPQVYTLPPSREEMTKNQVSLTCLVKGFY PSDIAVEWESNGQPENNYKTTPPVLDSDGSFFLYSKLTVDKSRWQQGNVFSCSVMHEAL HNHYTQKSLSLSPGK |
| 14 | Nucleic acid sequence encoding Unprocessed ActRIIA-hFc with TPA leader sequence | ATGGATGCAATGAAGAGAGGGCTCTGCTGTGTGCTGCTGCTGTGTGGAGCAGTCTTCGT TTCGCCCGGCGCCGCTATACTTGGTAGATCAGAAACTCAGGAGTGTCTTTTTTTAATGC TAATTGGGAAAAAGACAGAACCAATCAAACTGGTGTTGAACCGTGTTATGGTGACAAAG ATAAACGGCGGCATTGTTTTGCTACCTGGAAGAATATTTCTGGTTCCATTGAATAGTGA AACAAGGTTGTTGGCTGGATGATATCAACTGCTATGACAGGACTGATTGTGTAGAAAAA AAAGACAGCCCTGAAGTATATTTCTGTTGCTGTGAGGGCAATATGTGTAATGAAAAGTT TTCTTATTTTCCGGAGATGGAAGTCACACAGCCCACTTCAAATCCAGTTACACCTAAGC CACCCACCGGTGGTGGAACTCACACATGCCCACCGTGCCCAGCACCTGAACTCCTGGGG GGACCGTCAGTCTTCCTCTTCCCCCCAAAACCCAAGGACACCCTCATGATCTCCCGGAC CCCTGAGGTCACATGCGTGGTGGTGGACGTGAGCCACGAAGACCCTGAGGTCAAGTTCA ACTGGTACGTGGACGGCGTGGAGGTGCATAATGCCAAGACAAAGCCGCGGGAGGAGCAG TACAACAGCACGTACCGTGTGGTCAGCGTCCTCACCGTCCTGCACCAGGACTGGCTGAA TGGCAAGGAGTACAAGTGCAAGGTCTCCAACAAAGCCCTCCCAGTCCCCATCGAGAAAA CCATCTCCAAAGCCAAAGGGCAGCCCCGAGAACCACAGGTGTACACCCTGCCCCCATCC CGGGAGGAGATGACCAAGAACCAGGTCAGCCTGACCTGCCTGGTCAAAGGCTTCTATCC CAGCGACATCGCCGTGGAGTGGGAGAGCAATGGGCAGCCGGAGAACAACTACAAGACCA CGCCTCCCGTGCTGGACTCCGACGGCTCCTTCTTCCTCTATAGCAAGCTCACCGTGGAC AAGAGCAGGTGGCAGCAGGGGAACGTCTTCTCATGCTCCGTGATGCATGAGGCTCTGCA CAACCACTACACGCAGAAGAGCCTCTCCCTGTCTCCGGTAAATGAGAATTC |
| 15 | human ActRIIB soluble (extracellular), processed polypeptide sequence with the N-terminal 6 amino acids of the EC domain deleted and the C-terminal 4 amino acids of the EC domain deleted (amino acids 25-130 of SEQ ID NO: 28) and with an L79D mutation | ETRECIYYNANWELERTNQSGLERCEGEQDKRLHCYASWRNSSGTIELVKKGCWDDDFN CYDRQECVATEENPQVYFCCCEGNFCNERFTHLPEAGGPEVTYEPPP |
| 16 | human ActRIIB precursor protein sequence (A64) | MTAPWVALALLWGSLWPGSGRGEAETRECIYYNANWELERTNQSGLERCEGEQDKRLHC YASWANSSGTIELVKKGCWLDDFNCYDRQECVATEENPQVYFCCCEGNFCNERFTHLPE AGGPEVTYEPPPTAPTLLLTVLAYSLLPIGGLSLIVLLAFWMYRHRKPPYGHVDIHEDPG PPPPSPLVGLKPLQLLEIKARGRFGCVWKAQLMNDFVAVKIFPLQDKQSWQSEREIFST PGMKHENLLQFIAAEKRGSNLEVELWLITAFHDKGSLTDYLKGNIITWNELCHVAETMS RGLSYLHEDVPWCRGEGHKPSIAHRDFKSKNVLLKSDLTAVLADFGLAVRFEPGKPPGD THGQVGTRRYMAPEVLEGAINFQRDAFLRIDMYAMGLVLWELVSRCKAADGPVDEYMLP FEEEIGQHPSLEELQEVVHKKMRPTIKDHWLKHPGLAQLCVTIEECWDHDAEARLSAG CVEERVSLIRRSVNGTTSDCLVSLVTSVTNVDLPPKESSI |
| 17 | human ActRIIB soluble (extracellular), processed polypeptide sequence (amino acids 19-134 of SEQ ID NO: 16) | SGRGEAETRECIYYNANWELERTNQSGLERCEGEQDKRLHCYASWANSSGTIELVKKGC WLDDFNCYDRQECVATEENPQVYFCCCEGNFCNERFTHLPEAGGPEVTYEPPPTAPT |
| 18 | human ActRIIB soluble (extracellular), processed polypeptide sequence with the C-terminal 15 amino acids deleted (amino acids 19-119 of SEQ ID NO: 16) | SGRGEAETRECIYYNANWELERTNQSGLERCEGEQDKRLHCYASWANSSGTIELVKKGC WLDDFNCYDRQECVATEENPQVYFCCCEGNFCNERFTHLPEA |
| 19 | nucleic acid sequence encoding a human ActRIIB (A64) precursor protein | ATGACGGCGCCCTGGGTGGCCCTCGCCCTCCTCTGGGGATCGCTGTGGCCCGGCTCTGG GCGTGGGGAGGCTGAGACACGGGAGTGCATCTACTACAACGCCAACTGGGAGCTGGAGC GCACCAACCAGAGCGGCCTGGAGCGCTGCGAAGGCGAGCAGGACAAGCGGCTGCACTGC TACGCCTCCTGGGCCAACAGCTCTGGCACCATCGAGCTCGTGAAGAAGGGCTGCTGGCT AGATGACTTCAACTGCTACGATAGGCAGGAGTGTGTGGCCACTGAGGAGAACCCCCAGG TGTACTTCTGCTGCTGTGAAGGCAACTTCTGCAACGAGCGCTTCACTCATTTGCCAGAG GCTGGGGGCCCGGAAGTCACGTACGAGCCACCCCCGACAGCCCCACCCTGCTCACGGT GCTGGCCTACTCACTGCTGCCCATCGGGGGCCTTTCCCTCATCGTCCTGCTGGCCTTTT |

TABLE 1-continued

Sequence Information.

| SEQ ID NO. | DESCRIPTION | SEQUENCE |
|---|---|---|
|  |  | GGATGTACCGGCATCGCAAGCCCCCCTACGGTCATGTGGACATCCATGAGGACCCTGGG<br>CCTCCACCACCATCCCCTCTGGTGGGCCTGAAGCCACTGCAGCTGCTGGAGATCAAGGC<br>TCGGGGGCGCTTTGGCTGTGTCTGGAAGGCCCAGCTCATGAATGACTTTGTAGCTGTCA<br>AGATCTTCCCACTCCAGGACAAGCAGTCGTGGCAGAGTGAACGGGAGATCTTCAGCACA<br>CCTGGCATGAAGCACGAGAACCTGCTACAGTTCATTGCTGCCGAGAAGCGAGGCTCCAA<br>CCTCGAAGTAGAGCTGTGGCTCATCACGGCCTTCCATGACAAGGGCTCCCTCACGGATT<br>ACCTCAAGGGGAACATCATCACATGGAACGAACTGTGTCATGTAGCAGAGACGATGTCA<br>CGAGGCCTCTCATACCTGCATGAGGATGTGCCCTGGTGCCGTGGCGAGGGCCACAAGCC<br>GTCTATTGCCCACAGGGACTTTAAAAGTAAGAATGTATTGCTGAAGAGCGACCTCACAG<br>CCGTGCTGGCTGACTTTGGCTTGGCTGTTCGATTTGAGCCAGGGGAAACCTCCAGGGGAC<br>ACCCACGGACAGGTAGGCACGAGACGGTACATGGCTCCTGAGGTGCTCGAGGGAGCCAT<br>CAACTTCCAGAGAGATGCCTTCCTGCGCATTGACATGTATGCCATGGGGTTGGTGCTGT<br>GGGAGCTTGTGTCTCGCTGCAAGGCTGCAGACGGACCCGTGGATGAGTACATGCTGCCC<br>TTTGAGGAAGAGATTGGCCAGCACCCTTCGTTGGAGGAGCTGCAGGAGGTGGTGGTGCA<br>CAAGAAGATGAGGCCCACCATTAAAGATCACTGGTTGAAACACCCGGGCCTGGCCCAGC<br>TTTGTGTGACCATCGAGGAGTGCTGGGACCATGATGCAGAGGCTCGCTTGTCCGCGGGC<br>TGTGTGGAGGAGCGGGTGTCCCTGATTCGGAGGTCGGTCAACGGCACTACCTCGGACTG<br>TCTCGTTTCCCTGGTGACCTCTGTCACCAATGTGGACCTGCCCCCTAAAGAGTCAAGCA<br>TCTAA |
| 20 | fusion protein comprising a soluble extracellular domain of ActRIIB (A64; SEQ ID NO: 17) fused to an Fc domain | SGRGEAETRECIYYNANWELERTNQSGLRECEGEQDKRLHCYASWANSSGTIELVKKGC<br>WLDDFNCYDRQECVATEENPQVYFCCCEGNFCNERFTHLPEAGGPEVTYEPPPTAPTGG<br>GTHTCPPCPAPELLGGPSVFLFPPKPKDTLMISRTPEVTCVVVDVSHEDPEVKFNWYVD<br>GVEVHNAKTKPREEQYNSTYRVVSVLTVLHQDWLNGKEYKCKVSNKALPVPIEKTISKA<br>KGQPREPQVYTLPPSREEMTKNQVSLTCLVKGFYPSDIAVEWESNGQPENNYKTTPPVL<br>DSDGSFFLYSKLTVSKSRWQQGNVFSCSVMHEALHNHYTQKSLSLSPGK |
| 21 | fusion protein comprising a soluble extracellular domain of ActRIIB (A64) with the C-terminal 15 amino acids deleted (SEQ ID NO: 18) fused to an Fc domain | SGRGEAETRECIYYNANWELERTNQSGLRECEGEQDKRLHCYASWANSSGTIELVKKGC<br>WLDDFNCYDRQECVATEENPQVYFCCCEGNFCNERFTHLPEAGGGTHTCPPCPAPELLG<br>GPSVFLFPPKPKDTLMISRTPEVTCVVVDVSHEDPEVKFNWYVDGVEVHNAKTKPREEQ<br>YNSTYRVVSVLTVLHQDWLNGKEYKCKVSNKALPVPIEKTISKAKGQPREPQVYTLPPS<br>REEMTKNQVSLTCLVKGFYPSDIAVEWESNGQPENNYKTTPPVLDSDGSSFLYSKLTVD<br>KSRWQQGNVFSCSVMHEALHNHYTQKSLSLSPGK |
| 22 | human ActRIIB soluble (extracellular), processed polypeptide sequence with the N-terminal 6 amino acids of the EC domain deleted and the C-terminal 5 amino acids of the EC domain deleted (amino acids 25-129 of SEQ ID NO: 28) and with an L79D mutation | ETRECIYYNANWELERTNQSGLERCEGEQDKRLHCYASWRNSSGTIELVKKGCWDDDFN<br>CYDRQECVATEENPQVYFCCCEGNFCNERFTHLPEAGGPEVTYEPP |
| 23 | human ActRIIB soluble (extracellular), processed polypeptide sequence with the N-terminal 6 amino acids of the EC domain deleted and the C-terminal 3 amino acids of the EC domain deleted (amino acids 25-131 of SEQ ID NO: 28) and with an L79D mutation | ETRECIYYNANWELERTNQSGLERCEGEQDKRLHCYASWRNSSGTIELVKKGCWDDDFN<br>CYDRQECVATEENPQVYFCCCEGNFCNERFTHLPEAGGPEVTYEPPPT |
| 24 | Unprocessed ActRIIB-Fc fusion protein with the N-terminal 6 amino acids of the EC domain deleted and the C-terminal 3 amino acids of the EC domain deleted (amino acids 25-131 of SEQ ID NO: 28) and with an L79D mutation and | MDAMKRGLCCVLLLCGAVFVSPGAAETRECIYYNANWELERTNQSGLERCEGEQDKRLH<br>CYASWRNSSGTIELVKKGCWDDDFVCYDRQECVATEENPQVYFCCCEGNFCNERFTHLP<br>EAGGPEVTYEPPPTGGGTHTCPPCPAPELLGGPSVFLFPPKPKDTLMISRTPEVTCVVV<br>DVSHEDPEVKFNWYVDGVEVHNAKTKPREEQYNSTYRVVSVLTVLHQDWLNGKEYKCKV<br>SNKALPAPIEKTISKAKGQPREPQVYTLPPSREEMTKNQVSLTCLVKGFYPSDIAVEWE<br>SNGQPENNYKTTPPVLDSDGSSFLYSKLTVDKSRWQQGNVFSCSVMHEALHNHYTQKSL<br>SLSPGK |

TABLE 1-continued

Sequence Information.

| SEQ ID NO. | DESCRIPTION | SEQUENCE |
|---|---|---|
| | with TPA leader sequence | |
| 25 | Processed ActRIIB-Fc fusion protein with the N-terminal 6 amino acids of the EC domain deleted and the C-terminal 3 amino acids of the EC domain deleted (amino acids 25-131 of SEQ ID NO: 28) and with an L79D mutation | ETRECIYYNANWELERTNQSGLERCEGEQDKRLHCYASWRNSSGTIELVKKGCWDDDFN CYDRQECVATEENPQVYFCCCEGNFCNERFTHLPEAGGPEVTYEPPPTGGGTHTCPPCP APELLGGPSVFLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKAKGQPREPQV YTLPPSREEMTKNQVSLTCLVKGFYPSDIAVEWESNGQPENNYKTTPPVLDSDGSFFLY SKLTVDKSRWQQGNVFSCSVMHEALHNHYTQKSLSLSPGK |
| 26 | human ActRIIB soluble (extracellular), processed polypeptide sequence (amino acids 20-134 of SEQ ID NO: 16) | GRGEAETRECIYYNANWELERTNQSGLERCEGEQDKRHCYASWANSSGTIELVKKGCWL DDFNCYDRQECVATEENPQVYFCCCEGNFCNERFTHLPEAGGPEVTYEPPPTAPT |
| 27 | human ActRIIB soluble (extracellular), processed polypeptide sequence with the C-terminal 15 amino acids deleted (amino acids 20-119 of SEQ ID NO: 16) | GRGEAETRECIYYNANWELERTNQSGLERCEGEQDKRLHCYASWANSSGTIELVKKGCW LDDFNCYDRQECVATEENPQVYFCCCEGNFCNERFTHLPEA |
| 28 | human ActRIIB precursor protein sequence (R64) | MTAPWVALALLWGSLWPGSGRGEAETRECIYYNANWELERTNQSGLERCEGEQDKRLHC YASWRNSSGTIELVKKGVWLDDFNCYDRQECVATEENPQVYFCCCEGNFCNERFTHLPE AGGPEVTYEPPPTAPTLLTVLAYSLLPIGGLSLIVLLAFWMYRHRKPPYGHVDIHEDPG PPPPSPLVGLKPLQLLEIKARGRFGCVWKAQLMNDFVAVKIFPLQDKQSWQSEREIFST PGMKHENLLQFIAAEKRGSNLEVELWLITAFHDKGSLTDYLKGNIITWNELCHVAETMS RGLSYLHEDVPWCRGEGHKPSIAHRDFNSKNVLLKSDLTAVLADFGLAVRFEPGKPPGD THGQVGTRRYMAPEVLEGAINFQRDAFLRIDMYAMGLVLWELVSRCKAADGPVDEYMLP FEEEIGQHPSLEELQEVVVHKKMRPTIKDHWLKHPGLAQLCVTIEECWDHDAEARLSAG CVEERVSLIRRSVNGTTSDCLVSLVTSVTNVDLPPKESSI |
| 29 | human ActRIIB soluble (extracellular), processed polypeptide sequence (amino acids 19-134 of SEQ ID NO: 28) | SGRGEAETRECIYYNANWELERTNQSGLERCEGEQDKRLHCYASWRNSSGTIELVKKGC WLDDFNCYDRQECVATEENPQVYFCCCEGNFCNERFTHLPEAGGPEVTYEPPPTAPT |
| 30 | human ActRIIB soluble (extracellular), processed polypeptide sequence with the C-terminal 15 amino acids deleted (amino acids 19-119 of SEQ ID NO: 28) | SGRGEAETRECIYYNANWELERTNQSGLERCEGEQDKRLHCYASWRNSSGTIELVKKGC WLDDFNCYDRQECVATEENQPVYFCCCEGNFCNERFTHLPEA |
| 31 | human ActRIIB soluble (extracellular), processed polypeptide sequence (amino acids 20-134 of SEQ ID NO: 28) | GRGEAETRECIYYNANWELERTNQSGLERCEGEQDKRLHCYASWRNSSGITELVKKGCW LDDFNCYDRQECVATEENPQVYFCCCEGNFCNERFTHLPEAGGPEVTYEPPPTAPT |
| 32 | human ActRIIB soluble (extracellular), processed polypeptide sequence with the C-terminal 15 amino acids deleted (amino acids 20-119 of SEQ ID NO: 28) | GRGEAETRECIYYNANWELERTNQSGLERCEGEQDKRLHCYASWRNSSGITELVKKGCW LDDFNCYDRQECVATEENPQVYFCCCEGNFCNERFTHLPEA |
| 33 | human ActRIIB soluble (extracellular), processed polypeptide sequence with the N-terminal 6 amino acids | ETRECIYYNANWELERTNQSGLERCEGEQDKRLHCYASWANSSGTIELVKKGCWDDDFN CYDRQECVATEENPQVYFCCCEGNFCNERFTHLPEAGGPEVTYEPPPT |

TABLE 1-continued

Sequence Information.

| SEQ ID NO. | DESCRIPTION | SEQUENCE |
|---|---|---|
| | of the EC domain deleted and the C-terminal 3 amino acids of the EC domain deleted (amino acids 25-131 of SEQ ID NO: 16) and with an L79D mutation | |
| 34 | Unprocessed ActRIIB-Fc fusion protein with the N-terminal 6 amino acids of the EC domain deleted and the C-terminal 3 amino acids of the EC domain deleted (amino acids 25-131 of SEQ ID NO: 16) and with an L79D mutation and with TPA leader sequence | MDAMKRGLCCVLLLCGAVFVSPGAAETRECIYYNANWELERTNQSLGERCEGEQDKRLH CYASWANSSGITELVKKGCWDDDFNVYDRQECVATEENPQVYFCCCEGNFCNERFTHLP EAGGPEVTYEPPPTGGGTHTCPPCPAPELLGGPSVFLFPPKPKDTLMISRTPEVTCVVV DVSHEDPEVKFNWYVDGVEVHNAKTKPREEQYNSTYRVVSVLTVLHQDWLNGKEYKCKV SNKALPAPIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEALHNHYTQKSL SLSPGK |
| 35 | Processed ActRIIB-Fc fusion protein with the N-terminal 6 amino acids of the EC domain deleted and the C-terminal 3 amino acids of the EC domain deleted (amino acids 25-131 of SEQ ID NO: 16) and with an L79D mutation | ETRECIYYNANWELERTNQSLGERCEGEQDKRLHCYASWANSSGITELVKKGCWDDDFN CYDRQECVATEENPQVYFCCCEGNFCNERFTHLPEAGGPEVTYEPPPTGGGTHTCPPCP APELLGGPSVFLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKAKGQPREPQV YTLPPSREEMTKNQVSLTCLVKGFYPSDIAVEWESNGQPENNYKTTPPVLDSDGSFFLY SKLTVDKSRWQQGNVFSCSVMHEALHNHYTQKSLSLSPGK |
| 36 | human ActRIIB soluble (extracellular), processed polypeptide sequence (amino acids 20-134 of SEQ ID NO: 28) with L79D mutation | GRGEAETRECIYYNANWELERTNQSGLERCEGEQDKRLHCYASWNRSSGTIELVKKGCW DDDFNCYDRQECVATEEPNQVYFCCCEGNFCNERFTHLPEAGGPEVTYEPPPTAPT |
| 37 | human ActRIIB soluble (extracellular), processed polypeptide sequence (amino acids 20-134 of SEQ ID NO: 16) with L79D mutation | GRGEAETRECIYYNANWELERTNQSLGERCEGEQDKRLHCYASWANSSGITELVKKGCW DDDFNCYDRQECVATEENPQVYFCCCEGNFCNERFTHLPEAGGPEVTYEPPPTAPT |
| 38 | human ActRIIB soluble (extracellular), processed polypeptide sequence (amino acids 20-134 of SEQ ID NO: 28) with L79D mutation fused to an Fc domian with a GGG linker | GRGEAETRECIYYNANWELERTNQSLGERCEGEQDKRLHCYASWRNSSGTIELVKKGCW DDDFNCYDRQECVATEENPQVYFCCCEGNFCNERFTHLPEAGGPEVTYEPPPTAPTGGG THTCPPCPAPELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPAPIEKTISKAK GQPREPQVYTLPPSREEMTKNQVSLTCLVKGFYPSDIAVEWESNGQPENNYKTTPPVLD SDGSFFLYSKLTVDKSRWQQGNVFSCSVMHEALHNHYTQKSLSLSPGK |
| 39 | human ActRIIB soluble (extracellular), processed polypeptide sequence (amino acids 20-134 of SEQ ID NO: 16) with L79D mutation fused to an Fc domain | GRGEAETRECIYYNANWELERTNQSLGERCEGEQDKRLHCYASWANSSGTIELVKKGCW DDDFNCYDRQECVATEENPQVYFCCCEGNFCNERFTHLPEAGGPEVTYEPPPTAPTGGG THTCPPCPAPELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPAPIEKTISKAK GQPREPQVYTLPPSREEMTKNQVSLTCLVKGFYPSDIAVEWESNGQPENNYKTTPPVLD SDGSFFLYSKLTVDKSRWQQGNVFSCSVMHEALHNHYTQKSLSLSPGK |
| 40 | human ActRIIB soluble (extracellular), processed polypeptide sequence (amino acids 20-134 of SEQ ID NO: 28) with L79D mutation fused to an | MDAMKRGLCCVLLLCGAVFVSPGASGRGEAETRECIYYNANWELERTNQSGLERCEGEQ DKRLHCYASWANSSGTIELVKKGCWDDDFNVYDRQECVATEENPQVYFCCCEGNFCNER FTHLPEAGGPEVTYEPPPTAPTGGGTHTCPPCPAPELLGGPSVFLFPPKPKDTLMISRT PEVTCVVVDVSHEDPEVKFNWYVDGVEVHNAKTKPREEQYNSTYRVVSVLTVLHQDWLN GKEYKCKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVMHEALH NHYTQKSLSLSPGK |

TABLE 1-continued

Sequence Information.

| SEQ ID NO. | DESCRIPTION | SEQUENCE |
|---|---|---|
| | Fc domain and with TPA leader sequence | |
| 41 | human ActRIIB soluble (extracellular), processed polypeptide sequence (amino acids 20-134 of SEQ ID NO: 168) with L79D mutation fused to an Fc domain and with TPA leader sequence | MDAMKRGLCCVLLLCGAVFVSPGASGRGEAETRECIYYNANWELERTNQSGLERCEGEQ DKRLHCYASWANSSGTIELVKKGCWDDDFNCYDRQECVATEENPQVYFCCCEGNFCNER FTHLPEAGGPEVTYEPPPTAPTGGGTHTCPPCPAPELLGGPSVFLFPPKPKDTLMISRT PEVTCVVVDVSHEDPEVKFNWYVDGVEVHNAKTKPREEQYNSTYRVVSVLTVLHQDWLN GKEYKCKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVMHEALH NHYTQKSLSLSPGK |
| 42 | human ActRIIB soluble (extracellular), processed polypeptide sequence having a variant C-terminal sequence (disclosed in WO2007/053775) | GRGEAETRECIYYNANWELERTNQSLGERCEGEQDKRLHCYASWRNSSGTIELVKKGCW LDDFNCYDRQECVATEENPQVYFCCCEGNFCNERFTHLPEAGGPEGPWASTTIPSGGPE ATAAAGDQGSGALSLCLEGPAHE |
| 43 | human ActRIIB soluble (extracellular), processed polypeptide sequence having a variant C-terminal sequence (disclosed in WO2007/053775) having an L79D mutation | GRGEAETRECIYYNANWELERTNQSGLERCEGEQDKRLHCYASWRNSSGTIELVKKGCW DDDFNCYDRQECVATEENPQVYFCCCEGNFCNERFTHLPEAGGPEGPWASTTIPSGGPE ATAAAGDQGSGALWLCLEGPAHE |
| 44 | human ActRIIB soluble (extracellular), processed polypeptide sequence having a variant C-terminal sequence (disclosed in WO2007/053775) having an L79D mutation fused to an Fc domain with a TGGG linker | GRGEAETRECIYYNANWELERTNQSGLERCEGEQDKRLHCYASWRNSSGTIELVKKGCW DDDFNCYDRQECVATEENPQVYFCCCEGNFCNERFTHLPEAGGPEGPWASTTIPSGGPE ATAAAGDQGSGALWLCLEGPAHETGGGTHTCPPCPAPELLGGPSVFLFPPKPKDTLMIS RTPEVTCVVVDVSHEDPEVKFNWYVDGVEVHNAKTKPREEQYNSTYRVVSVLTVLHQDW LNGKEYKCKVSNKALPAPIEKTISKAKGQPREPQVYTLPPSREEMTKNQVSLTCLVKGF YPSDIAVEWESNGQPENNYKTTPPVLDSDGSFFLYSKLTVDKSRWQQGNVFSCSVMHEA LHNHYTQKSLSLSPGK |
| 45 | Nucleic Acid Sequence Encoding SEQ ID NO: 24 | ATGGATGCAATGAAGAGAGGGCTCTGCTGTGTGCTGCTGCTGTGTGGAGCAGTCTTCGT TTCGCCCGGCGCCGCCGAAACCCGCGAATGTATTTATTACAATGCTAATTGGGAACTCG AACGGACGAACCAATCCGGGCTCGAACGGTGTGAGGGGGAACAGGATAAACGCCTCCAT TGCTATGCGTCGTGGAGGAACTCCTCCGGGACGATTGAACTGGTCAAGAAAGGGTGCTG GGACGACGATTTCAATTGTTATGACCGCCAGGAATGTGTCGCGACCGAAGAGAATCCGC AGGTCTATTTCTGTTGTTGCGAGGGGAATTTCTGTAATGAACGGTTTACCCACCTCCCC GAAGCCGGCGGGCCCGAGGTGACCTATGAACCCCCGCCCACCGGTGGTGGAACTCACAC ATGCCCACCGTGCCCAGCACCTGAACTCCTGGGGGGACCGTCAGTCTTCCTCTTCCCCC CAAAACCCAAGGACACCCTCATGATCTCCCGGACCCCTGAGGTCACATGCGTGGTGGTG GACGTGAGCCACGAAGACCCTGAGGTCAAGTTCAACTGGTACGTGGACGGCGTGGAGGT GCATAATGCCAAGACAAAGCCGCGGGAGGAGCAGTACAACAGCACGTACCGTGTGGTCA GCGTCCTCACCGTCCTGCACCAGGACTGGCTGAATGGCAAGGAGTACAAGTGCAAGGTC TCCAACAAAGCCCTCCCAGCCCCCATCGAGAAAACCATCTCCAAAGCCAAAGGGCAGCC CCGAGAACCACAGGTGTACACCCTGCCCCCATCCCGGGAGGAGATGACCAAGAACCAGG TCAGCCTGACCTGCCTGGTCAAAGGCTTCTATCCCAGCAGACATCGCCGTGGAGTGGGA GAGCAATGGGCAGCCGGAGAACAACTACAAGACCACGCCTCCCGTGCTGGACTCCGACG GCTCCTTCTTCCTCTATAGCAAGCTCACCGTGGACAAGAGCAGGTGGCAGCAGGGGAAC GTCTTCTCATGCTCCGTGATGCATGAGGCTCTGCACAACCACTACACGCAGAAGAGCCT CTCCCTGTCCCCGGGTAAATGA |
| 46 | fusion protein comprising a soluble extracellular domain of ActRIIB (R64; SEQ ID NO: 29) fused to an Fc domain | SGRGEAETRECIYYNANWELERTNQSGLERCEGEQDKRLHCYASWRNSSGTIELVKKGC WLDDFNCYDRQECVATEENPQVYFCCCEGNFCNERFTHLPEAGGPEVTYEPPPTAPTGG GTHTCPPCPAPELLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKALPVPIEKTISKA KGQPREPQVYTLPPSREEMTKNQVSLTCLVKGFYPSDIAVEWESNGQPENNYKTTPPVL DSDGSFFLYSKLTVDKSRWQQGNVFSCSVMHEALHNHYTQKSLSLSPGK |
| 47 | fusion protein comprising a soluble extracellular domain of ActRIIB (R64) with the C-terminal 15 | SGRGEAETRECIYYNANWELERTNQSGLERCEGEQDKRLHCYASWRNSSGTIELVKKGC WLDDFNCYDRQECVATEENPQVYFCCCEGNFCNERFTHLPEAGGGTHTCPPCPAPELLG GPSVFLFPPKPKDTLMISRTPEVTCVVVDVSHEDPEVKFNWYVDGVEVHNAKTKPREEQ YNSTYRVVSVLTVLHQDWLNGKEYKCKVSNKALPVPIEKTISKAKGQPREPQVYTLPPS REEMTKNQVSLTCLVKGFYPSDIAVEWESNGQPENNYKTTPPVLDSDGSFFLYSKLTVD |

TABLE 1-continued

Sequence Information.

| SEQ ID NO. | DESCRIPTION | SEQUENCE |
|---|---|---|
| | amino acids deleted (SEQ ID NO: 30) fused to an Fc domain | KSRWQQGNVFSCSVMHEALHNHYTQKSLSLSPGK |

10. EQUIVALENTS

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims. Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference in their entireties.

SEQUENCE LISTING

<160> NUMBER OF SEQ ID NOS: 47

<210> SEQ ID NO 1
<211> LENGTH: 513
<212> TYPE: PRT
<213> ORGANISM: Homo sapiens
<220> FEATURE:
<223> OTHER INFORMATION: human ActRIIA precursor polypeptide

<400> SEQUENCE: 1

```
Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
        195                 200                 205
```

Ala Gln Leu Leu Asn Glu Tyr Val Ala Val Lys Ile Phe Pro Ile Gln
    210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
        275                 280                 285

Leu Cys His Ile Ala Glu Thr Met Ala Arg Gly Leu Ala Tyr Leu His
    290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
            340                 345                 350

Ala Gly Asp Thr His Gly Gln Val Gly Thr Arg Arg Tyr Met Ala Pro
        355                 360                 365

Glu Val Leu Glu Gly Ala Ile Asn Phe Gln Arg Asp Ala Phe Leu Arg
    370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
            420                 425                 430

Val His Lys Lys Lys Arg Pro Val Leu Arg Asp Tyr Trp Gln Lys His
        435                 440                 445

Ala Gly Met Ala Met Leu Cys Glu Thr Ile Glu Glu Cys Trp Asp His
    450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495

Val Val Thr Met Val Thr Asn Val Asp Phe Pro Pro Lys Glu Ser Ser
            500                 505                 510

Leu

<210> SEQ ID NO 2
<211> LENGTH: 115
<212> TYPE: PRT
<213> ORGANISM: Homo sapiens
<220> FEATURE:
<223> OTHER INFORMATION: human ActRIIA soluble (extracellular),
      processed polypeptide sequence

<400> SEQUENCE: 2

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
        50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro
        115

<210> SEQ ID NO 3
<211> LENGTH: 100
<212> TYPE: PRT
<213> ORGANISM: Artificial Sequence
<220> FEATURE:
<223> OTHER INFORMATION: human ActRIIA soluble (extracellular),
      processed polypeptide sequence with the C-terminal 15 amino acids
      deleted

<400> SEQUENCE: 3

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met
            100

<210> SEQ ID NO 4
<211> LENGTH: 1542
<212> TYPE: DNA
<213> ORGANISM: Homo sapiens
<220> FEATURE:
<223> OTHER INFORMATION: nucleic acid sequence of human ActRIIA
      precursor protein

<400> SEQUENCE: 4
atgggagctg ctgcaaagtt ggcgtttgcc gtctttctta tctcctgttc ttcaggtgct      60
atacttggta gatcagaaac tcaggagtgt cttttcttta atgctaattg ggaaaaagac     120
agaaccaatc aaactggtgt tgaaccgtgt tatggtgaca agataaacg gcggcattgt     180 tttgctacct ggaagaatat ttctggttcc attgaaatag tgaaacaagg ttgttggctg     240
gatgatatca actgctatga caggactgat tgtgtagaaa aaaagacag ccctgaagta     300 tatttttgtt gctgtgaggg caatatgtgt aatgaaaagt tttcttattt tccagagatg     360
gaagtcacac agcccacttc aaatccagtt acacctaagc cacccatta caacatcctg     420 ctctattcct tggtgccact tatgttaatt gcggggattg tcatttgtgc attttgggtg     480
tacaggcatc acaagatggc ctaccctcct gtacttgttc aactcaaga cccaggacca     540 ccccacctt ctccattact agggttgaaa ccactgcagt tattagaagt gaaagcaagg     600

```
ggaagatttg gttgtgtctg gaaagcccag ttgcttaacg aatatgtggc tgtcaaaata    660
tttccaatac aggacaaaca gtcatggcaa aatgaatacg aagtctacag tttgcctgga    720
atgaagcatg agaacatatt acagttcatt ggtgcagaaa acgaggcac cagtgttgat     780 gtggatcttt ggctgatcac agcatttcat gaaaagggtt cactatcaga ctttcttaag    840
gctaatgtgg tctcttggaa tgaactgtgt catattgcag aaaccatggc tagaggattg    900
gcatatttac atgaggatat acctggccta aaagatggcc acaaacctgc catatctcac    960
agggacatca aaagtaaaaa tgtgctgttg aaaaacaacc tgacagcttg cattgctgac   1020
tttgggttgg ccttaaaatt tgaggctggc aagtctgcag gcgataccca tggacaggtt   1080
ggtacccgga ggtacatggc tccagaggta ttagagggtg ctataaactt cgaaagggat   1140 gcattttga ggatagatat gtatgccatg ggattagtcc tatgggaact ggcttctcgc    1200
tgtactgctg cagatggacc tgtagatgaa tacatgttgc catttgagga ggaaattggc   1260
cagcatccat ctcttgaaga catgcaggaa gttgttgtgc ataaaaaaaa gaggcctgtt   1320
ttaagagatt attggcagaa acatgctgga atggcaatgc tctgtgaaac cattgaagaa   1380
tgttgggatc acgacgcaga agccaggtta tcagctggat gtgtaggtga agaattacc    1440 cagatgcaga gactaacaaa tattattacc acagaggaca ttgtaacagt ggtcacaatg   1500
gtgacaaatg ttgactttcc tcccaaagaa tctagtctat ga                     1542

<210> SEQ ID NO 5
<211> LENGTH: 345
<212> TYPE: DNA
<213> ORGANISM: Homo sapiens
<220> FEATURE:
<223> OTHER INFORMATION: human ActRIIA soluble (extracellular)
      polypeptide

<400> SEQUENCE: 5
atacttggta gatcagaaac tcaggagtgt cttttcttta atgctaattg ggaaaaagac     60
agaaccaatc aaactggtgt tgaaccgtgt tatggtgaca agataaacg gcggcattgt    120 tttgctacct ggaagaatat ttctggttcc attgaaatag tgaaacaagg ttgttggctg    180
gatgatatca actgctatga caggactgat tgtgtagaaa aaaagacag ccctgaagta    240 tattttgtt gctgtgaggg caatatgtgt aatgaaaagt tttcttattt tccagagatg    300
gaagtcacac agcccacttc aaatccagtt acacctaagc caccc                   345

<210> SEQ ID NO 6
<211> LENGTH: 228
<212> TYPE: PRT
<213> ORGANISM: Artificial Sequence
<220> FEATURE:
<223> OTHER INFORMATION: fusion protein comprising a soluble
      extracellular domain of ActRIIA fused to an Fc domain
<220> FEATURE:
<221> NAME/KEY: VARIANT
<222> LOCATION: 44
<223> OTHER INFORMATION: Xaa = Asp or Ala
<220> FEATURE:
<221> NAME/KEY: VARIANT
<222> LOCATION: 102
<223> OTHER INFORMATION: Xaa = Lys or Ala
<220> FEATURE:
<221> NAME/KEY: VARIANT
<222> LOCATION: 215
<223> OTHER INFORMATION: Xaa = Asn or Ala

<400> SEQUENCE: 6

Thr His Thr Cys Pro Pro Cys Pro Ala Pro Glu Leu Leu Gly Gly Pro
```

```
  1               5                  10                 15
Ser Val Phe Leu Phe Pro Pro Lys Pro Lys Asp Thr Leu Met Ile Ser
                 20                 25             30

Arg Thr Pro Glu Val Thr Cys Val Val Asp Xaa Val Ser His Glu
             35              40              45

Asp Pro Glu Val Lys Phe Asn Trp Tyr Val Asp Gly Val Glu Val His
         50                  55              60

Asn Ala Lys Thr Lys Pro Arg Glu Glu Gln Tyr Asn Ser Thr Tyr Arg
65              70                  75                  80

Val Val Ser Val Leu Thr Val Leu His Gln Asp Trp Leu Asn Gly Lys
             85                  90                  95

Glu Tyr Lys Cys Lys Xaa Val Ser Asn Lys Ala Leu Pro Val Pro Ile
             100                 105             110

Glu Lys Thr Ile Ser Lys Ala Lys Gly Gln Pro Arg Glu Pro Gln Val
             115                 120                 125

Tyr Thr Leu Pro Pro Ser Arg Glu Glu Met Thr Lys Asn Gln Val Ser
             130             135                 140

Leu Thr Cys Leu Val Lys Gly Phe Tyr Pro Ser Asp Ile Ala Val Glu
145             150                 155                 160

Trp Glu Ser Asn Gly Gln Pro Glu Asn Asn Tyr Lys Thr Thr Pro Pro
                 165                 170                 175

Val Leu Asp Ser Asp Gly Pro Phe Phe Leu Tyr Ser Lys Leu Thr Val
             180                 185                 190

Asp Lys Ser Arg Trp Gln Gln Gly Asn Val Phe Ser Cys Ser Val Met
             195                 200                 205

His Glu Ala Leu His Asn Xaa His Tyr Thr Gln Lys Ser Leu Ser Leu
         210                 215                 220

Ser Pro Gly Lys
225

<210> SEQ ID NO 7
<211> LENGTH: 344
<212> TYPE: PRT
<213> ORGANISM: Artificial Sequence
<220> FEATURE:
<223> OTHER INFORMATION: Extracellular domain of human ActRIIA fused to
      a human Fc domain

<400> SEQUENCE: 7

Ile Leu Gly Arg Ser Glu Thr Gln Glu Cys Leu Phe Phe Asn Ala Asn
1               5                  10                  15

Trp Glu Lys Asp Arg Thr Asn Gln Thr Gly Val Glu Pro Cys Tyr Gly
             20                  25              30

Asp Lys Asp Lys Arg Arg His Cys Phe Ala Thr Trp Lys Asn Ile Ser
             35              40                  45

Gly Ser Ile Glu Ile Val Lys Gln Gly Cys Trp Leu Asp Asp Ile Asn
         50                  55              60

Cys Tyr Asp Arg Thr Asp Cys Val Glu Lys Lys Asp Ser Pro Glu Val
65              70                  75                  80

Tyr Phe Cys Cys Cys Glu Gly Asn Met Cys Asn Glu Lys Phe Ser Tyr
                 85                  90                  95

Phe Pro Glu Met Glu Val Thr Gln Pro Thr Ser Asn Pro Val Thr Pro
             100                 105             110

Lys Pro Pro Thr Gly Gly Gly Thr His Thr Cys Pro Pro Cys Pro Ala
             115                 120                 125
```

```
Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 8
<211> LENGTH: 21
<212> TYPE: PRT
<213> ORGANISM: Artificial Sequence
<220> FEATURE:
<223> OTHER INFORMATION: Leader sequence of Honey bee mellitin (HBML)

<400> SEQUENCE: 8

Met Lys Phe Leu Val Asn Val Ala Leu Val Phe Met Val Val Tyr Ile
1               5                   10                  15

Ser Tyr Ile Tyr Ala
            20

<210> SEQ ID NO 9
<211> LENGTH: 22
<212> TYPE: PRT
<213> ORGANISM: Artificial Sequence
<220> FEATURE:
<223> OTHER INFORMATION: Leader sequence of Tissue Plasminogen Activator
      (TPA)

<400> SEQUENCE: 9

Met Asp Ala Met Lys Arg Gly Leu Cys Cys Val Leu Leu Leu Cys Gly
1               5                   10                  15

Ala Val Phe Val Ser Pro
            20

<210> SEQ ID NO 10
<211> LENGTH: 20
<212> TYPE: PRT
```

<213> ORGANISM: Artificial Sequence
<220> FEATURE:
<223> OTHER INFORMATION: Native ActRIIA leader

<400> SEQUENCE: 10

Met Gly Ala Ala Ala Lys Leu Ala Phe Ala Val Phe Leu Ile Ser Cys
1               5                   10                  15

Ser Ser Gly Ala
            20

<210> SEQ ID NO 11
<211> LENGTH: 9
<212> TYPE: PRT
<213> ORGANISM: Artificial Sequence
<220> FEATURE:
<223> OTHER INFORMATION: ActRIIA-hFc and mActRIIA-Fc N-terminal sequence

<400> SEQUENCE: 11

Ile Leu Gly Arg Ser Glu Thr Gln Glu
1               5

<210> SEQ ID NO 12
<211> LENGTH: 329
<212> TYPE: PRT
<213> ORGANISM: Artificial Sequence
<220> FEATURE:
<223> OTHER INFORMATION: ActRIIA-Fc Protein with deletion of the
      C-terminal 15 amino acids of the extracellular domain of ActRIIA

<400> SEQUENCE: 12

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Thr Gly Gly Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Val Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met

```
225                 230                 235                 240
Thr Lys Asn Gln Val Ser Leu Thr Cys Leu Val Lys Gly Phe Tyr Pro
                245                 250                 255
Ser Asp Ile Ala Val Glu Trp Glu Ser Asn Gly Gln Pro Glu Asn Asn
                260                 265                 270
Tyr Lys Thr Thr Pro Pro Val Leu Asp Ser Asp Gly Ser Phe Phe Leu
                275                 280                 285
Tyr Ser Lys Leu Thr Val Asp Lys Ser Arg Trp Gln Gln Gly Asn Val
290                 295                 300
Phe Ser Cys Ser Val Met His Glu Ala Leu His Asn His Tyr Thr Gln
305                 310                 315                 320
Lys Ser Leu Ser Leu Ser Pro Gly Lys
                325

<210> SEQ ID NO 13
<211> LENGTH: 369
<212> TYPE: PRT
<213> ORGANISM: Artificial Sequence
<220> FEATURE:
<223> OTHER INFORMATION: Unprocessed ActRIIA-hFc with TPA leader
      sequence

<400> SEQUENCE: 13

Met Asp Ala Met Lys Arg Gly Leu Cys Cys Val Leu Leu Leu Cys Gly
1               5                   10                  15
Ala Val Phe Val Ser Pro Gly Ala Ala Ile Leu Gly Arg Ser Glu Thr
                20                  25                  30
Gln Glu Cys Leu Phe Phe Asn Ala Asn Trp Glu Lys Asp Arg Thr Asn
                35                  40                  45
Gln Thr Gly Val Glu Pro Cys Tyr Gly Asp Lys Asp Lys Arg Arg His
                50                  55                  60
Cys Phe Ala Thr Trp Lys Asn Ile Ser Gly Ser Ile Glu Ile Val Lys
65                  70                  75                  80
Gln Gly Cys Trp Leu Asp Asp Ile Asn Cys Tyr Asp Arg Thr Asp Cys
                85                  90                  95
Val Glu Lys Lys Asp Ser Pro Glu Val Tyr Phe Cys Cys Cys Glu Gly
                100                 105                 110
Asn Met Cys Asn Glu Lys Phe Ser Tyr Phe Pro Glu Met Glu Val Thr
                115                 120                 125
Gln Pro Thr Ser Asn Pro Val Thr Pro Lys Pro Pro Thr Gly Gly Gly
                130                 135                 140
Thr His Thr Cys Pro Pro Cys Pro Ala Pro Glu Leu Leu Gly Gly Pro
145                 150                 155                 160
Ser Val Phe Leu Phe Pro Pro Lys Pro Lys Asp Thr Leu Met Ile Ser
                165                 170                 175
Arg Thr Pro Glu Val Thr Cys Val Val Val Asp Val Ser His Glu Asp
                180                 185                 190
Pro Glu Val Lys Phe Asn Trp Tyr Val Asp Gly Val Glu Val His Asn
                195                 200                 205
Ala Lys Thr Lys Pro Arg Glu Glu Gln Tyr Asn Ser Thr Tyr Arg Val
                210                 215                 220
Val Ser Val Leu Thr Val Leu His Gln Asp Trp Leu Asn Gly Lys Glu
225                 230                 235                 240
Tyr Lys Cys Lys Val Ser Asn Lys Ala Leu Pro Val Pro Ile Glu Lys
                245                 250                 255
```

```
Thr Ile Ser Lys Ala Lys Gly Gln Pro Arg Glu Pro Gln Val Tyr Thr
            260                 265                 270

Leu Pro Pro Ser Arg Glu Glu Met Thr Lys Asn Gln Val Ser Leu Thr
        275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Lys

<210> SEQ ID NO 14
<211> LENGTH: 1113
<212> TYPE: DNA
<213> ORGANISM: Artificial Sequence
<220> FEATURE:
<223> OTHER INFORMATION: Nucleic acid sequence encoding Unprocessed
      ActRIIA-hFc with TPA leader sequence

<400> SEQUENCE: 14
atggatgcaa tgaagagagg gctctgctgt gtgctgctgc tgtgtggagc agtcttcgtt      60
tcgcccggcg ccgctatact tggtagatca gaaactcagg agtgtctttt tttaatgcta     120
attgggaaaa agacagaacc aatcaaactg gtgttgaacc gtgttatggt gacaaagata     180
aacggcggca ttgttttgct acctggaaga atatttctgg ttccattgaa tagtgaaaca     240
aggttgttgg ctggatgata tcaactgcta tgacaggact gattgtgtag aaaaaaaaga     300
cagccctgaa gtatatttct gttgctgtga gggcaatatg tgtaatgaaa agttttctta     360
ttttccggag atggaagtca cacagcccac ttcaaatcca gttacaccta agccacccac     420
cggtggtgga actcacacat gcccaccgtg cccagcacct gaactcctgg ggggaccgtc     480
agtcttcctc ttccccccaa aacccaagga caccctcatg atctcccgga cccctgaggt     540
cacatgcgtg gtggtggacg tgagccacga agaccctgag gtcaagttca actggtacgt     600
ggacggcgtg gaggtgcata atgccaagac aaagccgcgg gaggagcagt acaacagcac     660
gtaccgtgtg gtcagcgtcc tcaccgtcct gcaccaggac tggctgaatg caaggagta     720 caagtgcaag gtctccaaca aagccctccc agtccccatc gagaaaacca tctccaaagc     780
caaagggcag ccccgagaac acaggtgta ccctgccc ccatcccggg aggagatgac      840
caagaaccag gtcagcctga cctgcctggt caaaggcttc tatcccagcg acatcgccgt     900
ggagtgggag agcaatgggc agccggagaa caactacaag accacgcctc ccgtgctgga     960
ctccgacggc tccttcttcc tctatagcaa gctcaccgtg gacaagagca ggtggcagca    1020
ggggaacgtc ttctcatgct ccgtgatgca tgaggctctg cacaaccact acacgcagaa    1080
gagcctctcc ctgtctccgg taaatgagaa ttc                                 1113

<210> SEQ ID NO 15
<211> LENGTH: 106
<212> TYPE: PRT
<213> ORGANISM: Artificial Sequence
<220> FEATURE:
<223> OTHER INFORMATION: human ActRIIB soluble (extracellular processed
``` polypeptide with the N-terminal 6 aa of the EC domain deleted and
the C-terminal 4 aa of the EC domain deleted (aa 25-130 of SEQ ID
NO:28) and with an L79D mutation

<400> SEQUENCE: 15

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Asp Phe Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro
            100                 105
```

<210> SEQ ID NO 16
<211> LENGTH: 512
<212> TYPE: PRT
<213> ORGANISM: Homo sapiens
<220> FEATURE:
<223> OTHER INFORMATION: human ActRIIB precursor protein sequence (A64)

<400> SEQUENCE: 16

```
Met Thr Ala Pro Trp Val Ala Leu Ala Leu Leu Trp Gly Ser Leu Trp
1               5                   10                  15

Pro Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Ala
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
210                 215                 220
```

```
Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
            245                 250                 255

Leu Glu Val Glu Leu Trp Leu Ile Thr Ala Phe His Asp Lys Gly Ser
        260                 265                 270

Leu Thr Asp Tyr Leu Lys Gly Asn Ile Ile Thr Trp Asn Glu Leu Cys
    275                 280                 285

His Val Ala Glu Thr Met Ser Arg Gly Leu Ser Tyr Leu His Glu Asp
290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
            325                 330                 335

Leu Ala Asp Phe Gly Leu Ala Val Arg Phe Glu Pro Gly Lys Pro Pro
        340                 345                 350

Gly Asp Thr His Gly Gln Val Gly Thr Arg Arg Tyr Met Ala Pro Glu
    355                 360                 365

Val Leu Glu Gly Ala Ile Asn Phe Gln Arg Asp Ala Phe Leu Arg Ile
370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
            405                 410                 415

Glu Ile Gly Gln His Pro Ser Leu Glu Glu Leu Gln Glu Val Val Val
        420                 425                 430

His Lys Lys Met Arg Pro Thr Ile Lys Asp His Trp Leu Lys His Pro
    435                 440                 445

Gly Leu Ala Gln Leu Cys Val Thr Ile Glu Glu Cys Trp Asp His Asp
450                 455                 460

Ala Glu Ala Arg Leu Ser Ala Gly Cys Val Glu Arg Val Ser Leu
465                 470                 475                 480

Ile Arg Arg Ser Val Asn Gly Thr Thr Ser Asp Cys Leu Val Ser Leu
            485                 490                 495

Val Thr Ser Val Thr Asn Val Asp Leu Pro Pro Lys Glu Ser Ser Ile
        500                 505                 510
```

```
<210> SEQ ID NO 17
<211> LENGTH: 116
<212> TYPE: PRT
<213> ORGANISM: Homo sapiens
<220> FEATURE:
<223> OTHER INFORMATION: human ActRIIB soluble (extracellular),
      processed polypeptide sequence (amino acids 19-134 of SEQ ID
      NO:16)

<400> SEQUENCE: 17

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Ala Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
```

```
              65                  70                  75                  80

Val Tyr Phe Cys Cys Cys Glu Gly Asn Phe Cys Asn Glu Arg Phe Thr
                    85                  90                  95

His Leu Pro Glu Ala Gly Gly Pro Glu Val Thr Tyr Glu Pro Pro Pro
                100                 105                 110

Thr Ala Pro Thr
        115

<210> SEQ ID NO 18
<211> LENGTH: 101
<212> TYPE: PRT
<213> ORGANISM: Artificial Sequence
<220> FEATURE:
<223> OTHER INFORMATION: human ActRIIB soluble (extracellular) processed
      polypeptide with the C-terminal 15 aa deleted (aa 19-119 of SEQ ID
      NO:16)

<400> SEQUENCE: 18

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Ala Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                    85                  90                  95

His Leu Pro Glu Ala
                100

<210> SEQ ID NO 19
<211> LENGTH: 1539
<212> TYPE: DNA
<213> ORGANISM: Homo sapiens
<220> FEATURE:
<223> OTHER INFORMATION: nucleic acid sequence encoding a human ActRIIB
      (A64) precursor protein

<400> SEQUENCE: 19
atgacggcgc cctgggtggc cctcgccctc ctctggggat cgctgtggcc cggctctggg      60
cgtggggagg ctgagacacg ggagtgcatc tactacaacg ccaactggga gctggagcgc     120
accaaccaga gcggcctgga gcgctgcgaa ggcgagcagg acaagcggct gcactgctac     180
gcctcctggg ccaacagctc tggcaccatc gagctcgtga agaagggctg ctggctagat     240
gacttcaact gctacgatag gcaggagtgt gtggccactg aggagaaccc ccaggtgtac     300
ttctgctgct gtgaaggcaa cttctgcaac gagcgcttca ctcatttgcc agaggctggg     360
ggcccggaag tcacgtacga gccaccccca cagcccccca ccctgctcac ggtgctggcc     420
tactcactgc tgcccatcgg ggccttttcc ctcatcgtcc tgctggcctt ttggatgtac     480
cggcatcgca agccccccta cggtcatgtg gacatccatg aggaccctgg gcctccacca     540
ccatcccctc tggtgggcct gaagccactg cagctgctgg agatcaaggc tcggggcgc      600 tttggctgtg tctggaaggc ccagctcatg aatgactttg tagctgtcaa gatcttccca     660
ctccaggaca gcagtcgtg gcagagtgaa cgggagatct cagcacacc tggcatgaag      720
```

```
cacgagaacc tgctacagtt cattgctgcc gagaagcgag gctccaacct cgaagtagag    780
ctgtggctca tcacggcctt ccatgacaag ggctccctca cggattacct caagggggaac   840 atcatcacat ggaacgaact gtgtcatgta gcagagacga tgtcacgagg cctctcatac    900
ctgcatgagg atgtgccctg gtgccgtggc gagggccaca agccgtctat tgcccacagg    960
gactttaaaa gtaagaatgt attgctgaag agcgacctca cagccgtgct ggctgacttt   1020
ggcttggctg ttcgatttga gccagggaaa cctccagggg acacccacgg acaggtaggc   1080
acgagacggt acatggctcc tgaggtgctc gagggagcca tcaacttcca gagagatgcc   1140
ttcctgcgca ttgacatgta tgccatgggg ttggtgctgt gggagcttgt gtctcgctgc   1200
aaggctgcag acggacccgt ggatgagtac atgctgccct tgaggaaga gattggccag    1260 caccttcgt tggaggagct gcaggaggtg gtggtgcaca agaagatgag gcccaccatt    1320
aaagatcact ggttgaaaca cccgggcctg gcccagcttt gtgtgaccat cgaggagtgc   1380
tgggaccatg atgcagaggc tcgcttgtcc gcgggctgtg tggaggagcg ggtgtccctg   1440
attcggaggt cggtcaacgg cactacctcg gactgtctcg tttccctggt gacctctgtc   1500
accaatgtgg acctgccccc taaagagtca agcatctaa                          1539
```

<210> SEQ ID NO 20
<211> LENGTH: 344
<212> TYPE: PRT
<213> ORGANISM: Artificial Sequence
<220> FEATURE:
<223> OTHER INFORMATION: fusion protein comprising a soluble
      extracellular domain of ActRIIB (A64; SEQ ID NO:17) fused to an Fc
      domain

<400> SEQUENCE: 20

```
Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Ala Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr Gly Gly Gly Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205
```

```
Asp Trp Leu Asn Gly Lys Glu Tyr Lys Cys Lys Val Ser Asn Lys Ala
    210                 215                 220
Leu Pro Val Pro Ile Glu Lys Thr Ile Ser Lys Ala Lys Gly Gln Pro
225                 230                 235                 240
Arg Glu Pro Gln Val Tyr Thr Leu Pro Pro Ser Arg Glu Glu Met Thr
                245                 250                 255
Lys Asn Gln Val Ser Leu Thr Cys Leu Val Lys Gly Phe Tyr Pro Ser
            260                 265                 270
Asp Ile Ala Val Glu Trp Glu Ser Asn Gly Gln Pro Glu Asn Asn Tyr
        275                 280                 285
Lys Thr Thr Pro Pro Val Leu Asp Ser Asp Gly Ser Phe Phe Leu Tyr
    290                 295                 300
Ser Lys Leu Thr Val Asp Lys Ser Arg Trp Gln Gln Gly Asn Val Phe
305                 310                 315                 320
Ser Cys Ser Val Met His Glu Ala Leu His Asn His Tyr Thr Gln Lys
                325                 330                 335
Ser Leu Ser Leu Ser Pro Gly Lys
            340
```

<210> SEQ ID NO 21
<211> LENGTH: 329
<212> TYPE: PRT
<213> ORGANISM: Artificial Sequence
<220> FEATURE:
<223> OTHER INFORMATION: fusion protein comprising a soluble
      extracellular domain of ActRIIB (A64) with the C-terminal 15 amino
      acids deleted (SEQ ID NO:18) fused to an Fc domain

<400> SEQUENCE: 21

```
Ser Gly Arg Gly Glu Ala Glu Thr Arg Glu Cys Ile Tyr Tyr Asn Ala
1               5                   10                  15
Asn Trp Glu Leu Glu Arg Thr Asn Gln Ser Gly Leu Glu Arg Cys Glu
                20                  25                  30
Gly Glu Gln Asp Lys Arg Leu His Cys Tyr Ala Ser Trp Ala Asn Ser
            35                  40                  45
Ser Gly Thr Ile Glu Leu Val Lys Lys Gly Cys Trp Leu Asp Asp Phe
        50                  55                  60
Asn Cys Tyr Asp Arg Gln Glu Cys Val Ala Thr Glu Glu Asn Pro Gln
65                  70                  75                  80
Val Tyr Phe Cys Cys Cys Glu Gly Asn Phe Cys Asn Glu Arg Phe Thr
                85                  90                  95
His Leu Pro Glu Ala Gly Gly Thr His Thr Cys Pro Pro Cys Pro
            100                 105                 110
Ala Pro Glu Leu Leu Gly Gly Pro Ser Val Phe Leu Phe Pro Pro Lys
        115                 120                 125
Pro Lys Asp Thr Leu Met Ile Ser Arg Thr Pro Glu Val Thr Cys Val
    130                 135                 140
Val Val Asp Val Ser His Glu Asp Pro Glu Val Lys Phe Asn Trp Tyr
145                 150                 155                 160
Val Asp Gly Val Glu Val His Asn Ala Lys Thr Lys Pro Arg Glu Glu
                165                 170                 175
Gln Tyr Asn Ser Thr Tyr Arg Val Val Ser Val Leu Thr Val Leu His
            180                 185                 190
Gln Asp Trp Leu Asn Gly Lys Glu Tyr Lys Cys Lys Val Ser Asn Lys
        195                 200                 205
Ala Leu Pro Val Pro Ile Glu Lys Thr Ile Ser Lys Ala Lys Gly Gln
```

```
                210                 215                 220
Pro Arg Glu Pro Gln Val Tyr Thr Leu Pro Pro Ser Arg Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
                260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
        290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```

<210> SEQ ID NO 22
<211> LENGTH: 105
<212> TYPE: PRT
<213> ORGANISM: Artificial Sequence
<220> FEATURE:
<223> OTHER INFORMATION: human ActRIIB soluble (extracellular) processed
      polypeptide with the N-terminal 6 aa of the EC domain deleted and
      the C-terminal 5 aa of the EC domain deleted (aa 25-129 of SEQ ID
      NO:28) and with an L79D mutation

<400> SEQUENCE: 22

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro
            100                 105
```

<210> SEQ ID NO 23
<211> LENGTH: 107
<212> TYPE: PRT
<213> ORGANISM: Artificial Sequence
<220> FEATURE:
<223> OTHER INFORMATION: human ActRIIB soluble (extracellular) processed
      polypeptide with the N-terminal 6 aa of the EC domain deleted and
      the C-terminal 3 aa of the EC domain deleted (aa 25-131 of SEQ ID
      NO:28) and with an L79D mutation

<400> SEQUENCE: 23

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45
```

Val Lys Lys Gly Cys Trp Asp Asp Asp Phe Asn Cys Tyr Asp Arg Gln
          50                  55                  60

Glu Cys Val Ala Thr Glu Glu Asn Pro Gln Val Tyr Phe Cys Cys Cys
 65                  70                  75                  80

Glu Gly Asn Phe Cys Asn Glu Arg Phe Thr His Leu Pro Ala Gly
                 85                  90                  95

Gly Pro Glu Val Thr Tyr Glu Pro Pro Pro Thr
            100                 105

<210> SEQ ID NO 24
<211> LENGTH: 360
<212> TYPE: PRT
<213> ORGANISM: Artificial Sequence
<220> FEATURE:
<223> OTHER INFORMATION: Unprocessed ActRIIB-Fc fusion protein with the
      N-terminal 6 aa of the EC domain deleted and the C-terminal 3 aa
      of the EC domain deleted (aa 25-131 of SEQ ID NO:28) and with an
      L79D mutation and with TPA leader sequence

<400> SEQUENCE: 24

Met Asp Ala Met Lys Arg Gly Leu Cys Cys Val Leu Leu Leu Cys Gly
 1               5                  10                  15

Ala Val Phe Val Ser Pro Gly Ala Ala Glu Thr Arg Glu Cys Ile Tyr
            20                  25                  30

Tyr Asn Ala Asn Trp Glu Leu Glu Arg Thr Asn Gln Ser Gly Leu Glu
         35                  40                  45

Arg Cys Glu Gly Glu Gln Asp Lys Arg Leu His Cys Tyr Ala Ser Trp
 50                  55                  60

Arg Asn Ser Ser Gly Thr Ile Glu Leu Val Lys Lys Gly Cys Trp Asp
 65                  70                  75                  80

Asp Asp Phe Asn Cys Tyr Asp Arg Gln Glu Cys Val Ala Thr Glu Glu
                 85                  90                  95

Asn Pro Gln Val Tyr Phe Cys Cys Cys Glu Gly Asn Phe Cys Asn Glu
            100                 105                 110

Arg Phe Thr His Leu Pro Glu Ala Gly Gly Pro Glu Val Thr Tyr Glu
        115                 120                 125

Pro Pro Pro Thr Gly Gly Gly Thr His Thr Cys Pro Pro Cys Pro Ala
130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
        275                 280                 285

```
Asp Ile Ala Val Glu Trp Glu Ser Asn Gly Gln Pro Glu Asn Asn Tyr
    290                 295                 300
Lys Thr Thr Pro Pro Val Leu Asp Ser Asp Gly Ser Phe Phe Leu Tyr
305                 310                 315                 320
Ser Lys Leu Thr Val Asp Lys Ser Arg Trp Gln Gln Gly Asn Val Phe
                325                 330                 335
Ser Cys Ser Val Met His Glu Ala Leu His Asn His Tyr Thr Gln Lys
                340                 345                 350
Ser Leu Ser Leu Ser Pro Gly Lys
                355                 360

<210> SEQ ID NO 25
<211> LENGTH: 335
<212> TYPE: PRT
<213> ORGANISM: Artificial Sequence
<220> FEATURE:
<223> OTHER INFORMATION: Processed ActRIIB-Fc fusion protein with the
      N-terminal 6 aa of the EC domain deleted and the C-terminal 3 aa
      of the EC domain deleted (aa 25-131 of SEQ ID NO:28) and with an
      L79D mutation

<400> SEQUENCE: 25

Glu Thr Arg Glu Cys Ile Tyr Tyr Asn Ala Asn Trp Glu Leu Glu Arg
1               5                   10                  15
Thr Asn Gln Ser Gly Leu Glu Arg Cys Glu Gly Glu Gln Asp Lys Arg
                20                  25                  30
Leu His Cys Tyr Ala Ser Trp Arg Asn Ser Ser Gly Thr Ile Glu Leu
                35                  40                  45
Val Lys Lys Gly Cys Trp Asp Asp Asp Phe Asn Cys Tyr Asp Arg Gln
50                  55                  60
Glu Cys Val Ala Thr Glu Glu Asn Pro Gln Val Tyr Phe Cys Cys Cys
65                  70                  75                  80
Glu Gly Asn Phe Cys Asn Glu Arg Phe Thr His Leu Pro Glu Ala Gly
                85                  90                  95
Gly Pro Glu Val Thr Tyr Glu Pro Pro Pro Thr Gly Gly Thr His
                100                 105                 110
Thr Cys Pro Pro Cys Pro Ala Pro Glu Leu Leu Gly Gly Pro Ser Val
                115                 120                 125
Phe Leu Phe Pro Pro Lys Pro Lys Asp Thr Leu Met Ile Ser Arg Thr
130                 135                 140
Pro Glu Val Thr Cys Val Val Val Asp Val Ser His Glu Asp Pro Glu
145                 150                 155                 160
Val Lys Phe Asn Trp Tyr Val Asp Gly Val Glu Val His Asn Ala Lys
                165                 170                 175
Thr Lys Pro Arg Glu Glu Gln Tyr Asn Ser Thr Tyr Arg Val Val Ser
                180                 185                 190
Val Leu Thr Val Leu His Gln Asp Trp Leu Asn Gly Lys Glu Tyr Lys
                195                 200                 205
Cys Lys Val Ser Asn Lys Ala Leu Pro Ala Pro Ile Glu Lys Thr Ile
210                 215                 220
Ser Lys Ala Lys Gly Gln Pro Arg Glu Pro Gln Val Tyr Thr Leu Pro
225                 230                 235                 240
Pro Ser Arg Glu Glu Met Thr Lys Asn Gln Val Ser Leu Thr Cys Leu
                245                 250                 255
Val Lys Gly Phe Tyr Pro Ser Asp Ile Ala Val Glu Trp Glu Ser Asn
                260                 265                 270
```

```
Gly Gln Pro Glu Asn Asn Tyr Lys Thr Thr Pro Pro Val Leu Asp Ser
            275                 280                 285

Asp Gly Ser Phe Phe Leu Tyr Ser Lys Leu Thr Val Asp Lys Ser Arg
            290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
            325                 330                 335

<210> SEQ ID NO 26
<211> LENGTH: 115
<212> TYPE: PRT
<213> ORGANISM: Homo sapiens
<220> FEATURE:
<223> OTHER INFORMATION: human ActRIIB soluble (extracellular),
      processed polypeptide sequence (amino acids 20-134 of SEQ ID
      NO:16)

<400> SEQUENCE: 26

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 27
<211> LENGTH: 100
<212> TYPE: PRT
<213> ORGANISM: Artificial Sequence
<220> FEATURE:
<223> OTHER INFORMATION: human ActRIIB soluble (extracellular),
      processed polypeptide sequence with the C-terminal 15 aa deleted
      (aa 20-119 of SEQ ID NO:16)

<400> SEQUENCE: 27

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala
```

<210> SEQ ID NO 28
<211> LENGTH: 512
<212> TYPE: PRT
<213> ORGANISM: Homo sapiens
<220> FEATURE:
<223> OTHER INFORMATION: human ActRIIB precursor protein sequence (R64)

<400> SEQUENCE: 28

```
Met Thr Ala Pro Trp Val Ala Leu Ala Leu Leu Trp Gly Ser Leu Trp
1               5                   10                  15

Pro Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
```

```
                    355                 360                 365
Val Leu Glu Gly Ala Ile Asn Phe Gln Arg Asp Ala Phe Leu Arg Ile
            370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
            435                 440                 445

Gly Leu Ala Gln Leu Cys Val Thr Ile Glu Glu Cys Trp Asp His Asp
        450                 455                 460

Ala Glu Ala Arg Leu Ser Ala Gly Cys Val Glu Arg Val Ser Leu
465                 470                 475                 480

Ile Arg Arg Ser Val Asn Gly Thr Thr Ser Asp Cys Leu Val Ser Leu
            485                 490                 495

Val Thr Ser Val Thr Asn Val Asp Leu Pro Pro Lys Glu Ser Ser Ile
            500                 505                 510

<210> SEQ ID NO 29
<211> LENGTH: 116
<212> TYPE: PRT
<213> ORGANISM: Artificial Sequence
<220> FEATURE:
<223> OTHER INFORMATION: human ActRIIB soluble (extracellular),
      processed polypeptide sequence (amino acids 19-134 of SEQ ID
      NO:28)

<400> SEQUENCE: 29

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr
        115

<210> SEQ ID NO 30
<211> LENGTH: 101
<212> TYPE: PRT
<213> ORGANISM: Artificial Sequence
<220> FEATURE:
<223> OTHER INFORMATION: human ActRIIB soluble (extracellular),
      processed polypeptide sequence with the C-terminal 15 aa deleted
      (aa 19-119 of SEQ ID NO:28)

<400> SEQUENCE: 30

Ser Gly Arg Gly Glu Ala Glu Thr Arg Glu Cys Ile Tyr Tyr Asn Ala
1               5                   10                  15
```

-continued

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala
            100

<210> SEQ ID NO 31
<211> LENGTH: 115
<212> TYPE: PRT
<213> ORGANISM: Artificial Sequence
<220> FEATURE:
<223> OTHER INFORMATION: human ActRIIB soluble (extracellular),
      processed polypeptide sequence (amino acids 20-134 of SEQ ID
      NO:28)

<400> SEQUENCE: 31

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 32
<211> LENGTH: 100
<212> TYPE: PRT
<213> ORGANISM: Artificial Sequence
<220> FEATURE:
<223> OTHER INFORMATION: human ActRIIB soluble (extracellular),
      processed polypeptide sequence with the C-terminal 15 aa deleted
      (aa 20-119 of SEQ ID NO:28)

<400> SEQUENCE: 32

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

```
Cys Tyr Asp Arg Gln Glu Cys Val Ala Thr Glu Asn Pro Gln Val
 65                  70                  75                  80

Tyr Phe Cys Cys Glu Gly Asn Phe Cys Asn Glu Arg Phe Thr His
                 85                  90                  95

Leu Pro Glu Ala
            100

<210> SEQ ID NO 33
<211> LENGTH: 107
<212> TYPE: PRT
<213> ORGANISM: Artificial Sequence
<220> FEATURE:
<223> OTHER INFORMATION: human ActRIIB soluble (extracellular) processed
      polypeptide with the N-terminal 6 aa of the EC domain deleted and
      the C-terminal 3 aa of the EC domain deleted (aa 25-131 of SEQ ID
      NO:16) and with an L79D mutation

<400> SEQUENCE: 33

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
                20                  25                  30

Leu His Cys Tyr Ala Ser Trp Ala Asn Ser Ser Gly Thr Ile Glu Leu
             35                  40                  45

Val Lys Lys Gly Cys Trp Asp Asp Asp Phe Asn Cys Tyr Asp Arg Gln
 50                  55                  60

Glu Cys Val Ala Thr Glu Glu Asn Pro Gln Val Tyr Phe Cys Cys Cys
 65                  70                  75                  80

Glu Gly Asn Phe Cys Asn Glu Arg Phe Thr His Leu Pro Glu Ala Gly
                 85                  90                  95

Gly Pro Glu Val Thr Tyr Glu Pro Pro Thr
            100                 105

<210> SEQ ID NO 34
<211> LENGTH: 360
<212> TYPE: PRT
<213> ORGANISM: Artificial Sequence
<220> FEATURE:
<223> OTHER INFORMATION: Unprocessed ActRIIB-Fc fusion protein with the
      N-terminal 6 aa of the EC domain deleted and the C-terminal 3 aa
      of the EC domain deleted (aa 25-131 of SEQ ID NO:16) and with an
      L79D mutation and with TPA leader sequence

<400> SEQUENCE: 34

Met Asp Ala Met Lys Arg Gly Leu Cys Cys Val Leu Leu Leu Cys Gly
1               5                   10                  15

Ala Val Phe Val Ser Pro Gly Ala Ala Glu Thr Arg Glu Cys Ile Tyr
                20                  25                  30

Tyr Asn Ala Asn Trp Glu Leu Glu Arg Thr Asn Gln Ser Gly Leu Glu
             35                  40                  45

Arg Cys Glu Gly Glu Gln Asp Lys Arg Leu His Cys Tyr Ala Ser Trp
 50                  55                  60

Ala Asn Ser Ser Gly Thr Ile Glu Leu Val Lys Lys Gly Cys Trp Asp
 65                  70                  75                  80

Asp Asp Phe Asn Cys Tyr Asp Arg Gln Glu Cys Val Ala Thr Glu Glu
                 85                  90                  95

Asn Pro Gln Val Tyr Phe Cys Cys Cys Glu Gly Asn Phe Cys Asn Glu
            100                 105                 110

Arg Phe Thr His Leu Pro Glu Ala Gly Gly Pro Glu Val Thr Tyr Glu
            115                 120                 125
```

```
Pro Pro Pro Thr Gly Gly Thr His Thr Cys Pro Pro Cys Pro Ala
    130             135             140

Pro Glu Leu Leu Gly Gly Pro Ser Val Phe Leu Phe Pro Pro Lys Pro
145             150             155             160

Lys Asp Thr Leu Met Ile Ser Arg Thr Pro Glu Val Thr Cys Val Val
                165             170             175

Val Asp Val Ser His Glu Asp Pro Glu Val Lys Phe Asn Trp Tyr Val
            180             185             190

Asp Gly Val Glu Val His Asn Ala Lys Thr Lys Pro Arg Glu Glu Gln
        195             200             205

Tyr Asn Ser Thr Tyr Arg Val Val Ser Val Leu Thr Val Leu His Gln
    210             215             220

Asp Trp Leu Asn Gly Lys Glu Tyr Lys Cys Lys Val Ser Asn Lys Ala
225             230             235             240

Leu Pro Ala Pro Ile Glu Lys Thr Ile Ser Lys Ala Lys Gly Gln Pro
                245             250             255

Arg Glu Pro Gln Val Tyr Thr Leu Pro Pro Ser Arg Glu Glu Met Thr
            260             265             270

Lys Asn Gln Val Ser Leu Thr Cys Leu Val Lys Gly Phe Tyr Pro Ser
        275             280             285

Asp Ile Ala Val Glu Trp Glu Ser Asn Gly Gln Pro Glu Asn Asn Tyr
    290             295             300

Lys Thr Thr Pro Pro Val Leu Asp Ser Asp Gly Ser Phe Phe Leu Tyr
305             310             315             320

Ser Lys Leu Thr Val Asp Lys Ser Arg Trp Gln Gln Gly Asn Val Phe
                325             330             335

Ser Cys Ser Val Met His Glu Ala Leu His Asn His Tyr Thr Gln Lys
            340             345             350

Ser Leu Ser Leu Ser Pro Gly Lys
        355             360

<210> SEQ ID NO 35
<211> LENGTH: 335
<212> TYPE: PRT
<213> ORGANISM: Artificial Sequence
<220> FEATURE:
<223> OTHER INFORMATION: Processed ActRIIB-Fc fusion protein with the
      N-terminal 6 aa of the EC domain deleted and the C-terminal 3 aa
      of the EC domain deleted (aa 25-131 of SEQ ID NO:16) and with an
      L79D mutation

<400> SEQUENCE: 35

Glu Thr Arg Glu Cys Ile Tyr Tyr Asn Ala Asn Trp Glu Leu Glu Arg
1               5               10              15

Thr Asn Gln Ser Gly Leu Glu Arg Cys Glu Gly Glu Gln Asp Lys Arg
            20              25              30

Leu His Cys Tyr Ala Ser Trp Ala Asn Ser Ser Gly Thr Ile Glu Leu
        35              40              45

Val Lys Lys Gly Cys Trp Asp Asp Asp Phe Asn Cys Tyr Asp Arg Gln
    50              55              60

Glu Cys Val Ala Thr Glu Glu Asn Pro Gln Val Tyr Phe Cys Cys Cys
65              70              75              80

Glu Gly Asn Phe Cys Asn Glu Arg Phe Thr His Leu Pro Glu Ala Gly
                85              90              95

Gly Pro Glu Val Thr Tyr Glu Pro Pro Pro Thr Gly Gly Gly Thr His
            100             105             110
```

-continued

Thr Cys Pro Pro Cys Pro Ala Pro Glu Leu Leu Gly Gly Pro Ser Val
    115                 120                 125

Phe Leu Phe Pro Pro Lys Pro Lys Asp Thr Leu Met Ile Ser Arg Thr
130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
    290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 36
<211> LENGTH: 115
<212> TYPE: PRT
<213> ORGANISM: Artificial Sequence
<220> FEATURE:
<223> OTHER INFORMATION: human ActRIIB soluble (extracellular),
      processed polypeptide sequence (amino acids 20-134 of SEQ ID
      NO:28) with L79D mutation

<400> SEQUENCE: 36

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
    115

<210> SEQ ID NO 37
<211> LENGTH: 115
<212> TYPE: PRT
<213> ORGANISM: Artificial Sequence
<220> FEATURE:
<223> OTHER INFORMATION: human ActRIIB soluble (extracellular), processed polypeptide sequence (amino acids 20-134 of SEQ ID NO:16) with L79D mutation

<400> SEQUENCE: 37

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115
```

<210> SEQ ID NO 38
<211> LENGTH: 343
<212> TYPE: PRT
<213> ORGANISM: Artificial Sequence
<220> FEATURE:
<223> OTHER INFORMATION: human ActRIIB soluble (extracellular), processed polypeptide sequence (aa 20-134 of SEQ ID NO:28) with L79D mutation fused to an Fc domain with a GGG linker

<400> SEQUENCE: 38

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
            115                 120                 125

Glu Leu Leu Gly Gly Pro Ser Val Phe Leu Phe Pro Pro Lys Pro Lys
        130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
```

```
                         165                 170                 175
Gly Val Glu Val His Asn Ala Lys Thr Lys Pro Arg Glu Glu Gln Tyr
                180                 185                 190

Asn Ser Thr Tyr Arg Val Val Ser Val Leu Thr Val Leu His Gln Asp
            195                 200                 205

Trp Leu Asn Gly Lys Glu Tyr Lys Cys Lys Val Ser Asn Lys Ala Leu
        210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 39
<211> LENGTH: 343
<212> TYPE: PRT
<213> ORGANISM: Artificial Sequence
<220> FEATURE:
<223> OTHER INFORMATION: human ActRIIB soluble (extracellular),
      processed polypeptide sequence (aa 20-134 of SEQ ID NO:16) with
      L79D mutation fused to an Fc domain

<400> SEQUENCE: 39

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175
```

```
Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
            195                 200                 205

Trp Leu Asn Gly Lys Glu Tyr Lys Cys Lys Val Ser Asn Lys Ala Leu
210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
                260                 265                 270

Ile Ala Val Glu Trp Glu Ser Asn Gly Gln Pro Glu Asn Asn Tyr Lys
                275                 280                 285

Thr Thr Pro Pro Val Leu Asp Ser Asp Gly Ser Phe Phe Leu Tyr Ser
            290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 40
<211> LENGTH: 368
<212> TYPE: PRT
<213> ORGANISM: Artificial Sequence
<220> FEATURE:
<223> OTHER INFORMATION: human ActRIIB soluble (extracellular),
      processed polypeptide sequence (aa 20-134 of SEQ ID NO:28) with
      L79D mutation fused to an Fc domain and with TPA leader sequence

<400> SEQUENCE: 40

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Asp Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175
```

```
Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
            195                 200                 205

Lys Thr Lys Pro Arg Glu Glu Gln Tyr Asn Ser Thr Tyr Arg Val Val
            210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
            275                 280                 285

Leu Val Lys Gly Phe Tyr Pro Ser Asp Ile Ala Val Glu Trp Glu Ser
            290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
            355                 360                 365

<210> SEQ ID NO 41
<211> LENGTH: 368
<212> TYPE: PRT
<213> ORGANISM: Artificial Sequence
<220> FEATURE:
<223> OTHER INFORMATION: human ActRIIB soluble (extracellular),
      processed polypeptide sequence (aa 20-134 of SEQ ID NO:16) with
      L79D mutation fused to an Fc domain and with TPA leader sequence

<400> SEQUENCE: 41

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Ala Asn Ser Ser Gly Thr Ile Glu Leu Val Lys
65                  70                  75                  80

Lys Gly Cys Trp Asp Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
            115                 120                 125

Glu Val Thr Tyr Glu Pro Pro Thr Ala Pro Thr Gly Gly Gly Thr
            130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
```

```
                    165                 170                 175
        Thr Pro Glu Val Thr Cys Val Val Asp Val Ser His Glu Asp Pro
                        180                 185                 190

Glu Val Lys Phe Asn Trp Tyr Val Asp Gly Val Glu Val His Asn Ala
                        195                 200                 205

Lys Thr Lys Pro Arg Glu Glu Gln Tyr Asn Ser Thr Tyr Arg Val Val
                    210                 215                 220

Ser Val Leu Thr Val Leu His Gln Asp Trp Leu Asn Gly Lys Glu Tyr
        225                 230                 235                 240

Lys Cys Lys Val Ser Asn Lys Ala Leu Pro Ala Pro Ile Glu Lys Thr
                        245                 250                 255

Ile Ser Lys Ala Lys Gly Gln Pro Arg Glu Pro Gln Val Tyr Thr Leu
                        260                 265                 270

Pro Pro Ser Arg Glu Glu Met Thr Lys Asn Gln Val Ser Leu Thr Cys
                        275                 280                 285

Leu Val Lys Gly Phe Tyr Pro Ser Asp Ile Ala Val Glu Trp Glu Ser
                        290                 295                 300

Asn Gly Gln Pro Glu Asn Asn Tyr Lys Thr Thr Pro Pro Val Leu Asp
        305                 310                 315                 320

Ser Asp Gly Ser Phe Phe Leu Tyr Ser Lys Leu Thr Val Asp Lys Ser
                        325                 330                 335

Arg Trp Gln Gln Gly Asn Val Phe Ser Cys Ser Val Met His Glu Ala
                        340                 345                 350

Leu His Asn His Tyr Thr Gln Lys Ser Leu Ser Leu Ser Pro Gly Lys
                        355                 360                 365

<210> SEQ ID NO 42
<211> LENGTH: 141
<212> TYPE: PRT
<213> ORGANISM: Artificial Sequence
<220> FEATURE:
<223> OTHER INFORMATION: human ActRIIB soluble (extracellular),
      processed polypeptide sequence having a variant C-terminal
      sequence (disclosed in WO2007/053775)

<400> SEQUENCE: 42

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
                20                  25                  30

Glu Gln Asp Lys Arg Leu His Cys Tyr Ala Ser Trp Arg Asn Ser Ser
                35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
                100                 105                 110

Pro Ser Gly Gly Pro Glu Ala Thr Ala Ala Ala Gly Asp Gln Gly Ser
            115                 120                 125

Gly Ala Leu Trp Leu Cys Leu Glu Gly Pro Ala His Glu
            130                 135                 140

<210> SEQ ID NO 43
```

```
<211> LENGTH: 141
<212> TYPE: PRT
<213> ORGANISM: Artificial Sequence
<220> FEATURE:
<223> OTHER INFORMATION: human ActRIIB soluble (extracellular),
      processed polypeptide sequence having a variant C-terminal
      sequence (disclosed in WO2007/053775) having an L79D mutation

<400> SEQUENCE: 43

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Gly Asp Gln Gly Ser
        115                 120                 125

Gly Ala Leu Trp Leu Cys Leu Glu Gly Pro Ala His Glu
    130                 135                 140

<210> SEQ ID NO 44
<211> LENGTH: 370
<212> TYPE: PRT
<213> ORGANISM: Artificial Sequence
<220> FEATURE:
<223> OTHER INFORMATION: human ActRIIB soluble (extracellular),
      processed polypeptide sequence having a variant C-terminal
      sequence (disclosed in WO2007/053775) having an L79D mutation
      fused to an Fc domain with a TGGG linker

<400> SEQUENCE: 44

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Gly Asp Gln Gly Ser
        115                 120                 125

Gly Ala Leu Trp Leu Cys Leu Glu Gly Pro Ala His Glu Thr Gly Gly
    130                 135                 140

Gly Thr His Thr Cys Pro Pro Cys Pro Ala Pro Glu Leu Leu Gly Gly
145                 150                 155                 160
```

```
Pro Ser Val Phe Leu Phe Pro Pro Lys Pro Lys Asp Thr Leu Met Ile
            165                 170                 175

Ser Arg Thr Pro Glu Val Thr Cys Val Val Asp Val Ser His Glu
        180                 185                 190

Asp Pro Glu Val Lys Phe Asn Trp Tyr Val Asp Gly Val Glu Val His
            195                 200                 205

Asn Ala Lys Thr Lys Pro Arg Glu Glu Gln Tyr Asn Ser Thr Tyr Arg
        210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Pro Ala Pro Ile Glu
            245                 250                 255

Lys Thr Ile Ser Lys Ala Lys Gly Gln Pro Arg Glu Pro Gln Val Tyr
        260                 265                 270

Thr Leu Pro Pro Ser Arg Glu Glu Met Thr Lys Asn Gln Val Ser Leu
    275                 280                 285

Thr Cys Leu Val Lys Gly Phe Tyr Pro Ser Asp Ile Ala Val Glu Trp
290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Lys Leu Thr Val Asp
            325                 330                 335

Lys Ser Arg Trp Gln Gln Gly Asn Val Phe Ser Cys Ser Val Met His
        340                 345                 350

Glu Ala Leu His Asn His Tyr Thr Gln Lys Ser Leu Ser Leu Ser Pro
            355                 360                 365

Gly Lys
    370

<210> SEQ ID NO 45
<211> LENGTH: 1083
<212> TYPE: DNA
<213> ORGANISM: Artificial Sequence
<220> FEATURE:
<223> OTHER INFORMATION: Nucleic Acid Sequence Encoding SEQ ID NO:24

<400> SEQUENCE: 45
atggatgcaa tgaagagagg gctctgctgt gtgctgctgc tgtgtggagc agtcttcgtt      60
tcgcccggcg ccgccgaaac ccgcgaatgt atttattaca atgctaattg ggaactcgaa     120
cggacgaacc aatccgggct cgaacggtgt gaggggaac aggataaacg cctccattgc      180
tatgcgtcgt ggaggaactc ctccgggacg attgaactgg tcaagaaagg gtgctgggac     240
gacgatttca attgttatga ccgccaggaa tgtgtcgcga ccgaagagaa tccgcaggtc     300
tatttctgtt gttgcgaggg gaatttctgt aatgaacggt ttacccacct ccccgaagcc     360
ggcgggcccg aggtgaccta tgaaccccg cccaccggtg tggaactcac acatgcccca     420
ccgtgcccag cacctgaact cctggggga ccgtcagtct tcctcttccc cccaaaaccc      480
aaggacaccc tcatgatctc ccggaccct gaggtcacat gcgtggtggt ggacgtgagc      540
cacgaagacc ctgaggtcaa gttcaactgg tacgtggacg gcgtggaggt gcataatgcc      600
aagacaaagc cgcgggagga gcagtacaac agcacgtacc gtgtggtcag cgtcctcacc      660
gtcctgcacc aggactggct gaatggcaag gagtacaagt gcaaggtctc caacaaagcc      720
ctcccagccc ccatcgagaa aaccatctcc aaagccaaag gcagcccg agaaccacag       780
```

```
gtgtacaccc tgcccccatc ccgggaggag atgaccaaga accaggtcag cctgacctgc    840
ctggtcaaag gcttctatcc cagcgacatc gccgtggagt gggagagcaa tgggcagccg    900
gagaacaact acaagaccac gcctcccgtg ctggactccg acggctcctt cttcctctat    960
agcaagctca ccgtggacaa gagcaggtgg cagcagggga acgtcttctc atgctccgtg   1020
atgcatgagg ctctgcacaa ccactacacg cagaagagcc tctccctgtc cccgggtaaa   1080
tga                                                                 1083
```

<210> SEQ ID NO 46
<211> LENGTH: 344
<212> TYPE: PRT
<213> ORGANISM: Artificial Sequence
<220> FEATURE:
<223> OTHER INFORMATION: fusion protein comprising a soluble
      extracellular domain of ActRIIB (R64; SEQ ID NO:29) fused to an Fc
      domain

<400> SEQUENCE: 46

```
Ser Gly Arg Gly Glu Ala Glu Thr Arg Glu Cys Ile Tyr Tyr Asn Ala
 1               5                  10                  15

Asn Trp Glu Leu Glu Arg Thr Asn Gln Ser Gly Leu Glu Arg Cys Glu
                20                  25                  30

Gly Glu Gln Asp Lys Arg Leu His Cys Tyr Ala Ser Trp Arg Asn Ser
            35                  40                  45

Ser Gly Thr Ile Glu Leu Val Lys Lys Gly Cys Trp Leu Asp Asp Phe
        50                  55                  60

Asn Cys Tyr Asp Arg Gln Glu Cys Val Ala Thr Glu Glu Asn Pro Gln
 65                  70                  75                  80

Val Tyr Phe Cys Cys Cys Glu Gly Asn Phe Cys Asn Glu Arg Phe Thr
                 85                  90                  95

His Leu Pro Glu Ala Gly Gly Pro Glu Val Thr Tyr Glu Pro Pro Pro
            100                 105                 110

Thr Ala Pro Thr Gly Gly Gly Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
```

-continued

```
            290                 295                 300
Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 47
<211> LENGTH: 329
<212> TYPE: PRT
<213> ORGANISM: Artificial Sequence
<220> FEATURE:
<223> OTHER INFORMATION: fusion protein comprising a soluble
      extracellular domain of ActRIIB (R64) with the C-terminal 15 aa
      deleted (SEQ ID NO:30) fused to an Fc domain

<400> SEQUENCE: 47

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Val Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300
```

```
Phe Ser Cys Ser Val Met His Glu Ala Leu His Asn His Tyr Thr Gln
305                 310                 315                 320

Lys Ser Leu Ser Leu Ser Pro Gly Lys
                325
```

What is claimed:

1. A method of treating beta-thalassemia in a subject, comprising administering an ActRII signaling inhibitor to the subject, wherein the patient has been selected by using an in vitro cell culture method comprising the steps of:
- (a) co-culturing an erythroid progenitor cell (EPC) and a stromal cell in the presence of an activin type II receptor (ActRII) signaling inhibitor for a period of time; and
- (b) determining the level of GYPA, GATA1, GATA2, or alpha-globin in the EPC or determining the level of expansion of the EPC, wherein the stromal cell and/or the EPC has been obtained from the subject;

wherein the selected subject has:
- (i) an increase in the level of GYPA in the EPC of the in vitro cell culture method as compared to the level of GYPA in a control EPC;
- (ii) an increase in the level of GATA1 in the EPC of the in vitro cell culture method as compared to the level of GATA1 in a control EPC;
- (iii) a decrease in the level of GATA2 in the EPC of the in vitro cell culture method as compared to the level of GATA2 in a control EPC;
- (iv) a decrease in the level of alpha-globin in the EPC of the in vitro cell culture method as compared to the level of alpha-globin in a control EPC; or
- (v) an increase in the level of expansion of the EPC in the in vitro cell culture method as compared to the level of expansion in a control EPC;

or an in vitro cell culture method comprising the steps of:
- (a) culturing a stromal cell that has been obtained from the subject in the presence of an activin type II receptor (ActRII) signaling inhibitor for a period of time; and
- (b) determining the level of ICAM-1, IL-1Ra, survivin, Bcl-2, Bcl-xL, MCP-1, serpinE1, GRO-a, IL-8, IL-10, IL-2, RANTES, IP-10, IL-1a, IL-1b, MIF, G-CSF, GMCSF, C5a, IL-6, HO-2, HIF-1a, TRAIL R1, cleaved caspase-3, p27, p21, Bax, Bad, CIAP1, or PON2 in the supernatant obtained from the culture of step (a);

wherein the selected subject has:
- (i) an increase in the level of ICAM-1 in the supernatant of the in vitro cell culture method as compared to the level of ICAM-1 in a control supernatant
- (ii) an increase in the level of IL-1Ra in the supernatant of the in vitro cell culture as compared to the level of IL-1Ra in a control supernatant
- (iii) an increase in the level of survivin in the supernatant of the in vitro cell culture method as compared to the level of survivin in a control supernatant
- (iv) an increase in the level of Bcl-2 in the supernatant of the in vitro cell culture method as compared to the level of Bcl-2 in a control supernatant;
- (v) an increase in the level of Bcl-xL in the supernatant of the in vitro cell culture method as compared to the level of Bcl-xL in a control supernatant;
- (vi) an increase in the level of MCP-1 in the supernatant of the in vitro cell culture method as compared to the level of MCP-1 in a control supernatant;
- (vii) an increase in the level of serpinE1 in the supernatant of the in vitro cell culture method as compared to the level of serpinE1 in a control supernatant;
- (viii) an increase in the level of GRO-a in the supernatant of the in vitro cell culture method as compared to the level of GRO-a in a control supernatant;
- (ix) an increase in the level of IL-8 in the supernatant of the in vitro cell culture method as compared to the level of IL-8 in a control supernatant;
- (x) an increase in the level of IL-10 in the supernatant of the in vitro cell culture method as compared to the level of IL-10 in a control supernatant;
- (xi) an increase in the level of IL-2 in the supernatant of the in vitro cell culture method as compared to the level of IL-2 in a control supernatant;
- (xii) an increase in the level of CIAP1 in the supernatant of the in vitro cell culture method as compared to the level of CIAP1 in a control supernatant;
- (xiii) an increase in the level of PON2 in the supernatant of the in vitro cell culture method as compared to the level of PON2 in a control supernatant;
- (xiv) a decrease in the level of RANTES in the supernatant of the in vitro cell culture method as compared to the level of RANTES in a control supernatant;
- (xv) a decrease in the level of IP-10 in the supernatant of the in vitro cell culture method as compared to the level of IP-10 in a control supernatant;
- (xvi) a decrease in the level of IL-1a in the supernatant of the in vitro cell culture method as compared to the level of IL-1a in a control supernatant;
- (xvii) a decrease in the level of IL-1b in the supernatant of the in vitro cell culture method as compared to the level of IL-1b in a control supernatant;
- (xviii) a decrease in the level of MIF in the supernatant of the in vitro cell culture method as compared to the level of MIF in a control supernatant;
- (xix) a decrease in the level of G-CSF in the supernatant of the in vitro cell culture method as compared to the level of G-CSF in a control supernatant;
- (xx) a decrease in the level of GMCSF in the supernatant of the in vitro cell culture method as compared to the level of GMCSF in a control supernatant;
- (xxi) a decrease in the level of C5a in the supernatant of the in vitro cell culture method as compared to the level of C5a in a control supernatant;
- (xxii) a decrease in the level of IL-6 in the supernatant of the in vitro cell culture method as compared to the level of IL-6 in a control supernatant;
- (xxiii) a decrease in the level of HO-2 in the supernatant of the in vitro cell culture method as compared to the level of HO-2 in a control supernatant;
- (xxiv) a decrease in the level of HIF-1a in the supernatant of the in vitro cell culture method as compared to the level of HIF-1a in a control supernatant;
- (xxv) a decrease in the level of TRAIL R1 in the supernatant of the in vitro cell culture method as compared to the level of TRAIL R1 in a control supernatant;

(xxvi) a decrease in the level of cleaved caspase-3 in the supernatant of the in vitro cell culture method as compared to the level of cleaved caspase-3 in a control supernatant;
(xxvii) a decrease in the level of p27 in the supernatant of the in vitro cell culture method as compared to the level of p27 in a control supernatant;
(xxviii) a decrease in the level of p21 in the supernatant of the in vitro cell culture method as compared to the level of p21 in a control supernatant;
(xxix) a decrease in the level of Bax in the supernatant of the in vitro cell culture method as compared to the level of Bax in a control supernatant; and/or
(xxx) a decrease in the level of Bad in the supernatant of the in vitro cell culture method as compared to the level of bad in a control supernatant.

2. The method of claim 1, wherein the patient is being monitored using the in vitro cell culture method.

3. The method of claim 1, wherein the subject is a human.

4. The method of claim 1, wherein the stromal cell has been obtained from the bone marrow the subject.

5. The method of claim 1, wherein the erythroid progenitor cell has been obtained from peripheral blood of the subject.

6. The method of claim 1, wherein the ActRII signaling inhibitor is a polypeptide comprising an amino acid sequence selected from the group consisting of:
(a) 90% identical to SEQ ID NO:2;
(b) 95% identical to SEQ ID NO:2;
(c) 98% identical to SEQ ID NO:2;
(d) SEQ ID NO:2;
(e) 90% identical to SEQ ID NO:3;
(f) 95% identical to SEQ ID NO:3;
(g) 98% identical to SEQ ID NO:3;
(h) SEQ ID NO:3;
(i) 90% identical to SEQ ID NO:6;
(j) 95% identical to SEQ ID NO:6;
(k) 98% identical to SEQ ID NO:6;
(l) SEQ ID NO:6;
(m) 90% identical to SEQ ID NO:7;
(n) 95% identical to SEQ ID NO:7;
(o) 98% identical to SEQ ID NO:7;
(p) SEQ ID NO:7;
(q) 90% identical to SEQ ID NO:12;
(r) 95% identical to SEQ ID NO:12;
(s) 98% identical to SEQ ID NO:12;
(t) SEQ ID NO:12;
(u) 90% identical to SEQ ID NO:17;
(v) 95% identical to SEQ ID NO:17;
(w) 98% identical to SEQ ID NO:17;
(x) SEQ ID NO:17;
(y) 90% identical to SEQ ID NO:20;
(z) 95% identical to SEQ ID NO:20;
(aa) 98% identical to SEQ ID NO:20;
(bb) SEQ ID NO:20;
(cc) 90% identical to SEQ ID NO:21;
(dd) 95% identical to SEQ ID NO:21;
(ee) 98% identical to SEQ ID NO:21;
(ff) SEQ ID NO:21;
(gg) 90% identical to SEQ ID NO:25;
(hh) 95% identical to SEQ ID NO:25;
(ii) 98% identical to SEQ ID NO:25; and
(jj) SEQ ID NO:25.

7. The method of claim 1, wherein the ActRII signaling inhibitor is an ActRIIA signaling inhibitor.

8. The method of claim 7, wherein the ActRIIA signaling inhibitor is a polypeptide comprising an amino acid sequence selected from the group consisting of:
(a) 90% identical to SEQ ID NO:2;
(b) 95% identical to SEQ ID NO:2;
(c) 98% identical to SEQ ID NO:2;
(d) SEQ ID NO:2;
(e) 90% identical to SEQ ID NO:3;
(f) 95% identical to SEQ ID NO:3;
(g) 98% identical to SEQ ID NO:3;
(h) SEQ ID NO:3;
(i) 90% identical to SEQ ID NO:6;
(j) 95% identical to SEQ ID NO:6;
(k) 98% identical to SEQ ID NO:6;
(l) SEQ ID NO:6;
(m) 90% identical to SEQ ID NO:7;
(n) 95% identical to SEQ ID NO:7;
(o) 98% identical to SEQ ID NO:7; and
(p) SEQ ID NO:7.

9. The method of claim 1, wherein the ActRII signaling inhibitor is a polypeptide comprising the amino acid sequence of SEQ ID NO:7.

10. The method of claim 1, wherein the ActRII signaling inhibitor is a humanized fusion-protein consisting of the extracellular domain of ActRIIA and the human IgG1 Fc domain.

11. The method of claim 1, wherein the wherein the ActRII signaling inhibitor is a signaling inhibitor of ActRIIB.

12. The method of claim 11, wherein the ActRIIB signaling inhibitor is a polypeptide comprising an amino acid sequence selected from the group consisting of:
(a) 90% identical to SEQ ID NO:17;
(b) 95% identical to SEQ ID NO:17;
(c) 98% identical to SEQ ID NO:17;
(d) SEQ ID NO:17;
(e) 90% identical to SEQ ID NO:20;
(f) 95% identical to SEQ ID NO:20;
(g) 98% identical to SEQ ID NO:20;
(h) SEQ ID NO:20;
(i) 90% identical to SEQ ID NO:21;
(j) 95% identical to SEQ ID NO:21;
(k) 98% identical to SEQ ID NO:21;
(l) SEQ ID NO:21;
(m) 90% identical to SEQ ID NO:25;
(n) 95% identical to SEQ ID NO:25;
(o) 98% identical to SEQ ID NO:25; and
(p) SEQ ID NO:25.

13. The method of claim 1, wherein the ActRII signaling inhibitor is a polypeptide comprising the amino acid sequence of SEQ ID NO:25.

14. The method of any of claim 1, wherein the ActRII signaling inhibitor is a humanized fusion-protein consisting of the extracellular domain of ActRIIB and the human IgG1 Fc domain.

* * * * *